US008367374B2

(12) United States Patent
Umaña et al.

(10) Patent No.: US 8,367,374 B2
(45) Date of Patent: Feb. 5, 2013

(54) FUSION CONSTRUCTS AND USE OF SAME TO PRODUCE ANTIBODIES WITH INCREASED FC RECEPTOR BINDING AFFINITY AND EFFECTOR FUNCTION

(75) Inventors: Pablo Umaña, Zürich (CH); Peter Bruenker, Hittnau (CH); Claudia Ferrara, Zürich (CH); Tobias Suter, Baden (CH)

(73) Assignee: Roche GlycArt AG (CH)

( * ) Notice: Subject to any disclaimer, the term of this patent is extended or adjusted under 35 U.S.C. 154(b) by 431 days.

(21) Appl. No.: 10/761,435

(22) Filed: Jan. 22, 2004

(65) Prior Publication Data
US 2004/0241817 A1 Dec. 2, 2004

Related U.S. Application Data

(60) Provisional application No. 60/441,307, filed on Jan. 22, 2003, provisional application No. 60/491,254, filed on Jul. 31, 2003, provisional application No. 60/495,142, filed on Aug. 15, 2003.

(51) Int. Cl.
*C12P 21/04* (2006.01)
*C12P 21/08* (2006.01)
(52) U.S. Cl. .................................... 435/70.1; 435/70.21
(58) Field of Classification Search ........................ None
See application file for complete search history.

(56) References Cited

U.S. PATENT DOCUMENTS

| 4,676,980 A | 6/1987 | Segal et al. |
| 4,946,778 A | 8/1990 | Ladner et al. |
| 6,180,320 B1 | 1/2001 | Saito et al. |

FOREIGN PATENT DOCUMENTS

| WO | WO 94/11026 A2 | 5/1994 |
| WO | WO 96/40210 A1 | 12/1996 |
| WO | WO 99/54342 A1 | 10/1999 |
| WO | WO 0129242 A * | 4/2001 |
| WO | WO 01/31045 A1 | 5/2001 |
| WO | WO 02/00879 A2 | 1/2002 |
| WO | WO 02/079255 A1 | 10/2002 |
| WO | WO 03/078614 A2 | 9/2003 |
| WO | WO 2004/074499 A2 | 9/2004 |

OTHER PUBLICATIONS

Umana, P. et al., "Engineered glycoforms of an antineuroblastoma IgG1 with optimized antibody-dependent cellular cytotoxic activity", 1999, Nat. Biotech., vol. 17: pp. 176-180.*
Shields, R. et al., "Lack of Fucose on Human IgG1 N-linked Oligosaccharide Improves Binding to Human FcgammaRIII and Antibody-dependent Cellualr Toxicity", Jul. 2002, JBC, vol. 277, pp. 26733-26740.*
Lerouge, P. et al., "N-Glycosylation of Recombinant Pharmaceutical Glycoproteins Produced in Transgenic Plants: Towards an Humanisation of Plant N-Glycans", 2000, Curr. Pharm. Biotech., vol. 1: pp. 347-354.*
Grabenhorst, E. et al.,"The Cytoplasmic, Transmembrane, and Stem Regions of Glycosyltransferases Specify Their in Vivo Functional Sublocalization and Stability in the Golgi", 1999, J. Biol. Chem., vol. 274: pp. 36107-36116.*
Amigorena, S., "Fcγ Receptors and Cross-Presentation in Dendritic Cells," *J. Exp. Med.* 195:F1-F3, The Rockefeller University Press (Jan. 2002).
Andersen, D.C., and Krummen, L., "Recombinant protein expression for therapeutic applications," *Curr. Opin. Biotechnol.* 13:117-123, Elsevier Science Ltd. (Apr. 2002).
Arnon, R., et al., "Monoclonal Antibodies for Immunotargeting of Drugs in Cancer Therapy," in *Monoclonal Antibodies and Cancer Therapy*, Reisfeld, R.A., and Sell, S., eds., Alan R. Liss, Inc., New York, NY, pp. 243-256 (1985).
Borth, N., et al., "Efficient Selection of High-Producing Subclones During Gene Amplification of Recombinant Chinese Hamster Ovary Cells by Flow Cytometry and Cell Sorting," *Biotechnol. Bioeng.* 71:266-273, John Wiley & Sons, Inc. (2001).
Carson, W.E., et al., "Interleukin-2 enhances the natural killer cell response to Herceptin-coated Her2/*neu*-positive breast cancer cells," *Eur. J. Immunol.* 31:3016-3025, Wiley-VCH Verlag Gmbh (2001).
Cartron, G., et al., "Therapeutic activity of humanized anti-CD20 monoclonal antibody and polymorphism in IgG Fc receptor FcγRIIIa gene," *Blood* 99:754-758, American Society of Hematology (Feb. 2002).
Chadd, H.E., and Chamow, S.M., "Therapeutic antibody expression technology," *Curr. Opin. Biotechnol.* 12:188-194, Elsevier Science Ltd. (2001).
Chamow, S.M., and Ashkenazi, A., "Immunoadhesins: principles and applications," *Trends Biotechnol.* 14:52-60, Elsevier Science Ltd. (1996).
Clynes, R.A., et al., "Inhibitory Fc receptors modulate *in vivo* cytotoxicity against tumor targets," *Nat. Med.* 6:443-446, Nature Publishing Company (2000).
Cole, S.P.C., et al., "The EBV-Hybridoma Technique and Its Applications to Human Lung Cancer," in *Monoclonal Antibodies and Cancer Therapy*, Reisfeld, R.A., and Sell, S., eds., Alan R. Liss, Inc., New York, NY, pp. 77-96 (1985).
Colbère-Garapin, F., et al., "A New Dominant Hybrid Selective Marker for Higher Eukaryotic Cells," *J. Mol. Biol.* 150:1-14, Academic Press Inc. (London) Ltd. (1981).
Cote, R.J., et al., "Generation of human monoclonal antibodies reactive with cellular antigens," *Proc. Natl. Acad. Sci. USA* 80:2026-2030, The National Academy of Sciences (1983).
Cragg, M.S., et al., "Complement-mediated lysis by anti-CD20 mAb correlates with segregation into lipid rafts," *Blood* 101:1045-1052, The American Society of Hematology (Feb. 2003). Cumming, D.A., "Glycosylation of recombinant protein therapeutics: control and functional implications," *Glycobiology* 1:115-130, Oxford University Press (1991).
Daëron, M., "Fc Receptor Biology," *Annu. Rev. Immunol.* 15:203-234, Annual Reviews Inc. (1997).
de Haas, M., et al., "A Triallelic Fcγ Receptor Type IIIa Polymorphism Influences the Binding of Human IgG by NK Cell FcγRIIIa[1]," *J. Immunol.* 156:2948-2955, The American Association of Immunologist (1996).
Deo, Y.M., et al., "Clinical significance of IgG Fc receptors and FcγR-directed immunotherapies," *Immunol. Today* 18:127-135, Elsevier Science Ltd. (1997).

(Continued)

*Primary Examiner* — Michael Burkhart
(74) *Attorney, Agent, or Firm* — Sterne, Kessler, Goldstein & Fox P.L.L.C.

(57) ABSTRACT

The present invention relates to the field of glycosylation engineering of proteins. More particularly, the present invention relates to nucleic acid molecules, including fusion constructs, having catalytic activity and the use of same in glycosylation engineering of host cells to generate polypeptides with improved therapeutic properties, including antibodies with increased Fc receptor binding and increased effector function.

33 Claims, 43 Drawing Sheets

OTHER PUBLICATIONS

Dillman, R.O., "Magic Bullets at Last! Finally—Approval of a Monoclonal Antibody for the Treatment of Cancer!!!," *Cancer Biother. Radiopharm. 12*:223-225, Mary Ann Liebert, Inc. (1997).

Freireich, E.J., et al., "Quantitative Comparison of Toxicity of AntiCancer Agents in Mouse, Rats, Hamster, Dog, Monkey, and Man," *Cancer Chemother. Rep. 50*:219-244, National Cancer Institute (1966).

Frost, J.D., et al., "A Phase I/IB Trial of Murine Monoclonal Anti-GD2 Antibody 14.G2a plus Interleukin-2 in Children with Refractory Neuroblastoma," *Cancer 80*:317-333, John Wiley & Sons, Inc. (1997).

Giddings, G., "Transgenic plants as protein factories," *Curr. Opin. Biotechnol. 12*:450-454, Elsevier Science Ltd. (2001).

Goldenberg, M.M., "Trastuzumab, a Recombinant DNA-Derived Humanized Monoclonal Antibody, a Novel Agent for the Treatment of Metastatic Breast Cancer," *Clin. Ther. 21*:309-318, Excerpta Medica, Inc. (1999).

Grillo-López, A.J., et al., "Overview of the Clinical Development of Rituximab: First Monoclonal Antibody Approved for the Treatment of Lymphoma," *Semin. Oncol. 26*:66-73, W.B. Saunders Company (1999).

Hartman, S.C., and Mulligan, R.C., "Two dominant-acting selectable markers for gene transfer studies in mammalian cells," *Proc. Natl. Acad. Sci. USA 85*:8047-8051, National Academy of Sciences (1988).

Hazenbos, W.L.W., et al., "Murine IgG1 Complexes Trigger Immune Effector Functions Predominantly via FcγRIII (CD16)," *J. Immunol. 161*:3026-3032, The American Association of Immunologists (1998).

Hellström, K.E., and Hellström, I., "Chap. 15. Antibodies for Drug Delivery," Controlled Drug Delivery Fundamentals and Applications, $2^{nd}$ ed., Robinson, J.R., and Lee, V.H.L., eds., Marcel Dekker, Inc., New York, NY, pp. 623-653 (1987).

Huse, W.D., et al., "Generation of a Large Combinatorial Library of the Immunoglobulin Repertoire in Phage Lambda," *Science 246*:1275-1281, American Association for the Advancement of Science (1989).

Jefferis, R., et al., "IgG-Fc-mediated effector functions: molecular definition of interaction sites for effector ligands and the role of glycosylation," *Immunol. Rev. 163*:59-76, Munksgaard (1998).

Jenkins, N., et al., "Getting the glycosylation right: Implications for the biotechnology industry," *Nat. Biotechnol. 14*:975-981, Nature America Publishing (1996).

Kalergis, A.M., and Ravtech, J.V., "Inducing Tumor Immunity through the Selective Engagement of Activating Fcγ Receptors on Dendritic Cells," *J. Exp. Med. 195*:1653-1659, The Rockefeller University Press (Jun. 2002).

Kobayashi, N., et al., "Analysis of Assembly of Synthetic Antibody Fragments: Expression of Functional scFv with Predefined Specificity," *BioTech. 23*:500-503, Eaton Publishing Co. (1997).

Köhler, G., and Milstein, C., "Continuous cultures of fused cells secreting antibody of predefined specificity," *Nature 256*:495-497, Macmillan Journals Ltd. (1975).

Kozbor, D., and Roder, C.J., "The production of monoclonal antibodies from human lymphocytes," *Immunol. Today 4*:72-79, Elsevier Biomedical Press (1983).

Lerouge, P., et al., "N-Glycosylation of Recombinant Pharmaceutical Glycoproteins Produced in Transgenic Plants: Towards an Humanisation of Plant N-Glycans," *Curr. Pharm. Biotechnol. 1*:347-354, Bentham Science Publishers Ltd. (2000).

Lifely, M.R., et al., "Glycosylation and biological activity of CAMPATH-1H expressed in different cell lines and grown under different culture conditions," *Glycobiology 5*:813-822, Oxford University Press (1995).

Lis, H., and Sharon, N., "Protein glycosylation Structural and Functional aspects," *Eur. J. Biochem. 218*:1-27, FEBS (1993).

Lowy, I., et al., "Isolation of Transforming DNA: Cloning the Hamster aprt Gene," *Cell 22*:817-823, MIT (1980).

Lund, J., et al., "Multiple Interactions of IgG with Its Core Oligosaccharide Can Modulate Recognition by Complement and Human Fcγ Receptor I and Influence the Synthesis of Its Oligosaccharide Chains," *J. Immunol. 157*:4963-4969, American Association of Immunologists (1996).

Ma, J.K.-C., et al., "The Production of Recombinant Pharmaceutical Proteins in Plants," *Nat. Rev. Genet. 4*:794-805, Nature Publishing Group (Oct. 2003).

Maloney, D.G., et al., "Rituximab: Mechanism of Action and Resistance," *Semin. Oncol. 29*:2-9, W.B. Saunders Company (Feb. 2002).

Metes, D., et al., "Identification of the CD32/FcγRIIc-$Q^{13}$/$STP^{13}$ polymorphism using an allele-specific restriction enzyme digestion assay," *J. Immunol. Meth. 258*:85-95, Elsevier Science B.V. (2001).

Mulligan, R.C., and Berg, P., "Selection for animal cells that express the *Escherichia coli* gene coding for xanthine-guanine phosphoribosyltransferase," *Proc. Natl. Acad. Sci. USA 78*:2072-2076, National Academy of Science (1981).

Morrison, S.L., et al., "Chimeric human antibody molecules: Mouse antigen-binding domains with human constant region domains," *Proc. Natl. Acad. Sci. USA 81*:6851-6855, National Academy of Science (1984).

Neuberger, M.S., et al., "Recombinant antibodies possessing novel effector functions," *Nature 312*:604-608, Macmillan Journals Ltd. (1984).

Nilsson, T., et al., "Kin recognition between *medial* Golgi enzymes in HeLa cells," *EMBO J. 13*:562-574, Oxford University Press (1994).

O'Hare, K., et al., "Transformation of mouse fibroblasts to methotrexate resistance by a recombinant plasmid expressing a prokaryotic dihydrofolate reductase," *Proc. Natl. Acad. Sci. USA 78*:1527-1531, National Academy of Science (1981).

Opat, a.S., et al., "*Medial* Golgi but Not Late Golgi Glycosyltransferases Exist as High Molecular Weight Complexes," *J. Biol. Chem. 275*:11836-11845, The American Society for Biochemistry and Molecular Biology, Inc. (2000).

Order, S.E., "Chap. 15. Analysis, Results, and Future Prospective of the Therapeutic Use of Radiolabeled Antibody in Cancer Therapy," in *Monoclonal Antibodies for Cancer Detection and Therapy*, Baldwin, R.W., and Byers, V.S., eds., Academic Press Inc. (London) Ltd., pp. 303-316 (1985).

Pini, A., et al., "Design and Use of a Phage Display Library," *J. Biol. Chem. 273*:21769-21776, The American Society for Biochemistry and Molecular Biology, Inc. (1988).

Rabouille, C., et al., "Mapping the distribution of Golgi enzymes involved in the construction of complex oligosaccharides," *J. Cell Sci. 108*:1617-1627, The Company of Biologist Ltd. (1995).

Ratanatharathorn, V., et al., "Anti-CD20 Chimeric Monoclonal Antibody Treatment of Refractory Immune-Mediated Thrombocytopenia in a Patient with Chronic Graft-versus-Hot Disease," *Ann. Intern. Med. 133*:275-279, The American College of Physician—American Society of Internal Medicine (2000).

Ravetch, J.V., and Bolland, S., "IgG Fc Receptors," *Annu. Rev. Immunol. 19*:275-290, Annual Reviews (2001).

Reff, M.E., and Heard, C., "A review of modifications to recombinant antibodies: attempt to increase efficacy in oncology applications," *Crit. Rev. Oncol. Hematol. 40*:25-35, Elsevier Science Ireland Ltd. (2000).

Santerre, R.F., et al., "Expression of prokaryotic genes for hygromycin B and G418 resistance as dominant-selection markers in mouse L cells," *Gene 1069*:147-156, Elsevier Science Publishers (1984).

Schachter, H., "Biosynthetic controls that determine the branching and microheterogeneity of protein-bound oligosaccharides," *Biochem. Cell Biol. 64*:163-181, National Research Council of Canada (1986).

Selenko, N., et al., "Cross-Priming of Cytotoxic T Cells Promoted by Apoptosis-Inducing Tumor Cell Reactive Antibodies?," *J. Clin. Immunol. 22*:124-130, Plenum Publishing Corporation (May 2002).

Senter, P.D., "Activation of prodrugs by antibody-enzyme conjugates: a new approach to cancer therapy," *FASEB J. 4*:188-193, Federation of American Societies for Experimental Biology (1990).

Senter, P.D., et al., "Enhancement of the *in Vitro* and *in Vivo* Antitumor Activities of Phosphorylated Mitomycin C and Etoposide Derivatives by Monoclonal Antibody-Alkaline Phosphatase Conjugates," *Cancer Res. 49*:5789-5792, American Association for Cancer Research, Inc. (1989).

Senter, P.D., et al., "Anti-tumor effects of antibody-alkaline phosphatase conjugates in combination with etoposide phosphate," *Proc. Natl. Acad. Sci. USA 85*:4842-4846, The National Academy of Sciences (1988).

Shields, R.L., et al., "Lack of Fucose on Human IgG1 N-Linked Oligosaccharide Improves Binding to Human FcγRIII and Antibody-dependent Cellular Toxicity," *J Biol. Chem. 277*:26733-26740, The American Society for Biochemistry and Molecular Biology, Inc. (Jul. 2002).

Stabila, P.F., et al., "Cell surface expression of a human IgG Fc chimera activates macrophages through Fc receptors," *Nat. Biotechnol. 16*:1357-1360, Nature American Inc. (1998).

Surfus, J.E., et al., "Anti-Renal-Cell Carcinoma Chimeric Antibody G250 Facilitates Antibody-Dependent Cellular Cytotoxicity with In Vitro and In Vivo Interleukin-2-Activated Effectors," *J. Immunother. 19*:184-191, Lippincott-Raven Publishers (1996).

Szybalska, E.H., and Szybalski, W., "Genetics of Human Cell Lines, IV. DNA-Mediated Heritable Transformation of a Biochemical Trait," *Proc. Natl. Acad. Sci. USA 48*:2026-2034, National Academy of Science (1962).

Takeda, S.-I., et al., "Construction of chimaeric processed immunoglobulin genes containing mouse variable and human constant region sequences," *Nature 314*:452-454, Macmillan Journals Ltd. (1985).

Thorpe, P.E., and Ross, W.C.J., "The Preparation and Cytotoxic Properties of Antibody-Toxin Conjugates," *Immunol. Rev. 62*:119-158, Munksgaard (1982).

Thorpe, P.E., "Antibody Carriers of Cytotoxic Agents in Cancer Therapy: A Review," in *Monoclonal Antibodies '84: Biological and Clinical Applications*, Pinchea, A., et al., eds., Editrice Kurtis, Italy, Milano, pp. 475-506 (1985).

Umaña, P., et al., "Engineered glycoforms of an antineuroblastoma IgG1 with optimized antibody-dependent cellular cytotoxic activity," *Nat. Biotechnol. 17*:176-180, Nature America, Inc. (1999).

van Der Kolk, L.E., et al., "Complement activation plays a key role in the side-effects of rituximab treatment," *Br. J. Hematol. 115*:807-811, Blackwell Science Ltd. (2001).

Werner, R.G., et al., "Appropriate Mammalian Expression Systems for Biopharmaceuticals," *Arzneim.-Forsch./Drug Res. 48*:870-880, Editio Cantor Verlages (1998).

Wigler, M., et al., "Transformation of mammalian cells with an amplifiable dominant-acting gene," *Proc. Natl. Acad. Sci. USA 77*:3567-3570, National Academy of Science (1980).

Wigler, M., et al., "Transfer of Purified Herpes Virus Thymidine Kinase Gene to Cultured Mouse Cells," *Cell 11*:223-232, MIT (1977).

Wright, A., and Morrison, S.L., "Effect of glycosylation on antibody function: implications for genetic engineering," *Trends Biotechnol. 15*:26-32, Eslevier Science Ltd. (1997).

Wormland, M.R., et al., "Variations in Oligosaccharide-Protein Interactions in Immunoglobulin G Determine the Site-Specific Glycosylation Profiles and Modulate the Dynamic Motion of the Fc Oligosaccharides," *Biochemistry 36*:1370-1380, American Chemical Society (1997).

Zecca, M., et al., "Anti-CD20 monoclonal antibody for the treatment of severe, immune-mediated pure red cell aplasia and hemolytic anemia," *Blood 97*:3995-3997, The American Society of Hematology (2001).

Ferrara, C., et al., "Modulation of Therapeutic Antibody Effector Functions by Glycosylation Engineering: Influence of Golgi Enzyme Localization Domain and Co-Expression of Heterologous β1, 4-*N*-acetylglucosaminyltransferase III and Golgi α-mannosidase II," *Biotechnol. Bioeng. 93*(5):851-861, Wiley Periodicals, Inc. (Jan. 2006).

Sburlati, A.R., et al., "Synthesis of Bisected Glycoforms of Recombinant IFN-β by Overexpression of β-1,4-*N*-Acetylglucosaminytransferase III in Chinese Hamster Ovary Cells," *Biotechnol. Prog. 14*:189-192, American Chemical Society (1998).

Examination Report for European Application No. 04 704 310.4, mailed Nov. 10, 2008, European Patent Office, Munich, Germany.

Bakker, H., et al., Galactose-extended glycans of antibodies produced by transgenic plants, *Proc. Natl. Acad. Sci. USA 98*:2899-2904, The National Academy of Sciences (2001).

Palacpac, N.Q, et al., "Stable expression of human β1,4-galactosyltransferase in plant cells modifies N-linked glycosylation patterns," *Proc. Natl. Acad. Sci. USA 96*:4692-4697, The National Academy of Sciences (1999).

International Search Report for International Application No. PCT/IB2004/000844, European Patent Office, Netherlands, mailed on Jan. 5, 2005.

International Preliminary Report on Patentability for International Application No. PCT/IB2004/000844, European Patent Office, mailed on Jan. 12, 2005.

Burke, J., et al., "The Transmembrane and Flanking Sequences of β1,2-*N*-Acetylglucosaminyltransferase I Specify *medial*-Golgi Localization*," *J. Biol. Chem. 267*:24433-24440, The American Society for Biochemistry and Molecular Biology, Inc., United States (1992).

Malaise, M.G., et al., "*In vitro* studies on the Fc-receptor function of mononuclear phagocytes in rheumatoid arthritis: Relation between the Fc-receptor blockade and the concanavalin A-binding capacity of autologous immunoglobulin G," *J. Clin. Immunol., 6(6)*:442-456, Springer, Netherlands (1986).

Misago, M., et al., "Molecular cloning and expression of cDNAs encoding human alpha-mannosidase II and a previously unrecognized alpha-mannosidase II$^X$ isozyme," *Proc. Natl. Acad. Sci., 92*:11766-11770, National Academy of Sciences, United States (1995).

Davies, J., et al., "Expression of GnTIII in a Recombinant Anti-CD20 CHO Production Cell Line: Expression of Antibodies with Altered Glycoforms Leads to an Increase in ADCC Through Higher Affinity for FCγRIII," *Biotechnology and Bioengineering 74(4)*:288-294, John Wiley & Sons, Inc., USA (Aug. 2001).

Moreman, K.W. and Robbins, P.W., "Isolation, Characterization, and Expression of cDNAs Encoding Murine α-Mannosidase II, a Golgi Enzyme that Controls Conversion of High Mannose to Complex N-Glycans," *J. Cell. Biol. 115(6)*:1521-1534, The Rockefeller University Press, USA (Dec. 1991).

Nilsson, T., et al., "The membrane spanning domain of β-1,4-galactosyltransferase specifies *trans* Golgi localization," *The EMBO Journal 10*(12):3567-3575, Oxford University Press, England (Dec. 1991).

Umaña, P., et al., "Tetracycline-Regulated Overexpression of Glycosyltransferase in Chinese Hamster Ovary Cells," *Biotechnology and Bioengineering 65*(5):542-549, John Wiley & Sons, Inc., United States (Dec. 1999).

Partial European Search Report with Written Opinion for European Application No. EP 10 07 5272.4, European Patent Office, Germany, mailed on Nov. 9, 2010.

Partial European Search Report with Written Opinion for European Application No. EP 10 07 5273.2, European Patent Office, Germany, mailed on Oct. 2, 2010.

Partial European Search Report for European Application No. EP 10 07 5271.6, European Patent Office, Germany, mailed on Nov. 10, 2010.

Nilsson, T., et al., "The Role of the Membrane-spanning Domain and Stalk Region of *N*-acetylglucosaminyltransferase I in Retention, Kin Recognition and Structural Maintenance of the Golgi Apparatus in HeLa Cells," *J. Cell Sci. 109*:1975-1989, The Company of Biologists Ltd., England (1996).

\* cited by examiner

Figure 7
(a)
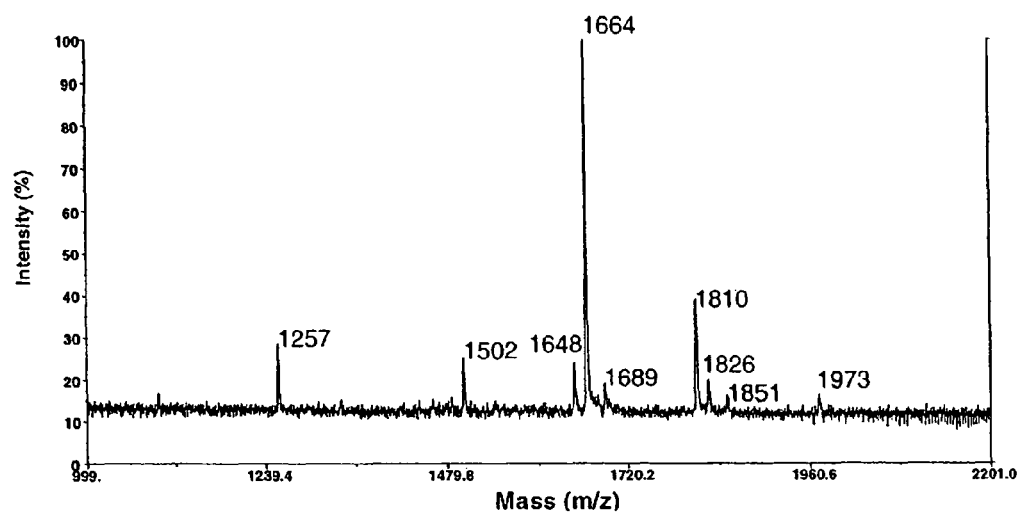
(b)
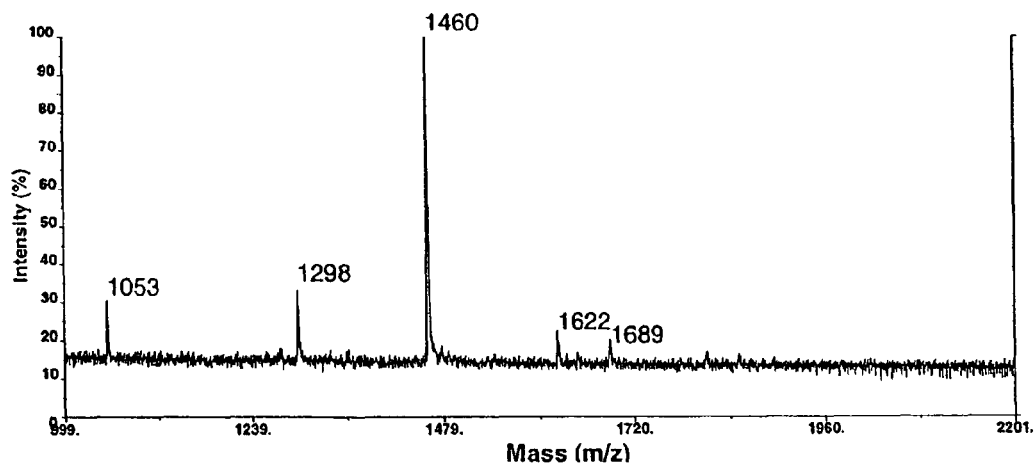

ManII-GnTIII:

Bold: ManII localization domain (cytoplasmic tail + transmembrane region + stem region)

**ATGAAGTTAAGCCGCCAGTTCACCGTGTTCGGCAGTGCGATCTTCTGTGTGGTGATTTTC
TCGCTCTACCTGATGCTGGACCGGGGTCACTTAGACTACCCCAGGAACCCGCGCCGCGAG
GGCTCCTTCCCTCAGGGCCAGCTCTCAATGTTGCAAGAAAAAATAGACCATTTGGAGCGT
TTGCTAGCTGAGAATAATGAGATCATCTCAAATATTAGAGACTCAGTCATCAATTTGAGT
GAGTCTGTGGAGGATGGTCCGAAAAGTTCACAAAGCAATTTCAGCCAAGGTGCTGGCTCA**
CCCCTGCTCCAGCCACTGTCCCCTAGCAAGGCCACCGAAGAACTGCACCGGGTGGACTTC
GTGTTGCCGGAGGACACCACAGAGTATTTTGTGCGCACCAAAGCTGGCGGTGTGTGCTTC
AAACCAGGTACCAGGATGCTGGAGAAACCTTCTCCAGGGCGGACAGAGGAGAAGACCAAG
GTGGCTGAGGGGTCCTCGGTCCGGGGTCCTGCTCGGAGGCCTATGCGGCATGTGTTGAGT
GCACGGGAGCGCCTGGGAGGCCGGGGCACTAGGCGCAAGTGGGTTGAGTGTGTGTGCCTG
CCAGGCTGGCACGGGCCCAGCTGCGGGGTGCCCACTGTGGTCCAGTATTCCAACCTGCCC
ACCAAGGAGCGCCTGGTACCCAGGGAGGTGCCGAGGCGGGTTATCAACGCCATCAACATC
AACCATGAGTTCGACCTGCTGGATGTGCGCTTCCATGAGCTGGGCGATGTTGTGGACGCC
TTTGTGGTCTGCGAATCCAATTTCACCGCCTACGGGGAGCCTCGGCCGCTCAAGTTCCGA
GAGATGCTGACCAATGGCACCTTCGAGTACATCCGCCACAAGGTGCTCTACGTCTTCCTG
GACCACTTCCCACCTGGTGGCCGTCAGGACGGCTGGATTGCAGACGACTACCTGCGTACC
TTCCTCACCCAGGATGGTGTCTCCCGCCTGCGCAACCTGCGACCTGATGACGTCTTTATC
ATCGACGACGCGGACGAGATCCCTGCGCGTGATGGTGTGCTGTTCCTCAAGCTCTACGAT
GGCTGGACAGAGCCCTTCGCCTTCCATATGCGCAAGTCCCTGTATGGTTTCTTTTGGAAG
CAACCAGGCACACTGGAGGTGGTGTCAGGCTGCACCATTGACATGCTGCAGGCTGTGTAT
GGGCTGGACGGCATCCGCCTGCGCCGCCGTCAGTACTACACCATGCCCAACTTTCGACAG
TATGAGAACCGCACCGGCCACATCCTAGTGCAGTGGTCTCTCGGCAGCCCCCTGCACTTC
GCGGGCTGGCACTGCTCCTGGTGCTTCACACCCGAGGGCATCTACTTCAAACTCGTGTCG
GCCCAGAATGGTGACTTCCCCCGCTGGGGTGACTACGAGGACAAGAGGGACCTCAATTAC
ATCCGAAGCTTGATTCGCACTGGGGGATGGTTCGACGGCACGCAGCAGGAGTACCCTCCT
GCAGACCCCAGTGAACACATGTATGCTCCTAAGTACCTGCTCAAGAACTATGACCAGTTC
CGCTACTTGCTCGAAAATCCCTACCGGGAGCCCAAGAGCACTGTAGAGGGTGGGCGCCGG
AACCAGGGCTCAGACGGAAGGTCATCTGCTGTCAGGGGCAAGTTGGATACAACGGAGGGC
CCGGAACAGAAACTGATCTCTGAAGAGGACCTGTAG

**MKLSRQFTVFGSAIFCVVIFSLYLMLDRGHLDYPRNPRREGSFPQGQLSMLQEKIDHLER
LLAENNEIISNIRDSVINLSESVEDGPKSSQSNFSQGAGS**PLLQPLSPSKATEELHRVDF
VLPEDTTEYFVRTKAGGVCFKPGTRMLEKPSPGRTEEKTKVAEGSSVRGPARRPMRHVLS
ARERLGGRGTRRKWVECVCLPGWHGPSCGVPTVVQYSNLPTKERLVPREVPRRVINAINI
NHEFDLLDVRFHELGDVVDAFVVCESNFTAYGEPRPLKFREMLTNGTFEYIRHKVLYVFL
DHFPPGGRQDGWIADDYLRTFLTQDGVSRLRNLRPDDVFIIDDADEIPARDGVLFLKLYD
GWTEPFAFHMRKSLYGFFWKQPGTLEVVSGCTIDMLQAVYGLDGIRLRRRQYYTMPNFRQ
YENRTGHILVQWSLGSPLHFAGWHCSWCFTPEGIYFKLVSAQNGDFPRWGDYEDKRDLNY
IRSLIRTGGWFDGTQQEYPPADPSEHMYAPKYLLKNYDQFRYLLENPYREPKSTVEGGRR
NQGSDGRSSAVRGKLDTTEGPEQKLISEEDL

Figure 24

GnTI-GnTIII

Bold: GnTI ManII localization domain (cytoplasmic tail + transmembrane region + stem region)

**ATGCTGAAGAAGCAGTCTGCAGGGCTTGTGCTGTGGGGCGCTATCCTCTTTGTGGCCTGG
AATGCCCTGCTGCTCCTCTTCTTCTGGACGCGCCCAGCACCTGGCAGGCCACCCTCAGTC
AGCGCTCTCGATGGCGACCCCGCCAGCCTCACCCGGGAAGTGATTCGCCTGGCCCAAGAC
GCCGAGGTGGAGCTGGAGCGGCAGCGTGGGCTGCTGCAGCAGATCGGGGATGCCCTGTCG
AGCCAGCGGGGAGGGTGCCCACCGCGGCCCCTCCCGCCCAGCCGCGTGTGCCTGTGACC
CCCGCG**CCCCTGCTCCAGCCACTGTCCCCTAGCAAGGCCACCGAAGAACTGCACCGGGTG
GACTTCGTGTTGCCGGAGGACACCACAGAGTATTTTGTGCGCACCAAAGCTGGCGGTGTG
TGCTTCAAACCAGGTACCAGGATGCTGGAGAAACCTTCTCCAGGGCGGACAGAGGAGAAG
ACCAAGGTGGCTGAGGGGTCCTCGGTCCGGGGTCCTGCTCGGAGGCCTATGCGGCATGTG
TTGAGTGCACGGGAGCGCCTGGGAGGCCGGGGCACTAGGCGCAAGTGGGTTGAGTGTGTG
TGCCTGCCAGGCTGGCACGGGCCCAGCTGCGGGGTGCCCACTGTGGTCCAGTATTCCAAC
CTGCCCACCAAGGAGCGCCTGGTACCCAGGGAGGTGCCGAGGCGGGTTATCAACGCCATC
AACATCAACCATGAGTTCGACCTGCTGGATGTGCGCTTCCATGAGCTGGGCGATGTTGTG
GACGCCTTTGTGGTCTGCGAATCCAATTTCACCGCCTACGGGGAGCCTCGGCCGCTCAAG
TTCCGAGAGATGCTGACCAATGGCACCTTCGAGTACATCCGCCACAAGGTGCTCTACGTC
TTCCTGGACCACTTCCCACCTGGTGGCCGTCAGGACGGCTGGATTGCAGACGACTACCTG
CGTACCTTCCTCACCCAGGATGGTGTCTCCCGCCTGCGCAACCTGCGACCTGATGACGTC
TTTATCATCGACGACGCGGACGAGATCCCTGCGCGTGATGGTGTGCTGTTCCTCAAGCTC
TACGATGGCTGGACAGAGCCCTTCGCCTTCCATATGCGCAAGTCCCTGTATGGTTTCTTT
TGGAAGCAACCAGGCACACTGGAGGTGGTGTCAGGCTGCACCATTGACATGCTGCAGGCT
GTGTATGGGCTGGACGGCATCCGCCTGCGCCGCCGTCAGTACTACACCATGCCCAACTTT
CGACAGTATGAGAACCGCACCGGCCACATCCTAGTGCAGTGGTCTCTCGGCAGCCCCCTG
CACTTCGCGGGCTGGCACTGCTCCTGGTGCTTCACACCCGAGGGCATCTACTTCAAACTC
GTGTCGGCCCAGAATGGTGACTTCCCCCGCTGGGGTGACTACGAGGACAAGAGGGACCTC
AATTACATCCGAAGCTTGATTCGCACTGGGGGATGGTTCGACGGCACGCAGCAGGAGTAC
CCTCCTGCAGACCCCAGTGAACACATGTATGCTCCTAAGTACCTGCTCAAGAACTATGAC
CAGTTCCGCTACTTGCTCGAAAATCCCTACCGGGAGCCCAAGAGCACTGTAGAGGGTGGG
CGCCGGAACCAGGGCTCAGACGGAAGGTCATCTGCTGTCAGGGGCAAGTTGGATACAACG
GAGGGCCCGGAACAGAAACTGATCTCTGAAGAGGACCTGTAG

**MLKKQSAGLVLWGAILFVAWNALLLLFFWTRPAPGRPPSVSALDGDPASLTREVIRLAQD
AEVELERQRGLLQQIGDALSSQRGRVPTAAPPAQPRVPVTPAPLL**QPLSPSKATEELHRV
DFVLPEDTTEYFVRTKAGGVCFKPGTRMLEKPSPGRTEEKTKVAEGSSVRGPARRPMRHV
LSARERLGGRGTRRKWVECVCLPGWHGPSCGVPTVVQYSNLPTKERLVPREVPRRVINAI
NINHEFDLLDVRFHELGDVVDAFVVCESNFTAYGEPRPLKFREMLTNGTFEYIRHKVLYV
FLDHFPPGGRQDGWIADDYLRTFLTQDGVSRLRNLRPDDVFIIDDADEIPARDGVLFLKL
YDGWTEPFAFHMRKSLYGFFWKQPGTLEVVSGCTIDMLQAVYGLDGIRLRRRQYYTMPNF
RQYENRTGHILVQWSLGSPLHFAGWHCSWCFTPEGIYFKLVSAQNGDFPRWGDYEDKRDL
NYIRSLIRTGGWFDGTQQEYPPADPSEHMYAPKYLLKNYDQFRYLLENPYREPKSTVEGG
RRNQGSDGRSSAVRGKLDTTEGPEQKLISEEDL

SEQUENCE LISTING

```
<160> NUMBER OF SEQ ID NOS: 20

<210> SEQ ID NO 1
<211> LENGTH: 11
<212> TYPE: PRT
<213> ORGANISM: Unknown
<220> FEATURE:
<223> OTHER INFORMATION: c-myc epitope tag

<400> SEQUENCE: 1

Pro Gln Lys Leu Ile Ser Glu Glu Asp Leu
1               5                   10

<210> SEQ ID NO 2
<211> LENGTH: 45
<212> TYPE: DNA
<213> ORGANISM: Artificial Sequence
<220> FEATURE:
<223> OTHER INFORMATION: GAB-177 PCR primer

<400> SEQUENCE: 2
gcgtgtgcct gtgaccccg cgccctgct ccagccactg tcccc           45

<210> SEQ ID NO 3
<211> LENGTH: 26
<212> TYPE: DNA
<213> ORGANISM: Artificial Sequence
<220> FEATURE:
<223> OTHER INFORMATION: GAB-178 PCR primer

<400> SEQUENCE: 3
gaaggtttct ccagcatcct ggtacc                              26

<210> SEQ ID NO 4
<211> LENGTH: 43
<212> TYPE: DNA
<213> ORGANISM: Artificial Sequence
<220> FEATURE:
<223> OTHER INFORMATION: GAB-179 PCR primer

<400> SEQUENCE: 4
ctgaggcgcg ccgccaccat gctgaagaag cagtctgcag ggc           43

<210> SEQ ID NO 5
<211> LENGTH: 48
```

-continued

```
<212> TYPE: DNA
<213> ORGANISM: Artificial Sequence
<220> FEATURE:
<223> OTHER INFORMATION: GAB-180 PCR primer

<400> SEQUENCE: 5
ggggacagtg gctggagcag gggcgcgggg gtcacaggca cacgcggc                48

<210> SEQ ID NO 6
<211> LENGTH: 50
<212> TYPE: DNA
<213> ORGANISM: Artificial Sequence
<220> FEATURE:
<223> OTHER INFORMATION: GAB-252 PCR primer

<400> SEQUENCE: 6
gctaggccgg ccgccaccat gaagttaagc cgccagttca ccgtgttcgg              50

<210> SEQ ID NO 7
<211> LENGTH: 65
<212> TYPE: DNA
<213> ORGANISM: Artificial Sequence
<220> FEATURE:
<223> OTHER INFORMATION: GAB-253 PCR primer

<400> SEQUENCE: 7
ggggacagtg gctggagcag gggtgagcca gcaccttggc tgaaattgct tgtgaactt   60 ttcgg                                                              65

<210> SEQ ID NO 8
<211> LENGTH: 66
<212> TYPE: DNA
<213> ORGANISM: Artificial Sequence
<220> FEATURE:
<223> OTHER INFORMATION: GAB-254 PCR primer

<400> SEQUENCE: 8
tccgaaaagt tcacaaagca atttcagcca aggtgctggc tcacccctgc tccagccact   60
gtcccc                                                              66

<210> SEQ ID NO 9
<211> LENGTH: 29
<212> TYPE: DNA
<213> ORGANISM: Artificial Sequence
<220> FEATURE:
<223> OTHER INFORMATION: GAB-255 PCR primer

<400> SEQUENCE: 9
atgccgcata ggcctccgag caggacccc                                    29

<210> SEQ ID NO 10
<211> LENGTH: 43
<212> TYPE: DNA
<213> ORGANISM: Artificial Sequence
<220> FEATURE:
<223> OTHER INFORMATION: GAB-261 PCR primer

<400> SEQUENCE: 10
gctaaatatt gaattccctt tatgtgtaac tcttggctga agc                    43

<210> SEQ ID NO 11
<211> LENGTH: 48
<212> TYPE: DNA
<213> ORGANISM: Artificial Sequence
<220> FEATURE:
<223> OTHER INFORMATION: GAB-262 PCR primer
```

<400> SEQUENCE: 11

```
tagcaatatt gaattcgcag gaaaaggaca agcagcgaaa attcacgc          48
```

<210> SEQ ID NO 12
<211> LENGTH: 1715
<212> TYPE: DNA
<213> ORGANISM: Artificial Sequence
<220> FEATURE:
<223> OTHER INFORMATION: Nucleotide sequence of GnTI-GnTIII

<400> SEQUENCE: 12

```
atgaagttaa gccgccagtt caccgtgttc ggcagtgcga tcttctgtgt ggtgattttc    60
tcgctctacc tgatgctgga ccggggtcac ttagactacc ccaggaaccc gcgccgcgag   120
ggctccttcc ctcagggcca gctctcaatg ttgcaagaaa aaatagacca tttggagcgt   180
ttgctagctg agaataatga gatcatctca aatattagag actcagtcat caatttgagt   240
gagtctgtgg aggatggtcc gaaaagttca caaagcaatt tcagccaagg tgctggctca   300
cccctgctcc agccactgtc ccctagcaag gccaccgaag aactgcaccg gtggacttc    360
gtgttgccgg aggacaccac agagtatttt gtgcgcacca agctggcgg tgtgtgcttc   420
aaaccaggta ccaggatgct ggagaaacct tctccagggc ggacagagga aagaccaag    480
gtggctgagg ggtcctcggt ccgggtcct gctcggagcc ctatgcggca tgtgttgagt   540
gcacgggagc gcctgggagg ccggggcact aggcgcaagt gggttgagtg tgtgtgcctg   600
ccaggctggc acgggcccag ctgcggggtg cccactgtgg tccagtattc caacctgccc   660
accaaggagc gcctggtacc cagggaggtg ccgaggcggg ttatcaacgc catcaacatc   720
aaccatgagt tcgacctgct ggatgtgcgc ttccatgagc tgggcgatgt tgtggacgcc   780
tttgtggtct gcgaatccaa tttcaccgcc tacggggagc tcggccgct caagttccga   840
gagatgctga ccaatggcac cttcgagtac atccgccaca aggtgctcta cgtcttcctg   900
gaccacttcc cacctggtgg ccgtcaggac ggctggattg cagacgacta cctgcgtacc   960
ttcctcaccc aggatggtgt ctcccgcctg cgcaacctgc gacctgatga cgtctttatc  1020
atcgacgacg cggacgagat ccctgcgcgt gatggtgtgc tgttcctcaa gctctacgat  1080
ggctggacag agcccttcgc cttccatatg cgcaagtccc tgtatggttt cttttggaag  1140
caaccaggca cacggaggtg tgtcaggct gcaccattga catgctgcag gctgtgtatg  1200
ggctggacgg catccgcctg cgccgccgtc agtactacac catgcccaac tttcgacagt  1260
atgagaaccg caccggccac atcctagtgc agtggtctct cggcagcccc ctgcacttcg  1320
cgggctggca ctgctcctgg tgcttcacac ccgagggcat ctacttcaaa ctcgtgtcgg  1380
cccagaatgg tgacttcccc cgctggggtg actacgagga caagagggac ctcaattaca  1440
tccgaagctt gattcgcact gggggatggt tcgacggcac gcagcaggag taccctcctg  1500
cagaccccag tgaacacatg tatgctccta agtacctgct caagaactat gaccagttcc  1560
gctacttgct cgaaaatccc taccgggagc ccaagagcac tgtagagggt gggcgccgga  1620
accagggctc agacggaagg tcatctgctg tcaggggcaa gttggataca acggagggcc  1680
cggaacagaa actgatctct gaagaggacc tgtag                              1715
```

<210> SEQ ID NO 13
<211> LENGTH: 571
<212> TYPE: PRT
<213> ORGANISM: Artificial Sequence
<220> FEATURE:
<223> OTHER INFORMATION: Amino acid sequence of GnTI-GnTIII

<400> SEQUENCE: 13

```
Met Lys Leu Ser Arg Gln Phe Thr Val Phe Gly Ser Ala Ile Phe Cys
1               5                   10                  15
Val Val Ile Phe Ser Leu Tyr Leu Met Leu Asp Arg Gly His Leu Asp
            20                  25                  30
Tyr Pro Arg Asn Pro Arg Arg Glu Gly Ser Phe Pro Gln Gly Gln Leu
        35                  40                  45
Ser Met Leu Gln Glu Lys Ile Asp His Leu Glu Arg Leu Leu Ala Glu
    50                  55                  60
Asn Asn Glu Ile Ile Ser Asn Ile Arg Asp Ser Val Ile Asn Leu Ser
65                  70                  75                  80
Glu Ser Val Glu Asp Gly Pro Lys Ser Ser Gln Ser Asn Phe Ser Gln
                85                  90                  95
Gly Ala Gly Ser Pro Leu Leu Gln Pro Leu Ser Pro Ser Lys Ala Thr
            100                 105                 110
Glu Glu Leu His Arg Val Asp Phe Val Leu Pro Glu Asp Thr Thr Glu
        115                 120                 125
Tyr Phe Val Arg Thr Lys Ala Gly Gly Val Cys Phe Lys Pro Gly Thr
    130                 135                 140
Arg Met Leu Glu Lys Pro Ser Pro Gly Arg Thr Glu Glu Lys Thr Lys
145                 150                 155                 160
Val Ala Glu Gly Ser Ser Val Arg Gly Pro Ala Arg Arg Pro Met Arg
                165                 170                 175
His Val Leu Ser Ala Arg Glu Arg Leu Gly Gly Arg Gly Thr Arg Arg
            180                 185                 190
Lys Trp Val Glu Cys Val Cys Leu Pro Gly Trp His Gly Pro Ser Cys
        195                 200                 205
Gly Val Pro Thr Val Val Gln Tyr Ser Asn Leu Pro Thr Lys Glu Arg
    210                 215                 220
Leu Val Pro Arg Glu Val Pro Arg Arg Val Ile Asn Ala Ile Asn Ile
225                 230                 235                 240
Asn His Glu Phe Asp Leu Leu Asp Val Arg Phe His Glu Leu Gly Asp
                245                 250                 255
Val Val Asp Ala Phe Val Val Cys Glu Ser Asn Phe Thr Ala Tyr Gly
            260                 265                 270
Glu Pro Arg Pro Leu Lys Phe Arg Glu Met Leu Thr Asn Gly Thr Phe
        275                 280                 285
Glu Tyr Ile Arg His Lys Val Leu Tyr Val Phe Leu Asp His Phe Pro
    290                 295                 300
Pro Gly Gly Arg Gln Asp Gly Trp Ile Ala Asp Asp Tyr Leu Arg Thr
305                 310                 315                 320
Phe Leu Thr Gln Asp Gly Val Ser Arg Leu Arg Asn Leu Arg Pro Asp
                325                 330                 335
Asp Val Phe Ile Ile Asp Asp Ala Asp Glu Ile Pro Ala Arg Asp Gly
            340                 345                 350
Val Leu Phe Leu Lys Leu Tyr Asp Gly Trp Thr Glu Pro Phe Ala Phe
        355                 360                 365
His Met Arg Lys Ser Leu Tyr Gly Phe Phe Trp Lys Gln Pro Gly Thr
    370                 375                 380
Leu Glu Val Val Ser Gly Cys Thr Ile Asp Met Leu Gln Ala Val Tyr
385                 390                 395                 400
Gly Leu Asp Gly Ile Arg Leu Arg Arg Gln Tyr Tyr Thr Met Pro
                405                 410                 415
```

```
Asn Phe Arg Gln Tyr Glu Asn Arg Thr Gly His Ile Leu Val Gln Trp
            420                 425                 430

Ser Leu Gly Ser Pro Leu His Phe Ala Gly Trp His Cys Ser Trp Cys
            435                 440                 445

Phe Thr Pro Glu Gly Ile Tyr Phe Lys Leu Val Ser Ala Gln Asn Gly
            450                 455                 460

Asp Phe Pro Arg Trp Gly Asp Tyr Glu Asp Lys Arg Asp Leu Asn Tyr
465                 470                 475                 480

Ile Arg Ser Leu Ile Arg Thr Gly Gly Trp Phe Asp Gly Thr Gln Gln
            485                 490                 495

Glu Tyr Pro Pro Ala Asp Pro Ser Glu His Met Tyr Ala Pro Lys Tyr
            500                 505                 510

Leu Leu Lys Asn Tyr Asp Gln Phe Arg Tyr Leu Leu Glu Asn Pro Tyr
            515                 520                 525

Arg Glu Pro Lys Ser Thr Val Glu Gly Gly Arg Arg Asn Gln Gly Ser
            530                 535                 540

Asp Gly Arg Ser Ser Ala Val Arg Gly Lys Leu Asp Thr Thr Glu Gly
545                 550                 555                 560

Pro Glu Gln Lys Leu Ile Ser Glu Glu Asp Leu
            565                 570
```

<210> SEQ ID NO 14
<211> LENGTH: 1722
<212> TYPE: DNA
<213> ORGANISM: Artificial Sequence
<220> FEATURE:
<223> OTHER INFORMATION: Nucleotide sequence of ManII-GnTIII

<400> SEQUENCE: 14

```
atgctgaaga agcagtctgc agggcttgtg ctgtggggcg ctatcctctt tgtggcctgg       60
aatgccctgc tgctcctctt cttctggacg cgcccagcac ctggcaggcc accctcagtc      120
agcgctctcg atggcgaccc cgccagcctc acccgggaag tgattcgcct ggcccaagac      180
gccgaggtgg agctggagcg gcagcgtggg ctgctgcagc agatcgggga tgccctgtcg      240
agccagcggg ggagggtgcc caccgcggcc cctcccgccc agccgcgtgt gcctgtgacc      300
cccgcgcccc tgctccagcc actgtcccct agcaaggcca ccgaagaact gcaccgggtg      360
gacttcgtgt tgccggagga caccacagag tattttgtgc gcaccaaagc tggcggtgtg      420
tgcttcaaac caggtaccag gatgctggag aaaccttctc caggggcgac agaggagaag      480
accaaggtgg ctgagggggtc ctcggtccgg gtcctgctc ggaggcctat gcggcatgtg      540
ttgagtgcac gggagcgcct ggaggccgga ggcactaggc gcaagtgggt tgagtgtgtg      600
tgcctgccag gctggcacgg gcccagctgc ggggtgccca ctgtggtcca gtattccaac      660
ctgcccacca aggagcgcct ggtacccagg gaggtgccga ggcgggttat caacgccatc      720
aacatcaacc atgagttcga cctgctggat gtgcgcttcc atgagctggg cgatgttgtg      780
gacgcctttg tggtctgcga atccaatttc accgcctacg gggagcctcg gccgctcaag      840
ttccgagaga tgctgaccaa tggcaccttc gagtacatcc gccacaaggt gctctacgtc      900
ttcctggacc acttcccacc tggtggccgt caggacggct ggattgcaga cgactacctg      960
cgtaccttcc tcacccagga tggtgtctcc cgcctgcgca acctgcgacc tgatgacgtc     1020
tttatcatcg acgacgcgga cgagatccct gcgcgtgatg tgtgtgctgt cctcaagctc     1080
tacgatggct ggacagagcc cttcgccttc catatgcgca gtccctgta tggtttcttt    1140
tggaagcaac caggcacact ggaggtggtg tcaggctgca ccattgacat gctgcaggct     1200
```

```
gtgtatgggc tggacggcat ccgcctgcgc cgccgtcagt actacaccat gcccaacttt    1260
cgacagtatg agaaccgcac cggccacatc ctagtgcagt ggtctctcgg cagccccctg    1320
cacttcgcgg gctggcactg ctcctggtgc ttcacacccg agggcatcta cttcaaactc    1380
gtgtcggccc agaatggtga cttcccccgc tggggtgact acgaggacaa gagggacctc    1440
aattacatcc gaagcttgat tcgcactggg ggatggttcg acggcacgca gcaggagtac    1500
cctcctgcag accccagtga acacatgtat gctcctaagt acctgctcaa gaactatgac    1560
cagttccgct acttgctcga aaatccctac cgggagccca gagcactgt agagggtggg    1620 cgccggaacc agggctcaga cggaaggtca tctgctgtca ggggcaagtt ggatacaacg    1680
gagggcccgg aacagaaact gatctctgaa gaggacctgt ag                       1722
```

<210> SEQ ID NO 15
<211> LENGTH: 573
<212> TYPE: PRT
<213> ORGANISM: Artificial Sequence
<220> FEATURE:
<223> OTHER INFORMATION: Amino acid sequence of ManII-GnTIII fusion

<400> SEQUENCE: 15

```
Met Leu Lys Lys Gln Ser Ala Gly Leu Val Leu Trp Gly Ala Ile Leu
1               5                   10                  15

Phe Val Ala Trp Asn Ala Leu Leu Leu Phe Phe Trp Thr Arg Pro
                20                  25                  30

Ala Pro Gly Arg Pro Pro Ser Val Ser Ala Leu Asp Gly Asp Pro Ala
            35                  40                  45

Ser Leu Thr Arg Glu Val Ile Arg Leu Ala Gln Asp Ala Glu Val Glu
    50                  55                  60

Leu Glu Arg Gln Arg Gly Leu Leu Gln Gln Ile Gly Asp Ala Leu Ser
65                  70                  75                  80

Ser Gln Arg Gly Arg Val Pro Thr Ala Ala Pro Pro Ala Gln Pro Arg
                85                  90                  95

Val Pro Val Thr Pro Ala Pro Leu Leu Gln Pro Leu Ser Pro Ser Lys
            100                 105                 110

Ala Thr Glu Glu Leu His Arg Val Asp Phe Val Leu Pro Glu Asp Thr
        115                 120                 125

Thr Glu Tyr Phe Val Arg Thr Lys Ala Gly Gly Val Cys Phe Lys Pro
    130                 135                 140

Gly Thr Arg Met Leu Glu Lys Pro Ser Pro Gly Arg Thr Glu Glu Lys
145                 150                 155                 160

Thr Lys Val Ala Glu Gly Ser Ser Val Arg Gly Pro Ala Arg Arg Pro
                165                 170                 175

Met Arg His Val Leu Ser Ala Arg Glu Arg Leu Gly Gly Arg Gly Thr
            180                 185                 190

Arg Arg Lys Trp Val Glu Cys Val Cys Leu Pro Gly Trp His Gly Pro
        195                 200                 205

Ser Cys Gly Val Pro Thr Val Val Gln Tyr Ser Asn Leu Pro Thr Lys
    210                 215                 220

Glu Arg Leu Val Pro Arg Glu Val Pro Arg Arg Val Ile Asn Ala Ile
225                 230                 235                 240

Asn Ile Asn His Glu Phe Asp Leu Leu Asp Val Arg Phe His Glu Leu
                245                 250                 255

Gly Asp Val Val Asp Ala Phe Val Val Cys Glu Ser Asn Phe Thr Ala
            260                 265                 270
```

-continued

```
Tyr Gly Glu Pro Arg Pro Leu Lys Phe Arg Glu Met Leu Thr Asn Gly
            275                 280                 285

Thr Phe Glu Tyr Ile Arg His Lys Val Leu Tyr Val Phe Leu Asp His
    290                 295                 300

Phe Pro Pro Gly Gly Arg Gln Asp Gly Trp Ile Ala Asp Asp Tyr Leu
305                 310                 315                 320

Arg Thr Phe Leu Thr Gln Asp Gly Val Ser Arg Leu Arg Asn Leu Arg
                325                 330                 335

Pro Asp Asp Val Phe Ile Ile Asp Ala Asp Glu Ile Pro Ala Arg
                340                 345                 350

Asp Gly Val Leu Phe Leu Lys Leu Tyr Asp Gly Trp Thr Glu Pro Phe
                355                 360                 365

Ala Phe His Met Arg Lys Ser Leu Tyr Gly Phe Phe Trp Lys Gln Pro
    370                 375                 380

Gly Thr Leu Glu Val Val Ser Gly Cys Thr Ile Asp Met Leu Gln Ala
385                 390                 395                 400

Val Tyr Gly Leu Asp Gly Ile Arg Leu Arg Arg Gln Tyr Tyr Thr
                405                 410                 415

Met Pro Asn Phe Arg Gln Tyr Glu Asn Arg Thr Gly His Ile Leu Val
                420                 425                 430

Gln Trp Ser Leu Gly Ser Pro Leu His Phe Ala Gly Trp His Cys Ser
    435                 440                 445

Trp Cys Phe Thr Pro Glu Gly Ile Tyr Phe Lys Leu Val Ser Ala Gln
    450                 455                 460

Asn Gly Asp Phe Pro Arg Trp Gly Asp Tyr Glu Asp Lys Arg Asp Leu
465                 470                 475                 480

Asn Tyr Ile Arg Ser Leu Ile Arg Thr Gly Gly Trp Phe Asp Gly Thr
                485                 490                 495

Gln Gln Glu Tyr Pro Pro Ala Asp Pro Ser Glu His Met Tyr Ala Pro
                500                 505                 510

Lys Tyr Leu Leu Lys Asn Tyr Asp Gln Phe Arg Tyr Leu Leu Glu Asn
        515                 520                 525

Pro Tyr Arg Glu Pro Lys Ser Thr Val Glu Gly Arg Arg Asn Gln
    530                 535                 540

Gly Ser Asp Gly Arg Ser Ser Ala Val Arg Gly Lys Leu Asp Thr Thr
545                 550                 555                 560

Glu Gly Pro Glu Gln Lys Leu Ile Ser Glu Glu Asp Leu
                565                 570

<210> SEQ ID NO 16
<211> LENGTH: 398
<212> TYPE: PRT
<213> ORGANISM: Unknown
<220> FEATURE:
<223> OTHER INFORMATION: GalT amino acid sequence from pBlueGalT

<400> SEQUENCE: 16

Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
                20                  25                  30

His Leu Gly Val Thr Leu Val Tyr Tyr Leu Ala Gly Arg Asp Leu Ser
            35                  40                  45

Arg Leu Pro Gln Leu Val Gly Val Ser Thr Pro Leu Gln Gly Gly Ser
    50                  55                  60

Asn Ser Ala Ala Ala Ile Gly Gln Ser Ser Gly Glu Leu Arg Thr Gly
```

```
                65                  70                  75                  80
Gly Ala Arg Pro Pro Pro Leu Gly Ala Ser Ser Gln Pro Arg Pro
                    85                  90                  95
Gly Gly Asp Ser Ser Pro Val Val Asp Ser Gly Pro Gly Pro Ala Ser
                100                 105                 110
Asn Leu Thr Ser Val Pro Val Pro His Thr Thr Ala Leu Ser Leu Pro
                115                 120                 125
Ala Cys Pro Glu Glu Ser Pro Leu Leu Val Gly Pro Met Leu Ile Glu
            130                 135                 140
Phe Asn Met Pro Val Asp Leu Glu Leu Val Ala Lys Gln Asn Pro Asn
145                 150                 155                 160
Val Lys Met Gly Gly Arg Tyr Ala Pro Arg Asp Cys Val Ser Pro His
                165                 170                 175
Lys Val Ala Ile Ile Pro Phe Arg Asn Arg Gln Glu His Leu Lys
                180                 185                 190
Tyr Trp Leu Tyr Tyr Leu His Pro Val Leu Gln Arg Gln Gln Leu Asp
                195                 200                 205
Tyr Gly Ile Tyr Val Ile Asn Gln Ala Gly Asp Thr Ile Phe Asn Arg
                210                 215                 220
Ala Lys Leu Leu Asn Val Gly Phe Gln Glu Ala Leu Lys Asp Tyr Asp
225                 230                 235                 240
Tyr Thr Cys Phe Val Phe Ser Asp Val Asp Leu Ile Pro Met Asn Asp
                245                 250                 255
His Asn Ala Tyr Arg Cys Phe Ser Gln Pro Arg His Ile Ser Val Ala
                260                 265                 270
Met Asp Lys Phe Gly Phe Ser Leu Pro Tyr Val Gln Tyr Phe Gly Gly
                275                 280                 285
Val Ser Ala Leu Ser Lys Gln Gln Phe Leu Thr Ile Asn Gly Phe Pro
            290                 295                 300
Asn Asn Tyr Trp Gly Trp Gly Gly Glu Asp Asp Asp Ile Phe Asn Arg
305                 310                 315                 320
Leu Val Phe Arg Gly Met Ser Ile Ser Arg Pro Asn Ala Val Val Gly
                325                 330                 335
Arg Cys Arg Met Ile Arg His Ser Arg Asp Lys Lys Asn Glu Pro Asn
                340                 345                 350
Pro Gln Arg Phe Asp Arg Ile Ala His Thr Lys Glu Thr Met Leu Ser
                355                 360                 365
Asp Gly Leu Asn Ser Leu Thr Tyr Gln Val Leu Asp Val Gln Arg Tyr
            370                 375                 380
Pro Leu Tyr Thr Gln Ile Thr Val Asp Ile Gly Thr Pro Ser
385                 390                 395

<210> SEQ ID NO 17
<211> LENGTH: 3435
<212> TYPE: DNA
<213> ORGANISM: Homo sapiens

<400> SEQUENCE: 17
atgaagttaa gccgccagtt caccgtgttc ggcagtgcga tcttctgtgt ggtgattttc      60
tcgctctacc tgatgctgga ccggggtcac ttagactacc ccaggaaccc cgcgccgcga     120
ggctccttcc ctcagggcca gctctcaatg ttgcaagaaa aaatagacca tttggagcgt     180
ttgctagctg agaataatga gatcatctca aatattagag actcagtcat caatttgagt     240
gagtctgtgg aggatggtcc gaaaagttca caaagcaatt tcagccaagg tgctggctca     300
```

```
catcttctgc cctcacaatt atccctctca gttgacactg cagactgtct gtttgcttca    360
caaagtggaa gtcacaattc agatgtgcag atgttggatg tttacagtct aatttctttt    420
gacaatccag atggtggagt ttggaagcaa ggatttgaca ttacttatga atctaatgaa    480
tgggacactg aaccccttca agtctttgtg gtgcctcatt cccataacga cccaggttgg    540
ttgaagactt tcaatgacta ctttagagac aagactcagt atattttta  taacatggtc    600 ctaaagctga agaagactc  acggaggaag tttatttggt ctgagatctc ttacctttca    660
aagtggtggg atattataga tattcagaag aaggatgctg ttaaaagttt aatagaaaat    720
ggtcagcttg aaattgtgac aggtggctgg gttatgcctg atgaagctac tccacattat    780
tttgccttaa ttgatcaact aattgaagga catcagtggc tggaaaataa tataggagtg    840
aaacctcggt ccggctgggc tattgatccc tttggacact caccaacaat ggcttatctt    900
ctaaaccgtg ctggactttc tcacatgctt atccagagag ttcattatgc agttaaaaaa    960
cactttgcac tgcataaaac attggagttt ttttggagac agaattggga tctgggatct   1020
gtcacagata ttttatgcca catgatgccc ttctacagct atgacatccc tcacacttgt   1080
ggacctgatc ctaaaatatg ctgccagttt gatttttaaac gtcttcctgg aggcagattt   1140
ggttgtccct ggggagtccc cccagaaaca atacatcctg gaaatgtcca aagcagggct   1200
cggatgctac tagatcagta ccgaaagaag tcaaagcttt ttcgtaccaa agttctcctg   1260
gctccactag gagatgattt ccgctactgt gaatacacgg aatgggattt acagtttaag   1320
aattatcagc agcttttga  ttatatgaat tctcagtcca gtttaaagt  taagatacag   1380 tttggaactt tatcagattt ttttgatgcg ctggataaag cagatgaaac tcagagagac   1440
aagggccagt cgatgttccc tgttttaagt ggagatttt  tcacttatgc cgatcgagat   1500
gatcattact ggagtggcta ttttacatcc agaccctttt acaaacgaat ggacagaatc   1560
atggaatctc atttaagggc tgctgaaatt ctttactatt tcgccctgag acaagctcac   1620
aaatacaaga taaataaatt tctctcatca tcactttaca cggcactgac agaagccaga   1680
aggaatttgg gactgtttca acatcatgat gctatcacag gaactgcaaa agactgggtg   1740
gttgtggatt atggtaccag acttttttcat tcgttaatgg ttttggagaa gataattgga   1800
aattctgcat tccttcttat tttgaaggac aaactcacat acgactctta ctctcctgat   1860
accttcctgg agatggattt gaaacaaaaa tcacaagatt ctctgccaca aaaaaatata   1920
ataaggctga gtgcggagcc aaggtacctt gtggtctata atcctttaga acaagaccga   1980
atctcgttgg tctcagtcta tgtgagttcc ccgacagtgc aagtgttctc tgcttcagga   2040
aaacctgtgg aagttcaagt cagcgcagtt tgggatacag caaatactat ttcagaaaca   2100
gcctatgaga tctctttcg  agcacatata ccgccattgg gactgaaagt gtataagatt   2160
ttggaatcag caagttcaaa ttcacattta gctgattatg tcttgtataa gaataaagta   2220
gaagatagcg aatttttcac cataaagaat atgataaaata ctgaagaagg tataacacta   2280
gagaactcct ttgttttact tcggtttgat caaactggac ttatgaagca atgatgact    2340 aaagaagatg taaacaccca tgaagtaaat gtgcaatttt catggtatgg aaccacaatt   2400
aaaagagaca aaagtggtgc ctacctcttc ttacctgatg gtaatgccaa gccttatgtt   2460
tacacaacac cgcccttgt  cagagtgaca catggaagga tttattcgga agtgacttgc   2520 tttttttgacc atgttactca tagagtccga ctataccaca tacagggaat agaaggacag   2580
tctgtggaag tttccaatat tgtggacatc cgaaaagtat ataaccgtga gattgcaatg   2640
aaaatttctt ctgatataaa aagccaaaat agattttata ctgacctaaa tgggtaccag   2700
```

-continued

```
attcaaccta gaatgacact gagcaaattg cctcttcaag caaatgtcta tcccatgacc    2760
acaatggcct atatccagga tgccaaacat cgtttgacac tgctctctgc tcagtcttta    2820
ggggtttcga gtttgaatag tggtcagatt gaagttatca tggatcgaag actcatgcaa    2880
gatgataatc gtggccttga gcaaggtatc caggataaca agattacagc taatctattt    2940
cgaatactac tagaaaaaag aagtgctgtt aatacggaag aagaaaagaa gtcggtcagt    3000
tatccttctc tccttagcca cataacttct tctctcatga atcatccagt cattccaatg    3060
gcaaataagt tcttctcacc taccctttga gctgcaaggtg aattctctcc attacagtca    3120
tctttgcctt gtgacattca tctggttaat ttgagaacaa tacagtcaaa ggtgggcaat    3180
gggcactcca atgaggcagc cttgatcctc cacagaaaag ggtttgattg tcggttctct    3240
agcaaaggca cagggctgtt ttgttctact actcagggaa agatattggt acagaaactt    3300
ttaaacaagt ttattgtcga aagtctcaca ccttcatcac tatccttgat gcattcacct    3360
cccggcactc agaatataag tgagatcaac ttgagtccaa tggaaatcag cacattccga    3420
atccagttga ggtga                                                    3435
```

<210> SEQ ID NO 18
<211> LENGTH: 1144
<212> TYPE: PRT
<213> ORGANISM: Homo sapiens

<400> SEQUENCE: 18

```
Met Lys Leu Ser Arg Gln Phe Thr Val Phe Gly Ser Ala Ile Phe Cys
1               5                   10                  15

Val Val Ile Phe Ser Leu Tyr Leu Met Leu Asp Arg Gly His Leu Asp
            20                  25                  30

Tyr Pro Arg Asn Pro Arg Arg Glu Gly Ser Phe Pro Gln Gly Gln Leu
        35                  40                  45

Ser Met Leu Gln Glu Lys Ile Asp His Leu Glu Arg Leu Leu Ala Glu
    50                  55                  60

Asn Asn Glu Ile Ile Ser Asn Ile Arg Asp Ser Val Ile Asn Leu Ser
65                  70                  75                  80

Glu Ser Val Glu Asp Gly Pro Lys Ser Ser Gln Ser Asn Phe Ser Gln
                85                  90                  95

Gly Ala Gly Ser His Leu Leu Pro Ser Gln Leu Ser Leu Ser Val Asp
            100                 105                 110

Thr Ala Asp Cys Leu Phe Ala Ser Gln Ser Gly Ser His Asn Ser Asp
        115                 120                 125

Val Gln Met Leu Asp Val Tyr Ser Leu Ile Ser Phe Asp Asn Pro Asp
    130                 135                 140

Gly Gly Val Trp Lys Gln Gly Phe Asp Ile Thr Tyr Glu Ser Asn Glu
145                 150                 155                 160

Trp Asp Thr Glu Pro Leu Gln Val Phe Val Pro His Ser His Asn
                165                 170                 175

Asp Pro Gly Trp Leu Lys Thr Phe Asn Asp Tyr Phe Arg Asp Lys Thr
            180                 185                 190

Gln Tyr Ile Phe Asn Asn Met Val Leu Lys Leu Lys Glu Asp Ser Arg
        195                 200                 205

Arg Lys Phe Ile Trp Ser Glu Ile Ser Tyr Leu Ser Lys Trp Trp Asp
    210                 215                 220

Ile Ile Asp Ile Gln Lys Lys Asp Ala Val Lys Ser Leu Ile Glu Asn
225                 230                 235                 240

Gly Gln Leu Glu Ile Val Thr Gly Gly Trp Val Met Pro Asp Glu Ala
```

```
                    245                 250                 255
Thr Pro His Tyr Phe Ala Leu Ile Asp Gln Leu Ile Glu Gly His Gln
                260                 265                 270

Trp Leu Glu Asn Asn Ile Gly Val Lys Pro Arg Ser Gly Trp Ala Ile
            275                 280                 285

Asp Pro Phe Gly His Ser Pro Thr Met Ala Tyr Leu Leu Asn Arg Ala
        290                 295                 300

Gly Leu Ser His Met Leu Ile Gln Arg Val His Tyr Ala Val Lys Lys
305                 310                 315                 320

His Phe Ala Leu His Lys Thr Leu Glu Phe Phe Trp Arg Gln Asn Trp
                325                 330                 335

Asp Leu Gly Ser Val Thr Asp Ile Leu Cys His Met Met Pro Phe Tyr
            340                 345                 350

Ser Tyr Asp Ile Pro His Thr Cys Gly Pro Asp Pro Lys Ile Cys Cys
        355                 360                 365

Gln Phe Asp Phe Lys Arg Leu Pro Gly Gly Arg Phe Gly Cys Pro Trp
    370                 375                 380

Gly Val Pro Pro Glu Thr Ile His Pro Gly Asn Val Gln Ser Arg Ala
385                 390                 395                 400

Arg Met Leu Leu Asp Gln Tyr Arg Lys Lys Ser Lys Leu Phe Arg Thr
                405                 410                 415

Lys Val Leu Leu Ala Pro Leu Gly Asp Asp Phe Arg Tyr Cys Glu Tyr
            420                 425                 430

Thr Glu Trp Asp Leu Gln Phe Lys Asn Tyr Gln Gln Leu Phe Asp Tyr
        435                 440                 445

Met Asn Ser Gln Ser Lys Phe Lys Val Lys Ile Gln Phe Gly Thr Leu
    450                 455                 460

Ser Asp Phe Phe Asp Ala Leu Asp Lys Ala Asp Glu Thr Gln Arg Asp
465                 470                 475                 480

Lys Gly Gln Ser Met Phe Pro Val Leu Ser Gly Asp Phe Phe Thr Tyr
                485                 490                 495

Ala Asp Arg Asp Asp His Tyr Trp Ser Gly Tyr Phe Thr Ser Arg Pro
            500                 505                 510

Phe Tyr Lys Arg Met Asp Arg Ile Met Glu Ser His Leu Arg Ala Ala
        515                 520                 525

Glu Ile Leu Tyr Tyr Phe Ala Leu Arg Gln Ala His Lys Tyr Lys Ile
    530                 535                 540

Asn Lys Phe Leu Ser Ser Ser Leu Tyr Thr Ala Leu Thr Glu Ala Arg
545                 550                 555                 560

Arg Asn Leu Gly Leu Phe Gln His His Asp Ala Ile Thr Gly Thr Ala
                565                 570                 575

Lys Asp Trp Val Val Asp Tyr Gly Thr Arg Leu Phe His Ser Leu
            580                 585                 590

Met Val Leu Glu Lys Ile Ile Gly Asn Ser Ala Phe Leu Leu Ile Leu
        595                 600                 605

Lys Asp Lys Leu Thr Tyr Asp Ser Tyr Ser Pro Asp Thr Phe Leu Glu
    610                 615                 620

Met Asp Leu Lys Gln Lys Ser Gln Asp Ser Leu Pro Gln Lys Asn Ile
625                 630                 635                 640

Ile Arg Leu Ser Ala Glu Pro Arg Tyr Leu Val Tyr Asn Pro Leu
                645                 650                 655

Glu Gln Asp Arg Ile Ser Leu Val Ser Val Tyr Val Ser Ser Pro Thr
            660                 665                 670
```

-continued

```
Val Gln Val Phe Ser Ala Ser Gly Lys Pro Val Glu Val Gln Val Ser
            675                 680                 685

Ala Val Trp Asp Thr Ala Asn Thr Ile Ser Glu Thr Ala Tyr Glu Ile
690                 695                 700

Ser Phe Arg Ala His Ile Pro Pro Leu Gly Leu Lys Val Tyr Lys Ile
705                 710                 715                 720

Leu Glu Ser Ala Ser Asn Ser His Leu Ala Asp Tyr Val Leu Tyr
                725                 730                 735

Lys Asn Lys Val Glu Asp Ser Gly Ile Phe Thr Ile Lys Asn Met Ile
                740                 745                 750

Asn Thr Glu Glu Gly Ile Thr Leu Glu Asn Ser Phe Val Leu Leu Arg
            755                 760                 765

Phe Asp Gln Thr Gly Leu Met Lys Gln Met Met Thr Lys Glu Asp Gly
770                 775                 780

Lys His His Glu Val Asn Val Gln Phe Ser Trp Tyr Gly Thr Thr Ile
785                 790                 795                 800

Lys Arg Asp Lys Ser Gly Ala Tyr Leu Phe Leu Pro Asp Gly Asn Ala
                805                 810                 815

Lys Pro Tyr Val Tyr Thr Thr Pro Phe Val Arg Val Thr His Gly
                820                 825                 830

Arg Ile Tyr Ser Glu Val Thr Cys Phe Phe Asp His Val Thr His Arg
                835                 840                 845

Val Arg Leu Tyr His Ile Gln Gly Ile Glu Gly Gln Ser Val Glu Val
    850                 855                 860

Ser Asn Ile Val Asp Ile Arg Lys Val Tyr Asn Arg Glu Ile Ala Met
865                 870                 875                 880

Lys Ile Ser Ser Asp Ile Lys Ser Gln Asn Arg Phe Tyr Thr Asp Leu
                885                 890                 895

Asn Gly Tyr Gln Ile Gln Pro Arg Met Thr Leu Ser Lys Leu Pro Leu
                900                 905                 910

Gln Ala Asn Val Tyr Pro Met Thr Thr Met Ala Tyr Ile Gln Asp Ala
            915                 920                 925

Lys His Arg Leu Thr Leu Leu Ser Ala Gln Ser Leu Gly Val Ser Ser
            930                 935                 940

Leu Asn Ser Gly Gln Ile Glu Val Ile Met Asp Arg Arg Leu Met Gln
945                 950                 955                 960

Asp Asp Asn Arg Gly Leu Glu Gln Gly Ile Gln Asp Asn Lys Ile Thr
                965                 970                 975

Ala Asn Leu Phe Arg Ile Leu Leu Glu Lys Arg Ser Ala Val Asn Thr
                980                 985                 990

Glu Glu Glu Lys Lys Ser Val Ser Tyr Pro Ser Leu Leu Ser His Ile
            995                 1000                1005

Thr Ser Ser Leu Met Asn His Pro Val Ile Pro Met Ala Asn Lys
    1010                1015                1020

Phe Phe Ser Pro Thr Leu Glu Leu Gln Gly Glu Phe Ser Pro Leu
    1025                1030                1035

Gln Ser Ser Leu Pro Cys Asp Ile His Leu Val Asn Leu Arg Thr
    1040                1045                1050

Ile Gln Ser Lys Val Gly Asn Gly His Ser Asn Glu Ala Ala Leu
    1055                1060                1065

Ile Leu His Arg Lys Gly Phe Asp Cys Arg Phe Ser Ser Lys Gly
    1070                1075                1080

Thr Gly Leu Phe Cys Ser Thr Thr Gln Gly Lys Ile Leu Val Gln
    1085                1090                1095
```

Lys Leu Leu Asn Lys Phe Ile Val Glu Ser Leu Thr Pro Ser Ser
        1100                1105                1110

Leu Ser Leu Met His Ser Pro Pro Gly Thr Gln Asn Ile Ser Glu
        1115                1120                1125

Ile Asn Leu Ser Pro Met Glu Ile Ser Thr Phe Arg Ile Gln Leu
        1130                1135                1140

Arg

<210> SEQ ID NO 19
<211> LENGTH: 1116
<212> TYPE: DNA
<213> ORGANISM: Artificial Sequence
<220> FEATURE:
<223> OTHER INFORMATION: Nucleotide sequence of ManII-GalT

<400> SEQUENCE: 19

```
atgaagttaa gccgccagtt caccgtgttc ggcagtgcga tcttctgtgt ggtgattttc      60
tcgctctacc tgatgctgga ccggggtcac ttagactacc ccaggaaccc gcgccgcgag     120
ggctccttcc ctcagggcca gctctcaatg ttgcaagaaa aaatagacca tttggagcgt     180
ttgctagctg agaataatga gatcatctca aatattagag actcagtcat caatttgagt     240
gagtctgtgg aggatggtcc gaaaagttca caaagcaatt tcagccaagg tgctggctca     300
cccgcctgcc ctgaggagtc cccgctgctt gtgggcccca tgctgattga gtttaacatg     360
cctgtggacc tggagctcgt ggcaaagcag aacccaaatg tgaagatggg cggccgctat     420
gccccccaggg actgcgtctc tcctcacaag gtggccatca tcattccatt ccgcaaccgg     480
caggagcacc tcaagtactg gctatattat ttgcacccag tcctgcagcg ccagcagctg     540
gactatggca tctatgttat caaccaggcg ggagacacta tattcaatcg tgctaagctc     600
ctcaatgttg ctttcaaga agccttgaag gactatgact acacctgctt tgtgtttagt     660
gacgtggacc tcattccaat gaatgaccat aatgcgtaca ggtgtttttc acagccacgg     720
cacatttccg ttgcaatgga taagtttgga ttcagcctac cttatgttca gtattttgga     780
ggtgtctctg ctctaagtaa acaacagttt ctaaccatca atggatttcc taataattat     840
tggggctggg gaggagaaga tgatgacatt tttaacagat tagtttttag aggcatgtct     900
atatctcgcc caaatgctgt ggtcggggag tgtcgcatga tccgccactc aagagacaaa     960
aaaaatgaac ccaatcctca gaggtttgac cgaattgcac acacaaagga gacaatgctc    1020
tctgatggtt tgaactcact cacctaccag gtgctggatg tacagagata cccattgtat    1080
acccaaatca cagtggacat cgggacaccg agctag                              1116
```

<210> SEQ ID NO 20
<211> LENGTH: 371
<212> TYPE: PRT
<213> ORGANISM: Artificial Sequence
<220> FEATURE:
<223> OTHER INFORMATION: Amino acid sequence of ManII-GalT

<400> SEQUENCE: 20

Met Lys Leu Ser Arg Gln Phe Thr Val Phe Gly Ser Ala Ile Phe Cys
1               5                   10                  15

Val Val Ile Phe Ser Leu Tyr Leu Met Leu Asp Arg Gly His Leu Asp
            20                  25                  30

Tyr Pro Arg Asn Pro Arg Arg Glu Gly Ser Phe Pro Gln Gly Gln Leu
        35                  40                  45

Ser Met Leu Gln Glu Lys Ile Asp His Leu Glu Arg Leu Leu Ala Glu

```
            50              55              60
Asn Asn Glu Ile Ile Ser Asn Ile Arg Asp Ser Val Ile Asn Leu Ser
 65              70              75              80

Glu Ser Val Glu Asp Gly Pro Lys Ser Ser Gln Ser Asn Phe Ser Gln
             85              90              95

Gly Ala Gly Ser Pro Ala Cys Pro Glu Glu Ser Pro Leu Leu Val Gly
            100             105             110

Pro Met Leu Ile Glu Phe Asn Met Pro Val Asp Leu Glu Leu Val Ala
            115             120             125

Lys Gln Asn Pro Asn Val Lys Met Gly Gly Arg Tyr Ala Pro Arg Asp
            130             135             140

Cys Val Ser Pro His Lys Val Ala Ile Ile Ile Pro Phe Arg Asn Arg
145             150             155             160

Gln Glu His Leu Lys Tyr Trp Leu Tyr Tyr Leu His Pro Val Leu Gln
            165             170             175

Arg Gln Gln Leu Asp Tyr Gly Ile Tyr Val Ile Asn Gln Ala Gly Asp
            180             185             190

Thr Ile Phe Asn Arg Ala Lys Leu Leu Asn Val Gly Phe Gln Glu Ala
            195             200             205

Leu Lys Asp Tyr Asp Tyr Thr Cys Phe Val Phe Ser Asp Val Asp Leu
            210             215             220

Ile Pro Met Asn Asp His Asn Ala Tyr Arg Cys Phe Ser Gln Pro Arg
225             230             235             240

His Ile Ser Val Ala Met Asp Lys Phe Gly Phe Ser Leu Pro Tyr Val
            245             250             255

Gln Tyr Phe Gly Gly Val Ser Ala Leu Ser Lys Gln Gln Phe Leu Thr
            260             265             270

Ile Asn Gly Phe Pro Asn Asn Tyr Trp Gly Trp Gly Gly Glu Asp Asp
            275             280             285

Asp Ile Phe Asn Arg Leu Val Phe Arg Gly Met Ser Ile Ser Arg Pro
            290             295             300

Asn Ala Val Val Gly Arg Cys Arg Met Ile Arg His Ser Arg Asp Lys
305             310             315             320

Lys Asn Glu Pro Asn Pro Gln Arg Phe Asp Arg Ile Ala His Thr Lys
            325             330             335

Glu Thr Met Leu Ser Asp Gly Leu Asn Ser Leu Thr Tyr Gln Val Leu
            340             345             350

Asp Val Gln Arg Tyr Pro Leu Tyr Thr Gln Ile Thr Val Asp Ile Gly
            355             360             365

Thr Pro Ser
    370
```

FUSION CONSTRUCTS AND USE OF SAME TO PRODUCE ANTIBODIES WITH INCREASED FC RECEPTOR BINDING AFFINITY AND EFFECTOR FUNCTION

CROSS-REFERENCE TO RELATED APPLICATIONS

This application claims the benefit of U.S. Provisional Application Nos. 60/441,307, filed Jan. 22, 2003; 60/491,254, filed Jul. 31, 2003; and 60/495,142, filed Aug. 15, 2003, the entire contents of each of which are hereby incorporated by reference.

BACKGROUND OF THE INVENTION

1. Field of the Invention

The present invention relates to the field of glycosylation engineering of proteins. More particularly, the present invention relates to nucleic acid molecules, including fusion constructs, having catalytic activity and the use of same in glycosylation engineering of host cells to generate polypeptides with improved therapeutic properties, including antibodies with increased Fc receptor binding and increased effector function.

2. Background Art

Glycoproteins mediate many essential functions in human beings, other eukaryotic organisms, and some prokaryotes, including catalysis, signaling, cell-cell communication, and molecular recognition and association. They make up the majority of non-cytosolic proteins in eukaryotic organisms. (Lis et al., *Eur. J. Biochem.* 218:1-27 (1993)). Many glycoproteins have been exploited for therapeutic purposes, and during the last two decades, recombinant versions of naturally-occurring, secreted glycoproteins have been a major product of the biotechnology industry. Examples include erythropoietin (EPO), therapeutic monoclonal antibodies (therapeutic m-Abs), tissue plasminogen activator (tPA), interferon-β, (IFN-β), granulocyte-macrophage colony stimulating factor (GM-CSF), and human chorionic gonadotrophin (hCG). (Cumming et al., *Glycobiology* 1:115-130 (1991)).

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions. (Jenkins et al., *Nature Biotechnol.* 14:975-81 (1996)).

Mammalian cells are the preferred hosts for production of therapeutic glycoproteins, due to their capability to glycosylate proteins in the most compatible form for human application. (Cumming et al., *Glycobiology* 1:115-30 (1991); Jenkins et al., *Nature Biotechnol.* 14:975-81 (1996)). Bacteria very rarely glycosylate proteins, and like other types of common hosts, such as yeasts, filamentous fungi, insect and plant cells, yield glycosylation patterns associated with rapid clearance from the blood stream, undesirable immune interactions, and in some specific cases, reduced biological activity.

Among mammalian cells, Chinese hamster ovary (CHO) cells have been most commonly used during the last two decades. In addition to giving suitable glycosylation patterns, these cells allow consistent-generation of genetically stable, highly productive clonal cell lines. They can be cultured to high densities in simple bioreactors using serum-free media, and permit the development of safe and reproducible bioprocesses. Other commonly used animal cells include baby hamster kidney (BHK) cells, NS0- and SP2/0-mouse myeloma cells. More recently, production from transgenic animals has also been tested. (Jenkins et al., *Nature Biotechnol.* 14:975-81 (1996)).

All antibodies contain carbohydrate structures at conserved positions in the heavy chain constant regions, with each isotype possessing a distinct array of N-linked carbohydrate structures, which variably affect protein assembly, secretion or functional activity. (Wright, A., and Morrison, S. L., *Trends Biotech.* 15:26-32 (1997)). The structure of the attached N-linked carbohydrate varies considerably, depending on the degree of processing, and can include high-mannose, multiply-branched as well as biantennary complex oligosaccharides. (Wright, A., and Morrison, S. L., *Trends Biotech.* 15:26-32 (1997)). Typically, there is heterogeneous processing of the core oligosaccharide structures attached at a particular glycosylation site such that even monoclonal antibodies exist as multiple glycoforms. Likewise, it has been shown that major differences in antibody glycosylation occur between cell lines, and even minor differences are seen for a given cell line grown under different culture conditions. (Lifely, M. R. et al., *Glycobiology* 5(8):813-22 (1995)).

Unconjugated monoclonal antibodies (mAbs) can be useful medicines for the treatment of cancer, as demonstrated by the U.S. Food and Drug Administration's approval of Rituximab (Rituxan™; IDEC Pharmaceuticals, San Diego, Calif., and Genentech Inc., San Francisco, Calif.), for the treatment of CD20 positive B-cell, low-grade or follicular Non-Hodgkin's lymphoma, Trastuzumab (Herceptin™; Genentech Inc,) for the treatment of advanced breast cancer (Grillo-Lopez, A.-J., et al., *Semin. Oncol.* 26:66-73 (1999); Goldenberg, M. M., *Clin. Ther.* 21:309-18 (1999)), Gemtuzumab (Mylotarg™, Celltech/Wyeth-Ayerst) for the treatment of relapsed acute myeloid leukemia, and Alemtuzumab (CAMPATH™, Millenium Pharmaceuticals/Schering AG) for the treatment of B cell chronic lymphocytic leukemia. The success of these products relies not only on their efficacy but also on their outstanding safety profiles (Grillo-Lopez, A.-J., et al., *Semin. Oncol.* 26:66-73 (1999); Goldenberg, M. M., *Clin. Ther.* 21:309-18 (1999)). In spite of the achievements of these drugs, there is currently a large interest in obtaining higher specific antibody activity than what is typically afforded by unconjugated mAb therapy.

One way to obtain large increases in potency, while maintaining a simple production process and potentially avoiding significant, undesirable side effects, is to enhance the natural, cell-mediated effector functions of mAbs by engineering their oligosaccharide component (Umaña, P. et al., *Nature Biotechnol.* 17:176-180 (1999)). IgG1 type antibodies, the most commonly used antibodies in cancer immunotherapy, are glycoproteins that have a conserved N-linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., *Glycobiology* 5:813-822 (1995); Jefferis, R., et al., *Immunol*

Rev. 163:59-76 (1998); Wright, A. and Morrison, S. L., *Trends Biotechnol.* 15:26-32 (1997)).

The present inventors showed previously that overexpression in Chinese hamster ovary (CHO) cells of β(1,4)-N-acetylglucosaminyltransferase III (GnTIII), a glycosyltransferase catalyzing the formation of bisected oligosaccharides, significantly increases the in vitro ADCC activity of an anti-neuroblastoma chimeric monoclonal antibody (chCE7) produced by the engineered CHO cells. (See Umaña, P. et al., *Nature Biotechnol.* 17:176-180 (1999), International Publication No. WO 99/54342, the entire contents of each of which are hereby incorporated by reference in their entirety). The antibody chCE7 belongs to a large class of unconjugated mAbs which have high tumor affinity and specificity, but have too little potency to be clinically useful when produced in standard industrial cell lines lacking the GnTIII enzyme (Umana, P., et al., *Nature Biotechnol.* 17:176-180 (1999)). That study was the first to show that large increases of ADCC activity could be obtained by engineering the antibody-producing cells to express GnTIII, which also led to an increase in the proportion of constant region (Fc)-associated, bisected oligosaccharides, including bisected non-fucosylated oligosaccharides, above the levels found in naturally-occurring antibodies.

The results of a number of studies suggest that Fc-receptor-dependent mechanisms contribute substantially to the action of cytotoxic antibodies against tumors and indicate that an optimal antibody against tumors would bind preferentially to activation Fc receptors and minimally to the inhibitory partner FcγRIIB. (Clynes, R. A., et al., *Nature Medicine* 6(4):443-446 (2000); Kalergis, A. M., and Ravetch, J. V., *J. Exp. Med.* 195(12):1653-1659 (June 2002). For example, the results of at least one study suggest that the FcγRIIIa receptor in particular is strongly associated with the efficacy of antibody therapy. (Cartron, G., et al., *Blood* 99(3):754-757 (February 2002)). That study showed that patients homozygous for FcγRIIIa have a better response to Rituximab than heterozygous patients. The authors concluded that the superior response was due to better in vivo binding of the antibody to FcγRIIIa, which resulted in better ADCC activity against lymphoma cells. (Cartron, G., et al., *Blood* 99(3):754-757 (February 2002)).

In addition to ADCC, successful anti-cancer monoclonal antibodies often induce Fc-independent direct signaling mechanisms that regulate target cell survival, proliferation, or death by activating cell signaling cascades or blocking access to growth factors. (Selenko, N., et al., *J. Clin. Immunol.* 22(3):124-130 (2002)). For example, treatment of $CD20^+$ B cells with Rituximab has been shown to induce complement-mediated lysis and Mab-induced induction of apoptosis as well as ADCC. (Selenko, N., et al., *J. Clin. Immunol.* 22(3):124-130 (2002)). Moreover, the Rituximab induced apoptosis of lymphoma cells not only kills the cells but also promotes uptake and cross-presentation of lymphoma cell-derived peptides by antigen-presenting dendritic cells (DC), induces maturation of DC, and allows the generation of specific cytotoxic T lymphocytes (CTL).

BRIEF SUMMARY OF THE INVENTION

Recognizing the tremendous therapeutic potential of antibodies with increased Fc receptor binding affinity and increased effector function, the present inventors developed a method for producing such antibodies which involves engineering the glycosylation profile of the antibody Fc region.

The present invention is broadly directed to methods for glycoengineering host cells to alter the glycosylation profile of one or more polypeptides produced by that host cell. The methods of the invention can be used to produced theraepeutic antibodies with modified glycosylation in the Fc region, including reduced fucosylation, wherein the antibodies have increased effector function and/or increased Fc receptor binding as a result of the modified glycosylation. The glycoengineered antibodies of the present invention are particularly useful in therapeutic treatments of tumors in patients. In one embodiments, the host cells of the invention are glycoengineered to express a nucleic acid molecule encoding a fusion polypeptide with GnTIII catalytic activity or GalT catalytic activity. In a preferred embodiment, the fusion constructs are coexpressed with a nucleic acid molecule encoding a polypeptide having human ManII catalytic activity and/or a nucleic acid molecule encoding a polypeptide with GnTII catalytic activity. In yet another embodiment, the glycoengineered polypeptides of the present invention are produced by a host cell glycoengineered to have increased expression of a nucleic acid molecule encoding a polypeptide with Man II catalytic activity.

Accordingly, in one aspect the invention is directed to an isolated nucleic acid comprising a sequence encoding a fusion polypeptide, wherein said fusion polypeptide has β(1,4)-N-acetylglucosaminyltransferase III ("GnTIII") activity and comprises the Golgi localization domain of a Golgi resident polypeptide. In one embodiment, the fusion polypeptide comprises the catalytic domain of β(1,4)-N-acetylglucosaminyltransferase III. In a further embodiment, the Golgi localization domain is selected from the group consisting of the localization domain of mannosidase II, the localization domain of β(1,2)-N-acetylglucosaminyltransferase I ("GnTI"), the localization domain of β(1,2)-N-acetylglucosaminyltransferase II ("GnTII"), the localization domain of mannosidase I, and the localization domain of α1-6 core fucosyltransferase. In a preferred embodiment the isolated nucleic acid sequence comprises the nucleotide sequence depicted in FIG. 24 or FIG. 25. In another preferred embodiment, the isolated nucleic acid sequence encodes a polypeptide having the amino acid sequence depicted in FIG. 24 or FIG. 25. In yet another preferred embodiment, the isolated nucleic acid sequence encodes a polypeptide having an amino acid sequence at least 80% identical to the amino acid sequence in FIG. 24 or FIG. 25.

In another aspect, the invention is directed to an isolated nucleic acid comprising a sequence encoding a fusion polypeptide, wherein said fusion polypeptide has β(1,4)-galactosyltransferase ("GalT") activity and comprises the Golgi localization domain of a Golgi resident polypeptide. In one embodiment, the fusion polypeptide comprises the catalytic domain of β(1,4)-galactosyltransferase. In another embodiment, the fusion polypeptide comprises the catalytic domain of β(1,4) galactosyltransferase. In a further embodiment, the Golgi localization domain is selected from the group consisting of the localization domain of mannosidase II, the localization domain of β(1,2)-N-acetylglucosaminyltransferase I ("GnTI"), the localization domain of β(1,2)-N-acetylglucosaminyltransferase II ("GnTII"), the localization domain of mannosidase I, and the localization domain of α1-6 core fucosyltransferase.

In another aspect, the present invention is directed to an expression vector comprising an isolated nucleic acid comprising a sequence encoding a fusion polypeptide, wherein said fusion polypeptide has β(1,4)-N-acetylglucosaminyl-transferase III activity and comprises the Golgi localization domain of a Golgi resident polypeptide. In one embodiment, the expression vector encodes a fusion polypeptide comprising the catalytic domain of β(1,4)-N-acetylglucosaminyltransferase III and the Golgi localization domain is selected from the group consisting of the localization domain of mannosidase II, the localization domain of β(1,2)-N-acetylglucosaminyltransferase I, the localization domain of β(1,2)-N-acetylglucosaminyltransferase II, the localization domain of mannosidase I, and the localization domain of α1-6 core fucosyltransferase.

In another aspect, the present invention is directed to an expression vector comprising an isolated nucleic acid comprising a sequence encoding a fusion polypeptide, wherein said fusion polypeptide has β(1,4)-galactosyltransferase activity and comprises the Golgi localization domain of a Golgi resident polypeptide. In one embodiment, the expression vector encodes a fusion polypeptide comprising the catalytic domain of β(1,4)-galactosyltransferase and the Golgi localization domain is selected from the group consisting of the localization domain of mannosidase II, the localization domain of β(1,2)-N-acetylglucosaminyltransferase I, the localization domain of β(1,2)-N-acetylglucosaminyltransferase II, the localization domain of mannosidase I, and the localization domain of α1-6 core fucosyltransferase.

In another aspect, the present invention is directed to a host cell comprising an above-described expression vector.

In another aspect, the present invention is directed to a host cell engineered to express at least one nucleic acid encoding a fusion polypeptide having β(1,4)-N-acetylglucosaminyltransferase III ("GnTIII") activity in an amount sufficient to modify the oligosaccharides in the Fc region of a polypeptide produced by the host cell, wherein said polypeptide produced by said host cell is selected from the group consisting of a whole antibody molecule, an antibody fragment containing the Fc region, and a fusion protein that includes a region equivalent to the Fc region of an immunoglobulin. In one embodiment, the fusion polypeptide having GnTIII activity comprises the catalytic domain of β(1,4)-N-acetylglucosaminyltransferase III and the Golgi localization domain of a heterologous Golgi resident polypeptide selected from the group consisting of the localization domain of mannosidase II, the localization domain of β(1,2)-N-acetylglucosaminyltransferase I, the localization domain of mannosidase I, the localization domain of β(1,2)-N-acetylglucosaminyltransferase II, and the localization domain of α1-6 core fucosyltransferase.

In another aspect, the present invention is directed to a host cell engineered to express at least one nucleic acid encoding a fusion polypeptide having β(1,4)-galactosyltransferase ("GalT") activity in an amount sufficient to modify the oligosaccharides in the Fc region of a polypeptide produced by the host cell, wherein said polypeptide produced by said host cell is selected from the group consisting of a whole antibody molecule, an antibody fragment containing the Fc region, and a fusion protein that includes a region equivalent to the Fc region of an immunoglobulin. In one embodiment, the fusion polypeptide having GalT activity comprises the catalytic domain of β(1,4)-galactosyltransferase and the Golgi localization domain of a heterologous Golgi resident polypeptide selected from the group consisting of the localization domain of mannosidase II, the localization domain of β(1,2)-N-acetylglucosaminyltransferase I, the localization domain of mannosidase I., the localization domain of β(1,2)-N-acetylglucosaminyltransferase II, and the localization domain of α1-6 core fucosyltransferase.

Preferably, the Golgi localization domain is from mannosidase II or β(1,2)-N-acetylglucosaminyltransferase I or, alternatively, galactosyltransferase.

In another aspect, the present invention is directed to a fusion polypeptide having β(1,4)-N-acetylglucosaminyltransferase III activity and comprising the Golgi localization domain of a heterologous Golgi resident polypeptide. In one embodiment, the fusion polypeptides of the invention comprise the catalytic domain of β(1,4)-N-acetylglucosaminyltransferase III. In another embodiment, the Golgi localization domain is selected from the group consisting of: the localization domain of mannosidase II, the localization domain of β(1,2)-N-acetylglucosaminyltransferase I, the localization domain of mannosidase I, the localization domain of β(1,2)-N-acetylglucosaminyltransferase II, and the localization domain of α1-6 core fucosyltransferase.

In another aspect, the present invention is directed to a fusion polypeptide having β(1,4)-galactosyltransferase activity and comprising the Golgi localization domain of a heterologous Golgi resident polypeptide. In one embodiment, the fusion polypeptides of the invention comprise the catalytic domain of β(1,4)-galactosyltransferase. In another embodiment, the Golgi localization domain is selected from the group consisting of: the localization domain of mannosidase II, the localization domain of β(1,2)-N-acetylglucosaminyltransferase I, the localization domain of mannosidase I, the localization domain of β(1,2)-N-acetylglucosaminyltransferase II, and the localization domain of α1-6 core fucosyltransferase.

Preferably, the Golgi localization domain is from mannosidase II or β(1,2)-N-acetylglucosaminyltransferase I ("GnTI") or, alternatively, galactosyltransferase ("GalT").

In another aspect, the present invention is directed to a method for producing a fusion polypeptide having β(1,4)-N-acetylglucosaminyltransferase III activity comprising culturing a host cell of the invention in a medium under conditions allowing the expression of the nucleic acid encoding the fusion polypeptide and recovering the fusion polypeptide from the resultant culture. In one embodiment, the fusion polypeptide comprises the catalytic domain of β(1,4)-N-acetylglucosaminyltransferase III. Preferably, the fusion polypeptide comprises the Golgi localization domain of a heterologous Golgi resident polypeptide selected from the group consisting of the localization domain of mannosidase II, the localization domain of β(1,2)-N-acetylglucosaminyltransferase I, the localization domain of mannosidase I, the localization domain of β(1,2)-N-acetylglucosaminyltransferase II, and the localization domain of α1-6 core fucosyltransferase.

In another aspect, the present invention is directed to a method for producing a fusion polypeptide having β(1,4)-galactosyltransferase activity comprising culturing a host cell of the invention in a medium under conditions allowing the expression of the nucleic acid encoding the fusion polypeptide and recovering the fusion polypeptide from the resultant culture. In one embodiment, the fusion polypeptide comprises the catalytic domain of β(1,4)-galactosyltransferase. Preferably, the fusion polypeptide comprises the Golgi localization domain of a heterologous Golgi resident polypeptide selected from the group consisting of the localization domain of mannosidase II, the localization domain of β(1,2)-N-acetylglucosaminyltransferase I, the localization domain of mannosidase I, the localization domain of β(1,2)-N-acetylglucosaminyltransferase II, and the localization domain of α1-6 core fucosyltransferase.

Preferably, the Golgi localization domain is from mannosidase II or β(1,2)-N-acetylglucosaminyltransferase I, or galactosyltransferase ("GalT").

In a further aspect, the invention is directed to a method for modifying the glycosylation profile of a polypeptide produced by a host cell comprising introducing into the host cell at least one nucleic acid or expression vector of the invention.

Preferably, the polypeptide is IgG or a fragment thereof containing the Fc region of the polypeptide. In a particularly preferred embodiment, the polypeptide is IgG1 or a fragment thereof containing the Fc region of the polypeptide. Alternatively, the polypeptide is a fusion protein that includes a region equivalent to the Fc region of a human IgG.

In another aspect, the invention is directed to a method for producing a polypeptide in a host cell, comprising: (a) culturing a host cell engineered to express at least one nucleic acid encoding a fusion polypeptide having β(1,4)-N-acetylglucosaminyltransferase III activity or, alternatively, β(1,4)-galactosyltransferase ("GalT") activity, under conditions which permit the production of a polypeptide selected from the group consisting of a whole antibody molecule, an antibody fragment containing the Fc region, and a fusion protein that includes a region equivalent to the Fc region of an immunoglobulin, wherein said fusion polypeptide is expressed in an amount sufficient to modify the oligosaccharides in the Fc region of said polypeptide produced by said host cell; and (b) isolating said polypeptide. Preferably, the fusion polypeptide comprises the catalytic domain of β(1,4)-N-acetylglucosaminyltransferase III or β(1,4)-galactosyltransferase ("GalT") and further comprises the Golgi localization domain of a heterologous Golgi resident polypeptide selected from the group consisting of the localization domain of mannosidase II, the localization domain of β(1,2)-N-acetylglucosaminyltransferase I, the localization domain of mannosidase I, the localization domain of β(1,2)-N-acetylglucosaminyltransferase II, and the localization domain of α1-6 core fucosyltransferase. In preferred embodiments, the polypeptide produced by the host cell has increased effector function and/or increased Fc receptor binding as a result of the modification. In particularly preferred embodiments, the increased effector function is increased Fc-mediated cellular cytotoxicity, increased binding to NK cells, increased binding to macrophages, increased binding to monocytes, increased binding to polymorphonuclear cells, increased direct signaling inducing apoptosis, increased dendritic cell maturation, and/or increased T cell priming, and the increased Fc receptor binding is increased binding to an Fc activating receptor such as FcγRIIIA. Preferably, the polypeptide exhibiting increased effector function and/or increased Fc receptor binding is an antibody, antibody-fragment, or fusion protein comprising a region equivalent to the Fc region of an immunoglobulin and has an increased proportion of nonfucosylated oligosaccharides in the Fc region.

In another aspect, the invention is directed to pharmaceutical compositions comprising the antibody, antibody fragment containing the Fc region, or fusion polypeptide containing the Fc region of an immunoglobulin of the invention, and to the use of such a pharmaceutical composition in the treatment of tumors, such as cancers, or other disorders. In one embodiment, the treatment is B cell depletion by administering a therapeutically effective amount of such a pharmaceutical composition to a patient, e.g., human, in need thereof.

In yet a further aspect, the invention provides a host cell comprising an expression vector comprising a nucleic acid molecule encoding a fusion polypeptide, wherein said fusion polypeptide has β(1,4)-N-acetylglucosaminyltransferase III (GnT III) activity and comprises the Golgi localization domain of a Golgi resident polypeptide; and an expression vector comprising a nucleic acid molecule encoding a polypeptide, wherein said polypeptide has mannosidase II (Man II) activity. In preferred embodiments, the fusion polypeptide comprises the catalytic domain of GnTIII and the Golgi localization domain is selected from the group consisting of the localization domain of ManII, the localization domain of GnTI, the localization domain of GnTII, the localization domain of ManI, and the localization domain of α-1,6-core-fucosyltransferase. In one embodiment, the host cell further comprises an expression vector encoding a polypeptide having GnTII activity. The nucleic acids molecules encoding the fusion polypeptide, the polypeptide having ManII activity, and the polypeptide having GnTII activity can each be in separate expression vectors or the same expression vector.

In an additional aspect, the invention is directed to a host cell comprising an expression vector comprising a nucleic acid molecule encoding a fusion polypeptide, wherein said fusion polypeptide has β(1,4)-galactosyltransferase (GalT) activity and comprises the Golgi localization domain of a Golgi resident polypeptide; and an expression vector comprising a nucleic acid molecule encoding a polypeptide, wherein said polypeptide has mannosidase II (Man II) activity. In preferred embodiments, the fusion polypeptide comprises the catalytic domain of GnTIII and the Golgi localization domain is selected from the group consisting of the localization domain of ManII, the localization domain of GnTI, the localization domain of GnTII, the localization domain of ManI, and the localization domain of α-1,6-core-fucosyltransferase. In one embodiment, the host cell further comprises an expression vector encoding a polypeptide having GnTII activity. The nucleic acids molecules encoding the fusion polypeptide, the polypeptide having ManII activity, and the polypeptide having GnTII activity can each be in separate expression vectors or the same expression vector.

In a further aspect, the invention is directed to a host cell engineered to express at least one nucleic acid encoding a fusion polypeptide having GnT III activity and at least one nucleic acid encoding a polypeptide having Man II activity in an amount sufficient to modify the oligosaccharides in the Fc region of a polypeptide produced by said host cell, wherein said polypeptide produced by said host cell is selected from the group consisting of a whole antibody molecule, an antibody fragment, and a fusion protein that includes a region equivalent to the Fc region of an immunoglobulin.

In an additional embodiment, the invention provides a host cell engineered to express at least one nucleic acid encoding a fusion polypeptide having GnTIII activity, at least one nucleic acid encoding a polypeptide having ManII activity and at least one nucleic acid encoding a polypeptide having GnT II activity in an amount sufficient to modify the oligosaccharides in the Fc region of a polypeptide produced by said host cell, wherein said polypeptide produced by said host cell is selected from the group consisting of a whole antibody molecule, an antibody fragment, and a fusion protein that includes a region equivalent to the Fc region of an immunoglobin.

In a further aspect, the invention provides a host cell engineered to express at least one nucleic acid encoding a fusion polypeptide having GalT activity and at least one nucleic acid encoding a polypeptide having Man II activity in an amount sufficient to modify the oligosaccharides in the Fc region of a polypeptide produced by said host cell, wherein said polypeptide produced by said host cell is selected from the group consisting of a whole antibody molecule, an antibody fragment, and a fusion protein that includes a region equivalent to the Fc region of an immunoglobin.

In an additional aspect, the invention provides a host cell engineered to express at least one nucleic acid encoding a fusion polypeptide having GalT activity, at least one nucleic acid encoding a polypeptide having Man II activity and at least one nucleic acid encoding a polypeptide having GnT II activity, in an amount sufficient to modify the oligosaccharides in the Fc region of a polypeptide produced by said host cell, wherein said polypeptide produced by said host cell is selected from the group consisting of a whole antibody molecule, an antibody fragment, and a fusion protein that includes a region equivalent to the Fc region of an immunoglobin.

In a further aspect, the invention is directed to a method for producing a polypeptide in a host cell, comprising culturing a host cell engineered to express at least one nucleic acid encoding a fusion polypeptide having GnT III activity and at least one a nucleic acid encoding a polypeptide having Man II activity under conditions which permit the production of a polypeptide selected from the group consisting of a whole antibody molecule, an antibody fragment, and a fusion protein that includes a region equivalent to the Fc region of an immunoglobulin, wherein said fusion polypeptide is expressed in an amount sufficient to modify the oligosaccharides in the Fc region of said polypeptide produced by said host cell; and isolating said polypeptide.

In another aspect, the invention is directed to a method for producing a polypeptide in a host cell, comprising culturing a host cell engineered to express at least one nucleic acid encoding a fusion polypeptide having GalT activity and at least one nucleic acid encoding a polypeptide having Man II activity under conditions which permit the production of a polypeptide selected from the group consisting of a whole antibody molecule, an antibody fragment, and a fusion protein that includes a region equivalent to the Fc region of an immunoglobulin, wherein said fusion polypeptide is expressed in an amount sufficient to modify the oligosaccharides in the Fc region of said polypeptide produced by said host cell; and isolating said polypeptide.

In an additional aspect, a method for producing a polypeptide having increased Fc-mediated cellular cytotoxicity in a host cell, comprising culturing a host cell engineered to express at least one nucleic acid encoding GalT and at least one nucleic acid encoding Man II under conditions which permit the production of a polypeptide selected from the group consisting of a whole antibody molecule, an antibody fragment that included the Fc region of an immunoglobulin, wherein the expression level of one or both of GalT or Man II is sufficient to modify the oligosaccharides in the Fc region of said polypeptide produced by said host cell and wherein said polypeptide has increased Fc-mediated cellular cytotoxicity as a result of said modification; and isolating said polypeptide having increased Fc-mediated cellular cytotoxicity.

In another aspect, the present invention is directed to a method for producing a polypeptide in a host cell, comprising: (a) culturing a host cell engineered to express at least one nucleic acid encoding a polypeptide having α-Mannosidase II activity under conditions which permit the production of a polypeptide selected from the group consisting of a whole antibody molecule, an antibody fragment, and a fusion protein that includes a region equivalent to the Fc region of an immunoglobulin, wherein said polypeptide having α-Mannosidase II activity is expressed in an amount sufficient to modify the oligosaccharides in the Fc region of said polypeptide produced by said host cell; and (b) isolating said polypeptide produced by said host cell.

In another aspect, the present invention is directed to a host cell engineered to express at least one nucleic acid encoding a polypeptide having α-Mannosidase II activity under conditions which permit the production of a polypeptide selected from the group consisting of a whole antibody molecule, an antibody fragment, and a fusion protein that includes a region equivalent to the Fc region of an immunoglobulin, wherein said polypeptide having α-Mannosidase II activity is expressed in an amount sufficient to modify the oligosaccharides in the Fc region of said polypeptide produced by said host cell In yet another aspect, the present invention is directed to polypeptides produced by such host cells, particularly antibodies having increased effector function and/or increased Fc receptor binding as a result of said modified oligosaccharides.

BRIEF DESCRIPTION OF THE FIGURES

FIG. 7. MALDI/TOF-MS spectra of neutral oligosaccharide mix derived from recombinant, glycoengineered anti-CD20 IgG1 antibody produced in HEK293-EBNA engineered with a nucleic acid encoding a fusion polypeptide ("M2-GnTIII") with GnTIII activity and localized via a Golgi alpha-mannosidaseII(ManII)-Golgi localization domain. Cells were co-transfected with antibody expression vector pETR1520 and with GnTIII expression vector pETR1519. Antibody was purified from culture medium and oligosaccharides were prepared and analyzed as described in the Materials and Methods section of Example 1. (a) Oligosaccharide profile of PNGaseF-release oligosaccharides with no additional enzymatic treatment. (b) Oligosaccharide profile of PNGaseF-release oligosaccharides further digested with EndoH.

FIG. 24. The nucleic acid sequence and amino acid sequence, respectively, of the Mannosidase II-GnTIII fusion polypeptide of the invention.

FIG. 25. The nucleic acid sequence and amino acid sequence, respectively, of the GnT-I-GnT-III fusion polypeptide of the invention.

DETAILED DESCRIPTION OF THE INVENTION

Figure 1:
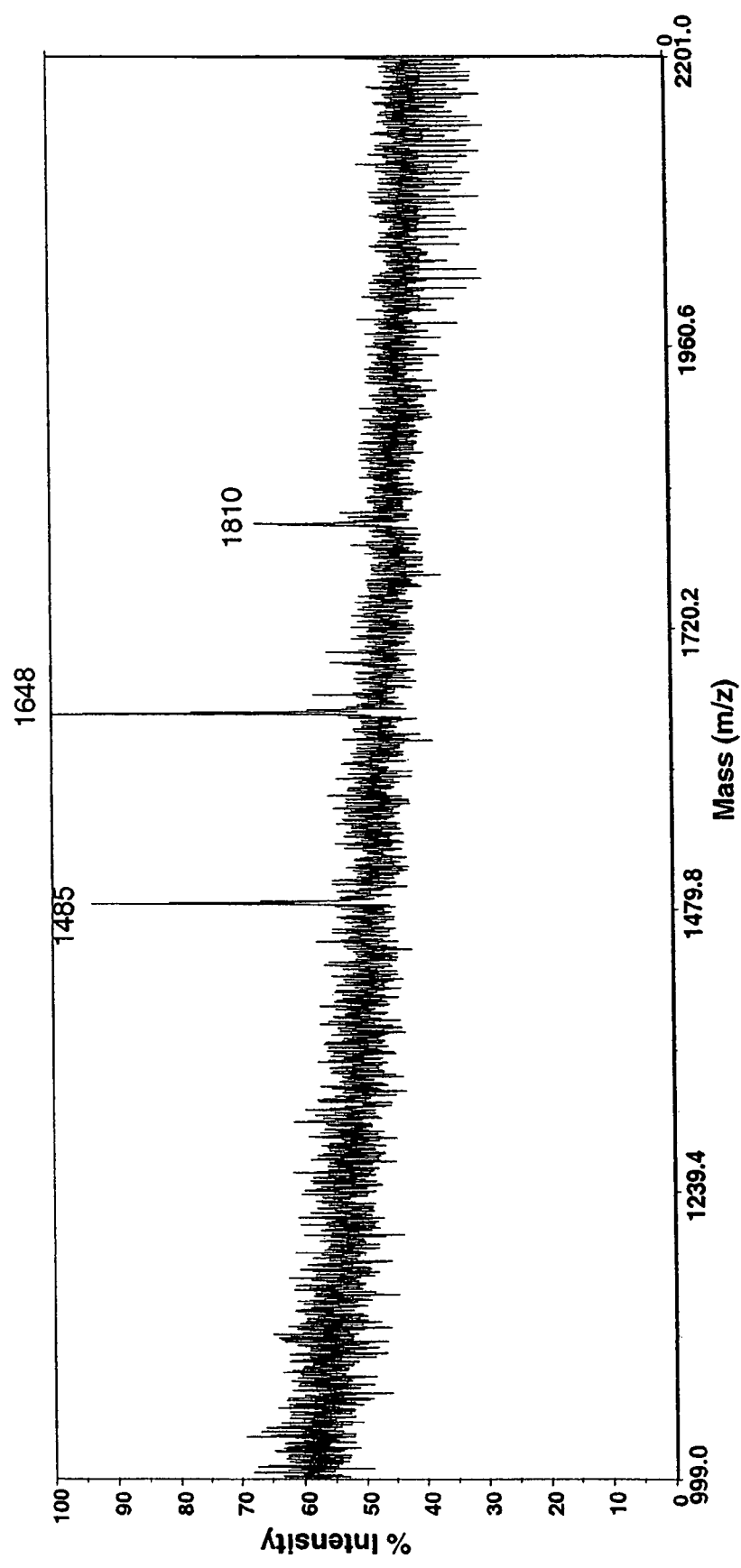
FIG. 1. MALDI/TOF-MS spectrum of neutral oligosaccharide mix derived from recombinant, unmodified (non-glycoengineered) anti-CD20 IgG1 antibody produced in BHK. Cells were transfected with antibody expression vector pETR1502. Antibody was purified from culture medium and oligosaccharides were prepared and analyzed as described in the Materials and Methods section of Example 1.

Terms are used herein as generally used in the art, unless otherwise defined as follows.

As used herein, the term antibody is intended to include whole antibody molecules, including monoclonal, polyclonal and multispecific (e.g., bispecific) antibodies, as well as antibody fragments having the Fc region and fusion proteins that include a region equivalent to the Fc region of an immunoglobulin. Also encompassed are humanized and chimeric antibodies.

As used herein, the term Fc region is intended to refer to a C-terminal region of an IgG heavy chain. Although the boundaries of the Fc region of an IgG heavy chain might vary slightly, the human IgG heavy chain Fc region is usually defined to stretch from the amino acid residue at position Cys226 to the carboxyl-terminus.

As used herein, the term region equivalent to the Fc region of an immunoglobulin is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity. (See, e.g., Bowie, J. U. et al., *Science* 247:1306-10 (1990).

As used herein, a fusion polypeptide "having β(1,4)-N-acetylglucosaminyltransferase III activity" refers to fusion polypeptides that are able to catalyze the addition of a N-acetylglucosamine (GlcNAc) residue in β-1-4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of β(1,4)-N-acetylglucosaminyltransferase III, but rather substantially similar to the dose-dependence in a given activity as compared to the β(1,4)-N-acetylglucosaminyltransferase III (i.e., the candidate polypeptide will exhibit greater activity or not more than about 25-fold less and, preferably, not more than about tenfold less activity, and most preferably, not more than about three-fold less activity relative to the β(1,4)-N-acetylglucosaminyltransferase III.)

As used herein, a fusion polypeptide "having β(1,4)-galactosyltransferase activity" or "having GalT activity" refers to fusion polypeptides that are able to catalyze the addition of a galactose residue from UDP galactose to the non-reducing terminal GlcNAc found in N-linked oligosaccharides. This includes fusion polypeptides exhibiting enzymatic activity similar to, but not necessarily identical to, an activity of β(1,4)-galactosyltransferase, also known as UDP-Gal: GlcNAc β-1,4-galactosyltransferase (E.C. 2.4.1.38), according to the Nomenclature Committee of the International Union of Biochemistry and Molecular Biology (NC-IUBMB), as measured in a particular biological assay, with or without dose dependency. In the case where dose dependency does exist, it need not be identical to that of β(1,4)-galactosyltransferase, but rather substantially similar to the dose-dependence in a given activity as compared to the β(1,4)-galactosyltransferase (i.e., the candidate polypeptide will exhibit greater activity or not more than about 25-fold less and, preferably, not more than about tenfold less activity, and most preferably, not more than about three-fold less activity relative to the β(1,4)-N-acetylglucosaminyltransferase III.)

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be the entire sequence shown in either FIG. 24 or FIG. 25.

As a practical matter, whether any particular nucleic acid molecule or polypeptide is at least 80%, 85%, 90%, 95%, 96%, 97%, 98% or 99% identical to a nucleotide sequence or polypeptide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., *Comp. App. Biosci.* 6:237-245 (1990). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to a reference polypeptide can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., *Comp. App. Biosci.* 6:237-245 (1990). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, CutoffScore=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

As used herein, a nucleic acid that "hybridizes under stringent conditions" to a nucleic acid sequence of the invention, refers to a polynucleotide that hybridizes in an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

As used herein, the term Golgi localization domain refers to the amino acid sequence of a Golgi resident polypeptide which is responsible for anchoring it in location within the Golgi complex. Generally, localization domains comprise amino terminal "tails" of an enzyme.

As used herein, the term effector function refers to those biological activities attributable to the Fc region (a native sequence Fc region or amino acid sequence variant Fc region) of an antibody. Examples of antibody effector functions include, but are not limited to, Fc receptor binding affinity, antibody-dependent cellular cytotoxicity (ADCC), antibody-dependent cellular phagocytosis (ADCP), cytokine secretion, immune-complex-mediated antigen uptake by antigen-presenting cells, down-regulation of cell surface receptors, etc.

As used herein, the terms engineer, engineered, engineering and glycosylation engineering are considered to include any manipulation of the glycosylation pattern of a naturally occurring polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation.

As used herein, the term host cell covers any kind of cellular system which can be engineered to generate modified glycoforms of proteins, protein fragments, or peptides of interest, including antibodies, antibody fragments, and fusion proteins. Typically, the host cells have been manipulated to express optimized levels of GnT III. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

As used herein, the term Fc-mediated cellular cytotoxicity includes antibody-dependent cellular cytotoxicity and cellular cytotoxicity mediated by a soluble Fc-fusion protein containing a human Fc-region. It is an immune mechanism leading to the lysis of "antibody-targeted cells" by "human immune effector cells", wherein:

The "human immune effector cells" are a population of leukocytes that display Fc receptors on their surface through which they bind to the Fc-region of antibodies or of Fc-fusion proteins and perform effector functions. Such a population may include, but is not limited to, peripheral blood mononuclear cells (PBMC) and/or natural killer (NK) cells.

The "antibody-targeted cells" are cells bound by the antibodies or Fc-fusion proteins. The antibodies or Fc fusion-proteins bind to target cells via the protein part N-terminal to the Fc region.

As used herein, the term increased Fc-mediated cellular cytotoxicity is defined as either an increase in the number of "antibody-targeted cells" that are lysed in a given time, at a given concentration of antibody, or of Fc-fusion protein, in the medium surrounding the target cells, by the mechanism of Fc-mediated cellular cytotoxicity defined above, and/or a reduction in the concentration of antibody, or of Fc-fusion protein, in the medium surrounding the target cells, required to achieve the lysis of a given number of "antibody-targeted cells", in a given time, by the mechanism of Fc-mediated cellular cytotoxicity. The increase in Fc-mediated cellular cytotoxicity is relative to the cellular cytotoxicity mediated by the same antibody, or Fc-fusion protein, produced by the same type of host cells, using the same standard production, purification, formulation and storage methods, which are known to those skilled in the art, but that has not been produced by host cells engineered to express the glycosyltransferase GnTIII by the methods described herein.

By antibody having increased antibody dependent cellular cytotoxicity (ADCC) is meant an antibody having increased ADCC as determined by any suitable method known to those of ordinary skill in the art. One accepted in vitro ADCC assay is as follows:

1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
   i) the PBMCs are isolated using standard density centrifugation procedures and are suspended at $5 \times 10^6$ cells/ml in RPMI cell culture medium;
   ii) the target cells are grown by standard tissue culture methods, harvested from the exponential growth phase with a viability higher than 90%, washed in RPMI cell culture medium, labelled with 100 micro-Curies of $^{51}Cr$, washed twice with cell culture medium, and resuspended in cell culture medium at a density of $10^5$ cells/ml;
   iii) 100 microliters of the final target cell suspension above are transferred to each well of a 96-well microtiter plate;
   iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
   v) for the maximum release (MR) controls, 3 additional wells in the plate containing the labelled target cells, receive 50 microliters of a 2% (V/V) aqueous solution of non-ionic detergent (Nonidet, Sigma, St. Louis), instead of the antibody solution (point iv above);
   vi) for the spontaneous release (SR) controls, 3 additional wells in the plate containing the labelled target cells, receive 50 microliters of RPMI cell culture medium instead of the antibody solution (point iv above);
   vii) the 96-well microtiter plate is then centrifuged at $50 \times g$ for 1 minute and incubated for 1 hour at 4° C.;
   viii) 50 microliters of the PBMC suspension (point i above) are added to each well to yield an effector:target cell ratio of 25:1 and the plates are placed in an incubator under 5% $CO_2$ atmosphere at 37° C. for 4 hours;
   ix) the cell-free supernatant from each well is harvested and the experimentally released radioactivity (ER) is quantified using a gamma counter;
   x) the percentage of specific lysis is calculated for each antibody concentration according to the formula (ER−MR)/(MR−SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);
4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress the glycosyltransferase GnTIII.

As used herein, the term anti-CD20 antibody is intended to mean an antibody which specifically recognizes a cell surface non-glycosylated phosphoprotein of 35,000 Daltons, typically designated as the human B lymphocyte restricted differentiation antigen Bp35, commonly referred to as CD20.

The present invention is based on the discovery that engineering antibody-producing cells to express a novel fusion polypeptide having β(1,4)-N-acetylglucosaminyltransferase III (GnTIII) activity or, alternatively, β(1,4)-galactosyltransferase ("GalT") activity, and comprising the Golgi localization domain of a Golgi resident polypeptide results in antibodies with increased Fc receptor binding affinity and increased effector function. Alternatively, antibodies with increased effector function and/or increased Fc receptor binding can be obtained by engineering the antibody-producing cells to have increased expression of a nucleic acid molecule encoding a polypeptide having α-Mannosidase II catalytic activity. In preferred embodiments, the fusion constructs having GnTIII or GalT activity are coexpressed with nucleic acid molecules encoding ManII or GnTII.

Accordingly, in one embodiment, the present invention is directed to an isolated nucleic acid comprising a sequence encoding a fusion polypeptide, wherein the fusion polypeptide has β(1,4)-N-acetylglucosaminyltransferase III (GnTIII) activity and comprises the Golgi localization domain of a Golgi resident polypeptide. In a preferred embodiment, the fusion polypeptide comprises the catalytic domain of β(1,4)-N-acetylglucosaminyltransferase III and the Golgi localization domain is the localization domain of mannosidase II. In a further embodiment, the Golgi localization domain is the localization domain of GalT.

Preferably, the isolated nucleic acid has the nucleotide sequence shown in FIG. 24 and SEQ ID NO:14 In another preferred embodiment, the fusion polypeptide comprises the catalytic domain of β(1,4)-N-acetylglucosaminyltransferase III and the Golgi localization domain is the localization domain of β(1,2)-N-acetylglucosaminyltransferase I (GnTI). Preferably, the nucleic acid has the nucleotide sequence shown in FIG. 25 and SEQ ID NO:12. Alternatively, the Golgi localization domain of another Golgi resident polypeptide may be used. In another preferred embodiment, the Golgi localization domain is selected from the group consisting of the localization domain of β(1,2)-N-acetylglucosaminyltransferase II, the localization domain of mannosidase I, and the localization domain of α1-6 core fucosyltransferase.

In another preferred embodiment, the present invention is directed to an isolated nucleic acid comprising a sequence that encodes a polypeptide having the amino acid sequence shown in FIG. 24 and SEQ ID NO:15 or FIG. 25 and SEQ ID NO:13. The present invention also encompasses an isolated nucleic acid comprising a sequence that hybridizes under stringent conditions to a hybridization probe the nucleotide sequence of which consists of the nucleotide sequence shown in FIG. 24 and SEQ ID NO:14 or FIG. 25 and SEQ ID NO:12. The invention is further directed to an isolated nucleic acid comprising a sequence at least 80%, 85%, 90%, 95%, 96%, 97%, 98% or 99% identical to the nucleotide sequence shown in FIG. 24 and SEQ ID NO:14 or FIG. 25 and SEQ ID NO:12. In another embodiment, the invention is directed to an isolated nucleic acid comprising a sequence that encodes a polypeptide having an amino acid sequence at least 80%, 85%, 90%, 95%, 96%, 97%, 98% or 99% identical to the amino acid sequence FIG. 24 and SEQ ID NO:15 or FIG. 25 and SEQ ID NO:13. The invention also encompasses an isolated nucleic acid comprising a sequence that encodes a polypeptide having the amino acid sequence of FIG. 24 and SEQ ID NO:15 or FIG. 25 and SEQ ID NO:13, with conservative amino acid substitutions.

In another embodiment, the present invention is directed to an expression vector which comprises an isolated nucleic acid of the invention, such as those described above.

In a further embodiment, the present invention is directed to a fusion polypeptide having β(1,4)-N-acetylglucosaminyltransferase III activity or, alternatively, β(1,4)-galactosyltransferase ("GalT") activity, and comprising the Golgi localization domain of a heterologous Golgi resident polypeptide. In preferred embodiments, the fusion polypeptides of the invention comprise the catalytic domain of β(1,4)-N-acetylglucosaminyltransferase III. In a particularly preferred embodiment, the fusion polypeptides further comprise the Golgi localization domain of mannosidase II or β(1,2)-N-acetylglucosaminyltransferase I(GnTI). In an alternative embodiment, the Golgi localization domain is selected from the group consisting of the localization domain of mannosidase I, the localization domain of β(1,2)-N-acetylglucosaminyltransferase II, and the localization domain of α1-6 core fucosyltransferase. The fusion polypeptides of the present invention may be prepared by culturing the host cells of the present invention in a medium under conditions allowing the expression of the nucleic acid encoding said fusion polypeptide and recovering said fusion polypeptide from the resultant culture.

The present invention is further directed to a method for modifying the glycosylation profile of a polypeptide produced by a host cell, comprising introducing into said host cell a nucleic acid or vector of the invention. Preferably, the modified polypeptide is IgG or a fragment thereof comprising the Fc region. Most preferably, the polypeptide is IgG1, or a fragment thereof comprising the Fc region. In another preferred embodiment, the modified polypeptide is a fusion protein that includes a region equivalent to the Fc region of a human IgG.

The present invention is further directed to host cells comprising the nucleic acids and expression vectors of the invention. In one embodiment, the present invention is directed to a host cell engineered to express at least one nucleic acid encoding a fusion polypeptide having β(1,4)-N-acetylglucosaminyltransferase III activity or, alternatively, β(1,4)-galactosyltransferase ("GalT") activity, in an amount sufficient to modify the oligosaccharides in the Fc region of a polypeptide produced by said host cell, wherein said polypeptide is selected from the group consisting of a whole antibody molecule, an antibody fragment, and a fusion protein that includes a region equivalent to the Fc region of an immunoglobulin. In a preferred embodiment, the polypeptide produced by said host cell is IgG or a fragment thereof. Most preferably, the polypeptide produced by said host cell is IgG1 or a fragment thereof. Alternatively, the polypeptide produced by said host cell is a fusion protein that includes a region equivalent to the Fc region of a human IgG, e.g., IgG1.

The modified polypeptides produced by the host cells of the invention exhibit increased Fc receptor binding affinity and/or increased effector function as a result of the modification. Preferably, the increased Fc receptor binding affinity is increased binding to a Fcγ activating receptor, such as the FcγRIIIa receptor. The increased effector function is preferably an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased crosslinking of target-bound antibodies, increased direct signaling inducing apoptosis, increased dendritic cell maturation, and increased T cell priming.

In a particularly preferred embodiment, the host cell of the invention is a CHO cell, a BHK cell, a NS0 cell, a SP2/0 cell, a YO myeloma cell, a P3X63 mouse myeloma cell, a PER cell, a PER.C6 cell or a hybridoma cell and the polypeptide produced by said host cell is an anti-CD20 antibody such as IDEC-C2B8. In another preferred embodiment, the host cell is the chimeric anti-human EGFR monoclonal antibody C225.

In addition to comprising a nucleic acid encoding a fusion polypeptide of the invention, the host cells of the invention may further comprise at least one transfected nucleic acid encoding an antibody molecule, an antibody fragment retaining a functional Fc region, or a fusion protein that includes a region equivalent to the Fc region of an immunoglobulin. In preferred embodiments, the at least one transfected nucleic acid encodes an anti-CD20 antibody, the chimeric anti-human neuroblastoma monoclonal antibody chCE7, the chimeric anti-human renal cell carcinoma monoclonal antibody chG250, the chimeric anti-human colon, lung, and breast carcinoma monoclonal antibody ING-1, the humanized anti-human 17-1A antigen monoclonal antibody 3622W94, the humanized anti-human colorectal tumor antibody A33, the anti-human melanoma antibody directed against GD3 ganglioside R24, the chimeric anti-human squamous-cell carcinoma monoclonal antibody SF-25, an anti-human EGFR antibody, an anti-human EGFRvIII antibody, an anti-human PSMA antibody, an anti-human PSCA antibody, an anti-human CD22 antibody, an anti-human CD30 antibody, an anti-TAG72 antibody, an anti-high molecular weight melanoma associated antigen (HMWMAA) antibody, an anti-GD3 ganglioside antibody, an anti-GD2 ganglioside antibody, an anti-GM2 ganglioside antibody, an anti-human ganglioside antibody, an anti-EGFRvIII antibody, an anti-integrin antibody, an anti-CD80 antibody, an anti-LeY antibody, an anti-mucin antibody, an anti-MUC18 antibody, an anti-human CD33 antibody, an anti-human CD38 antibody, an anti-human CD40 antibody, an anti-human CD45 antibody, an anti-human CD52 antibody, an anti-human CD138 antibody, an anti-human HLA-DR variant antibody, an anti-human EpCAM antibody, an anti-human CEA antibody, an anti-human MUC1 antibody, an anti-human MUC1 core protein antibody, an anti-human aberrantly glycosylated MUC1 antibody, an antibody against human fibronectin variants containing the ED-B domain, or an anti-human HER2/neu antibody.

The present invention is also directed to a method for producing a polypeptide in a host cell comprising (a) culturing a host cell engineered to express at least one nucleic acid encoding a fusion polypeptide having β(1,4)-N-acetylglucosaminyltransferase III activity or, alternatively, β(1,4)-galactosyltransferase ("GalT") activity, under conditions which permit the production of a polypeptide selected from the group consisting of a whole antibody molecule, an antibody fragment retaining a functional Fc region, and a fusion protein that includes a region equivalent to the Fc region of an immunoglobulin, wherein said fusion polypeptide having GnTIII activity or, alternatively, GalT activity is expressed in an amount sufficient to modify the oligosaccharides in the Fc region of said polypeptide produced by said host cell; and (b) isolating said polypeptide. In a preferred embodiment, the fusion polypeptide comprises the catalytic domain of β(1,4)-

N-acetylglucosaminyltransferase III. In a particularly preferred embodiment, the fusion polypeptide further comprises the Golgi localization domain of a Golgi resident polypeptide. Preferably, the Golgi localization domain is the localization domain of mannosidase II or β(1,2)-N-acetylglucosaminyltransferase I (GnTI). Alternatively, the Golgi localization domain is selected from the group consisting of: the localization domain of mannosidase I, the localization domain of β(1,2)-N-acetylglucosaminyltransferase II, and the localization domain of α 1-6 core fucosyltransferase. The polypeptides produced by the methods of the present invention have increased Fc receptor binding affinity and/or increased effector function. Preferably, the increased effector function is one or more of the following: increased Fc-mediated cellular cytotoxicity (including increased antibody-dependent cellular cytotoxicity), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. The increased Fc receptor binding affinity is preferably increased binding to Fc activating receptors such as FcγRIIIa.

In another embodiment, the present invention is directed to a polypeptide produced by the methods of the invention which has an increased proportion of bisected oligosaccharides in the Fc region of said polypeptide. In yet another embodiment, the polypeptide produced by the methods of the invention has an increased proportion of nonfucosylated oligosaccharides in the Fc region as a result of said modification. The nonfucosylated oligosaccharides may be of the hybrid or complex type. In a particularly preferred embodiment, the polypeptide produced by the host cells and methods of the invention has an increased proportion of bisected, nonfucosylated oligosaccharides in the Fc region. The bisected, nonfucosylated oligosaccharides may be either hybrid or complex. Specifically, the methods of the present invention may be used to produce polypeptides in which at least 15%, more preferably at least 20%, more preferably at least 25%, more preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 95%, more preferably at least 96%, more preferably at least 97%, more preferably at least 98%, more preferably at least 99%, of the oligosaccharides in the Fc region of the polypeptide are nonfucosylated. The methods of the present invention may also be used to produce polypeptides in which at least 15%, more preferably at least 20%, more preferably at least 25%, more preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 900%, more preferably at least 95%, more preferably at least 96%, more preferably at least 97%, more preferably at least 98%, more preferably at least 99%, of the oligosaccharides in the Fc region of the polypeptide are bisected. Still further, the methods of the present invention may be used to produce polypeptides in which at least 15%, more preferably at least 20%, more preferably at least 25%, more preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 900%, more preferably at least 95%, more preferably at least 96%, more preferably at least 97%, more preferably at least 98%, more preferably at least 99%, of the oligosaccharides in the Fc region of the polypeptide are bisected, nonfucosylated. The methods of the present invention may also be used to produce polypeptides in which at least 15%, more preferably at least 20%, more preferably at least 25%, more preferably at least 30%, more preferably at least 35% of the oligosaccharides in the Fc region of the polypeptide are bisected hybrid nonfucosylated.

In another embodiment, the present invention is directed to an antibody engineered to have increased effector function and/or increased Fc receptor binding affinity, produced by the methods of the invention. Preferably, the increased effector function is one or more of the following: increased Fc-mediated cellular cytotoxicity (including increased antibody-dependent cellular cytotoxicity), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. In a preferred embodiment, the increased Fc receptor binding affinity is increased binding to an Fc activating receptor, most preferably FcγRIIIa. The invention is further directed to antibody fragments containing the Fc region and fusion proteins that include a region equivalent to the Fc region of an immunoglobulin. Such antibody fragments and fusion proteins exhibit increased Fc receptor binding affinity and/or increased effector function.

The present invention is further directed to pharmaceutical compositions comprising the antibodies, antibody fragments retaining the Fc region, and fusion proteins having a region equivalent to the Fc region of an immunoglobulin of the present invention and a pharmaceutically acceptable carrier.

The present invention is further directed to the use of such pharmaceutical compositions in the method of treatment of cancer. Specifically, the present invention is directed to a method for the treatment of cancer comprising administering a therapeutically effective amount of the pharmaceutical composition of the invention.

The present invention is also directed to a host cell comprising an expression vector comprising a nucleic acid molecule encoding a fusion polypeptide, wherein the fusion polypeptide has β(1,4)-N-acetylglucosaminyltransferase III (GnT III) activity and comprises the Golgi localization domain of a Golgi resident polypeptide; and an expression vector comprising a nucleic acid molecule encoding a polypeptide, wherein the polypeptide has mannosidase II (Man II) activity. In preferred embodiments, the nucleic acid molecule encoding the fusion polypeptide and the nucleic acid molecule encoding the polypeptide having mannosidase II activity are on the same or separate expression vectors. In another preferred embodiment, the fusion polypeptide comprises the catalytic domain of GnT III. In an additional preferred embodiment the Golgi localization domain is the localization domain of Man II, βƎ(1,2)-N-acetylglucosaminyltransferase I, β(1,2)-N- acetylglucosaminyltransferase II, mannosidase I or α1,6-N core fucosyltransferase. In a further preferred embodiment, the host cell is selected from the group consisting of a mammalian cell, a yeast cell, an insect cell and a plant cell. Preferably, the host cell is a CHO cell, a BHK cell, a NS0 cell, an SP2/0 cell, a YO myeloma cell, a P3X63 mouse myeloma cell, a PER cell, a PER.C6 cell, or a hybridoma cell.

The invention further provides a host cell comprising an expression vector comprising a nucleic acid molecule encoding a fusion polypeptide having β(1,4)-N-acetylglucosaminyltransferase III (GnT III) activity and comprises the Golgi localization domain of a Golgi resident polypeptide, an expression vector comprising a nucleic acid molecule encoding a polypeptide, wherein the polypeptide has mannosidase II (Man II) activity, and an expression vector comprising a nucleic acid molecule encoding a polypeptide, wherein the polypeptide has β(1,2)-N-acetylglucosaminyl-transferase II (GnT II) activity. In preferred embodiments, the nucleic acid molecule encoding a fusion polypeptide, the nucleic acid molecule encoding a polypeptide having Man II activity and the nucleic acid molecule encoding a polypeptide having GnT II activity are on the same or separate expression vectors. Also preferred is that the nucleic acid molecule encoding a fusion polypeptide is on one expression vector, and the nucleic acid molecule encoding a polypeptide having Man II activity and the nucleic acid molecule encoding a polypeptide having GnT II activity are on the same expression vector. Also preferred is that the nucleic acid molecule encoding a ManII is on one expression vector, and the nucleic acid molecule encoding a fusion polypeptide and the nucleic acid molecule encoding a polypeptide having GnT II activity are on the same expression vector. In another embodiment, the GnT II is on one expression vector, and the nucleic acid molecule encoding a fusion polypeptide and the nucleic acid molecule encoding a polypeptide having Man II activity are on the same expression vector.

In an additional aspect, the invention is directed to a host cell comprising an expression vector comprising a nucleic acid molecule encoding a fusion polypeptide, wherein the fusion polypeptide has β(1,4)-galactosyltransferase (GalT) activity and comprises the Golgi localization domain of a Golgi resident polypeptide; and an expression vector comprising a nucleic acid molecule encoding a polypeptide, wherein the polypeptide has mannosidase II (Man II) activity. In preferred embodiments, the nucleic acid molecule encoding a fusion polypeptide and the nucleic acid molecule encoding a polypeptide having mannosidase II activity are on the same expression vector or separate expression vectors. Preferably, the fusion polypeptide comprises the catalytic domain of GalT. In an additional embodiment, the Golgi localization domain is the localization domain of Man II, β(1,2)-N-acetylglucosaminyltransferase I, β(1,2)-N-acetylglucosaminyltransferase II, mannosidase I or α1,6-core fucosyltransferase. In a preferred embodiment, the host cell is selected from the group consisting of a mammalian cell, a yeast cell, an insect cell or a plant cell. Preferably, the host cell is a CHO cell, a BHK cell, a NS0 cell, an SP2/0 cell, a YO myeloma cell, a P3X63 mouse myeloma cell, a PER cell, a PER.C6 cell, or a hybridoma cell.

In an additional aspect, the invention is directed to a host cell comprising an expression vector comprising a nucleic acid molecule encoding a fusion polypeptide, wherein the fusion polypeptide has β(1,4)-galactosyltransferase (GalT) activity and comprises the Golgi localization domain of a Golgi resident polypeptide; and an expression vector comprising a nucleic acid molecule encoding a polypeptide, wherein the polypeptide has mannosidase II (Man II) activity; and an expression vector comprising a nucleic acid molecule encoding a polypeptide, wherein the polypeptide has β(1,2)-N-acetylglucosaminyl-transferase II (GnT II) activity. Preferably, each nucleic acid is on the same expression vector. In a separate embodiment, each nucleic acid molecule is on a separate vector. The invention further provides that the nucleic acid molecule encoding a fusion polypeptide is on one expression vector, and the nucleic acid molecule encoding a polypeptide having Man II activity and the nucleic acid molecule encoding a polypeptide having GnT II activity are on the same expression vector. The invention also provides that the nucleic acid molecule encoding a ManII is on one expression vector, and the nucleic acid molecule encoding a fusion polypeptide and the nucleic acid molecule encoding a polypeptide having GnT II activity are on the same expression vector. The invention also provides that the nucleic acid molecule encoding the GnT II is on one expression vector, and the nucleic acid molecule encoding a fusion polypeptide and the nucleic acid molecule encoding a polypeptide having Man II activity are on the same expression vector. In a preferred embodiment, the fusion polypeptide comprises the catalytic domain of GalT. In a further preferred embodiment, the Golgi localization domain is the localization domain of Man II, β(1,2)-N-acetylglucosaminyltransferase I, β(1,2)-N-acetylglucosaminyltransferase II, mannosidase I or α1,6-N core fucosyltransferase.

The invention further provides a host cell engineered to express at least one nucleic acid encoding a fusion polypeptide having GnT III activity and at least one nucleic acid encoding a polypeptide having Man II activity in an amount sufficient to modify the oligosaccharides in the Fc region of a polypeptide produced by the host cell, wherein the polypeptide produced by the host cell is selected from the group consisting of a whole antibody molecule, an antibody fragment, and a fusion protein that includes a region equivalent to the Fc region of an immunoglobin.

The invention also provides a host cell engineered to express at least one nucleic acid encoding a fusion polypeptide having GnT III activity, at least one nucleic acid encoding a polypeptide having Man II and at least one nucleic acid encoding a polypeptide having GnT II activity in an amount sufficient to modify the oligosaccharides in the Fc region of a polypeptide produced by the host cell, wherein the polypeptide produced by the host cell is selected from the group consisting of a whole antibody molecule, an antibody fragment, and a fusion protein that includes a region equivalent to the Fc region of an immunoglobin.

The present invention additionally provides a host cell engineered to express at least one nucleic acid encoding a fusion polypeptide having GalT activity and at least one nucleic acid encoding a polypeptide having Man II activity in an amount sufficient to modify the oligosaccharides in the Fc region of a polypeptide produced by the host cell, wherein the polypeptide produced by the host cell is selected from the group consisting of a whole antibody molecule, an antibody fragment, and a fusion protein that includes a region equivalent to the Fc region of an immunoglobin.

In a separate embodiment, the present invention also provides a host cell engineered to express at least one nucleic acid encoding a fusion polypeptide having GalT activity, at least one nucleic acid encoding a polypeptide having Man II and at least one nucleic acid encoding a polypeptide having GnT II activity in an amount sufficient to modify the oligosaccharides in the Fc region of a polypeptide produced by the host cell, wherein the polypeptide produced by the host cell is selected from the group consisting of a whole antibody molecule, an antibody fragment, and a fusion protein that includes a region equivalent to the Fc region of an immunoglobin. Preferably, the polypeptide produced by the host cell exhibits increased Fc receptor binding affinity as a result of the modification. In an additionally preferred embodiment, the polypeptide produced by the host cell exhibits increased effector function as a result of the modification. Preferably, the increased effector function is one or more of increased Fc-mediated cellular cytotoxicity, increased binding to NK cells, increased binding to macrophages, increased binding to polymorphonuclear cells, increased binding to monocytes, increased direct signaling induced apoptosis, increased dendritic cell maturation, and/or increased T cell priming.

In an additional embodiment, the invention is directed to a method for producing a polypeptide in a host cell, comprising culturing a host cell engineered to express at least one nucleic acid encoding a fusion polypeptide having GnT III activity and at least one nucleic acid encoding a polypeptide having Man II activity under conditions which permit the production of a polypeptide selected from the group consisting of a whole antibody molecule, an antibody fragment, and a fusion protein that includes a region equivalent to the Fc region of an immunoglobulin, wherein the fusion polypeptide is expressed in an amount sufficient to modify the oligosaccharides in the Fc region of the polypeptide produced by the host cell; and isolating the polypeptide. Preferably, the host cell is further engineered to express at least one nucleic acid encoding a polypeptide having GnT II activity. In an additionally preferred embodiment, the fusion polypeptide comprises the catalytic domain of GnT III. In a further preferred embodiment, the fusion polypeptide further comprises the Golgi localization domain of a heterologous Golgi resident polypeptide. Preferably, the Golgi localization domain is the localization domain of mannosidase II, β∃(1,2)-N-acetylglucosaminyltransferase I, mannosidase I, β(1,2)-N-acetylglucosaminyltransferase II or α1-6 core fucosyltransferase. Preferably, the polypeptide has increased effector function as a result of the above modification.

The invention is further directed to a method for producing a polypeptide in a host cell, comprising culturing a host cell engineered to express at least one nucleic acid encoding a fusion polypeptide having GalT activity and at least one a nucleic acid encoding a polypeptide having Man II activity under conditions which permit the production of a polypeptide selected from the group consisting of a whole antibody molecule, an antibody fragment, and a fusion protein that includes a region equivalent to the Fc region of an immunoglobulin, wherein the fusion polypeptide is expressed in an amount sufficient to modify the oligosaccharides in the Fc region of the polypeptide produced by the host cell; and isolating the polypeptide. In an additional embodiment, the host cell is further engineered to express at least one nucleic acid encoding a polypeptide having GnT II activity. Preferably, the fusion polypeptide comprises the catalytic domain of GalT. Also preferred is that the fusion polypeptide further comprises the Golgi localization domain of a heterologous Golgi resident polypeptide. Preferably, the Golgi localization domain is the localization domain of mannosidase II, β(1,2)-N-acetylglucosaminyltransferase I, mannosidase I, β(1,2)-N-acetylglucosaminyltransferase II or α1-6 core fucosyltransferase. Preferably, the polypeptide has increased effector function as a result of the above modification. Specifically, in a preferred embodiment, the polypeptide produced by the host cell has an increased proportion of bisected, nonfucosylated oligosaccharides in the Fc region of the polypeptide. Preferably, the bisected, nonfucosylated oligosaccharides are hybrid. Even more preferably, the bisected, nonfucosylated oligosaccharides are complex. In a preferred embodiment, at least from about 10% to 95% of the oligosaccharides in the Fc region of the polypeptide are bisected, nonfucosylated. Especially preferred is that about 20%, 25%, 30%, 35%, 40%, 45%, 50%, 55%, 60%, 65%, 70%, 75%, 80%, 85%, 90%, 95% of the oligosaccharides in the Fc region of the glycoengineered polypeptides of the present invention are bisected, nonfucosylated.

In an additionally preferred embodiment, the present invention provides that the antibodies engineered according to the methods of the present invention have increased effector function.

In an additional embodiment, the invention further provides pharmaceutical compositions comprising the antibodies engineered according to the methods of the present invention. Preferably, the pharmaceutical compositions of the present invention comprise a pharmaceutically acceptable carrier.

The invention further provides a method for the treatment of cancerous tumors comprising administering a therapeutically effective amount of the pharmaceutical compositions of the present invention to a patient in need thereof.

The invention is further directed to a method for producing a polypeptide having increased Fc-mediated cellular cytotoxicity in a host cell, comprising culturing a host cell engineered to express at least one nucleic acid encoding GalT and at least one nucleic acid encoding Man II under conditions which permit the production of a polypeptide selected from the group consisting of a whole antibody molecule, an antibody fragment that included the Fc region of an immunoglobulin, wherein the expression level of one or both of GalT or Man II is sufficient to modify the oligosaccharides in the Fc region of the polypeptide produced by the host cell and wherein the polypeptide has increased Fc-mediated cellular cytotoxicity as a result of the modification; and isolating the polypeptide having increased Fc-mediated cellular cytotoxicity. In an additionally preferred embodiment, the expression level of GalT produces an antibody molecule or antibody fragment that includes the Fc region of an immunoglobin having increased Fc-mediated cellular cytotoxicity.

The invention is further directed to a method for producing a polypeptide having increased Fc-mediated cellular cytotoxicity in a host cell, comprising culturing a host cell engineered to express at least one nucleic acid encoding GalT and at least one nucleic acid encoding Man II under conditions which permit the production of a polypeptide selected from the group consisting of a whole antibody molecule, an antibody fragment that included the Fc region of an immunoglobulin, wherein the expression level of one or both of GalT or Man II is sufficient to modify the oligosaccharides in the Fc region of the polypeptide produced by the host cell and wherein the polypeptide has increased Fc-mediated cellular cytotoxicity as a result of the modification; and isolating the polypeptide having increased Fc-mediated cellular cytotoxicity. In a preferred embodiment, the above host cell further comprises at least one nucleic acid encoding GnT III, wherein the GnT III is expressed in an amount sufficient to modify the oligosaccharides in the Fc region of the polypeptide produced by the host cell and wherein the polypeptide has increased Fc-mediated cellular cytotoxicity as a result of the modification. Preferably, the expression level of one or more of GalT, Man II or GnT III is sufficient to form bisected oligosaccharides in the Fc region of the polypeptide. Even more preferably, the proportion of bisected oligosaccharides in the Fc region to total oligosaccharides in the Fc region is at least about 25, 35, 45, 55, 60, 65, 70, 75, 80, 85, 90 or 95 percent. Preferably, the proportion of bisected oligosaccharides in the Fc region to total oligosaccharides in the Fc region is at least about 45 percent. In a preferred embodiment, the bisected oligosaccharides are complex or hybrid. Preferably, the host cell is a mammalian cell, a yeast cell, an insect cell or a plant cell. Even more preferably, the host cell is a plant cell.

In another aspect, the present invention is directed to a method for producing a polypeptide in a host cell, comprising:
  a. culturing a host cell engineered to express at least one nucleic acid encoding a polypeptide having α-Mannosidase II activity under conditions which permit the production of a polypeptide selected from the group consisting of a whole antibody molecule, an antibody fragment, and a fusion protein that includes a region equivalent to the Fc region of an immunoglobulin, wherein said polypeptide having α-Mannosidase II activity is expressed in an amount sufficient to modify the oligosaccharides in the Fc region of said polypeptide produced by said host cell; and
  b. isolating said polypeptide produced by said host cell.

The present invention is also directed to polypeptides, particularly antibodies, having increased effector function and/or increased Fc receptor binding as a result of said modified oligosacchardes as well as their use in therapeutic compositions to treat disorders, particularly tumors.

Identification and Generation of Nucleic Acids Encoding a Protein for which Modification of the Glycosylation Pattern is Desired The present invention provides methods for the generation and use of host cell systems for the production of glycoforms of antibodies, antibody fragments containing the Fc region, and fusion proteins which a region equivalent to the Fc region, having increased Fc receptor binding affinity, preferably Fc activating receptors, and/or having increased effector functions, including antibody-dependent cellular cytotoxicity. Identification of target epitopes and generation of antibodies having potential therapeutic value, for which modification of the glycosylation pattern is desired, and isolation of their respective coding nucleic acid sequence is within the scope of the invention.

Various procedures known in the art may be used for the production of antibodies to target epitopes of interest. Such antibodies include but are not limited to polyclonal, monoclonal, chimeric, humanized, fully-human, single chain, Fab fragments and fragments produced by an ScFv, Fab, VH, IgG expression library. Such antibodies may be useful, e.g., as diagnostic or therapeutic agents. As therapeutic agents, neutralizing antibodies, i.e., those which compete for binding with a ligand, substrate or adapter molecule, are of especially preferred interest.

For the production of antibodies, various host animals are immunized by injection with the target protein of interest including, but not limited to, rabbits, mice, rats, etc. Polyclonal antibodies may be raised in animals by multiple subcutaneous (sc) or intraperitoneal (ip) injections of the relevant antigen and an adjuvant. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, saponin, oil emulsions, keyhole limpet hemocyanin, dinitrophenol, and potentially useful human adjuvants such as BCG (bacille Calmette-Guerin) and *Corynebacterium parvum*. Animals are immunized against the antigen, immunogenic conjugates, or derivatives by combining, e.g., 100 g or 5 g of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to different protein and/or through a different cross-linking reagent. Conjugates can also be made in recombinant cell culture as protein fusions.

Monoclonal antibodies to the target of interest may be prepared using any technique which provides for the production of antibody molecules by continuous cell lines in culture. These include, but are not limited to, the hybridoma technique originally described by Kohler and Milstein, *Nature* 256:495-97 (1975), the human B-cell hybridoma technique (Kosbor et al., *Immunology Today* 4:72 (1983); Cote et al., *Proc. Natl. Acad. Sci. U.S.A.* 80:2026-30 (1983) and the EBV-hybridoma technique (Cole et al., *Monoclonal Antibodies and Cancer Therapy* 77-96 (Alan R. Liss, Inc., 1985)). In addition, techniques developed for the production of "chimeric antibodies" (Morrison et al., *Proc. Natl. Acad. Sci. U.S.A.* 81:6851-55 (1984); Neuberger et al., *Nature* 312:604-08 (1984); Takeda et al., *Nature* 314:452-54 (1985) by splicing the genes from a mouse antibody molecule of appropriate antigen specificity together with genes from a human antibody molecule of appropriate biological activity can be used. These techniques can be used to produce chimeric antibodies comprised of an antibody molecule of other mammals as well. Alternatively, techniques described for the production of single chain antibodies (U.S. Pat. No. 4,946,778) can be adapted to produce single chain antibodies having a desired specificity. The invention is further directed to humanized antibodies that have been glycoengineered according to the methods of the present invention. Techniques for generating humanized antibodies are disclosed, for example, in U.S. Pat. No. 6,180,320 to Queen et al., the entire contents of which are incorporated herein by their entirety.

Antibody fragments which contain specific binding sites of the target protein of interest may be generated by known techniques. For example, such fragments include, but are not limited to, F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., *Science* 246:1275-81 (1989) to allow rapid and easy identification of monoclonal Fab fragments with the desired specificity to the target protein of interest.

Once an antibody or antibody fragment has been identified for which modification in the glycosylation pattern are desired, the coding nucleic acid sequence is identified and isolated using techniques well known in the art.

a. Generation of Cell Lines for the Production of Proteins with Altered Glycosylation Pattern The present invention provides host cell expression systems for the generation of proteins having modified glycosylation patterns. In particular, the present invention provides host cell systems for the generation of glycoforms of proteins having an improved therapeutic value. Therefore, in one aspect, the invention provides host cell expression systems selected or engineered to express, e.g., a fusion polypeptide having β(1,4)-N-acetylglucosaminyltransferase III (GnTIII) activity and comprising the Golgi localization domain of a heterologous Golgi resident polypeptide. Specifically, such host cell expression systems may be engineered to comprise a recombinant nucleic acid molecule encoding such fusion polypeptide, operatively linked to a constitutive or regulated promoter system.

In one specific embodiment, the present invention provides a host cell that has been engineered to express at least one nucleic acid encoding a fusion polypeptide having β(1,4)-N-acetylglucosaminyltransferase III (GnTIII) activity and comprising the Golgi localization domain of a heterologous Golgi resident polypeptide. In one aspect, the host cell is engineered with a nucleic acid molecule comprising at least one gene encoding a fusion polypeptide having β(1,4)-N-acetylglucosaminyltransferase III (GnTIII) activity and comprising the Golgi localization domain of a heterologous Golgi resident polypeptide.

Generally, any type of cultured cell line can be used as a background to engineer the host cell lines of the present invention. In a preferred embodiment, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells of the invention. (See Ma, J. K.-C., et al., *Nature Genetics* 4:794-805 (October 2003) and references cited therein) (the entire contents of which are hereby incorporated by reference).

The invention is contemplated to encompass any engineered host cells expressing a fusion polypeptide having β(1,4)-N-acetylglucosaminyltransferase III (GnTIII) activity and comprising the Golgi localization domain of a heterologous Golgi resident polypeptide as defined herein.

One or several nucleic acids encoding a fusion polypeptide having β(1,4)-N-acetylglucosaminyltransferase III (GnTIII) activity and comprising the Golgi localization domain of a heterologous Golgi resident polypeptide may be expressed under the control of a constitutive promoter or, alternately, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different nucleic acids encoding fusion polypeptides having β(1,4)-N-acetylglucosaminyltransferase III (GnTIII) activity and comprising the Golgi localization domain of a heterologous Golgi resident polypeptide are comprised within the host cell system, some of them may be expressed under the control of a constitutive promoter, while others are expressed under the control of a regulated promoter. The maximal expression level is considered to be the highest possible level of stable fusion polypeptide expression that does not have a significant adverse effect on cell growth rate, and will be determined using routine experimentation. Expression levels are determined by methods generally known in the art, including Western blot analysis using an antibody specific for the polypeptide having GnTIII activity or an antibody specific for a peptide tag fused to the polypeptide having GnTIII activity, Northern blot analysis using a nucleic acid probe specific for the gene encoding the polypeptide having GnTIII activity or a nucleic acid probe specific for a nucleic acid encoding a peptide tag fused to the polypeptide having GnTIII activity, or measurement of GnTIII activity. Alternatively, a lectin may be employed which binds to biosynthetic products of the GnTIII, for example, $E_4$-PHA lectin. Alternatively, a functional assay which measures the increased Fc receptor binding or increased effector function mediated by antibodies produced by the cells engineered with the nucleic acid encoding a polypeptide with GnTIII activity, may be used. In a further alternative, the nucleic acid may be operatively linked to a reporter gene; the expression levels of the fusion polypeptide having β(1,4)-N-acetylglucosaminyltransferase III (GnTIII) activity and comprising the Golgi localization domain of a heterologous Golgi resident polypeptide are determined by measuring a signal correlated with the expression level of the reporter gene. The reporter gene may transcribed together with the nucleic acid(s) encoding the fusion polypeptide as a single mRNA molecule; their respective coding sequences may be linked either by an internal ribosome entry site (IRES) or by a cap-independent translation enhancer (CITE). The reporter gene may be translated together with at least one nucleic acid encoding the fusion polypeptide having β(1,4)-N-acetylglucosaminyltransferase III (GnTIII) activity and comprising the Golgi localization domain of a heterologous Golgi resident polypeptide such that a single polypeptide chain is formed. The nucleic acids encoding the fusion polypeptides of the present invention may be operatively linked to the reporter gene under the control of a single promoter, such that the nucleic acid encoding the fusion polypeptide and the reporter gene are transcribed into an RNA molecule which is alternatively spliced into two separate messenger RNA (mRNA) molecules; one of the resulting mRNAs is translated into the reporter protein, and the other is translated into the fusion polypeptide If several different nucleic acids encoding a fusion polypeptide having β(1,4)-N-acetylglucosaminyltransferase III (GnTIII) activity and comprising the Golgi localization domain of a heterologous Golgi resident polypeptide are expressed, they may be arranged in such way that they are transcribed as one or as several mRNA molecules. If they are transcribed as a single mRNA molecule, their respective coding sequences may be linked either by an internal ribosome entry site (IRES) or by a cap-independent translation enhancer (CITE). They may be transcribed from a single promoter into an RNA molecule which is alternatively spliced into several separate messenger RNA (mRNA) molecules, which then are each translated into their respective encoded fusion polypeptides.

In other embodiments, the present invention provides host cell expression systems for the generation of therapeutic antibodies, having increased Fc receptor binding affinity, particularly binding to Fc activating receptors, and increased effector function, including antibody-dependent cellular cytotoxicity. Generally, the host cell expression systems have been engineered and/or selected to express nucleic acids encoding the antibody for which the production of altered glycoforms is desired, along with at least one nucleic acid encoding a fusion polypeptide having β(1,4)-N-acetylglucosaminyltransferase III (GnTIII) activity and comprising the Golgi localization domain of a heterologous Golgi resident polypeptide. In one embodiment, the host cell system is transfected with at least one nucleic acid encoding such fusion polypeptide. Typically, the transfected cells are selected to identify and isolate clones that stably express the fusion polypeptide of the invention.

Any type of cultured cell line can be used as background to engineer the host cell lines of the present invention. In a preferred embodiment, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells may be used. Typically, such cell lines are engineered to further comprise at least one transfected nucleic acid encoding a whole antibody molecule, an antibody fragment containing the Fc region of an immunoglobulin, or a fusion protein that includes a region equivalent to the Fc region of an immunoglobulin. Typically such antibody production cell lines are derived from clones producing and secreting the antibody at high specific productivities in the range between 20 to 120 pg/(cell.day). In an alternative embodiment, a hybridoma cell line expressing a particular antibody of interest is used as background cell line to generate the engineered host cells of the invention.

In one embodiment the nucleic acids encoding the antibody, antibody fragment or Fc-fusion polypeptide are cloned into antibody-expression vectors and then are transfected into the host cells and cell clones with high and stable specific antibody productivity are selected and screened for. Such selected clones are then transfected with glycoprotein-modifying glycosyltransferase expression vectors containing nucleic acids encoding, for example, (a) a fusion polypeptide with beta 1,4-N-acetylglucosaminyltransferase III (GnTIII) activity, or (b) a fusion polypeptide with beta 1,4-galactosyltransferase (GalT) activity, or (c) a polypeptide with Golgi alpha-mannosidase II (ManII) activity, or (d) a fusion polypeptide with GnTIII activity and a further polypeptide with ManII activity, or (e) a fusion polypeptide with GalT activity and a further polypeptide with ManII activity. Clones clones are then selected and screened for stable expression of the antibody-encoding genes at levels leading to high antibody specific productivities, and with stable expression of the glycoprotein-modifying glycosyltransferase genes at expression levels leading to modification of the Fc region glycosylation pattern, including an increase in the fraction of non-fucosylated oligosaccharides which may be either bisected or non-bisected and which further may be of complex or hybrid type, which is associated with an increase in Fc receptor binding, particularly an increase in Fc-FcγRIII binding affinity, and an increase in Fc receptor mediated effector functions, including but not limited to Fc-dependent cellular cytotoxicity. Selection and screening methods are described below.

In another embodiment the order of the two transfections described above, namely the antibody expression vectors transfection and the glycoprotein-modifying glycosyltransferase expression vectors transfection, is reversed, i.e., host cells are first transfected with the glycoprotein-modifying glycosyltransferase expression vectors and then with the antibody expression vectors. In such approach the clones from the first transfection may be screened for adequate stable expression levels of the glycosyltransferase genes by any of the methods described further below, or alternatively by transiently transfecting replicates of such clones with antibody expression vectors and then applying the screening methods described further below in order to identify clones with stable expression level of the glycosyltransferase genes at levels that lead to a modification of the Fc region glycosylation pattern and to an increase in Fc receptor, including FcγRIII receptors, binding affinity and an increase in Fc receptor-mediated effector functions, including Fc-dependent cellular cytotoxicity.

In a further embodiment, the antibody-encoding genes and the glycosyltransferase genes are transfected together in a single transfection step, either in a single expression vector or in separate vectors.

Typically, at least one nucleic acid in the host cell system encodes a fusion polypeptide having β(1,4)-N-acetylglucosaminyltransferase III (GnTIII) activity or, alternatively, β(1,4)-galactosyltransferase activity, and comprising the Golgi localization domain of a heterologous Golgi resident polypeptide or, alternatively, it encodes a polypeptide with Golgi α-mannosidase II activity.

One or several nucleic acids encoding a fusion polypeptide of the invention may be expressed under the control of a constitutive promoter, or alternately, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different nucleic acids encoding a fusion polypeptide having β(1,4)-N-acetylglucosaminyltransferase III (GnTIII) activity and comprising the Golgi localization domain of a heterologous Golgi resident polypeptide are comprised within the host cell system, some of them may be expressed under the control of a constitutive promoter, while others are expressed under the control of a regulated promoter. The maximal expression level is considered to be the highest possible level of stable fusion polypeptide expression that does not have a significant adverse effect on cell growth rate, and will be determined using routine experimentation. Expression levels are determined by methods generally known in the art, including Western blot analysis using e.g., an antibody specific for the polypeptide having GnTIII activity or an antibody specific for a peptide tag fused to the polypeptide having GnTIII activity, Northern blot analysis using a nucleic acid probe specific for e.g., the gene encoding the polypeptide having GnTIII activity or a nucleic acid probe specific for a nucleic acid encoding a peptide tag fused to the polypeptide having GnTIII activity, or measurement of GnTIII enzymatic activity. Alternatively, a lectin may be employed which binds to biosynthetic products of GnTIII, for example, $E_4$-PHA lectin. Alternatively, a functional assay which measures the increased Fc receptor binding or increased effector function mediated by antibodies produced by the cells engineered with the nucleic acid encoding a polypeptide with GnTIII activity may be used. In a further alternative, the nucleic acid may be operatively linked to a reporter gene; the expression levels of the fusion polypeptide of the invention are determined by measuring a signal correlated with the expression level of the reporter gene. The reporter gene may be transcribed together with the nucleic acid(s) encoding said glycoprotein-modifying glycosyl transferase as a single mRNA molecule; their respective coding sequences may be linked either by an internal ribosome entry site (IRES) or by a cap-independent translation enhancer (CITE). The reporter gene may be translated together with at least one nucleic acid encoding a fusion polypeptide having β(1,4)-N-acetylglucosaminyltransferase III (GnTII) activity and comprising the Golgi localization domain of a heterologous Golgi resident polypeptide such that a single polypeptide chain is formed. The nucleic acid encoding the fusion polypeptide may be operatively linked to the reporter gene under the control of a single promoter, such that the nucleic acid encoding the fusion polypeptide of the invention and the reporter gene are transcribed into an RNA molecule which is alternatively spliced into two separate messenger RNA (mRNA) molecules; one of the resulting mRNAs is translated into said reporter protein, and the other is translated into said fusion polypeptide.

If several different nucleic acids encoding a fusion polypeptide having β(1,4)-N-acetylglucosaminyltransferase III (GnTIII) activity and comprising the Golgi localization domain of a heterologous Golgi resident polypeptide are expressed, they may be arranged in such way that they are transcribed as one or as several mRNA molecules. If they are transcribed as single mRNA molecule, their respective coding sequences may be linked either by an internal ribosome entry site (IRES) or by a cap-independent translation enhancer (CITE). They may be transcribed from a single promoter into an RNA molecule which is alternatively spliced into several separate messenger RNA (mRNA) molecules, which then are each translated into their respective encoded fusion polypeptides.

i. Expression Systems

Methods which are well known to those skilled in the art can be used to construct expression vectors containing the coding sequence of the protein of interest and the coding sequence of a fusion polypeptide having β(1,4)-N-acetylglucosaminyltransferase III (GnTIII) activity and comprising the Golgi localization domain of a heterologous Golgi resident polypeptide along with appropriate transcriptional/translational control signals. These methods include in vitro recombinant DNA techniques, synthetic techniques and in vivo recombination/genetic recombination. See, for example, the techniques described in Maniatis et al., Molecular Cloning A Laboratory Manual, Cold Spring Harbor Laboratory, N.Y. (1989) and Ausubel et al., Current Protocols in Molecular Biology, Greene Publishing Associates and Wiley Interscience, N.Y. (1989).

A variety of host-expression vector systems may be utilized to express the coding sequence of the protein of interest and the coding sequence of the fusion polypeptide of the present invention. Preferably, mammalian cells are used as host cell systems transfected with recombinant plasmid DNA or cosmid DNA expression vectors containing the coding sequence of the protein of interest and the coding sequence of the fusion polypeptide. Most preferably, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as host cell system. Some examples of expression systems and selection methods are described in the following references, and references therein: Borth et al., *Biotechnol. Bioen.* 71(4):266-73 (2000-2001), in Werner et al., *Arzneimittelforschung/Drug Res.* 48(8):870-80 (1998), in Andersen and Krummen, *Curr. Op. Biotechnol.* 13:117-123 (2002), in Chadd and Chamow, *Curr. Op. Biotechnol.* 12:188-194 (2001), and in Giddings, *Curr. Op. Biotechnol.* 12: 450-454 (2001). In alternate embodiments, other eukaryotic host cell systems may be contemplated, including, yeast cells transformed with recombinant yeast expression vectors containing the coding sequence of the protein of interest and the coding sequence of the fusion polypeptide of the invention; insect cell systems infected with recombinant virus expression vectors (e.g., baculovirus) containing the coding sequence of the protein of interest and the coding sequence of the fusion polypeptide of the invention; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of the protein of interest and the coding sequence of the fusion polypeptide of the invention; or animal cell systems infected with recombinant virus expression vectors (e.g., adenovirus, vaccinia virus) including cell lines engineered to contain multiple copies of the DNA encoding the protein of interest and the coding sequence of the fusion polypeptide of the invention either stably amplified (CHO/dhfr) or unstably amplified in double-minute chromosomes (e.g., murine cell lines).

For the methods of this invention, stable expression is generally preferred to transient expression because it typically achieves more reproducible results and also is more amenable to large scale production, i.e., production of the glycoengineered antibodies of the present invention in production scale cell lines. Rather than using expression vectors which contain viral origins of replication, host cells can be transformed with the respective coding nucleic acids controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows selection of cells which have stably integrated the plasmid into their chromosomes and grow to form foci which in turn can be cloned and expanded into cell lines.

A number of selection systems may be used, including, but not limited to, the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:2026 (1962)), and adenine phosphoribosyltransferase (Lowy et al., *Cell* 22:817 (1980)) genes, which can be employed in tk⁻, hgprt⁻ or aprt⁻ cells, respectively. Also, antimetabolite resistance can be used as the basis of selection for dhfr, which confers resistance to methotrexate (Wigler et al., *Natl. Acad. Sci. USA* 77:3567 (1989); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (Colberre-Garapin et al., *J. Mol. Biol.* 150:1 (1981)); and hygro, which confers resistance to hygromycin (Santerre et al., *Gene* 30:147 (1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047 (1988)); the glutamine synthase system; and ODC (ornithine decarboxylase) which confers resistance to the ornithine decarboxylase inhibitor, 2-(difluoromethyl)-DL-ornithine, DFMO (McConlogue, in: *Current Communications in Molecular Biology*, Cold Spring Harbor Laboratory ed. (1987)).

ii. Identification of Transfectants or Transformants that Express the Protein Having a Modified Glycosylation Pattern The host cells which contain the coding sequence and which express the biologically active gene products may be identified by at least four general approaches; (a) DNA-DNA or DNA-RNA hybridization; (b) the presence or absence of "marker" gene functions; (c) assessing the level of transcription as measured by the expression of the respective mRNA transcripts in the host cell; and (d) detection of the gene product as measured by immunoassay or by its biological activity.

In the first approach, the presence of the coding sequence of the protein of interest and the coding sequence of the fusion polypeptide of the invention inserted in the expression vector can be detected by DNA-DNA or DNA-RNA hybridization using probes comprising nucleotide sequences that are homologous to the respective coding sequences, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the coding sequence of the protein of interest and the coding sequence of the fusion polypeptide of the invention are inserted within a marker gene sequence of the vector, recombinants containing the respective coding sequences can be identified by the absence of the marker gene function. Alternatively, a marker gene can be placed in tandem with the coding sequences under the control of the same or different promoter used to control the expression of the coding sequences. Expression of the marker in response to induction or selection indicates expression of the coding sequence of the protein of interest and the coding sequence of the fusion polypeptide.

In the third approach, transcriptional activity for the coding region of the protein of interest and the coding sequence of the fusion polypeptide of the invention can be assessed by hybridization assays. For example, RNA can be isolated and analyzed by Northern blot using a probe homologous to the coding sequences of the protein of interest and the coding sequence of the fusion polypeptide of the invention or particular portions thereof. Alternatively, total nucleic acids of the host cell may be extracted and assayed for hybridization to such probes.

In the fourth approach, the expression of the protein products of the protein of interest and the coding sequence of the fusion polypeptide having β(1,4)-N-acetylglucosaminyltransferase III (GnTIII) activity and comprising the Golgi localization domain of a heterologous Golgi resident polypeptide can be assessed immunologically, for example by Western blots, immunoassays such as radioimmuno-precipitation, enzyme-linked immunoassays and the like. The ultimate test of the success of the expression system, however, involves the detection of the biologically active gene products.

b. Generation and Use of Proteins and Protein Fragments Having Altered Glycosylation Patterns
i. Generation and Use of Antibodies Having Increased Effector Function Including Antibody-Dependent Cellular Cytotoxicity In preferred embodiments, the present invention provides glycoforms of antibodies and antibody fragments having increased Fc receptor binding and/or effector function including antibody-dependent cellular cytotoxicity.

Clinical trials of unconjugated monoclonal antibodies (mAbs) for the treatment of some types of cancer have recently yielded encouraging results. Dillman, *Cancer Biother. & Radiopharm.* 12:223-25 (1997); Deo et al., *Immunology Today* 18:127 (1997). A chimeric, unconjugated IgG1 has been approved for low-grade or follicular B-cell non-Hodgkin's lymphoma. Dillman, *Cancer Biother. & Radiopharm.* 12:223-25 (1997), while another unconjugated mAb, a humanized IgG1 targeting solid breast tumors, has also been showing promising results in phase III clinical trials. Deo et al., *Immunology Today* 18:127 (1997). The antigens of these two mAbs are highly expressed in their respective tumor cells and the antibodies mediate potent tumor destruction by effector cells in vitro and in vivo. In contrast, many other unconjugated mAbs with fine tumor specificities cannot trigger effector functions of sufficient potency to be clinically useful. Frost et al., *Cancer* 80:317-33 (1997); Surfus et al., *J. Immunother.* 19:184-91 (1996). For some of these weaker mAbs, adjunct cytokine therapy is currently being tested. Addition of cytokines can stimulate antibody-dependent cellular cytotoxicity (ADCC) by increasing the activity and number of circulating lymphocytes. Frost et al., *Cancer* 80:317-33 (1997); Surfus et al., *J. Immunother.* 19:184-91 (1996). ADCC, a lytic attack on antibody-targeted cells, is triggered upon binding of leukocyte receptors to the constant region (Fc) of antibodies. Deo et al., *Immunology Today* 18:127 (1997).

A different, but complementary, approach to increase ADCC activity of unconjugated IgG1s is to engineer the Fc region of the antibody. Protein engineering studies have shown that FcγRs interact with the lower hinge region of the IgG CH2 domain. Lund et al., *J. Immunol.* 157:4963-69 (1996). However, FcγR binding also requires the presence of oligosaccharides covalently attached at the conserved Asn 297 in the CH2 region. Lund et al., *J. Immunol.* 157:4963-69 (1996); Wright and Morrison, *Trends Biotech.* 15:26-31 (1997), suggesting that either oligosaccharide and polypeptide both directly contribute to the interaction site or that the oligosaccharide is required to maintain an active CH2 polypeptide conformation. Modification of the oligosaccharide structure can therefore be explored as a means to increase the affinity of the interaction.

An IgG molecule carries two N-linked oligosaccharides in its Fc region, one on each heavy chain. As any glycoprotein, an antibody is produced as a population of glycoforms which share the same polypeptide backbone but have different oligosaccharides attached to the glycosylation sites. The oligosaccharides normally found in the Fc region of serum IgG are of complex bi-antennary type (Wormald et al., *Biochemistry* 36:130-38 (1997), with low level of terminal sialic acid and bisecting N-acetylglucosamine (GlcNAc), and a variable degree of terminal galactosylation and core fucosylation. Some studies suggest that the minimal carbohydrate structure required for FcγR binding lies within the oligosaccharide core. Lund et al., *J. Immunol.* 157:4963-69 (1996)

The mouse- or hamster-derived cell lines used in industry and academia for production of unconjugated therapeutic mAbs normally attach the required oligosaccharide determinants to Fc sites. IgGs expressed in these cell lines lack, however, the bisecting GlcNAc found in low amounts in serum IgGs. Lifely et al., *Glycobiology* 318:813-22 (1995). In contrast, it was recently observed that a rat myeloma-produced, humanized IgG1 (CAMPATH-1H) carried a bisecting GlcNAc in some of its glycoforms. Lifely et al., *Glycobiology* 318:813-22 (1995). The rat cell-derived antibody reached a similar maximal in vitro ADCC activity as CAMPATH-1H antibodies produced in standard cell lines, but at significantly lower antibody concentrations.

The CAMPATH antigen is normally present at high levels on lymphoma cells, and this chimeric mAb has high ADCC activity in the absence of a bisecting GlcNAc. Lifely et al., *Glycobiology* 318:813-22 (1995). In the N-linked glycosylation pathway, a bisecting GlcNAc is added by the enzyme β(1,4)-N-acetylglucosaminyltransferase III (GnT III). Schachter, *Biochem. Cell Biol.* 64:163-81 (1986).

Previous studies used a single antibody-producing CHO cell line, that was previously engineered to express, in an externally-regulated fashion, different levels of a cloned GnT III gene enzyme (Umana, P., et al., *Nature Biotechnol.* 17:176-180 (1999)). This approach established for the first time a rigorous correlation between expression of GnTIII and the ADCC activity of the modified antibody.

Further antibodies of the invention having increased Fc receptor binding affinity and increased effector function include, but are not limited to, anti-human neuroblastoma monoclonal antibody (chCE7) produced by the methods of the invention, a chimeric anti-human renal cell carcinoma monoclonal antibody (ch-G250) produced by the methods of the invention, a humanized anti-HER2 monoclonal antibody (e.g., Trastuzumab (HERCEPTIN)) produced by the methods of the invention, a chimeric anti-human colon, lung, and breast carcinoma monoclonal antibody (ING-1) produced by the methods of the invention, a humanized anti-human 17-1A antigen monoclonal antibody (3622W94) produced by the methods of the invention, a humanized anti-human colorectal tumor antibody (A33) produced by the methods of the invention, an anti-human melanoma antibody (R24) directed against GD3 ganglioside produced by the methods of the invention, and a chimeric anti-human squamous-cell carcinoma monoclonal antibody (SF-25) produced by the methods of the invention, an anti-human small cell lung carcinoma monoclonal antibody (BEC2, ImClone Systems, Merck KgaA) produced by the methods of the invention, an anti-human non-Hodgkin's lymphoma monoclonal antibody (Bexxar (tositumomab, Coulter Pharmaceuticals), Oncolym (Techniclone, Alpha Therapeutic)) produced by the methods of the invention, an anti-human squamous cell head and neck carcinoma monoclonal antibody (C225, ImClone Systems) prepared by the methods of the invention, an anti-human rectal and colon carcinoma monoclonal antibody (Panorex (edrecolomab), Centocor, Glaxo Wellcome) prepared by the methods of the invention, an anti-human ovarian carcinoma monoclonal antibody (Theragyn, Antisoma) produced by the methods of the invention, an anti-human acute myelogenous leukemia carcinoma monoclonal antibody (SmartM195, Protein Design Labs, Kanebo) produced by the methods of the invention, an anti-human malignant glioma monoclonal antibody (Cotara, Techniclone, Cambridge Antibody Technology) produced by the methods of the invention, an anti-human B cell non-Hodgkins lymphoma monoclonal antibody (IDEC-Y2B8, IDEC Pharmaceuticals) produced by the methods of the invention, an anti-human solid tumors monoclonal antibody (CEA-Cide, Immunomedics) produced by the methods of the invention, an anti-human colorectal carcinoma monoclonal antibody (Iodine 131-MN-14, Immunomedics) produced by the methods of the invention, an anti-human ovary, kidney, breast, and prostate carcinoma monoclonal antibody (MDX-210, Medarex, Novartis) produced by the methods of the invention, an anti-human colorectal and pancreas carcinoma monoclonal antibody (TTMA, Pharmacie & Upjohn) produced by the methods of the invention, an anti-human TAG-72 expressing carcinoma monoclonal antibody (MDX-220, Medarex) produced by the methods of the invention, an anti-human EGFr-expressing carcinoma monoclonal antibody (MDX-447) produced by the methods of the invention, Anti-VEGF monoclonal antibody (Genentech) produced by the methods of the invention, an anti-human breast, lung, prostate and pancreas carcinoma and malignant melanoma monoclonal antibody (BrevaRex, AltaRex) produced by the methods of the invention, and an anti-human acute myelogenous leukemia monoclonal antibody (Monoclonal Antibody Conjugate, Immunex) produced by the methods of the invention. In addition, the invention is directed to antibody fragment and fusion proteins comprising a region that is equivalent to the Fc region of immunoglobulins.

ii. Generation and Use of Fusion Proteins Comprising a Region Equivalent to an Fc Region of an Immunoglobulin that Promote Fc-Mediated Cytotoxicity As discussed above, the present invention relates to a method for increasing the Fc receptor binding affinity and/or effector function of therapeutic antibodies. This is achieved by engineering the glycosylation pattern of the Fc region of such antibodies, in particular by engineering the antibody-producing cells to produce a polypeptide with, e.g., GnTIII activity or Gal T activity, or ManII activity, that modifies the oligosaccharides attached to the Fc region of such antibodies. This strategy can be applied to increase Fc-mediated cellular cytotoxicity against undesirable cells mediated by any molecule carrying a region that is an equivalent to the Fc region of an immunoglobulin, not only by therapeutic antibodies, since the changes introduced by the engineering of glycosylation affect only the Fc region and therefore its interactions with the Fc receptors on the surface of effector cells involved in the ADCC mechanism. Fc-containing molecules to which the presently disclosed methods can be applied include, but are not limited to, (a) soluble fusion proteins made of a targeting protein domain fused to the N-terminus of an Fc-region (Chamov and Ashkenazi, *Trends Biotech*. 14: 52 (1996) and (b) plasma membrane-anchored fusion proteins made of a type II transmembrane domain that localizes to the plasma membrane fused to the N-terminus of an Fc region (Stabila, P. F., *Nature Biotech*. 16: 1357 (1998)).

In the case of soluble fusion proteins (a) the targeting domain directs binding of the fusion protein to undesirable cells such as cancer cells, i.e., in an analogous fashion to therapeutic antibodies. The application of presently disclosed method to enhance the effector function, including Fc-mediated cellular cytotoxic activity, mediated by these molecules would therefore be identical to the method applied to therapeutic antibodies.

In the case of membrane-anchored fusion proteins (b) the undesirable cells in the body have to express the gene encoding the fusion protein. This can be achieved either by gene therapy approaches, i.e., by transfecting the cells in vivo with a plasmid or viral vector that directs expression of the fusion protein-encoding gene to undesirable cells, or by implantation in the body of cells genetically engineered to express the fusion protein on their surface. The later cells would normally be implanted in the body inside a polymer capsule (encapsulated cell therapy) where they cannot be destroyed by an Fc-mediated cellular cytotoxicity mechanism. However should the capsule device fail and the escaping cells become undesirable, then they can be eliminated by Fc-mediated cellular cytotoxicity. Stabila et al., *Nature Biotech*. 16: 1357 (1998). In this case, the presently disclosed method would be applied either by incorporating into the gene therapy vector an additional gene expression cassette directing adequate or maximal expression levels of the fusion polypeptide of the invention or by engineering the cells to be implanted to express adequate or maximal levels of the fusion polypeptide of the invention.

Therapeutic Applications of Antibodies, Antibody Fragments, and Fusion Polypeptides Produced According to the Methods of the Invention.

The antibodies (i.e., the antibodies, antibody fragments, and fusion proteins comprising a region equivalent to the Fc region of an immunoglobulin) of the present invention can be used alone to target and kill tumor cells in vivo. The antibodies can also be used in conjunction with an appropriate therapeutic agent to treat human carcinoma. For example, the antibodies can be used in combination with standard or conventional treatment methods such as chemotherapy, radiation therapy or can be conjugated or linked to a therapeutic drug, or toxin, as well as to a lymphokine or a tumor-inhibitory growth factor, for delivery of the therapeutic agent to the site of the carcinoma.

Techniques for conjugating such therapeutic agents to antibodies are well known [see, e.g., Arnon et al., "Monoclonal Antibodies for Immunotargeting of Drugs in Cancer Therapy", in *Monoclonal Antibodies and Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); and Thorpe et al., "The Preparation And Cytotoxic Properties Of Antibody-Toxin Conjugates", Immunol. Rev., 62:119-58 (1982)].

Alternatively, a glycoengineered antibody can be coupled to high-energy radiation, e.g., a radioisotope such as <131>I, which, when localized at the tumor site, results in a killing of several cell diameters [see, e.g., Order, "Analysis, Results, and Future Prospective of The Therapeutic Use of Radiolabeled Antibody in Cancer Therapy", in *Monoclonal Antibodies For Cancer Detection And Therapy*, Baldwin et al. (eds.), pp. 303-16 (Academic Press 1985)]. According to yet another embodiment, the antibodies of the invention can be conjugated to a second antibody to form an antibody heteroconjugate for the treatment of tumor cells as described by Segal in U.S. Pat. No. 4,676,980.

Still other therapeutic applications for the antibodies of the invention include conjugation or linkage, e.g., by recombinant DNA techniques, to an enzyme capable of converting a prodrug into a cytotoxic drug and the use of that antibody-enzyme conjugate in combination with the prodrug to convert the prodrug to a cytotoxic agent at the tumor site [see, e.g., Senter et al., "Anti-Tumor Effects of Antibody-alkaline Phosphatase", *Proc. Natl. Acad. Sci. USA* 85:4842-46 (1988); "Enhancement of the in vitro and in vivo Antitumor Activities of Phosphorylated Mitocycin C and Etoposide Derivatives by Monoclonal Antibody-Alkaline Phosphatase Conjugates", Cancer Research 49:5789-5792 (1989); and Senter, "Activation of Prodrugs by Antibody-Enzyme Conjugates: A New Approach to Cancer Therapy," *FASEB J.* 4:188-193 (1990)].

Still another therapeutic use for the antibodies of the invention involves use, either in the presence of complement or as part of an antibody-drug or antibody-toxin conjugate, to remove tumor cells from the bone marrow of cancer patients. According to this approach, autologous bone marrow may be purged ex vivo by treatment with the antibody and the marrow infused back into the patient [see, e.g., Ramsay et al., "Bone Marrow Purging Using Monoclonal Antibodies", J. Clin. Immunol., 8(2):81-88 (1988)].

Furthermore, chimeric antibodies, recombinant immunotoxins and other recombinant constructs of the invention containing the specificity of the antigen-binding region of the desired monoclonal antibody may be used therapeutically. For example, the single-chain immunotoxins of the invention, may be used to treat human carcinoma in vivo.

Similarly, a fusion protein comprising at least the antigen-binding region of an antibody of the invention joined to at least a functionally active portion of a second protein having anti-tumor activity, e.g., a lymphokine or oncostatin can be used to treat human carcinoma in vivo. Furthermore, recombinant techniques known in the art can be used to construct bispecific antibodies wherein one of the binding specificities of the antibody is directed to a tumor-associated antigen, while the other binding specificity of the antibody is that of a molecule other than said tumor-associated antigen.

The present invention provides a method for selectively killing tumor cells expressing an antigen that specifically binds to the monoclonal antibody of the present invention or functional equivalent. This method comprises reacting the glycoengineered antibodies of the present invention or immunoconjugates (e.g. the immunotoxin) comprising same with said tumor cells. These tumor cells may be from a human carcinoma.

Additionally, this invention provides a method of treating carcinomas (for example human carcinomas) in vivo. This method comprises administering to a subject a pharmaceutically effective amount of a composition containing at least one of the glycoengineered antibodies of the invention or an immunoconjugates (e.g. the immunotoxin) comprising same.

In a further aspect, the invention is directed to an improved method for treating an autoimmune disease produced in whole or in part by pathogenic autoantibodies based on B-cell depletion comprising administering a therapeutically effective amount of immunologically active antibody to a human subject in need thereof, the improvement comprising administering a therapeutically effective amount of an antibody having increased ADCC prepared in accordance with the methods of the invention. In a preferred embodiment, the antibody is an anti-CD20 antibody. Examples of autoimmune diseases or disorders include, but are not limited to, immune-mediated thrombocytopenias, such as acute idiopathic thrombocytopenic purpurea and chronic idiopathic thrombocytopenic purpurea, dermatomyositis, Sydenham's chorea, lupus nephritis, rheumatic fever, polyglandular syndromes, Henoch-Schonlein purpura, post-streptococcal nephritis, erythema nodosum, Takayasu's arteritis, Addison's disease, erythema multiforme, polyarteritis nodosa, ankylosing spondylitis, Goodpasture's syndrome, thromboangitis ubiterans, primary biliary cirrhosis, Hashimoto's thyroiditis, thyrotoxicosis, chronic active hepatitis, polymyositis/dermatomyositis, polychondritis, pamphigus vulgaris, Wegener's granulomatosis, membranous nephropathy, amyotrophic lateral sclerosis, tabes dorsalis, polymyaglia, pernicious anemia, rapidly progressive glomerulonephritis and fibrosing alveolitis, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type 1 diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious amenia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc. In this aspect of the invention, the antibodies of the invention are used to deplete the blood of normal B-cells for an extended period.

In accordance with the practice of this invention, the subject may be a human, equine, porcine, bovine, murine, canine, feline, and avian subjects. Other warm blooded animals are also included in this invention.

The present invention also provides a method for treating a subject suffering from a cancer. The subject may be a human, dog, cat, mouse, rat, rabbit, horse, goat, sheep, cow, chicken. The cancer may be identified as a breast, bladder, retinoblastoma, papillary cystadenocarcinoma of the ovary, Wilm's tumor, or small cell lung carcinoma and is generally characterized as a group of cells having tumor associated antigens on the cell surface. This method comprises administering to the subject a cancer killing amount of a tumor targeted antibody joined to a cytotoxic agent. Generally, the joining of the tumor targeted antibody with the cytotoxic agent is made under conditions which permit the antibody so joined to bind its target on the cell surface. By binding its target, the tumor targeted antibody acts directly or indirectly to cause or contribute to the killing of the cells so bound thereby curing the subject.

Also provided is a method of inhibiting the proliferation of mammalian tumor cells which comprises contacting the mammalian tumor cells with a sufficient concentration of the glycoengineered antibodies of the invention or an immunoconjugate comprising same so as to inhibit proliferation of the mammalian tumor cells.

The subject invention further provides methods for inhibiting the growth of human tumor cells, treating a tumor in a subject, and treating a proliferative type disease in a subject. These methods comprise administering to the subject an effective amount of the composition of the invention.

It is apparent therefore that the present invention encompasses pharmaceutical compositions, combinations and methods for treating human carcinomas. For example, the invention includes pharmaceutical compositions for use in the treatment of human carcinomas comprising a pharmaceutically effective amount of an antibody of the present invention and a pharmaceutically acceptable carrier.

The compositions may contain the antibody or antibody fragments, either unmodified, conjugated to a therapeutic agent (e.g., drug, toxin, enzyme or second antibody) or in a recombinant form (e.g., chimeric antibodies, fragments of chimeric antibodies, bispecific antibodies). The compositions may additionally include other antibodies or conjugates for treating carcinomas (e.g., an antibody cocktail).

The antibody, antibody conjugate and immunotoxin compositions of the invention can be administered using conventional modes of administration including, but not limited to, intravenous, intraperitoneal, oral, intralymphatic or administration directly into the tumor. Intravenous administration is preferred.

The compositions of the invention may be in a variety of dosage forms which include, but are not limited to, liquid solutions or suspension, tablets, pills, powders, suppositories, polymeric microcapsules or microvesicles, liposomes, and injectable or infusible solutions. The preferred form depends upon the mode of administration and the therapeutic application.

The compositions of the invention also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment and the judgment of the treating physician. Accordingly, the dosages of the compositions should be titrated to the individual patient. Nevertheless, an effective dose of the compositions of this invention may be in the range of from about 1 to about 2000 mg/kg.

The molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the molecules of the present invention depends upon the location of the tumor being treated, the severity and course of the cancer, the subject's health and response to treatment and the judgment of the treating physician. Accordingly, the dosages of the molecules should be titrated to the individual subject.

The interrelationship of dosages for animals of various sizes and species and humans based on mg/kg of surface area is described by Freireich, E. J., et al. Cancer Chemother., Rep. 50 (4): 219-244 (1966). Adjustments in the dosage regimen may be made to optimize the tumor cell growth inhibiting and killing response, e.g., doses may be divided and administered on a daily basis or the dose reduced proportionally depending upon the situation (e.g., several divided doses may be administered daily or proportionally reduced depending on the specific therapeutic situation).

It would be clear that the dose of the composition of the invention required to achieve cures may be further reduced with schedule optimization.

In accordance with the practice of the invention, the pharmaceutical carrier may be a lipid carrier. The lipid carrier may be a phospholipid. Further, the lipid carrier may be a fatty acid. Also, the lipid carrier may be a detergent. As used herein, a detergent is any substance that alters the surface tension of a liquid, generally lowering it.

In one example of the invention, the detergent may be a nonionic detergent. Examples of nonionic detergents include, but are not limited to, polysorbate 80 (also known as Tween 80 or (polyoxyethylenesorbitan monooleate), Brij, and Triton (for example Triton WR-1339 and Triton A-20).

Alternatively, the detergent may be an ionic detergent. An example of an ionic detergent includes, but is not limited to, alkyltrimethylammonium bromide.

Additionally, in accordance with the invention, the lipid carrier may be a liposome. As used in this application, a "liposome" is any membrane bound vesicle which contains any molecules of the invention or combinations thereof.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

Example 1

Materials and Methods

1. Construction of Antibody Expression Vectors.
Anti-CD20 Antibody Expression Vector pETR1502

The C2B8 anti-CD20 antibody expression vector, pETR1502, consists of four independent, separate expression cassettes (one for the C2B8 antibody light chain, one for the C2B8 antibody heavy chain, one for the neomycin resistance gene and one for the murine dhfr gene). All genes are under control of the promoter of the myeloproliferative sarcoma virus (MPSV) and contain a synthetic consensus polyadenylation signal derived from the polyadenylation signal of the rabbit β-globin gene.

CDNAs encoding the variable heavy (VH) and variable light (VL) chain regions of the anti-CD20 antibody C2B8 were assembled from a set of overlapping single-stranded oligonucleotides in a one-step process using PCR (Kobayashi, N., et al., *Biotechniques* 23:500-503(1997)). The original sequence coding for C2B8 VL and VH regions were obtained from a published international patent application (International Publication Number: WO 94/11026). Assembled VL and VH cDNA fragments were subcloned into pBluescriptIIKS(+) to give pBlue-C2B8VH and pBlue-C2B8VL plasmids and sequenced.

The variable chains of C2B8 were amplified from the corresponding pBlue-C2B8VH and pBlue-C2B8VL plasmids using primers that introduce an AscI restriction site at the 5' end and appropriate restriction sites at the junction of the variable to constant region (BsiWI for the light chain and NheI for the heavy chain). The IgGI constant regions were amplified from a human leukocyte cDNA library (Quickclone, Clontech) using primers that introduce suitable restriction sites at the 5' and 3' ends (BsiWI and BamHI for the constant light chain and NheI and BamHI for the constant heavy chain).

After confirmation of the correct DNA sequences, the C2B8 antibody light and heavy chains were each combined with the MPSV promoter and polyadenylation signals. In a first step, two different expression vectors were constructed: one for the C2B8 light chain (pETR1315) and another for the C2B8 heavy chain (pETR1316). In a second step, a neomycin resistance expression cassette (neomycin resistance gene derived from Tn5 transposon and put under control of the minimal MPSV promoter) was introduced into the vector pETR1315 resulting in the plasmid pETR1481. A dhfr gene expression cassette under control of the MPSV promoter was inserted into the vector pETR1316 to give the plasmid pETR1328. In a final step, both expression modules (C2B8-light chain+neo and C2B8-heavy chain+dhfr) were combined in one vector resulting in the plasmid pETR1502.

Anti-CD20 Antibody Expression Vector pETR1520 pETR1520 combines a C2B8 anti-CD20 antibody expression vector with an origin of replication from the Epstein Barr virus (oriP) for episomal vector replication and maintenance in cells producing the Epstein Barr virus nuclear antigen (EBNA). For construction of the C2B8 expression vector, pETR1520, the C2B8 expression module from pETR1416 was inserted as a HinDIII fragment into oriP-containing vector pETR1507. The vector pETR1416 is similar to pETR1502 with the exception that in this plasmid the neomycin resistance gene is under control of the full, instead of the minimal, MPSV promoter.

Anti-Fibronectin Antibody Expression Vector pETR1546

This vector is the same as vector pETR1520, except that the variable heavy and light chain coding regions of the C2B8 anti-CD20 antibody have been replaced by the respective coding regions of antibody L19, a human antibody recognizing the ED-B domain of fibronectin. The variable region-encoding DNA fragments were synthesized by overlap extension PCR method using synthetic oligonucleotides based on the sequence of the variable regions of the L19 antibody (Pini, A. et al. *J. Biol. Chem.* 273(34):21769-76 (1998)).

Anti-EGFR Antibody (C225) Expression Vector pURSI28

Figure 16:
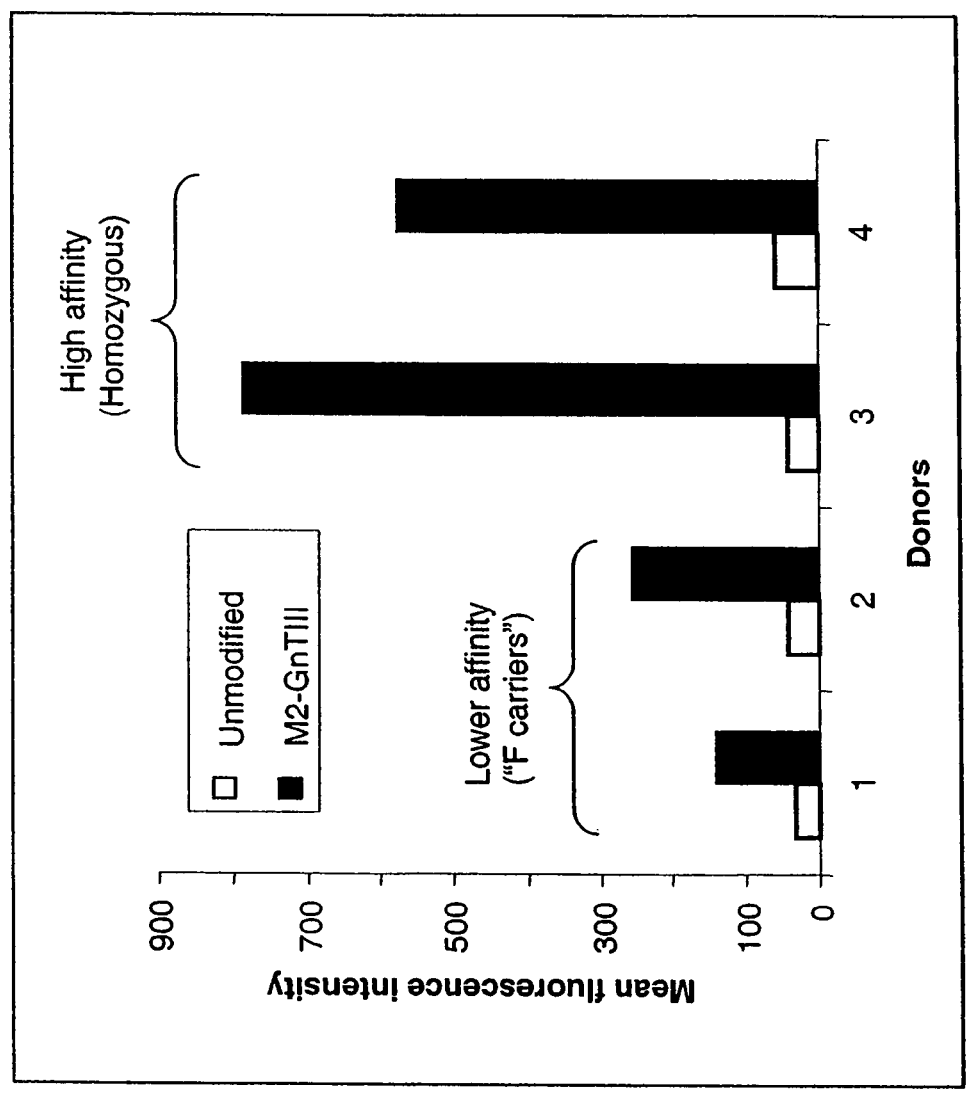
FIG. 16. Binding of "M2-GnTIII"-glycoengineered vs. unmodified recombinant, anti-CD20 chimeric IgG1 antibodies to FcgammaRIIIa receptor on NK cells from different donors. Both antibodies were produced in HEK293-EBNA cells. Production and glycosylation profile of the glycoenginereed antibody is depicted in FIG. 6 and those of the unmodified antibody in FIG. 5. The binding assay was performed as described in the Materials and Methods section of Example 1. Human NK cells expressing FcgammaRIIIa receptor on their surface were isolated from donors of a genotype known not to produce FcgammaRIIc receptor (i.e., homozygous for a gene variant that contains an in-frame stop codon within the FcgammaRIIc coding sequence). Two donors were genotyped as homozygous for the 158V-"higher-affinity" variant of the FcgammaRIIIa receptor. The other two donors were genotyped as 158V/F heterozygous for the 158V-"higher-affinity" and 158F-"lower-affinity" variants of the FcgammaRIIIa receptor. Geometric mean fluorescence intensity, measured by FACS using an FITC-labelled anti-human IgG antibody fragment, increases with the amount of recombinant antibody bound to the NK cells. Binding detected in this assay is FcgammaRIIIa-specific as demonstrated by use of a competing FcgammaRIIIa-specific antibody fragment (see FIG. 13).
Figure 17:
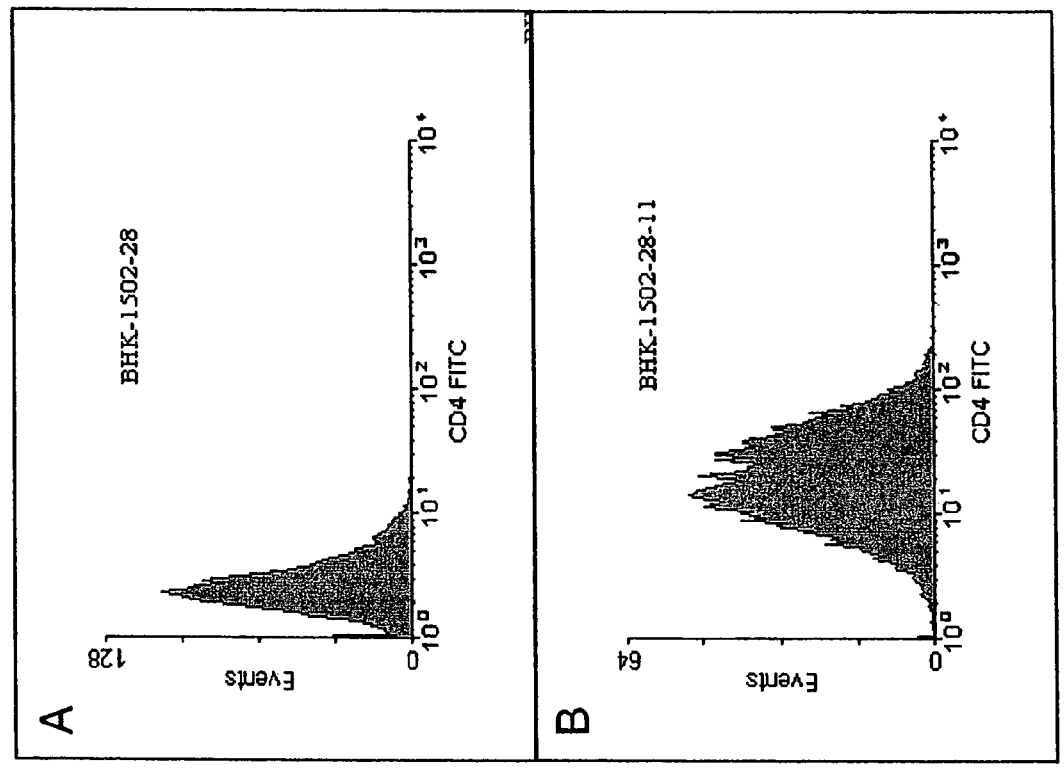
FIG. 17. FACS analysis of truncated-CD4 (tCD4) expression of (a) BHK-1502-28 (wild type) and, (b) clone BHK-1502-28-11 (M2-GnTIII-glycoengineered) stable, chimeric anti-CD20 IgG1 antibody-producing cell lines. Expression of tCD4 is operably-linked to M2-GnTIII expression via an IRES element in pETR1537 GnTIII expression vector and is therefore used as an indirect marker for GnTIII expression. Mean and geometric mean fluorescence intensities were, respectively, 27.6 and 19.9 for the glycoengineered and 4.7 and 4.1 for the wild type cell lines.

This vector is the same as vector pETR1520, except that the variable heavy and light chain coding regions of the C2B8 anti-CD20 antibody have been replaced by the respective coding regions of the antibody C225, a chimeric antibody recognizing the human epidermal growth factor receptor. The variable region-encoding DNA fragments were synthesized by overlap extension PCR method using synthetic oligonucleotides based on the sequence of the variable regions of the C225 antibody (sequences can be found in a published patent application with international publication number WO 96/40210, FIGS. 16 and 17 of that patent application for the heavy and light chains, respectively).

2. Construction of GnTIII-Fusion Expression Vectors pETR1166. Vector for Constitutive Expression of GnTIII For construction of the GnTIII expression vector pETR1166, rat GnTIII was amplified from a rat kidney cDNA library (Clontech) by PCR. A C-terminal c-myc-epitope tag was added immediately upstream of the stop codon of the gene (amino acid sequence: PEQKLISEEDL) for later, convenient detection of GnTIII by Western Blots. After confirmation of the correct sequence of GnTIII the gene was inserted under control of the MPSV promoter and a synthetic rabbit beta-globin polyadenylation signal was added. The final GnTIII expression vector also contained a separate puromycin resistance cassette for selection, with the puromycin resistance gene also under the control of the MPSV promoter and synthetic rabbit beta-globin polyadenylation signal.

pETR1425: Replacement of the First 76 Amino Acids of GnTIII by the First 102 Amino Acids of the Human GnTI.

The construction of this hybrid glycosyltransferase gene was performed by subsequent overlapping PCR reactions. In one reaction, the stem region of human GnTI was amplified using the primers GAB-179 and GAB-180. During this PCR reaction a Kozak consensus sequence and an AscI restriction site were also introduced at the 5' end. The resulting PCR fragment has a 23 bp overlap with GnTIII starting at position 229. In a second PCR reaction, the GnTIII region from position 229 to 380 was amplified with the primers GAB-177 and GAB-178 generating a PCR fragment with a unique BstXI site at the 3' end and an 22 bp overlap with the GnTI stem region at the 5' end. Both PCR fragments were purified and used as templates in a third PCR reaction (primers GAB-179 and GAB-178). The resulting fragment was purified and digested with AscI and ligated to the vector pETR1001 (cut with AscI and SmaI) resulting in the plasmid pETR1404. After the sequence of the insert has been confirmed the MPSV promoter element was added to pETR1404 as an AscI (partial digestion)/PmeI fragment yielding in the plasmid pETR1423. The SphI/BstXI fragment from pETR1166, an expression vector carrying the original rat GnTIII gene, was then replaced by the corresponding fragment of pETR1423 resulting in the plasmid pETR1425 containing the GnTI-GnTIII fusion under control of the MPSV promoter and a puromycin resistance cassette for selection.

```
Primer sequences:
GAB-177:
GCGTGTGCCTGTGACCCCCGCGCCCCTGCTCCAGCCACTGTCCCC

GAB-178:
GAAGGTTTCTCCAGCATCCTGGTACC

GAB-179:
CTGAGGCGCGCCGCCACCATGCTGAAGAAGCAGTCTGCAGGGC

GAB-180:
GGGGACAGTGGCTGGAGCAGGGGCGCGGGGGTCACAGGCACACGCGGC
``` pETR1506: Replacement of the 76 N-terminal Amino Acids of GnTIII by the First 100 Amino Acids of Human Mannosidase II.

The construction of pETR1506 was performed analogously to the construction of pETR1425. The stem region of the human mannosidase II gene was amplified with the primers GAB-252 and GAB-253 using the vector pBlue-man as a template. During this PCR a FseI site and a Kozak consensus sequence were introduced at the 5' end. The resulting PCR fragment overlaps the GnTIII gene starting at position 229 by 23 bp. In a second PCR reaction a part of the GnTIII gene (position 229-460) was amplified with the primers GAB-254 and GAB-255. This PCR reaction generated a fragment containing a 43 bp overlap with the mannosidase II gene at the 5' end and a unique StuI site at the 3' end. Both fragments were purified and used as templates in a third PCR with the primers GAB-252 and GAB-255. The resulting fragment was inserted into pIC19H giving the vector pETR1484. After the correct sequence of the insert has been confirmed the complete fusion gene was constructed by ligating the FseI/StuI fragment of pETR1484 with the StuI/BamHI fragment from pETR1166 in the vector pETR12177 (FseI/BamHI). The resulting plasmid (pETR1500) contained the hybrid manII-GnTIII gene (SEQ ID NO: 14) under control of the MPSV promoter. For selection of the plasmid in mammalian cells a puromycin resistance cassette was inserted as a SpeI fragment from pETR1166, yielding the plasmid pETR1506.

```
Primer sequences:
GAB-252:
GCTAGGCCGGCCGCCACCATGAAGTTAAGCCGCCAGTTCACCGTGTTCGG

GAB-253:
GGGGACAGTGGCTGGAGCAGGGGTGAGCCAGCACCTTGGCTGAAATTGCT

TTGTGAACTTTTCGG

GAB-254:
TCCGAAAAGTTCACAAAGCAATTTCAGCCAAGGTGCTGGCTCACCCCTGC

TCCAGCCACTGTCCCC

GAB-255:
ATGCCGCATAGGCCTCCGAGCAGGACCCC
``` pETR1519: Combination of the Hybrid manII-GnTIII Fusion Gene with the Replication Origin oriP from Epstein Barr Virus.

Using the primers GAB-261 and GAB-262 a 2 kb fragment containing oriP was amplified from the plasmid pCEP4 (Invitrogen). During this PCR reaction at both ends of the fragment SspI and EcoRI sites were introduced. For sequencing, the oriP fragment was inserted into the vector pIC19H. After the correct sequence has been confirmed oriP was inserted as a SspI fragment into the vector pETR1001 (digested with BsmBI and 5' overlapping ends filled in using Klenow polymerase). The resulting plasmid was designated pETR1507. A SphI/NruI manII-GnTIII expression cassette from pETR1510 was inserted into pETR1507 digested with the same restriction endonucleases giving the plasmid pETR1519.

```
Primer sequences:
GAB-261:
GCTAAATATTGAATTCCCTTTATGTGTAACTCTTGGCTGAAGC

GAB-262:
TAGCAATATTGAATTCGCAGGAAAAGGACAAGCAGCGAAAATTCACGC
``` pETR1537: Combination of the Hybrid manII-GnTIII Fusion Gene and a Truncated CD4 Cell-Surface Marker Gene The pETR1506 expression vector was modified for additional expression of a truncated CD4 cell-surface marker gene. Briefly, the hybrid manII-GnTIII fusion gene expression cassette was converted from a monocistronic to a bicistronic expression cassette by inserting, downstream of the stop codon of the manII-GnTIII fusion, a polio virus IRES element followed by a cDNA encoding a truncated human CD4 protein (comprising the human CD4 leader sequence for secretion followed by the transmembrane and extracellular domains).

3. Transfection of Mammalian Cells with GnTIII-Fusion- and Antibody-Expression Vectors Transfection of BHK Cells Exponentially growing cells (viability 90-95%) were seeded in the appropriate number of T75 flasks at a concentration of $0.9 \times 10^6$ cells/ml 24 h prior to electroporation. As culture medium, Invitrus (Cell Culture Technologies, Switzerland) supplemented with 10% fetal calf serum (FCS) was used. Cells were counted prior to electroporation. $8 \times 10^6$ cells were harvested by centrifugation (5 min, 200×g) and the supernatant was discarded. The cells were resuspended in 800 µl Invitrus medium and were transferred to a sterile electroporation cuvette (0.4 cm gap) already containing 8 µg circular plasmid DNA and incubated for 5 min at room temperature. The cells were electroporated using a Gene Pulser II (Bio-Rad) with the following conditions: 400 V, 960 µF with two pulses in a 30 sec interval. After the electroporation the cells were immediately transferred into a T25 flask containing 5 ml of outgrow medium (Invitrus/20% (V/V) FCS/1.25% (V/V) DMSO) and were incubated at 37° C. in a 5% $CO_2$-atmosphere incubator. For production of unmodified (non-glycoengineered) antibodies, the cells were transfected only with antibody expression vectors. For the production of the glycoengineered antibodies, the cells were co-transfected with two plasmids, one for antibody expression and the other of fusion GnTIII polypeptide (SEQ ID NO: 15) expression, at a ratio of 3:1, respectively.

Transfection of HEK293-EBNA Cells

Exponentially growing HEK293-EBNA cells were transfected by the calcium phosphate method. Cells were grown as adherent monolayer cultures in T flasks using DMEM culture medium supplemented with 10% FCS, and were transfected when they were between 50 and 80% confluent. For the transfection of a T75 flask, 8 million cells were seeded 24 hours before transfection in 14 ml DMEM culture medium supplemented with FCS (at 10% V/V final), 250 µg/ml neomycin, and cells were placed at 37° C. in an incubator with a 5% $CO_2$ atmosphere overnight. For each T75 flask to be transfected, a solution of DNA, $CaCl_2$ and water was prepared by mixing 47 µg total plasmid vector DNA, 235 µl of a 1M $CaCl_2$ solution, and adding water to a final volume of 469 µl. To this solution, 469 µl of a 50 mM HEPES, 280 mM NaCl, 1.5 mM $Na_2HPO_4$ solution at pH 7.05 was added, mixed immediately for 10 sec and left to stand at room temperature for 20 sec. The suspension was diluted with 12 ml of DMEM supplemented with 2% FCS, and added to the T75 in place of the existing medium. The cells were incubated at 37° C., 5% $CO_2$ for about 17 to 20 hours, then medium was replaced with 12 ml DMEM, 10% FCS. For production of unmodified (non-glycoengineered) antibodies, the cells were transfected only with antibody expression vectors. For the production of the glycoengineered antibodies, the cells were co-transfected with two plasmids, one for antibody expression and the other of fusion GnTIII polypeptide expression, at a ratio of 4:1, respectively. At day 5 post-transfection, supernatant was harvested, centrifuged for 5 min at 1200 rpm, followed by a second centrifugation for 10 min at 4000 rpm and kept at 4° C.

Generation of a Stable Mammalian Cell Line Expressing a Recombinant Anti-CD20 Antibody BHK cells (BHK21-13c) were transfected by electroporation with pETR1502 C2B8 antibody-expression vector, which contains a neomycin-resistance gene expression cassette. Neomycin-resistant clones were first selected to obtain a set of clones that had chromosomally integrated the pETR1502 vector DNA. Clones were then screened for recombinant antibody production using an ELISA assay. Briefly, 24 hours post electroporation, viable cells were counted and the transfection efficiency was determined by counting fluorescent cells of a parallel, control electroporation done with a pEYFP-expression vector. Cells were diluted in Invitrus selection medium containing 10% FCS and 1 mg/ml of neomycin. Usually eight 96-well plates were seeded with different concentrations of viable, transfected cells ($1 \times 10^3$, $5 \times 10^2$ and $1 \times 10^2$ cells per well) and incubated at 37° C. until clones could be identified. Once the clones had grown to almost confluent, the supernatants were analysed by ELISA for antibody production. ELISA positive clones were expanded first to 24-well and subsequently to 6-well plates, and then to T25 flasks. After five days of growth in T25 flasks, the final antibody titer was determined using an ELISA assay. Using this electroporation and selection procedure a C2B8 anti-CD20 antibody-expressing BHK cell clone (BHK-1502-28) was isolated that produced 13 μg/ml of antibody under the above culture conditions.

Generation of a Stable Mammalian Cell Line Expressing a Recombinant Anti-CD20 Antibody and a GnTIII-Fusion The clone BHK-1502-28, constitutively expressing anti-CD20 monoclonal antibody genes and the neomycin resistance gene, was transfected with the pETR1537 expression vector by electroporation. pETR1537 is a vector for constitutive expression of the ManII-GntIII gene and a truncated form of human CD4, the later IRES-dependently expressed. The vector also contains a puromycin-resistance gene expression cassette. Puromycin-resistant clones were first selected to obtain a set of clones that had chromosomally integrated the pETR1537 vector DNA. Clones were then screened for surface expression of truncated CD4 (tCD4), which serves as a marker for expression level of the bicistronic ManII-GnTIII+tCD4 gene expression unit. Recombinant antibody production of the selected clones was verified using an ELISA assay.

Briefly, pETR1537 vector DNA was linearized with XmnI. A control transfection with a EYFP expression vector was performed in parallel. Transfection efficiency was determined after 24 hours by counting cells expressing EYFP over total cells. 58% of all cells were expressing EYFP. Cell viability was of 91%. One day after transfection, cells transfected with pETR1537 or pEYFP were serially diluted at 1:100, 1:500, 1:1000 and 1:5000 dilutions and seeded in 96-well plates, in a final volume of 0.2 ml of selection medium (Invitrus, 10% FCS, 20 μg/ml puromycin, 1 mg/ml neomycin). Clones were visible after two weeks. They were expanded and screened for truncated-CD4 (tCD4) expression and antibody expression.

For the screening of tCD4 expression level, approximately 500,000 cells were washed with FACS buffer and incubated with 5 μl of FITC anti-human CD4 (Becton Dickinson, Switzerland) for 20 min on ice. After two washes cells were resuspended in 0.5 ml FACS buffer and analyzed with a FACS (FIG. 17A-B). A clone with a good expression level of tCD4 was isolated (BHK-1502-28-11). After 5 days of growth in a T25 flask, it produced about anti-CD20 antibody at a final titer of 17 μg/ml, as determined by ELISA.

4. Production and Purification of Unmodified and Glycoengineered Antibodies

Harvesting of Culture Medium

In the case of BHK cells transfected with an antibody expression vector or co-transfected with an antibody expression vector plus a GnTIII-fusion expression vector, the culture supernatant was harvested after culturing the transfected cells for 96 h post transfection. Depending on the expected productivity, several electroporations (10-15) were done for the same vector.

In the case of HEK293-EBNA cells transfected with an antibody expression vector or co-transfected with an expression vector plus a GnTIII-fusion expression vector, the culture medium was replaced by fresh culture medium approximately 16 hours post-transfection and the later medium was then harvested after culturing the transfected cells for a further 120 hours.

For the stable BHK-1502-28-11 cell line, a culture was seeded at 500,000 cells/ml and supernatant harvested after 4 days of culture when the cell density was $1.7 \times 10^6$ viable cells/ml and the cell viability of 69%.

Antibody Purification

Monoclonal antibody was purified from culture supernatant using two sequential chromatographic steps. The first step consisted of Protein A chromatography using a pH-gradient elution that effectively separates bovine and human IgGs. This was followed by a cation exchange chromatographic step to exchange the sample buffer to phosphate buffered saline (PBS).

5. Oligosaccharide Analysis

Oligosaccharides were enzymatically released from the antibodies by PNGaseF digestion, with the antibodies being either immobilized on a PVDF membrane or in solution.

The resulting digest solution containing the released oligosaccharides either prepared directly for MALDI/TOF-MS analysis or was further digested with EndoH glycosidase prior to sample preparation for MALDI/TOF-MS analysis.

Oligosaccharide Release Method for PVDF Membrane-Immobilized Antibodies

The wells of a 96-well plate made with a PVDF (Immobilon P, Millipore, Bedford, Mass.) membrane were wetted with 100 μl methanol and the liquid was drawn through the PVDF membrane using vacuum applied to the Multiscreen vacuum manifold (Millipore, Bedford, Mass.). The PVDF membranes were washed three times with 300 μl of water. The wells were then washed with 50 μl RCM buffer (8M Urea, 360 mM Tris, 3.2 mM EDTA, pH 8.6). Between 30-40 μg antibody was loaded in a well containing 10 μl RCM buffer. The liquid in the well was drawn through the membrane by applying vacuum, and the membrane was subsequently washed twice with 50 μl RCM buffer. The reduction of disulfide bridges was performed by addition of 50 μl of 0.1M dithiothreitol in RCM and incubation at 37° C. for 1 h.

Following reduction, a vacuum was applied to remove the dithiothreitol solution from the well. The wells were washed three times with 300 μl water before performing the carboxymethylation of the cysteine residues by addition of 50 μl 0.1M iodoacetic acid in RCM buffer and incubation at room temperature in the dark for 30 min.

After carboxymethylation, the wells were drawn with vacuum and subsequently washed three times with 300 μl water. The PVDF membrane was then blocked, to prevent adsorption of the endoglycosidase, by incubating 100 μl of a 1% aqueous solution of polyvinylpyrrolidone 360 at room temperature for 1 hour. The blocking reagent was then removed by gentle vacuum followed by three washes with 300 μl water.

N-linked oligosaccharides were released by addition of 2.5 mU peptide-N-glycosydase F (recombinat N-Glycanase, GLYKO, Novato, Calif.) and 0.1 mU Sialidase (GLYKO, Novato, Calif.), to remove any potential charged monosaccharide residues, in a final volume of 25 μl in 20 mM NaHCO$_3$, pH7.0). Digestion was performed for 3 hours at 37° C.

Oligosaccharide Release Method for Antibodies in Solution

Between 40 and 50 μg of antibody were mixed with 2.5 mU of PNGaseF (Glyko, U.S.A.) in 2 mM Tris, pH7.0 in a final volume of 25 microliters, and the mix was incubated for 3 hours at 37° C.

Use of Endoglycosidase H Digestion of PNGaseF-Released Oligosaccharides for the Assignment of Hybrid Bisected Oligosaccharide Structures to MALDI/TOF-MS Neutral Oligosaccharide Peaks The PNGaseF released oligosaccharides were subsequently digested with Endoglycosidase H (EC 3.2.1.96). For the EndoH digestion, 15 mU of EndoH (Roche, Switzerland) were added to the PNGaseF digest (antibody in solution method above) to give a final volume of 30 microliters, and the mix was incubated for 3 hours at 37° C. EndoH cleaves between the N-acetylglucosamine residues of the chitobiose core of N-linked oligosaccharides. The enzyme can only digest oligomannose and most hybrid type glycans, whereas complex type oligosaccharides are not hydrolyzed.

Sample Preparation for MALDI/TOF-MS

The enzymatic digests containing the released oligosaccharides were incubated for a further 3 h at room after the addition of acetic acid to a final concentration of 150 mM, and were subsequently passed through 0.6 ml of cation exchange resin (AG50W-X8 resin, hydrogen form, 100-200 mesh, Bio-Rad, Switzerland) packed into a micro-bio-spin chromatography column (BioRad, Switzerland) to remove cations and proteins. One microliter of the resulting sample was applied to a stainless steel target plate, and mixed on the plate with 1 μl of sDHB matrix. sDHB matrix was prepared by dissolving 2 mg of 2,5-dihydroxybenzoic acid plus 0.1 mg of 5-methoxysalicylic acid in 1 ml of ethanol/10 mM aqueous sodium chloride 1:1 (v/v). The samples were air dried, 0.2 μl ethanol was applied, and the samples were finally allowed to re-crystallize under air.

MALDI/TOF-MS

The MALDI-TOF mass spectrometer used to acquire the mass spectra was a Voyager Elite (Perspective Biosystems). The instrument was operated in the linear configuration, with an acceleration of 20 kV and 80 ns delay. External calibration using oligosaccharide standards was used for mass assignment of the ions. The spectra from 200 laser shots were summed to obtain the final spectrum.

6. PBMC Preparation

Peripheral blood mononuclear cells (PBMC) were prepared using Histopaque-1077 (Sigma Diagnostics Inc., St. Louis, Mo. 63178 USA) and following essentially the manufacturers instructions. In brief, venous blood was taken with heparinized syringes from volunteers who were asked to run for 1 minute at full power in order to increase the percentage of natural killer cells (NK) in the blood. The blood was diluted 1:0.75-1.3 with PBS not containing Ca or Mg and layered on Histopaque-1077. The gradient was centrifuged at 400×g for 30 min at room temperature (RT) without breaks. The interphase containing the PBMC was collected and washed with PBS (50 ml per cells from two gradients) and harvested by centrifugation at 300×g for 10 minutes at RT. After resuspension of the pellet with PBS, the PBMC were counted and washed a second time by centrifugation at 200×g for 10 minutes at RT. The cells were then resuspended in the appropriate medium for the subsequent procedures.

7. NK Cell Isolation

Human NK cells were isolated from PBMC applying a negative selection procedure using magnetic beads not binding to CD16- and CD56-positive cells (MACS system from Miltenyi Biotec GmbH, 51429 Bergisch Gladbach, GER). PBMC were washed once in ice-cold MACS buffer (PBS containing 2% FCS and 2 mM EDTA), resuspended at 20 Mio cells per ml of a 1:1 mixture of FCS and MACS buffer and incubated for 10 min at 4° C. The cells were then pelleted and resuspended in 80 μl per 10 million cells with MACS buffer containing 10% FCS. Then 20 μl Hapten-antibody solution per 10 million cells were added. The cells were incubated for 10 minutes at 4° C. with repeated swirling of the tube. After two washes with MACS buffer in at least 10× the labelling volume, the cells were resuspended in MACS buffer containing 10% FCS at 10 million cells per 80 μl and 20 μl anti-hapten-microbeads per 10 million cells were added. The tube was incubated for 15 minutes at 4° C. with repeated swirling of the tube. After one wash with MACS buffer the cells were resuspended at up to 100 million cells in 500 μl MACS buffer and loaded onto a LS MACS column which was placed in a MINI-MACS magnet and equilibrated with 3 ml MACS buffer. The column was washed with 3×3 ml MACS buffer. The cells in the flow-through fraction were collected and subsequently used as NK cells. Purity as determined by CD56 expression was between 88-95%.

8. ADCC Assay

PBMC or NK as effector cells were prepared as described above. The effector to target ratio was 25:1 and 10:1 for PBMC and NK cells, respectively. The effector cells were prepared in AIM-V medium at the appropriate concentration in order to add 50 μl per well of round bottom 96 well plates. Target cells for C2B8 antibodies were SKW6.4 or Namalwa B lymphoma cells grown in DMEM containing 10% FCS. Target cells were washed in PBS, counted and resuspended in AIM-V at 0.3 million per ml in order to add 30000 cells in 100 μl per microwell. Antibodies were diluted in AIM-V, added in 50 μl to the pre-plated target cells and allowed to bind to the targets for 10 minutes at RT. Then the effector cells were added and the plate was incubated for 4 hours at 37° C. in a humified atmosphere containing 5% $CO_2$. Killing of target cells was assessed by measurement of lactate dehydrogenase (LDH) release from damaged cells using the Cytotoxicity Detection kit (Roche Diagnostics, Rotkreuz, Switzerland). After the 4-hour incubation the plates were centrifuged at 800×g. 100 μl supernatant from each well was transferred to a new transparent flat bottom 96 well plate. 100 μl color substrate buffer from the kit were added per well. The Vmax values of the color reaction were determined in an ELISA reader at 490 nm for at least 10 min using SOFTmax PRO software (Molecular Devices, Sunnyvale, Calif. 94089, USA). Spontaneous LDH release was measured from wells containing only target and effector cells but no antibodies. Maximal release was determined from wells containing only target cells and 1% Triton X-100. Percentage of specific antibody-mediated killing was calculated as follows: ((x−SR)/(MR−SR)*100, where x is the mean of Vmax at a specific antibody concentration, SR is the mean of Vmax of the spontaneous release and MR is the mean of Vmax of the maximal release.

9. FcγRIIIA Binding on NK Cells

Freshly isolated NK cells were centrifuged 5 minutes at 200×g and pretreated with 0.09% (wt/vol) lactic acid solution (140 mM NaCl, 5 mM KCl, pH 3.9), by incubating $3\times10^5$ cells/ml at room temperature for 5 minutes, to remove NK cell-associated IgG. (De Haas M., *J. Immunol.* 156:2948 (1996)).

Cells were washed two times with PBS, 0.1% BSA, 0.01% sodium azide and concentration was adjusted to $2\times10^6$ cells/ml in PBS, 0.15 BSA, 0.01% sodium azide. $5\times10^5$ cells were incubated with 0, 0.1, 0.3, 1, 3, 10 μg/ml antibody variants for 30 min at 4° C. Cells were then washed two times and antibody binding was detected by incubating with 1:200 fluorescein isothiocyanate-conjugated F(ab')$_2$ goat anti-human IgG (Jackson ImmunoReasearch, West Grove, Pa.) and anti-human CD56-PE at 5 µl/5×10$^5$ cells (BD Pharmingen, san Diego, Calif.) for 30 minutes at 4° C. (Shields R. et al. *J. Biol. Chem.* 277(30):26733-26740 (2002)).

The fluorescence intensity referring to the bound antibody variants was determined for CD56+ cells on a FACSCalibur (BD Bioscience, San Jose, Calif.).

10. FcgammaRIIb Binding on Raji Lymphoma Cells

Raji B-cell human lymphoma cells were washed 20 min at 37° C. in PBS (concentration 0.3 Mio cells/ml). Cells were then resuspended at 2.22 million cells/ml in PBS, 0.1% BSA, 0.01% NaN$_3$, and 180 µl added per FACS tube. Ten-fold antibody dilutions (0, 0.1, 0.3, 1, 3, 10, 30 µg/ml) of L19-unmodified and L19 glycoengineered monoclonal antibodies were added to the Raji cells and incubated at 4° C. for 30 min (final cells concentration 2 million cells/ml). After two washes, 1:200 of fluorescein isothiocyanate-conjugated F(ab')$_2$ goat anti-human IgG (Jackson ImmunoReasearch, West Grove, Pa.) was added to the cells and incubated at 4° C. for 30 min. After one wash, cells were resuspended in 0.5 ml PBS, 0.1% BSA, 0.01% NaN$_3$ and the fluorescence intensity referring to the bound antibody variants was determined on a FACSCalibur (BD Bioscience, San Jose, Calif.) for living cells.

11. Complement Dependent Cytotoxicity Assay

Target cells were counted, washed with PBS, resuspended in AIM-V (Invitrogen) at 1 million cells per ml. 50 µl cells were plated per well in a flat bottom 96 well plate. Antibody dilutions were prepared in AIM-V and added in 50 µl to the cells. Antibodies were allowed to bind to the cells for 10 minutes at room temperature. Human serum complement (Quidel) was freshly thawed, diluted 3-fold with AIM-V and added in 50 µl to the wells. Rabbit complement (Cedarlane Laboratories) was prepared as described by the manufacturer, diluted 3-fold with AIM-V and added in 50 µl to the wells. As a control, complement sources were heated for 30 min at 56° C. before addition to the assay.

The assay plates were incubated for 2 h at 37° C. Killing of cells was determined by measuring LDH release. Briefly, the plates were centrifuged at 300×g for 3 min. 50 µl supernatant per well were transferred to a new 96 well plate and 50 µl of the assay reagent from the Cytotoxicity Kit (Roche) were added. A kinetic measurement with the ELISA reader determined the Vmax corresponding with LDH concentration in the supernatant. Maximal release was determined by incubating the cells in presence of 1% Trition X-100.

Results and Discussion

Glycoengineered versions of an anti-CD20 chimeric IgG1 antibody (C2B8 chimeric antibody, also known as rituximab) were produced by co-transfecting cultures of mammalian cells with vectors for expression of antibody genes and with vectors for expression of genes encoding various polypeptides with GnTIII activity. An unmodified (non-glycoengineered) version of the same antibody was produced by transfecting mammalian cells only with the vector for antibody gene expression. The transfected cells were kept in culture for at least three days and the secreted, recombinant antibodies were purified from the culture medium by Protein A affinity chromatography. Expression of genes encoding polypeptides with GnTIII activity did not have any significant effect on cell viability, cell growth or antibody production, relative to cells not producing such polypeptides.

The purified antibodies were then analyzed for their glycosylation patterns. These antibodies carry N-linked oligosaccharides attached only to Asn297 residue of the human IgG1 Fc region. The oligosaccharides were enzymatically removed from antibodies by PNGaseF digestion and were subsequently analyzed by MALDI/TOF-MS. Using this technique, it is possible to determine the fraction of different oligosaccharide species within the total, original Fc-oligosaccharide population, and it is also possible to assign structures to different peaks in the spectra (Umana, P. et al., *Nature Biotechnol.* 17:176-180(1999)).

Figure 2:
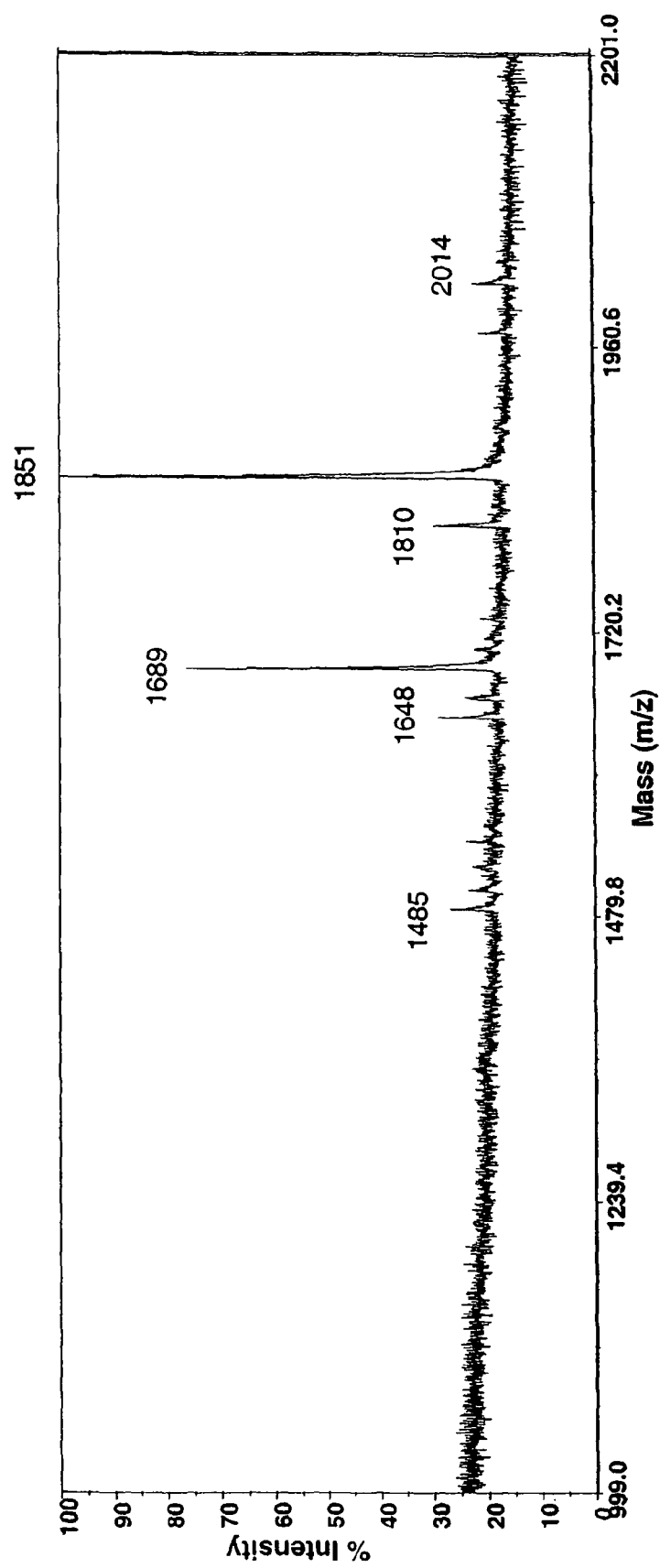
FIG. 2. MALDI/TOF-MS spectrum of neutral oligosaccharide mix derived from recombinant, glycoengineered anti-CD20 IgG1 antibody produced in BHK engineered with a nucleic acid encoding wild type ("wt") GnTIII. Cells were co-transfected with antibody expression vector pETR1502 and with GnTIII expression vector pETR1166. Antibody was purified from culture medium and oligosaccharides were prepared and analyzed as described in the Materials and Methods section of Example 1.
Figure 3:
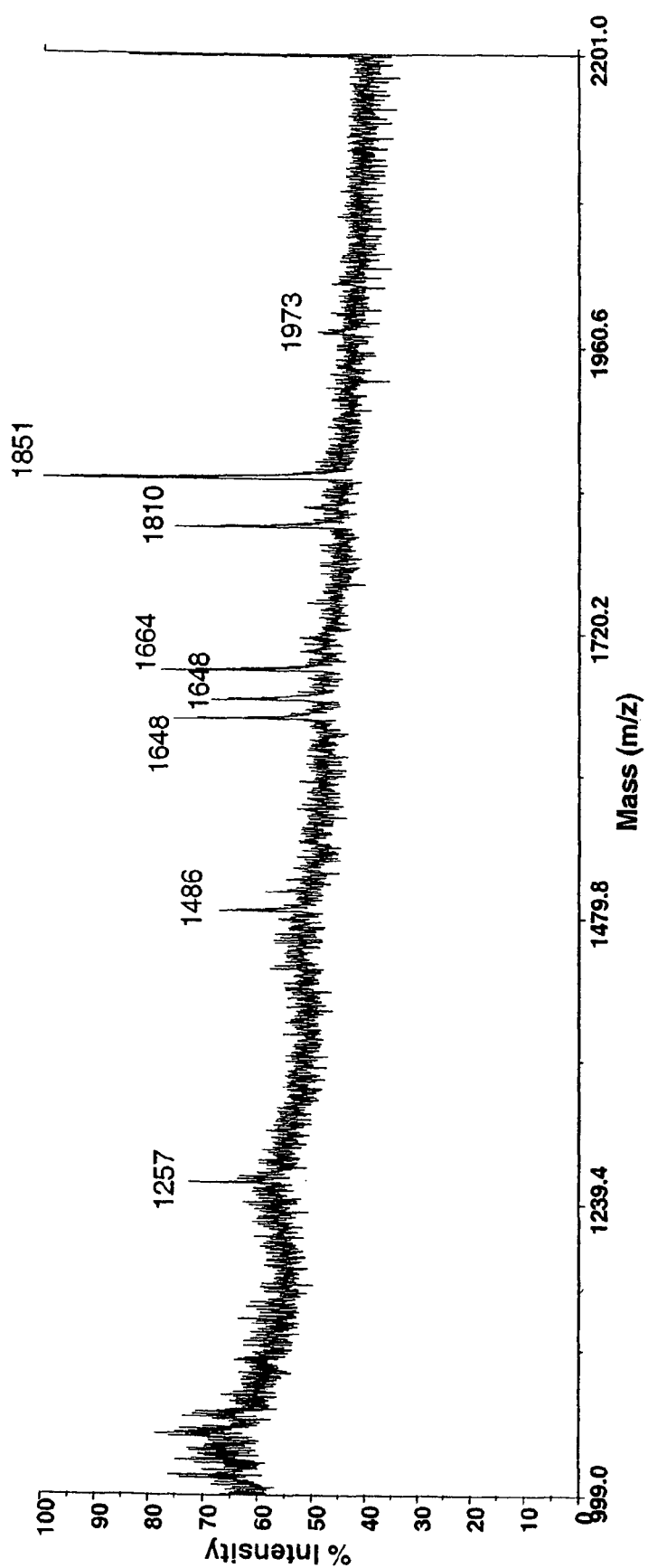
FIG. 3. MALDI/TOF-MS spectrum of neutral oligosaccharide mix derived from recombinant, glycoengineered anti-CD20 IgG1 antibody produced in BHK engineered with a nucleic acid encoding a fusion polypeptide ("G1-GnTIII") with GnTIII activity and localized via a GnTI-Golgi localization domain. Cells were co-transfected with antibody expression vector pETR1502 and with GnTIII expression vector pETR1425. Antibody was purified from culture medium and oligosaccharides were prepared and analyzed as described in the Materials and Methods section of Example 1.
Figure 4:
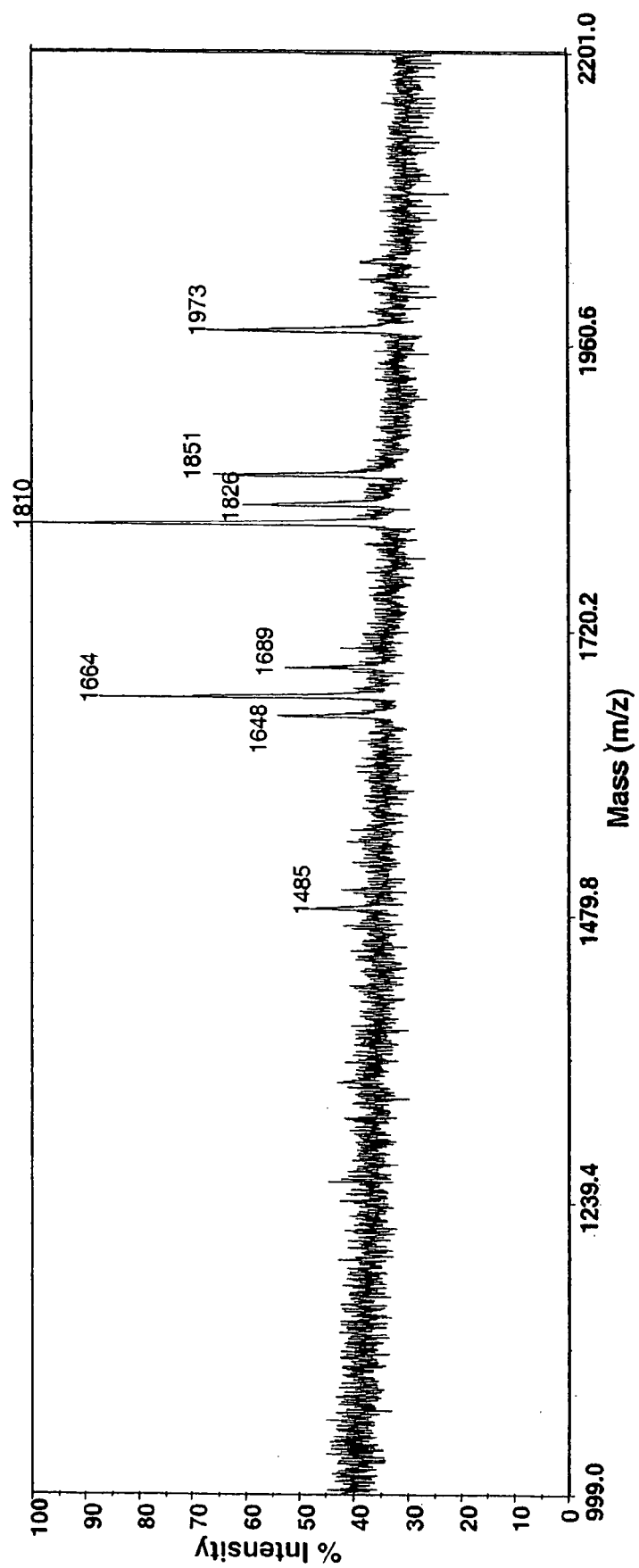
FIG. 4. MALDI/TOF-MS spectrum of neutral oligosaccharide mix derived from recombinant, glycoengineered anti-CD20 IgG1 antibody produced in BHK engineered with a nucleic acid encoding a fusion polypeptide ("M2-GnTIII") with GnTIII activity and localized via a Golgi alpha-mannosidaseII(ManII)-Golgi localization domain. Cells were co-transfected with antibody expression vector pETR1502 and with GnTIII expression vector pETR1506. Antibody was purified from culture medium and oligosaccharides were prepared and analyzed as described in the Materials and Methods section of Example 1.

FIG. 1 shows the neutral oligosaccharide MALDI/TOF-MS profiles from the recombinant C2B8 anti-CD20 chimeric IgG1 antibody produced in BHK cells. These cells were transfected with antibody expression vector pETR1502. FIGS. 2 to 4 show the corresponding profiles for the same antibody produced by BHK cells engineered with nucleic acids encoding polypeptides with GnTIII activity. The profile in FIG. 2 results from the use of a nucleic acid encoding wild-type GnTIII expressed from vector pETR1166. The profile in FIG. 3 results from the use of a nucleic acid encoding a fusion polypeptide comprising at the N-terminus the localization domain of GnTI fused to the C-terminal catalytic domain of GnTIII. This fusion gene was expressed from vector pETR1425. The profile in FIG. 4 results from the use of a nucleic acid encoding a fusion polypeptide comprising at the N-terminus the localization domain of Golgi α-mannosidaseII (ManII) fused to the catalytic domain of GnTIII. This fusion gene was expressed from vector pETR1506.

The unmodified antibody has a typical oligosaccharide profile (FIG. 1), with peaks at m/z ratios of 1485, 1648 and 1810 being consistent with biantennary, core-fucosylated, complex oligosaccharides with 0, 1- and 2-galactose residues, respectively. Similar profiles are found for the Fc-region oligosaccharides of non-engineered IgG1 antibodies produced in other standard mammalian, industrial cell lines such as CHO and mouse myeloma cells (Lifely, M. R. et al., *Glycobiology* 5:813-822 (1995)). Engineering of the antibody producing cells by expression of wild-type GnTIII leads mainly to bisected, core-fucosylated, complex biantennary oligosaccharides (FIG. 2), with peaks at m/z ratios of 1689, 1851 and 2014 being the bisected counterparts of the non-bisected, fucosylated oligosaccharide peaks found in the unmodified antibody. Engineering of the antibody-producing cells by expression of a nucleic acid encoding a GnTI-GnTIII fusion polypeptide, where the GnTIII catalytic domain is localized via the GnTI Golgi localization domain, also leads mainly to bisected complex biantennary oligosaccharides (note peaks at m/z 1689 and 1851 in FIG. 3). However, relative to the wild-type GnTIII, use of a GnTI-GnTIII fusion leads to an increase in bisected, non-fucosylated and bisected, hybrid structures (compare the proportions of peaks with m/z of 1664, 1810, 1826 and 1973, relative to the total, between FIGS. 2 and 3). The synthesis of bisected, non-fucosylated and bisected, hybrid structures results from the competition, for GnTI-modified oligosaccharide substrates, between the recombinant GnTIII-catalytic domain and (i) the endogenous core, α1,6-fucosyltransferase, (ii) Golgi α-mannosidase II (ManII) and (iii) GnTII, since once an oligosaccharide is modified with a bisecting GlcNAc added via a GnTIII-catalyzed reaction, these three other enzymes can no longer act to modify the bisected oligosaccharides. Therefore blocking action of ManII by addition of the bisecting GlcNAc also effectively blocks GnTII, since GnTII acts downstream of ManII in the N-linked oligosaccharide biosynthetic pathway. The peaks at m/z 1664 and 1826 are non-fucosylated, whereas the peaks at m/z 1810 and 1973 are fucosylated. EndoH glycosidase digestion, which can distinguish between hybrid and complex oligosaccharides (FIG. 8A), was used to confirm that the increase in these peaks is due to an increase in the proportion of Fc-attached bisected, non-fucosylated and bisected, hybrid oligosaccharides (see below).

In contrast to the other GnTIII activity-encoding nucleic acids used here, engineering of the antibody-producing cells by expression of a nucleic acid encoding a ManII-GnTIII fusion polypeptide (SEQ ID NO: 14), where the GnTIII catalytic domain is localized via the ManII Golgi localization domain, leads mainly to bisected, non-fucosylated and bisected, hybrid structures (note peaks at m/z 1664 1810, 1826 and 1973 in FIG. 4). Therefore, relative to the wild-type GnTIII and to the GnTI-GnTIII fusion (SEQ ID NOS:12 and 13), the ManII-GnTIII fusion was more efficient in the synthesis of Fc-attached bisected, non-fucosylated and bisected, hybrid oligosaccharides (compare the proportions of peaks with m/z of 1664 and 1810 relative to the total between FIGS. 2, 3 and 4). The proportions of the bisected, non-fucosylated Fc-oligosaccharides resulting from the expression of the nucleic acids encoding wild-type GnTIII, the GnTI-GnTIII fusion and the ManII-GnTIII fusion were approximately 4, 13, and 33%, respectively. No bisected oligosaccharides were detected in the unmodified (non-engineered) antibody.

Increasing the expression of the ManII-GnTIII fusion construct in the antibody-producing cells led to further increases in the proportion of bisected, non-fucosylated oligosaccharides. This was demonstrated by expressing the ManII-GnTIII construct from a vector (pETR1519) with an OriP for episomal replication in transfected HEK293-EBNA cells. This expression system is known to lead to high levels of expression, and was also used for expression of the antibody genes from vector pETR1520. The oligosaccharide profile from the purified, unmodified (non-glycoengineered) antibody expressed at high levels in this system is shown in FIG. 5, which again shows the typical oligosaccharide profile with non-bisected, fucosylated oligosaccharide peaks having 0, 1 and 2 galactose residues (e.g., compare FIGS. 1 and 5 showing the similar oligosaccharide profiles of the unmodified antibody expressed in BHK cells or at higher levels in HEK293-EBNA cells). Engineering the antibody producing cells with the nucleic acid encoding the ManII-GnTIII fusion expressed at higher levels in this system led to the production of antibodies where the majority of the Fc-oligosaccharides were bisected, non-fucosylated (see FIG. 6, where bisected, non-fucosylated hybrid oligosaccharide peaks at m/z 1664 and 1826 together constitute over 90% of the total oligosaccharides).

Figure 8:
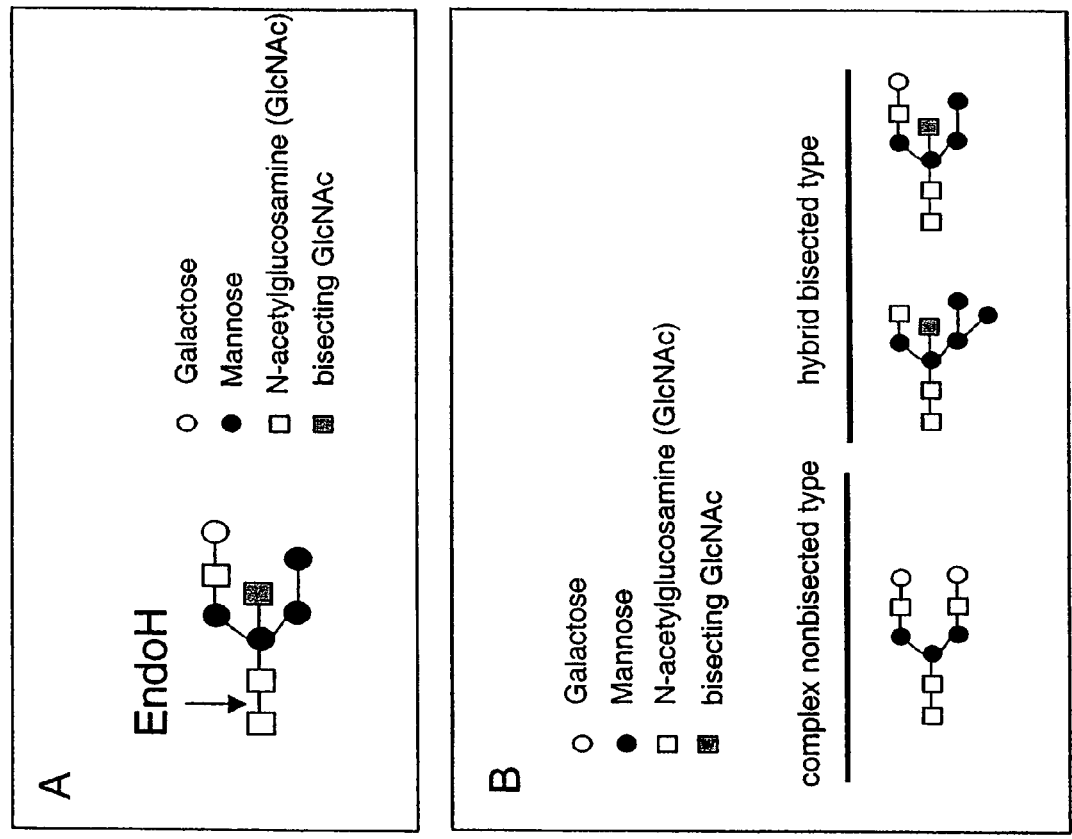
FIG. 8. (a) Schematic description of the EndoH-catalyzed digestion of oligosaccharides. EndoH can digest hybrid (and hybrid bisected), but not complex or complex bisected oligosaccharides. (b) By distinguishing between complex- and hybrid-type oligosaccharides, Endo-H treatment allows to make structural assignments to oligosaccharides peaks that have the same m/z ratios in the MALDI/TOF-MS spectra originally resulting from PNGAseF treatment.

As mentioned above, endoglycosidase H (EndoH) was used to confirm the assignment of bisected non-fucosylated and bisected, hybrid structures to the different oligosaccharide peaks observed in the MALDI profiles. The MALDI/TOF-MS neutral oligosaccharide profiles of PNGaseF– and of PNGaseF+EndoH-digested glycans derived from an anti-CD20 chimeric IgG1 antibody, produced by HEK293 cells glycoengineered by GnTIII(M2) overexpression, are shown in FIG. 7. The peak at m/z 1664 can be assigned to two different glycans, namely non-fucosylated hybrid-bisected or non-fucosylated complex, non-bisected. The different structures show the same m/z ratio due to the same monosaccharide composition (FIG. 8B).

The digestion of the PNGaseF-released glycans with Endoglycosidase H generates new structures, with the major peak being shifted from m/z 1664 to 1460 (FIG. 7B). The difference corresponds to the mass of a GlcNAc residue. As mentioned above, EndoH cannot cleave the complex type oligosaccharides. Therefore, the major peak at m/z 1664 can be assigned to the non-fucosylated hybrid bisected type after Endoglycosidase H digestion.

Other peaks that could be assigned to complex or hybrid bisected glycans. At m/z 1810; after EndoH digestion the peak disappeared so the structures can be assigned to the fucosylated hybrid bisected type. The subtraction of one GlcNAc and one fucose (from the core α-1,6 fucosylated, reducing-end GlcNAc residue) residue from the m/z 1810 peak generates a structure of m/z 1460. At m/z 1502, disappearance of this peak by EndoH digestion (GlcNAc residue eliminated) and the appearance of a peak at m/z 1298, demonstrate that the 1502 peak can be assigned to a non-fucosylated hybrid bisected type. At m/z 1647, the disappearance of the peak after EndoH digestion demonstrates that this peak is a fucosylated hybrid bisected structure. The removal of one GlcNAc and one fucose residue generates a structure of m/z 1298. The peak at m/z 1826, a non-fucosylated hybrid bisected type, was digested by EndoH. This generated a structure with m/z 1622. The peak at m/z 1053 after EndoH digestion can be assigned to the high mannose type (1257 m/z), digested by EndoH. The peak at m/z 1689 (complex bisected) was not affected by EndoH digestion, as expected. In synthesis, from the data obtained in Table 1, we conclude that 88% of the oligosaccharide structures carry a bisecting GlcNAc, 60% of which are non-fucosylated hybrid bisected structures, 22% fucosylated hybrid bisected and 6% fucosylated complex bisected oligosaccharide structures.

TABLE 1

Oligosaccharide assignments

| m/z | Possible structures | Relative % before EndoH | Expected m/z after EndoH | Observed m/z after EndoH | Relative % after EndoH | Assignment |
|---|---|---|---|---|---|---|
| 1256 | High mannose | 9 | 1053 | 1053 | 11 | High mannose (9%) |
| 1502 | Non-fuc. hybrid bisected or Non-fuc. complex | 7 | 1298 or 1502 | 1298 — | 13 | Non-fuc. hybrid bisected (7%) |
| 1647 | Fuc. hybrid bisected or Fuc. complex | 7 | 1298 or 1647 | 1298 — | 13 | Fuc. hybrid bisected (7%) |
| 1664 | Non-fuc. hybrid bisected or Non-fuc, complex | 49 | 1460 or 1664 | 1460 — | 60 | Non-fuc. hybrid bisected (49%) |
| 1689 | Fuc. complex bisected | 3 | 1689 | 1689 | 5 | Fuc. complex bisected (3%) |

TABLE 1-continued

Oligosaccharide assignments

| m/z | Possible structures | Relative % before EndoH | Expected m/z after EndoH | Observed m/z after EndoH | Relative % after EndoH | Assignment |
|---|---|---|---|---|---|---|
| 1810 | Fuc. hybrid bisected or Fuc. complex | 15 | 1460 or 1810 | 1460 1810 | 60 2 | Fuc. hybrid bisected (13%) and Fuc. complex (2%) |
| 1826 | Non-fuc. hybrid bisected | 4 | 1622 | 1622 | 7 | Non-fuc. hybrid bisected (4%) |
| 1851 | Fuc. complex bisected | 3 bisected | 1851 | 1851 | 2 | Fuc. complex (3%) |
| 1972 | Fuc. hybrid bisected | 3 | 1622 | 1622 | 7 | Fuc. hybrid bisected (3%) |

Mass balances (in mol fraction in %):
a) Peaks at m/z 1502 and 1647: 7 + 7% = 14% (expected). EndoH digestion for both peaks generates m/z 1298 (obtained 13% after EndoH)
b) Peaks at m/z 1664 and 1810: 49 + 13% = 62%. EndoH generates m/z 1460 (obtained 60%)
c) Peaks at m/z 1826 and 1972: 4 + 3% = 7%. EndoH generates m/z 1622 (7%) Summary.
Total relative percentage of structures bearing a bisecting GlcNAc: 88%
Non-fucosylated hybrid bisected: 60%
Fucosylated hybrid bisected: 22%
Fucosylated complex bisected: 6%

The above data (FIGS. 1 to 6) show that both the level of GnTIII expression and the particular localization domain that is used to target the GnTIII catalytic domain to the Golgi, influence the competition for GnTI-modified oligosaccharide substrates between the recombinant GnTIII-catalytic domain and the endogenous core α1,6-fucosyltransferase, (ManII) and GnTII enzymes. Higher expression of GnTIII favors it in this competition, leading to higher levels of bisected, hybrid and bisected, non-fucosylated oligosaccharides and to a concomitant reduction of the levels of bisected complex and bisected, fucosylated oligosaccharides. This was also noted previously for the wild type GnTIII (Umana, P. et al., Nature Biotechnol. 17:176-180(1999)). Yet, in spite of leading to similar overall levels of bisected oligosaccharides, localizing the GnTIII catalytic domain via the GnTI or via the ManII localization domains led to more effective competition, relative to the wild-type GnTIII, for the GnTI-modified oligosaccharide substrates against the endogenous core α1,6-fucosyltransferase, ManII and GnTII enzymes.

The higher efficiency of the GnTI-GnTIII fusion, compared to wild-type GnTIII, for the synthesis of bisected, hybrid and bisected, non-fucosylated oligosaccharides can be explained by an earlier Golgi distribution, in the cis-to-trans direction of glycoprotein substrate transport, of GnTI relative to GnTIII. The fine Golgi distributions of GnTI and ManII have been determined previously by quantitative immuno-electron microscopy (Rabouille, C. et al. J. Cell Sci. 108: 1617-27 (1995)). Both enzymes co-distribute along the Golgi, being localized mainly in the medial and trans cisternae of the Golgi stack, with a higher levels in the medial relative to the trans cisternae. The fine quantitative spatial distributions of core α1,6-fucosyltransferase, GnTII and wild-type GnTIII have not yet been determined. The above however does not explain why the ManII-GnTIII fusion is significantly more efficient than the GnTI-GnTIII fusion for the synthesis of bisected, hybrid and bisected, non-fucosylated oligosaccharides, since both GnTI and ManII have identical spatial distributions along the Golgi subcompartments.

The higher efficiency of the ManII-GnTIII fusion indicates the existence of relatively organized functional glycosylation reaction subcompartments within the physical subcompartments of the medial- and trans-Golgi cisternae. The so-called "medial-Golgi glycosylation enzymes", GnTI, GnTII and ManII are believed to exist in the Golgi as high-molecular weight complexes. However, if the localization domains allow these enzymes to form part of these complexes, this would be the same for the GnTI- and the ManII-GnTIII fusions. Expression of the recombinant GnTI-GnTIII fusion did not lead to displacement of the endogenous wild-type GnTI enzyme to any extent significant to the synthesis of Fc-oligosaccharides, since all GnTIII constructs used here led to a majority of the oligosaccharides being modified both by GnTI and GnTIII reactions.

Our data indicates that, by virtue of the ManII localization domain, a finer functional pairing occurs between the catalytic domains of the endogenous GnTI and the recombinant ManII-GnTIII fusion. Organized pairings of enzymes catalyzing subsequent reactions in a biosynthetic pathway, in a way that favors transfer of the product of the first reaction to the second catalytic site relative to diffusion of such product away from the enzymes, is known to occur in other biosynthetic pathways such as glycolysis and polyketide biosynthesis. GnTI and ManII have been reported to form "kin oligomers", at least when relocalizing one of these enzymes to the endoplasmic reticulum (Nilsson, T. et al. EMBO J. 13(3). 562-74 (1994)). A pair of charged amino acid residues in each of the stem regions of these two enzymes was found to be critical for this kin recognition. The residues in GnTI were of opposite charge to those of ManII. We have identified similar residues at equivalent positions of the stem regions of the other Golgi glycosylation enzymes involved in this part of the N-linked oligosaccharide biosynthetic pathway, namely core α1,6-fucosyltransferase (same charges as GnTI instead of complementary charges as in the case of ManII), ManI and GnTII. We have also identified that these residues are conserved across species. Although it has been suggested that these residues are not essential for incorporation into the high molecular weight complexes formed by the enzymes or even for Golgi localization (Opat, A. S. et al. J. Biol. Chem. 275 (16):11836-45 (2000)), it is possible that they are involved in a finer pairing of the catalytic domains during oligosaccharide biosynthesis. Such pairing does not need to be irreversible, but can be mediated by transient, dynamic interactions between the enzymes. There could be additional determinants for pairing elsewhere in the stem or catalytic region. However, any contribution to a specific GnTI-ManII pairing from the catalytic domain of ManII would be lost in the recombinant fusion bearing the GnTIII catalytic domain.

Figure 5:
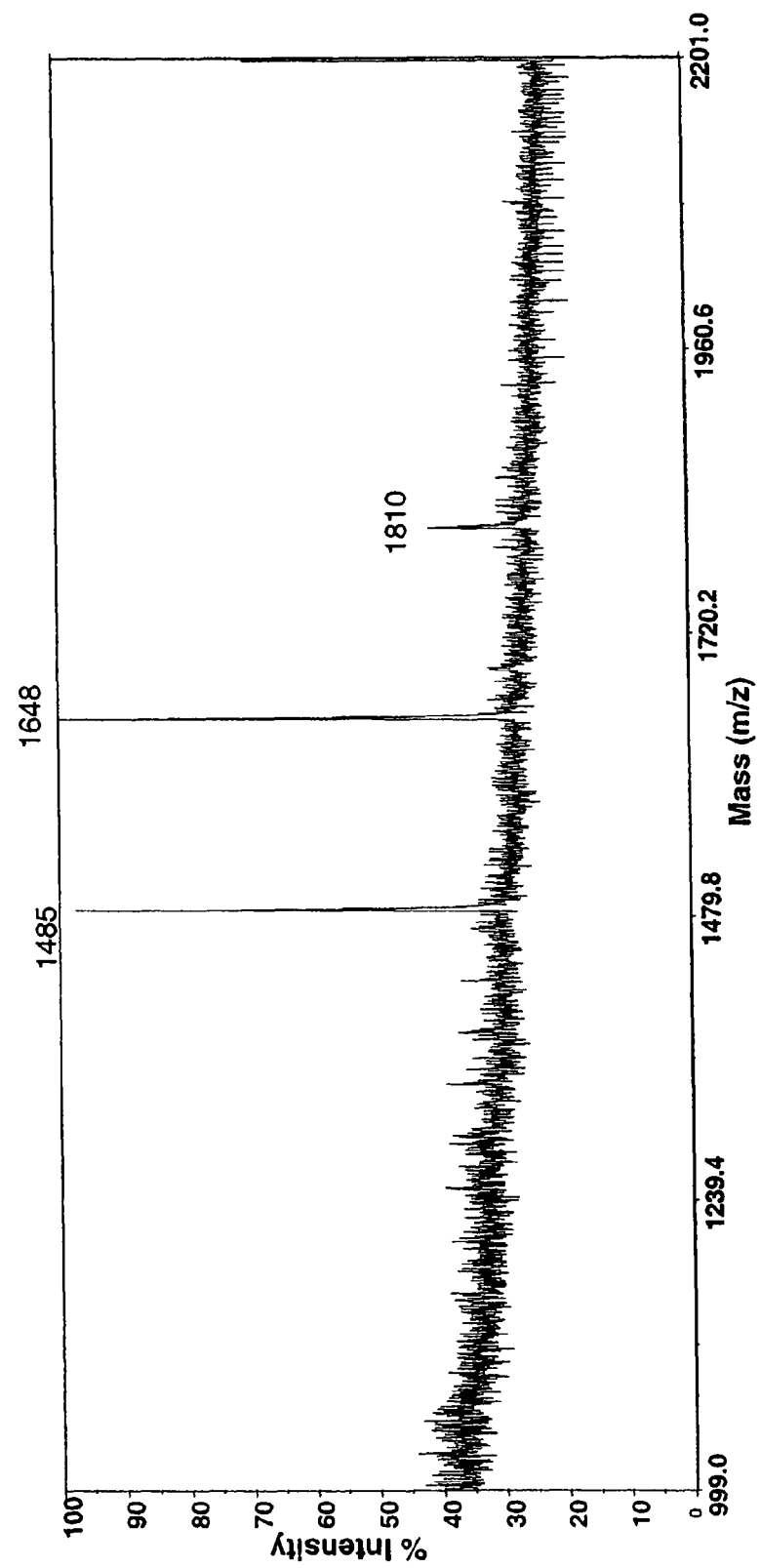
FIG. 5. MALDI/TOF-MS spectrum of neutral oligosaccharide mix derived from recombinant, unmodified (non-glycoengineered) anti-CD20 IgG1 antibody produced in HEK293-EBNA cells. Cells were transfected with antibody expression vector pETR1520. Antibody was purified from culture medium and oligosaccharides were prepared and analyzed as described in the Materials and Methods section of Example 1.
Figure 6:
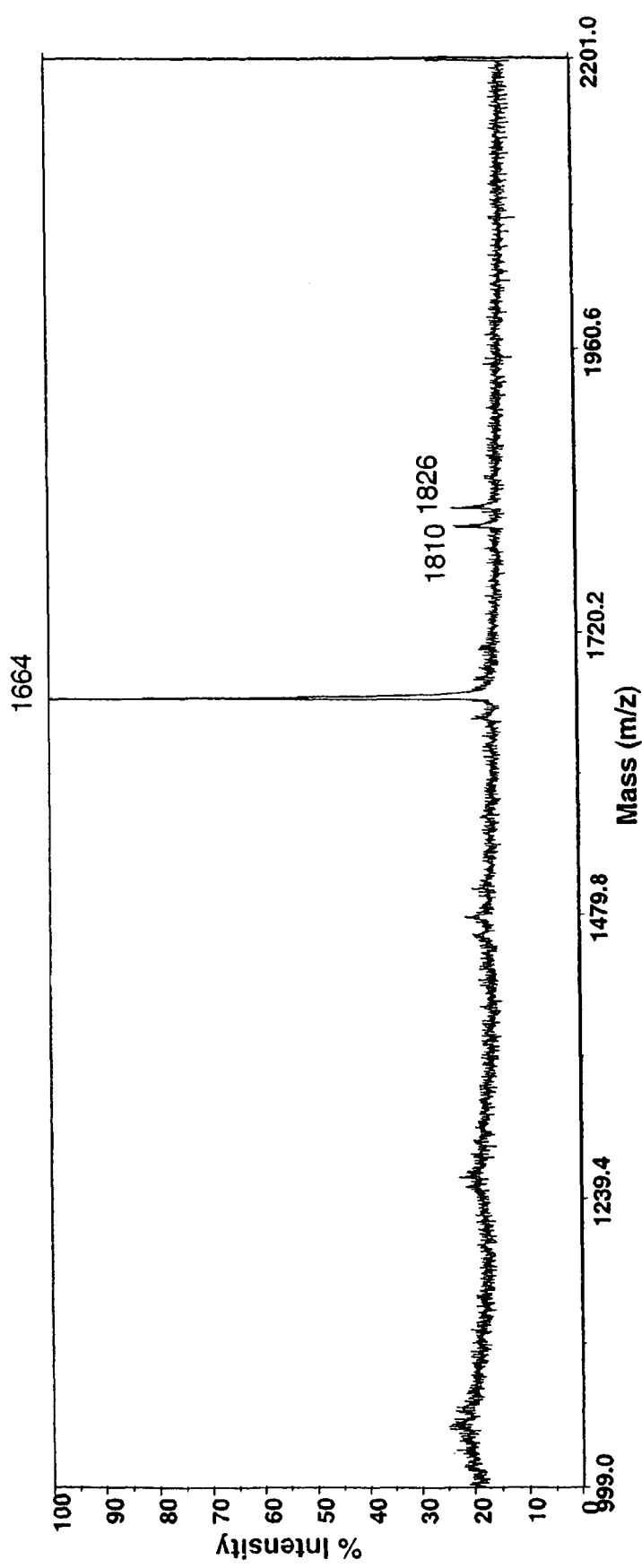
FIG. 6. MALDI/TOF-MS spectrum of neutral oligosaccharide mix derived from recombinant, glycoengineered anti-CD20 IgG1 antibody produced in HEK293-EBNA engineered with a nucleic acid encoding a fusion polypeptide ("M2-GnTIII") with GnTIII activity and localized via a Golgi alpha-mannosidaseII(ManII)-Golgi localization domain. Cells were co-transfected with antibody expression vector pETR1520 and with GnTIII expression vector pETR1519. Antibody was purified from culture medium and oligosaccharides were prepared and analyzed as described in the Materials and Methods section of Example 1.
Figure 9:
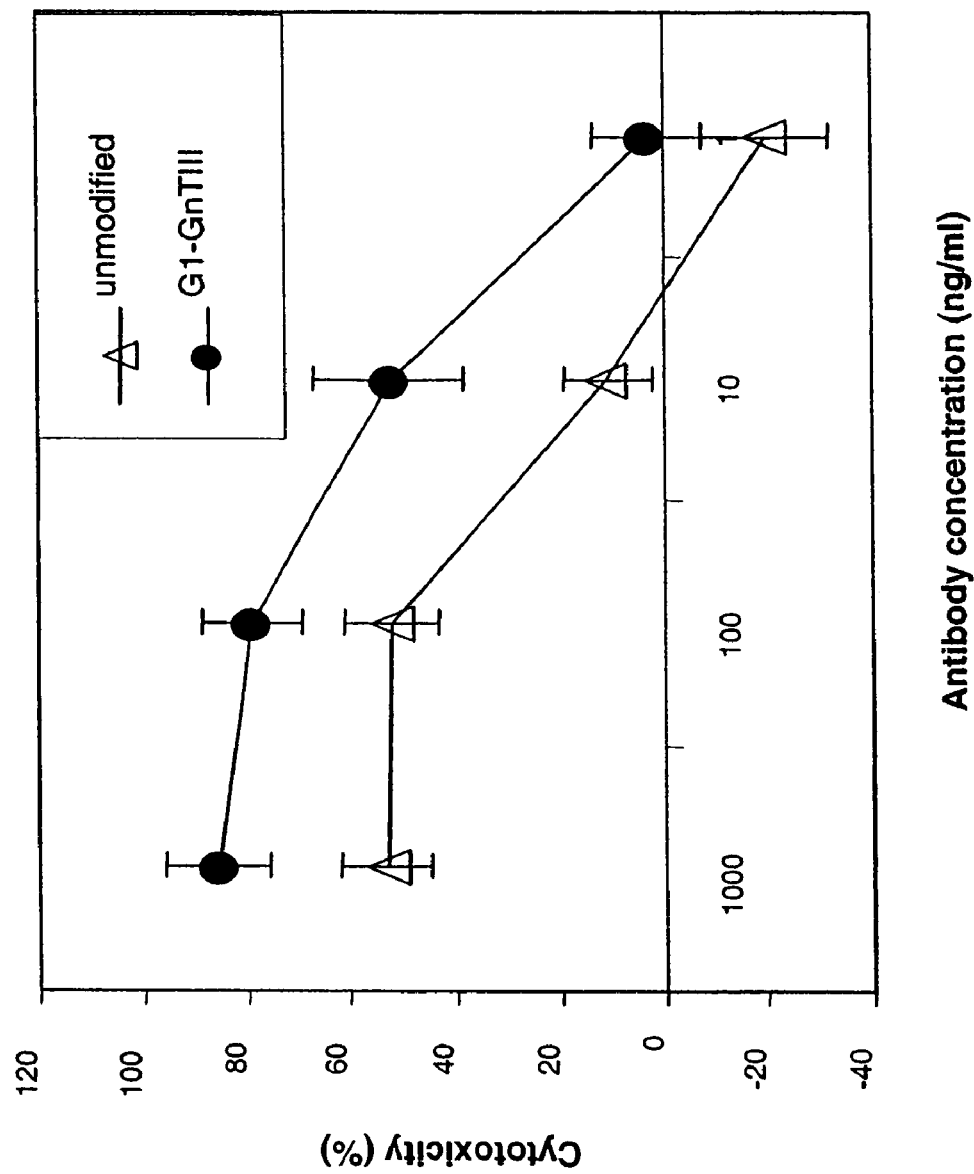
FIG. 9. Antibody-dependent cellular cytotoxicity (ADCC) of "G1-GnTIII"-glycoengineered vs. unmodified recombinant, anti-CD20 chimeric IgG1 antibodies. Both antibodies were produced in BHK cells. Production and glycosylation profile of the glycoenginereed antibody is depicted in FIG. 3 and those of the unmodified antibody in FIG. 1. Target cells (T) were SKW6.4 human lymphoblastoid cells. Effector cells (E) were freshly-isolated human PBMC. An E:T ratio of 25:1 was used in a 4-hour incubation ADCC assay measuring cytotoxicity by lactate dehydrogenase (LDH) release relative to a maximum release (using a detergent instead of antibody) and a spontaneous release (culture medium instead of antibody) controls. Assay details are described in Materials and Methods section of Example 1.
Figure 10:
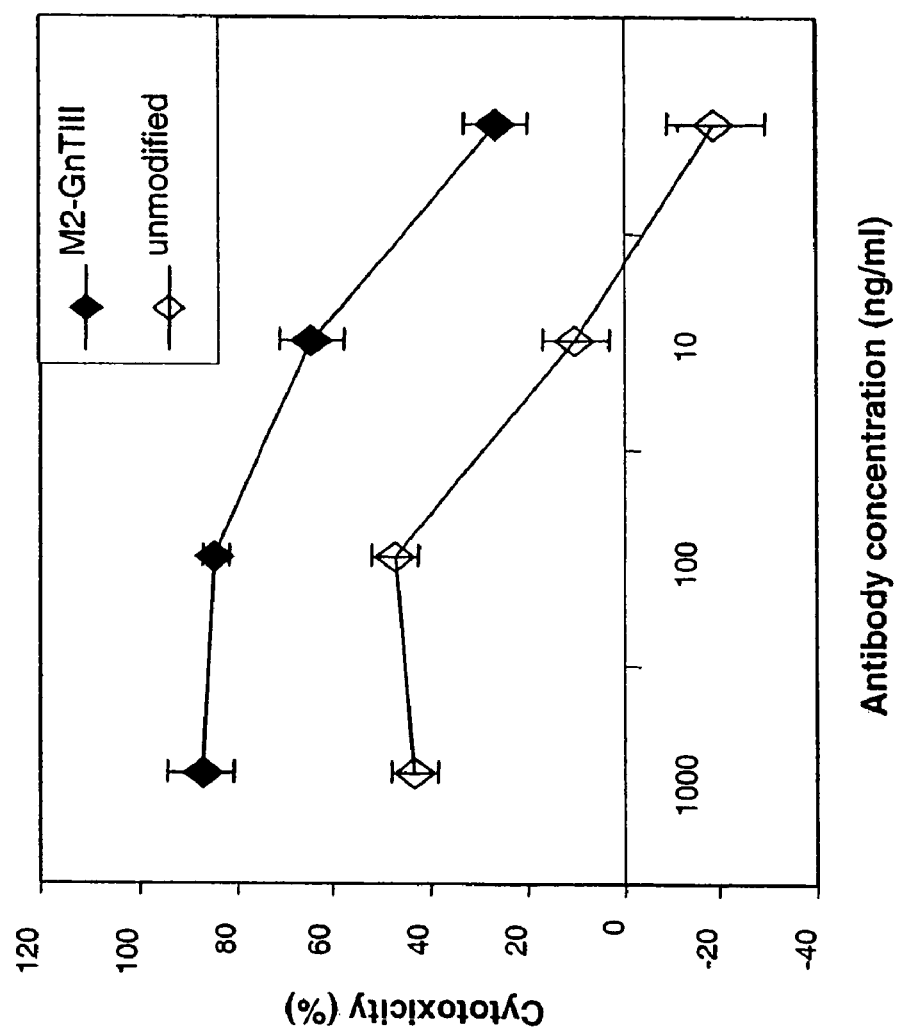
FIG. 10. Antibody-dependent cellular cytotoxicity (ADCC) of "M2-GnTIII"-glycoengineered vs. unmodified recombinant, anti-CD20 chimeric IgG1 antibodies. Both antibodies were produced in HEK293-EBNA cells. Production and glycosylation profile of the glycoenginereed antibody is depicted in FIG. 6 and those of the unmodified antibody in FIG. 5. Target cells (T) were SKW6.4 human lymphoblastoid cells. Effector cells (E) were freshly-isolated human PBMC. An E:T ratio of 25:1 was used in a 4-hour incubation ADCC assay measuring cytotoxicity by lactate dehydrogenase (LDH) release relative to a maximum release (using a detergent instead of antibody) and a spontaneous release (culture medium instead of antibody) controls. Assay details are described in Materials and Methods section of Example 1.
Figure 11:
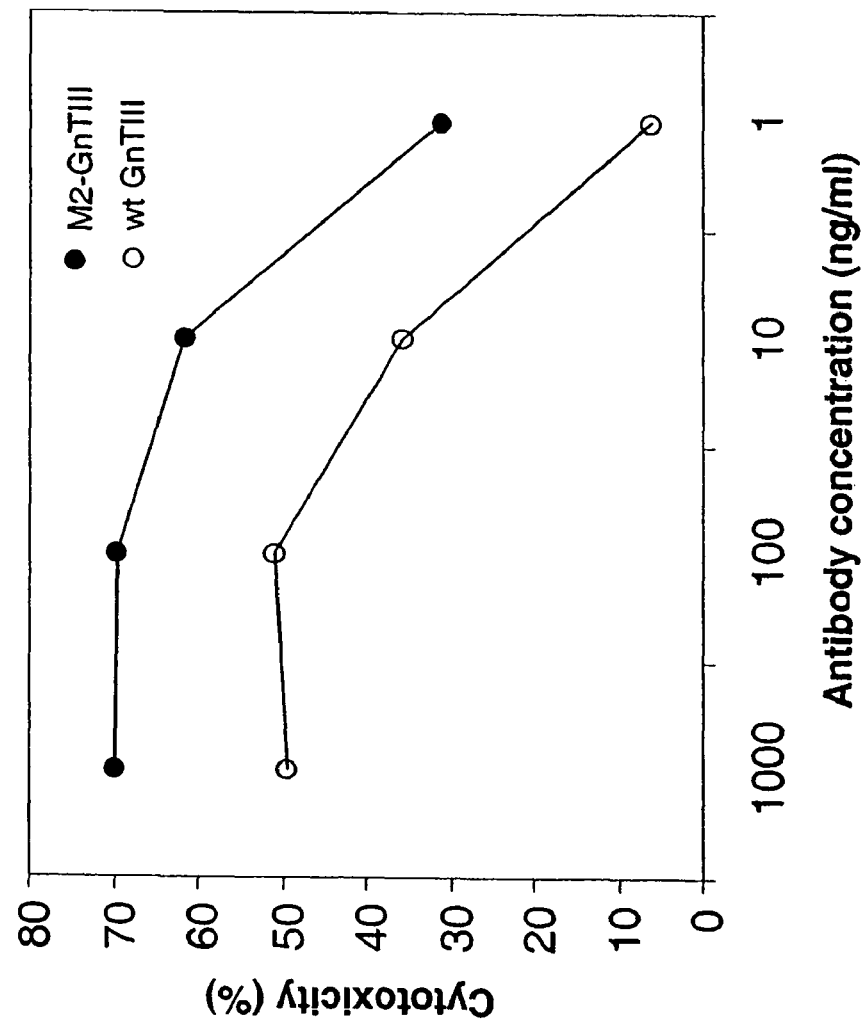
FIG. 11. Antibody-dependent cellular cytotoxicity (ADCC) of "M2-GnTIII"-glycoengineered vs. "wt-GnTIII"-glycoengineered recombinant, anti-CD20 chimeric IgG1 antibodies. Both antibodies were produced in BHK cells. Production and glycosylation profile of the M2-GnTIII-glycoenginereed antibody is depicted in FIG. 4 and those of the wt-GnTIII-glycoengineered antibody in FIG. 2. Target cells (T) were SKW6.4 human lymphoblastoid cells. Effector cells (E) were freshly-isolated human PBMC. An E:T ratio of 25:1 was used in a 4-hour incubation ADCC assay measuring cytotoxicity by lactate dehydrogenase (LDH) release relative to a maximum release (using a detergent instead of antibody) and a spontaneous release (culture medium instead of antibody) controls. Assay details are described in Materials and Methods section of Example 1.

FIGS. 9 to 11 demonstrate increased antibody-dependent cellular cytotoxicity (ADCC) resulting from overexpression in the antibody-producing cells of a nucleic acid encoding a polypeptide with GnTIII activity that is localized to the Golgi via different localization domains. Increased ADCC resulting from expression of recombinant polypeptide with GnTIII activity and localized to the Golgi via the GnTI Golgi localization domain is shown in FIG. 9. The oligosaccharide profile of the control antibody used for the ADCC assay of FIG. 9 is shown in FIG. 1. The oligosaccharide profile of the glycoengineered antibody used for the ADCC assay of FIG. 9 is shown in FIG. 3. Increased ADCC resulting from expression of recombinant polypeptide with GnTIII activity and localized to the Golgi via a glycosidase, ManII, Golgi localization domain is shown in FIG. 10. The oligosaccharide profile of the control antibody used for the ADCC assay of FIG. 10 is shown in FIG. 5. The oligosaccharide profile of the glycoengineered antibody used for the ADCC assay of FIG. 10 is shown in FIG. 6.

FIG. 11 shows that expression of a recombinant polypeptide with GnTIII activity and localized to the Golgi via a ManII Golgi localization domain leads to increased ADCC activity relative to the use of the wild-type GnTIII polypeptide with its own GnTIII Golgi localization domain. The oligosaccharide profile of the antibody glycoengineered by expression of wild-type GnTIII and used for the ADCC assay of FIG. 11, is shown in FIG. 2. The oligosaccharide profile of the glycoengineered by expression of the fusion polypeptide with GnTIII activity, localized to the Golgi via the ManII localization domain, and used for the ADCC assay of FIG. 11, is shown in FIG. 4. These data also show that antibodies with bisected oligosaccharides, including bisected, hybrid and bisected, non-fucosylated oligosaccharides, have increased ADCC activity compared to antibodies with complex, fucosylated, non-bisected oligosaccharides. It should be noted that all of the bisected oligosaccharides of the more active antibody used in the ADCC assay of FIG. 10 are bisected, non-fucosylated hybrid oligosaccharides. As mentioned previously, use of the fusion polypeptide with GnTIII activity and localized to the Golgi via the ManII localization domain leads the more efficient synthesis of the non-fucosylated, bisected oligosaccharides, and FIG. 11 shows that antibodies with increased levels of these bisected, non-fucosylated oligosaccharides are more active in ADCC relative to antibodies with lower levels of these oligosaccharides. The ADCC activity increases correlate with increases in this bisected, non-fucosylated oligosaccharide fraction within the Fc-associated oligosaccharide population, and large increases are seen when this fraction is higher than 15 to 20%.

Figure 12:
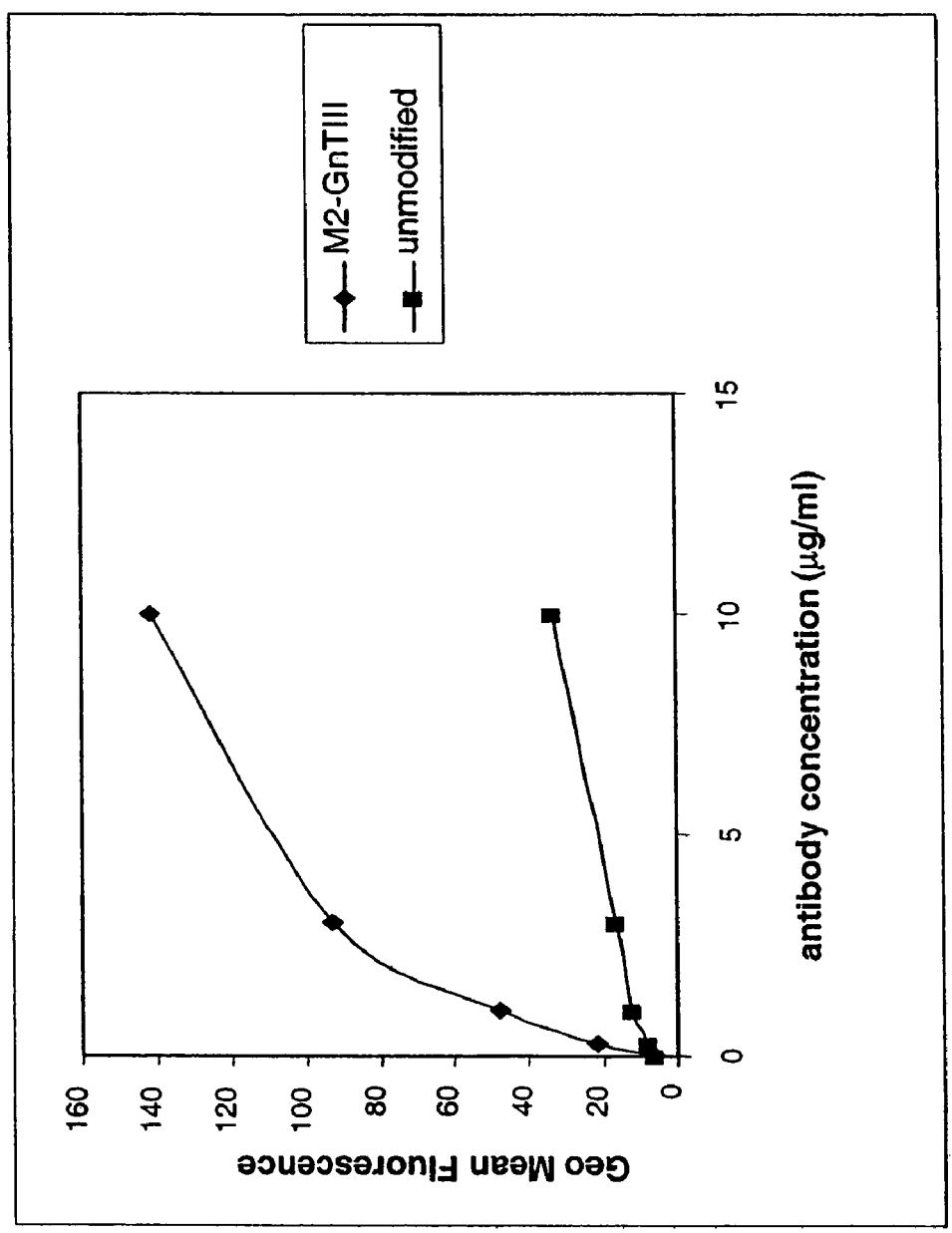
FIG. 12. Binding of "M2-GnTIII"-glycoengineered vs. unmodified recombinant, anti-CD20 chimeric IgG1 antibodies to FcgammaRIIIa receptor on NK cells. Both antibodies were produced in HEK293-EBNA cells. Production and glycosylation profile of the glycoenginereed antibody is depicted in FIG. 6 and those of the unmodified antibody in FIG. 5. The binding assay was performed as described in the Materials and Methods section of Example 1. Human NK cells expressing FcgammaRIIIa receptor on their surface were isolated from a donor of a genotype known not to produce FcgammaRIIc receptor (i.e., homozygous for a gene variant that contains an in-frame stop codon within the FcgammaRIIc coding sequence). Geometric mean fluorescence intensity, measured by FACS using an FITC-labelled anti-human IgG antibody fragment, increases with the amount of recombinant antibody bound to the NK cells. Binding detected in this assay is FcgammaRIIIa-specific as demonstrated by use of a competing FcgammaRIIIa-specific antibody fragment (see FIG. 13).
Figure 13:
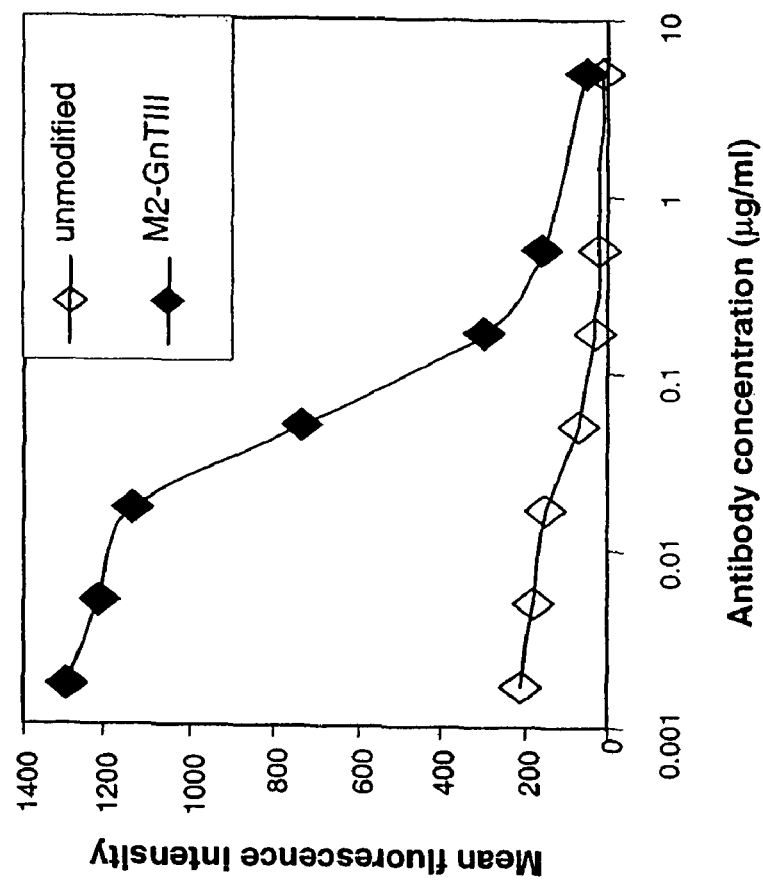
FIG. 13. Binding of "M2-GnTIII"-glycoengineered vs. unmodified recombinant, anti-CD20 chimeric IgG1 antibodies to FcgammaRIIIa receptor on NK cells in the presence of increasing concentrations of a competing anti-FcgammaRIII antibody fragment. Both recombinant antibodies were produced in HEK293-EBNA cells. Production and glycosylation profile of the glycoenginereed antibody is depicted in FIG. 6 and those of the unmodified antibody in FIG. 5. The binding assay was performed as described in the Materials and Methods section of Example 1, but co-incubating the purified NK cells with recombinant antibody (always at a final concentration of 3 µg/ml) and with increasing and varying concentrations (see graph) of competing 3G8-Fab2 anti-FcgammaRIII antibody fragment). Human NK cells expressing FcgammaRIIa receptor on their surface were isolated from a donor of a genotype known not to produce FcgammaRIIc receptor (i.e., homozygous for a gene variant that contains an in-frame stop codon within the FcgammaRIIc coding sequence). Geometric mean fluorescence intensity, measured by FACS using an FITC-labelled anti-human IgG antibody fragment, increases with the amount of recombinant antibody bound to the NK cells.
Figure 14:
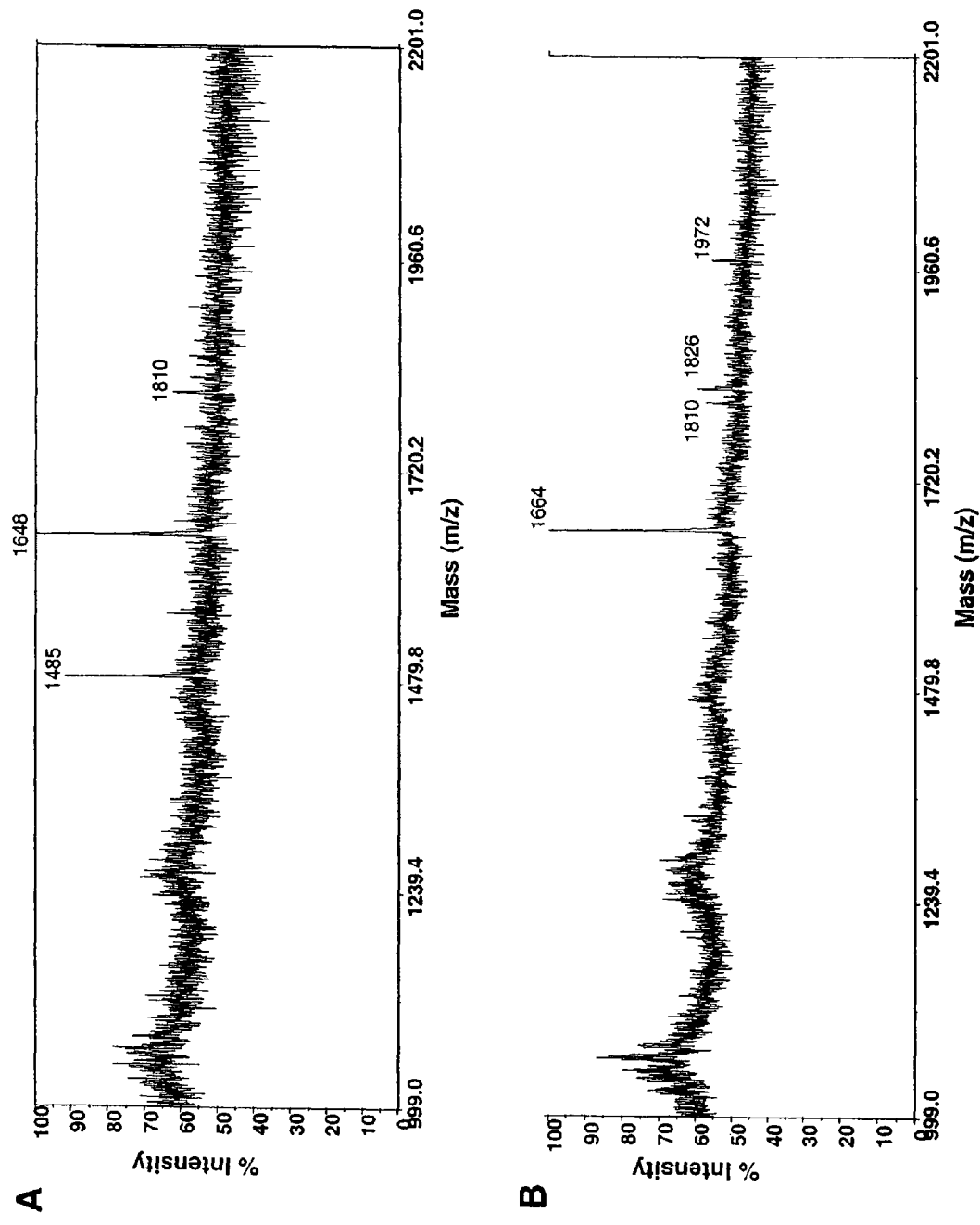
FIG. 14. MALDI/TOF-MS spectra of neutral oligosaccharide mixtures derived from recombinant, IgG1 "L19" antibodies recognizing ED-B+isoform of fibronectin and produced in HEK293-EBNA cells. (a) Unmodified antibody produced in HEK293-EBNA cells transfected with antibody expression vector pETR1546. (b) M2-GnTIII-glycoengineered antibody produced in HEK293-EBNA cells co-transfected with antibody expression vector pETR1546 and GnTIII expression vector pETR1519. Both antibodies were purified from culture medium by protein A affinity chromatography followed by size-exclusion chromatography step on a Superdex200 matrix (Amersham) exchanging the buffer to phosphate buffered saline (PBS). Oligosaccharides were prepared and analyzed as described in the Materials and Methods section of Example 1.

Natural killer (NK) cells are known to be important mediators of ADCC. These cells carry on their surface the activating Fcgamma receptor IIIA, also known as CD16a. Binding of the Fc region, of the target-cell bound antibodies, to FcgammaRIIIA receptors on NK cells is essential for crosslinking of these receptors on the NK cell and subsequent induction of ADCC. Therefore it is important to evaluate the binding of the antibodies produced by the methods described here to Fc receptors, in particular to receptors in the native form in which the human immune effector cells display them. FIG. 12 demonstrates that glycoengineered antibodies produced by expression in the antibody producing cells of a nucleic acid encoding a fusion polypeptide with GnTIII activity have increased binding affinity to the human activating Fc receptor FcgammaRIIIA. As mentioned above for the ADCC assays, these antibodies have increased levels of bisected, non-fucosylated oligosaccharides that result from the expression in the antibody-producing cells of the fusion polypeptide with GnTIII activity. The NK cells used in this assay were from a donor of a genotype that does not express the FcgammaRIIc receptor on their NK cells (Metes, D. et al. *J. Immunol. Methods* 258(1-2):85-95 (2001)). Therefore the only Fc receptor on the surface of these cells is the activating FcgammaRIIIA receptor. FIG. 13 shows that the binding assay measures specific binding affinity to this receptor. This is shown by competition with a FcgammaRIII-specific blocking antibody fragment (3G8 Fab2-fragment).

Strong evidence of the impact of enhanced Fc-FcR interactions on the outcome of anti-tumor antibody therapy comes from the correlation, found in lymphoma patients receiving rituximab, between efficacy and the homozygous higher-affinity FcgammaRIIIA receptor genotype (Cartron, G. et al. *Blood* 99(3):754-8 (2002)). This was the single parameter found to correlate with a vastly enhanced objective response rate and increased proportion of molecular responses. Increased efficacy due to enhanced FcgammaRIIIA-Fc interactions can be derived from the functions carried out by various types of immune cells, including natural killer (NK) cells, macrophages, monocytes and dendritic cells. Crosslinking of the activating FcgammaRIIIA receptor on NK cells, macrophages and monocytes can lead to tumor cell lysis by ADCC (widely believed to be the prime FcR-dependent killing mechanism in vivo)(Maloney, D. G. et al. *Semin. Oncol.* 29(1 Suppl. 2):2-9 (2002), Amigorena S., *J. Exp. Med.* 195(1):F1-3 (2002)) and also to antibody-dependent cellular phagocytosis (Hazenbos, W. L. et al. J. Immunol. 161(6): 3026-32(1998), Reff, M. E. and Heard, C. *Crit Rev Oncol Hematol.* 40(1):25-35(2001)) and to cytokine release in the vicinity of tumor cells (Carson, W. E. et al. *Eur. J. Immunol.* 31:3016-3025(2001)). These cytokines can in turn lead to direct cytotoxic effects on tumor cells, to anti-angiogenic effects which inhibit tumor growth by deprivation of oxygen and nutrients, and to enhanced tumor antigen presentation as part of an active T-cell mediated immune response against tumor cells. Dendritic cells are crucial for antigen presentation to T-cells, and cross-linking of FcgammaRIIIA on their surface (e.g., from antibody-bound, dying tumor cells initially attacked in vivo via ADCC) can lead to enhanced dendritic cell maturation, antigen uptake and presentation to T-cells, and cross-priming of cytotoxic T-cells, the later being a potentially very efficient mechanism to activate anti-tumor immunity (Amigorena S., *J. Exp. Med.* 195(1):F1-3 (2002), Kalergis, A. M. and Ravetch, J. V. *J. Exp. Med.* 195(12):1653-1659(2002), Selenko, N. e. al. *J. Clin. Immunol.* 22(3):124-130(2002)). Cross-linking of target-cell bound antibodies by Fc receptors on immune effector cells can also lead to increased direct killing of the target cells, for example via apoptosis induced by antibody-mediated cross-linking of the target-antigen molecules (Reff, M. E. and Heard, C. *Crit Rev Oncol Hematol.* 40(1):25-35(2001), Cragg, M. S. et al. *Blood* 101(3):1045-1052 (2003)). Of all these immune effector cells, NK cells alone possess only activating FcgammaRs on their surface. In the other types of cells, the activating FcgammaRIII is present together with the inhibitory FcgammaRIIb receptor, and induction of anti-tumor effector functions results from a positive balance of the activating over inhibitory signals.

Figure 15:
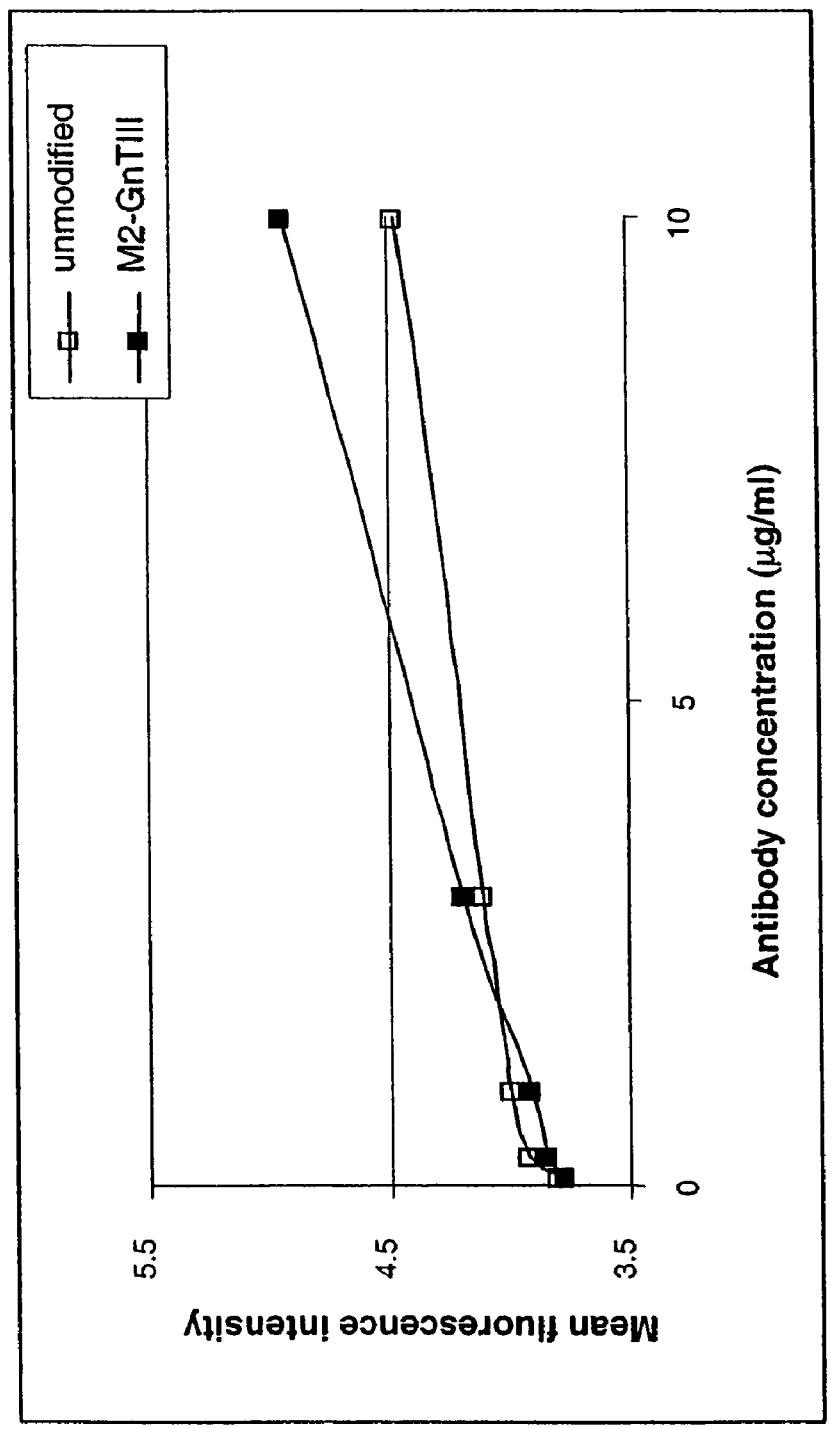
FIG. 15. Binding of "M2-GnTIII"-glycoengineered vs. unmodified recombinant, anti-ED-B+fibronectin IgG1 antibodies to FcgammaRIIb receptor on Raji human lymphoma cells. Both antibodies were produced in HEK293-EBNA cells. Production and glycosylation profile of the glycoenginereed antibody is depicted in FIG. 14b and those of the unmodified antibody in FIG. 14a. The binding assay was performed as described in the Materials and Methods section of Example 1. Geometric mean fluorescence intensity, measured by FACS using an FITC-labelled anti-human IgG antibody fragment, increases with the amount of recombinant antibody bound to the Raji B-cell lymphoma cells.

FIG. 15 shows that the increased Fc receptor binding is selective for the activating receptor compared to the inhibitory FcgammaRIIb. Such selectivity is important for effector functions carried out by immune cells other than NK cells, as explained above. Moreover, the increases in binding achieved by glycoengineering the Fc antibody region, using the methods described here, are far greater than those observed naturally for the homozygous higher-affinity FcgammaRIIIA genotype patients/donors receiving standard, unmodified antibody (FIG. 16) and that have already been associated with increased efficacy of anti-cancer antibodies (Cartron, G. et al. *Blood* 99(3):754-8 (2002)).

The binding domain of the activating FcgammaRIIIB receptor is almost identical to that of the FcgammaRIIIA. Therefore, the above data also indicates that glycoengineered antibodies described here can lead to increased effector functions mediated by effector cells displaying the FcgammaRIIIB, such as polymorphonuclear (PMN) cells, including release of toxic products and phagocytosis ((Reff, M. E. and Heard, C. *Crit Rev Oncol Hematol.* 40(1):25-35 (2001), Daeron, F M. *Annu. Rev. Immunol.* 15:203-34 (1997), Ravetch, J. V. and Bolland S. *Annu. Rev. Immunol.* 19:275-90 (2001)).

Figure 18:
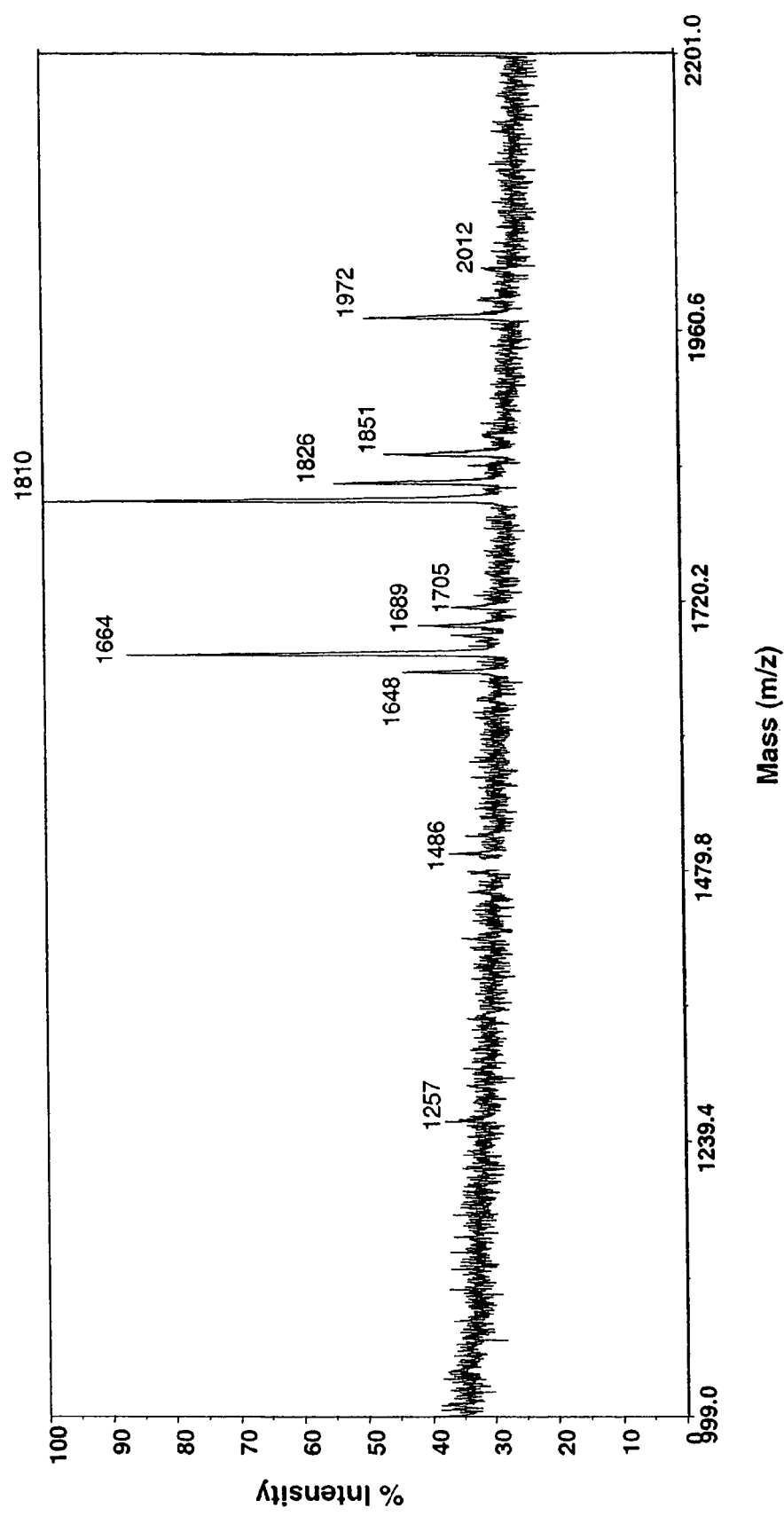
FIG. 18. MALDI/TOF-MS spectrum of neutral oligosaccharide mixture derived from M2-GnTIII-glycoengineered recombinant, anti-CD20 chimeric IgG1 antibody produced by BHK-1502-28-11 cell line. Cell line, antibody purification and oligosaccharide preparation and analysis are described in the Materials and Methods section of Example 1.

FIG. 18 shows the oligosaccharide profile of an anti-CD20 antibody produced from BHK cells growing in suspension and engineered for constitutive, high-level expression of both the recombinant antibody and a fusion polypeptide with GnTIII activity. The oligosaccharide profile shows increased levels of bisected non-fucosylated and bisected hybrid oligosaccharides for the antibody from the cells engineered with the fusion GnTIII (see Table 2 also). These structures are not found in non-glycoengineered antibodies produced by non-glycoengineered BHK cells (see FIG. 1). The engineered cells expressing the GnTII fusion exhibited normal growth in suspension and good antibody productivity.

The relative percentages of the oligosaccharides of the glycoengineered monoclonal antibody produced by the stable BHK-1502-28-11 cell line are presented in Table 2.

TABLE 2

Relative percentages of the peaks obtained by MALDI/TOF-MS.

| | Peak (m/z) | Relative percentage |
|---|---|---|
| 1 | 1257 | 2.5% |
| 2 | 1486 | 2.8% |
| 3 | 1647 | 6% |
| 4 | 1664 | 22.30% |
| 5 | 1680 | 2.5% |
| 6 | 1689 | 4.8% |
| 7 | 1705 | 3% |
| 8 | 1810 | 27.8% |
| 9 | 1826 | 10% |
| 10 | 1851 | 7.5% |
| 11 | 1972 | 9% |
| 12 | 2012 | 1.75% |

Total bisected: 88.6% (4 + 5 + 6 + 7 + 8 + 9 + 10 + 11 + 12)
Total non-fucosylated bisected: 37.8% (4 + 5 + 7 + 9)
Total fucosylated bisected: 50.8% (6 + 8 + 10 + 11 + 12)
Complex bisected: 17% (6 + 7 + 10 + 12)
Hybrid bisected: 71.6% (4 + 5 + 8 + 9 + 11)

Figure 19:
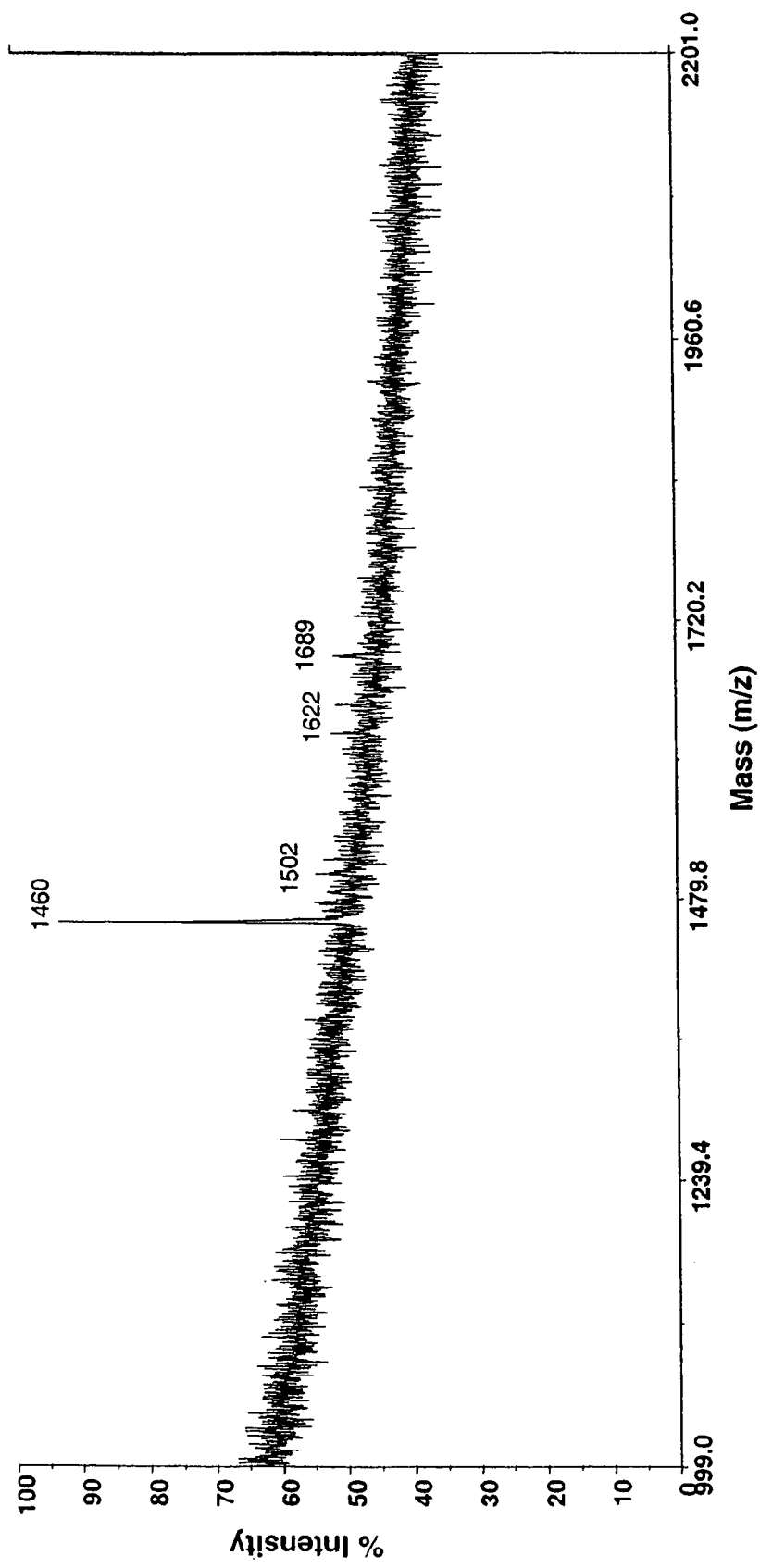
FIG. 19. MALDI/TOF-MS spectrum of neutral oligosaccharide mixture derived, by PNGaseF-release oligosaccharides and further digestion with EndoH, from M2-GnTIII-glycoengineered recombinant, anti-CD20 chimeric IgG1 antibody produced by BHK-1502-28-11 cell line. Cell line, antibody purification and oligosaccharide preparation and analysis are described in the Materials and Methods section of Example 1.
Figure 20:
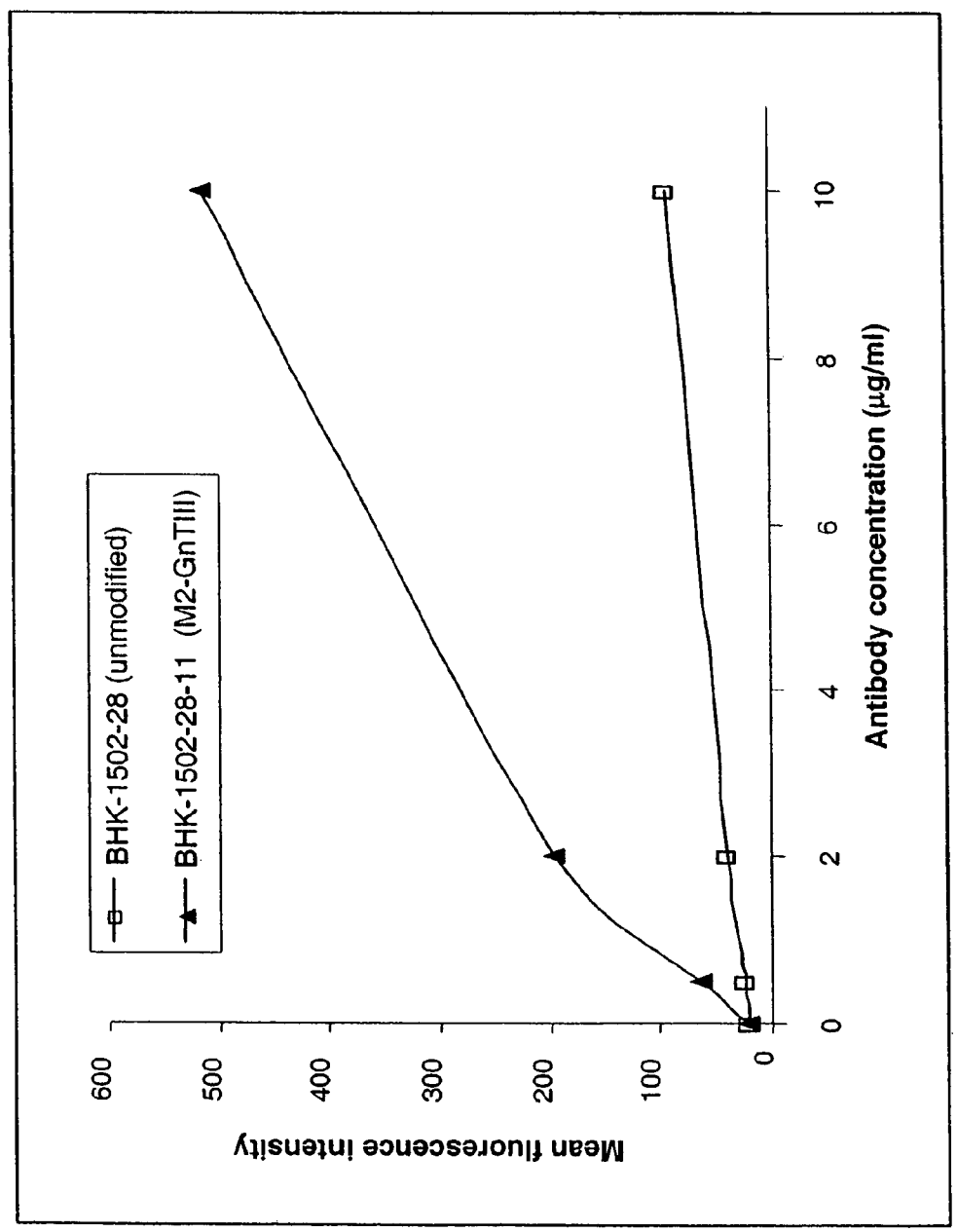
FIG. 20. Binding of "M2-GnTIII"-glycoengineered vs. unmodified recombinant, anti-CD20 chimeric IgG1 antibodies, produced by stable cell lines, to FcgammaRIIIa receptor on NK cells. Glycosylation profile of the glycoenginereed antibody is shown in FIGS. 18 and 19. The binding assay was performed as described in the Materials and Methods section of Example 1. Human NK cells expressing FcgammaRIIIa receptor on their surface were isolated from a donor of a genotype known not to produce FcgammaRIIc receptor (i.e., homozygous for a gene variant that contains an in-frame stop codon within the FcgammaRIIc coding sequence). Geometric mean fluorescence intensity, measured by FACS using an FITC-labelled anti-human IgG antibody fragment, increases with the amount of recombinant antibody bound to the NK cells. Binding detected in this assay is FcgammaRIIIa-specific as demonstrated by use of a competing FcgammaRIIIa-specific antibody fragment (see FIG. 13).

The oligosaccharide analysis showed that 88.6% of the structures carry a bisecting GlcNAc residue 50.8% are fucosylated and 37.8% are non-fucosylated. The digestion of the PNGaseF-released oligosaccharide with EndoglycosidaseH demonstrated that most of the peaks obtained are of the hybrid bisected type (FIG. 19). FIG. 20 shows increased binding affinity of the glycoengineered antibody, produced by the BHK-1502-28-11 cell line, to the activating Fc receptor FcgammaRIIIA on human NK cells. Cell lines growing in suspension and with constitutive stable expression of both the antibody genes and the fusion GnTIII polypeptide are ideal for large-scale production of therapeutic antibodies. Using standard cell engineering methods, the glycoengineering can be implemented either by introducing the fusion GnTIII gene into a cell line containing the antibody genes, or by introducing the antibody genes into a cell line containing the fusion GnTIII gene (a "pre-glycoengineered production cell line"), or by introducing the antibody and GnTIII fusion genes at the same time.

Figure 21:
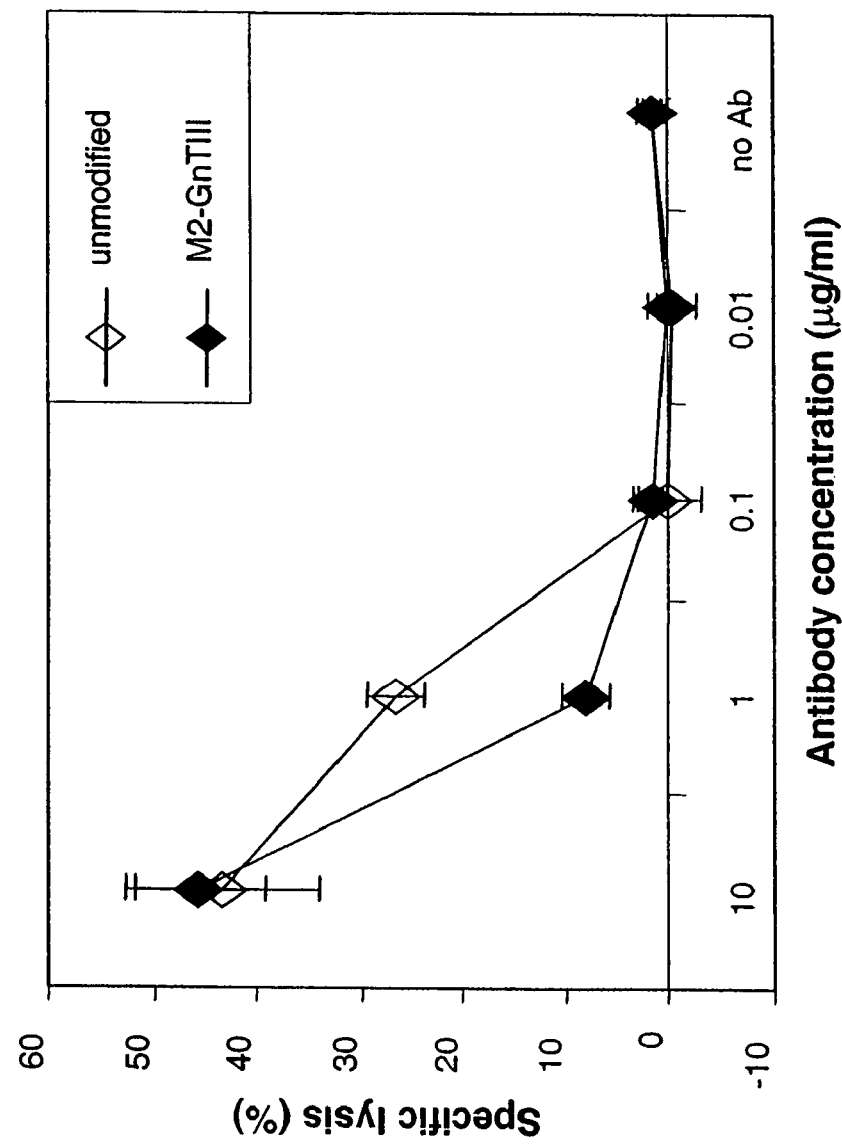
FIG. 21. Complement-mediated lysis (CML) of "M2-GnTIII"-glycoengineered vs. unmodified recombinant, anti-CD20 chimeric IgG1 antibodies. Both antibodies were produced in HEK293-EBNA cells. Production and glycosylation profile of the glycoeninereed antibody is depicted in FIG. 6 and those of the unmodified antibody in FIG. 5. Target cells (T) were SKW6.4 human lymphoblastoid cells. Human complement was used for the assay. Lysis was measured by LDH release. Assay details are described in Materials and Methods section of Example 1.

An anti-CD20 antibody produced in cells engineered for high level expression of the nucleic acid encoding a fusion polypeptide with GnTIII activity and localized to the Golgi via the ManII localization domain was tested also for complement mediated lysis (CML), a different effector function that is not dependent on Fc receptors on immune effector cells. The vast majority of the oligosaccharides of this glycoengineered antibody were of bisected hybrid non-fucosylated type. Reduced CML activity was observed for this anti-CD20 antibody compared to the unmodified antibody (FIG. 21). For some applications antibodies with increased ADCC but with reduced CML may be desirable, for example to reduce side effects, such as vasculitis in the blood vessels at the tumor site, mediated by CML. Other significant CML-mediated side-effects have been observed for anti-CD20 antibody therapy (van der Kolk L. E. et al. *Br J Haematol.* 115 (4):807-11 (2001)). However, the oligosaccharide profiles above also show that is also possible to engineer the antibody producing cells to express the GnTIII fusion polypeptide at an intermediate expression level that leads to intermediate levels of bisected hybrid non-fucosylated oligosaccharides (higher than 15%), but with a significant fraction of complex oligosaccharides within the Fc oligosaccharide population of the glycoengineered antibody. Such complex oligosaccharides are associated with normal, not reduced, levels of CML. Therefore the data indicates that antibodies with increased ADCC can be produced in this way which should maintain very similar levels of CML activity compared to non-engineered antibodies.

Figure 22:
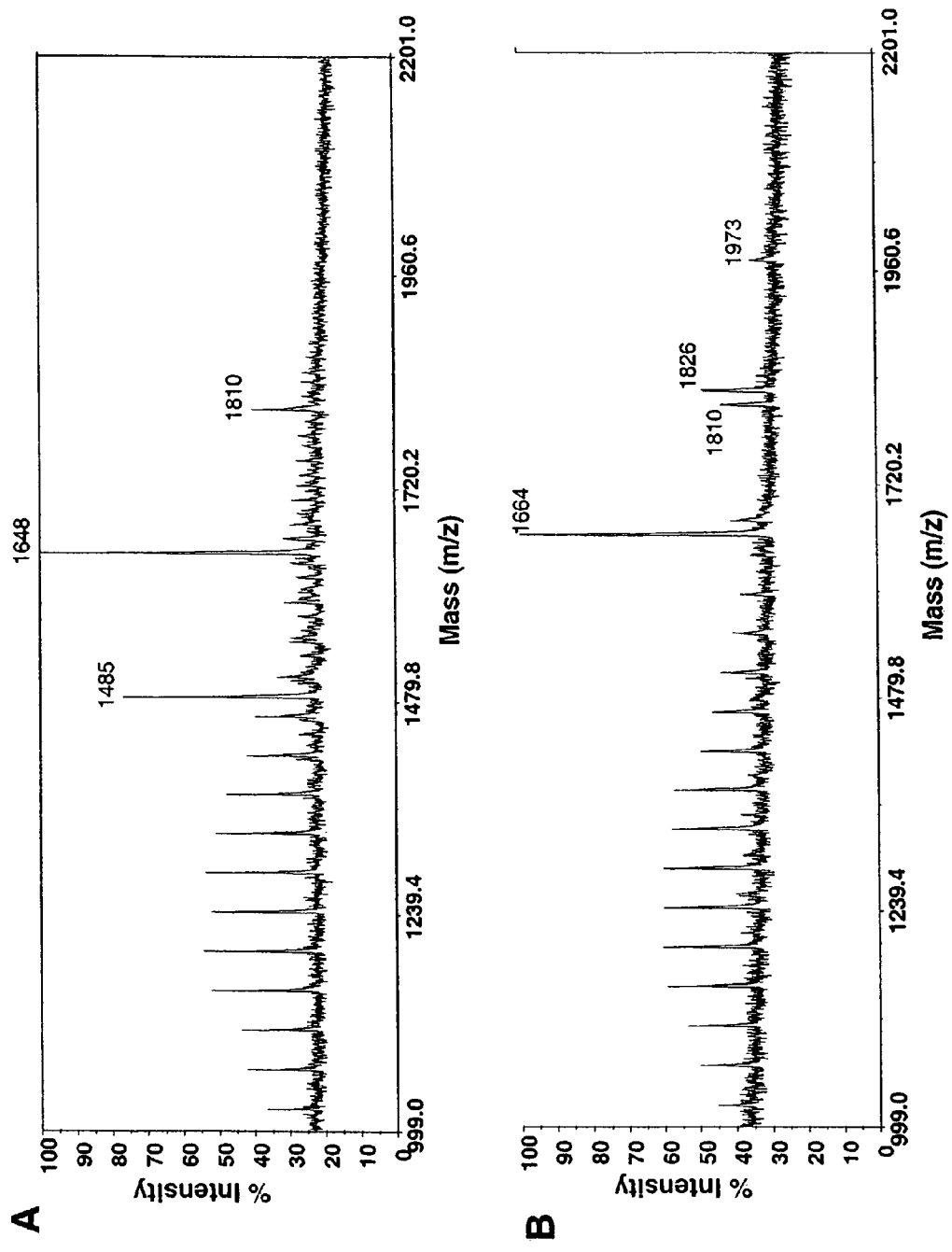
FIG. 22. MALDI/TOF-MS spectra of neutral oligosaccharide mixtures derived from recombinant, chimeric IgG1 "C225" antibodies, recognizing human epidermal growth factor receptor (EGFR), and produced in HEK293-EBNA cells. (a) Unmodified antibody produced in HEK293-EBNA cells transfected with antibody expression vector pURSI28. (b) M2-GnTIII-glycoengineered antibody produced in HEK293-EBNA cells co-transfected with antibody expression vector pETRURSI28 and GnTIII expression vector pETR1519. Both antibodies were purified from culture medium by protein A affinity chromatography followed by size-exclusion chromatography step on a Superdex200 matrix (Amersham) exchanging the buffer to phosphate buffered saline (PBS). Oligosaccharides were prepared and analyzed as described in the Materials and Methods section of Example 1.
Figure 23:
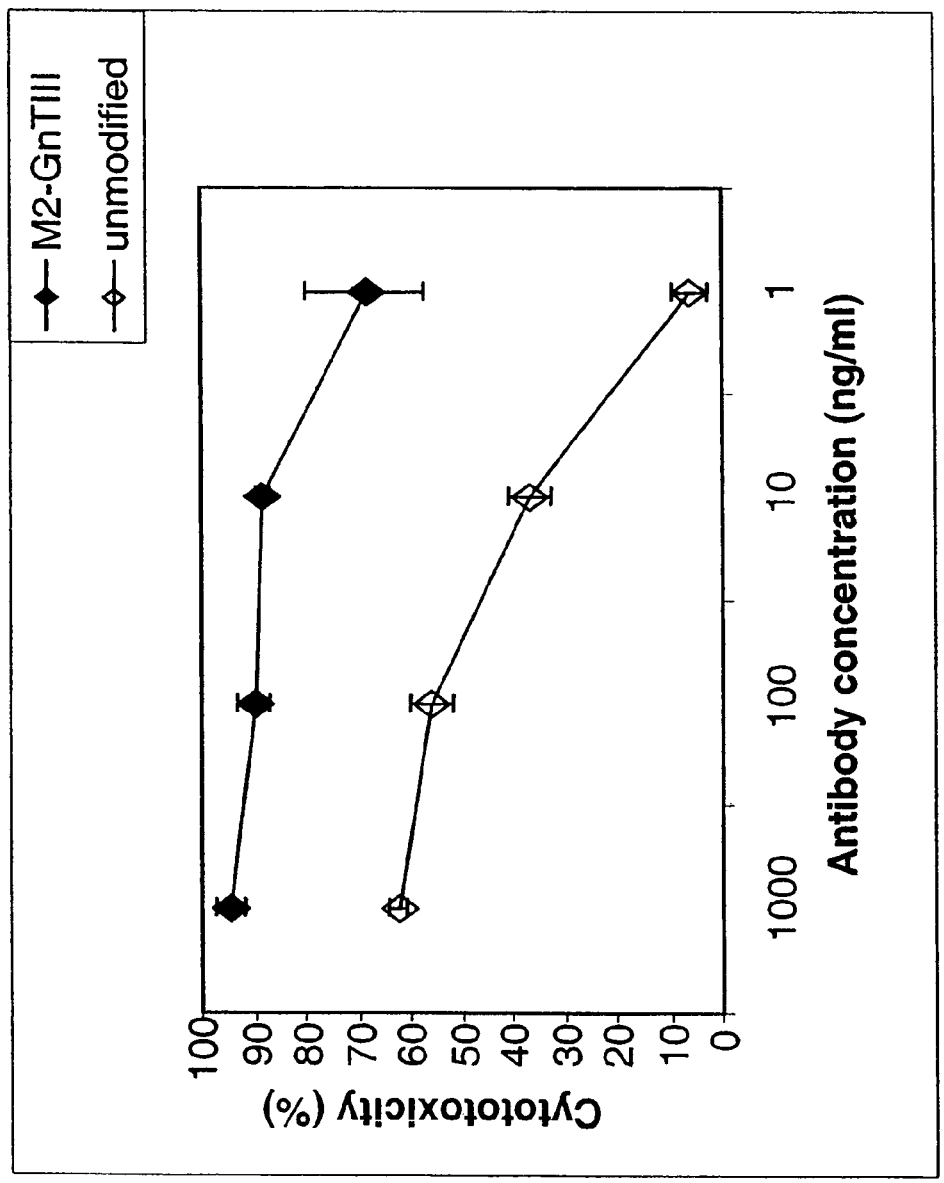
FIG. 23. Antibody-dependent cellular cytotoxicity (ADCC) of "M2-GnTIII"-glycoengineered vs. unmodified recombinant, anti-EGFR chimeric IgG1 "C225" antibodies. Both antibodies were produced in HEK293-EBNA cells. Production and glycosylation profile of the glycoenginereed antibody is depicted in FIG. 22b and those of the unmodified antibody in FIG. 22a. Target cells (T) were A431 human squamous carcinoma cells (ECACC No. 85090402). Effector cells (E) were freshly-isolated human PBMC. An E:T ratio of 25:1 was used in a 4-hour incubation ADCC assay measuring cytotoxicity by lactate dehydrogenase (LDH) release relative to a maximum release (using a detergent instead of antibody) and a spontaneous release (culture medium instead of antibody) controls. Assay details are described in Materials and Methods section of Example 1.

A second chimeric IgG1 antibody, C225, also known as cetuximab, that recognizes the human epidermal growth factor receptor (EGFR) was glycoengineered by the methods described here. FIG. 22 shows the oligosaccharide profiles of the unmodified anti-EGFR antibody C225 and of the glycoengineered version of the same antibody. The later was produced in cells expressing a nucleic acid encoding a fusion polypeptide with GnTIII activity and localized to the Golgi via a ManII localization domain. FIG. 23 shows increased ADCC of the anti-EGFR antibody resulting from this glycoengineering. Glycoengineered antibodies produced by the methods described here, and having increased ADCC and increased binding affinity to activating Fc receptors, are promising molecules for antibody therapy of cancer and of auto-immune diseases, since they should lead to increased efficacy, relative to the corresponding unmodified (non-glycoengineered) version of those antibodies, for these therapies. Additionally it should be possible to reduce the therapeutic doses for the glycoengineered antibodies compared to the unmodified ones, and this would positively impact the economics of antibody production.

Example 2

Treatment of Immune-Mediated Thrombocytopenia in a Patient with Chronic Graft-Versus-Host Disease Autoimmune thrombocytopenia in chronic graft-versus-host disease represents an instance of B-cell dysregulation leading to clinical disease. To treat immune-mediated thrombocytopenia in a subject with chronic graft-versus-host disease, an anti-CD20 chimeric monoclonal antibody prepared by the methods of the present invention and having increased ADCC is administered to the subject as described in Ratanatharathorn, V. et al., *Ann. Intern. Med.* 133(4):275-79 (2000) (the entire contents of which is hereby incorporated by reference). Specifically, a weekly infusion of the antibody, 375 mg/m$^2$ is administered to the subject for 4 weeks. The antibody therapy produces a marked depletion of B cells in the peripheral blood and decreased levels of platelet-associated antibody.

Example 3

Treatment of Severe, Immune-Mediated, Pure Red Cell Aplasia and Hemolytic Anemia Immune-mediated, acquired pure red cell aplasia (PRCA) is a rare disorder frequently associated with other autoimmune phenomena. To treat immune-mediated, acquired pure red cell aplasia in a subject, an anti-CD20 chimeric monoclonal antibody prepared by the methods of the present invention and having increased ADCC is administered to the subject as described in Zecca, M. et al., *Blood* 12:3995-97 (1997) (the entire contents of which are hereby incorporated by reference). Specifically, a subject with PRCA and autoimmune hemolytic anemia is given two doses of antibody, 375 mg/m$^2$, per week. After antibody therapy, substitutive treatment with intravenous immunoglobulin is initiated. This treatment produces a marked depletion of B cells and a significant rise in reticulocyte count accompanied by increased hemoglobin levels.

Example 4

Materials and Methods

1. Construction of GalT-Fusion Expression Vectors
Vector for Constitutive Expression of GalT
For construction of the GalT expression vector, GalT cDNA is amplified from a cDNA library (Clontech) by PCR. A C-terminal c-myc-epitope tag is added immediately upstream of the stop codon of the gene (amino acid sequence: PEQKLISEEDL) for later, convenient detection of GalT by Western Blots. After confirmation of the correct sequence of GalT the gene is inserted under control of the MPSV promoter and a synthetic rabbit beta-globin polyadenylation signal is added. The final GalT expression vector also contains a separate puromycin resistance cassette for selection, with the puromycin resistance gene also under the control of the MPSV promoter and synthetic rabbit beta-globin polyadenylation signal.
Replacement of Amino Acids Encoding the Localization Domain of GalT with the Amino Acids Encoding the Localization Domain of the Human GnTI.
The construction of this hybrid galactosyltransferase gene is performed, for example, by overlapping PCR reactions, resulting in the plasmid containing the GnTI-GalT fusion under control of the MPSV promoter and a puromycin resistance cassette for selection.
Replacement of the Amino Acids Encoding the Localization Domain of GalT with the Amino Acids Encoding the Localization Domain of Human Mannosidase II.
The construction of the GalT expression vector is performed. The resulting plasmid contains the hybrid manII-GalT gene under control of the MPSV promoter.
Combination of the Hybrid manII-GalT Fusion Gene with the Replication Origin oriP from Epstein Barr virus.

A DNA fragment with oriP is subcloned as described in Example 1 into the hybrid ManII-GalT expression vector described above.
Combination of the Hybrid manII-GalT Fusion Gene and a Truncated CD4 cell-Surface Marker Gene
The expression vector is modified for additional expression of a truncated CD4 cell-surface marker gene. Briefly, the hybrid manII-GalT fusion gene expression cassette is converted from a monocistronic to a bicistronic expression cassette by inserting, downstream of the stop codon of the manII-GalT fusion, a polio virus IRES element followed by a cDNA encoding a truncated human CD4 protein (comprising the human CD4 leader sequence for secretion followed by the transmembrane and extracellular domains).
3. Transfection of Mammalian Cells with GalT-Fusion- and Antibody-Expression Vectors
Transfection of BHK Cells
Exponentially growing cells (viability 90-95%) are cultured, harvested and subsequently transfected as described in Example 1. For the production of the glycoengineered antibodies, the cells are co-transfected with two plasmids, one for antibody expression and the other for fusion GalT polypeptide expression, at a ratio of 3:1, respectively.
Transfection of HEK293-EBNA Cells
Exponentially growing HEK293-EBNA cells are transfected as described in Example 1. For the production of the glycoengineered antibodies, the cells are co-transfected with two plasmids, one for antibody expression and the other of fusion GalT polypeptide expression, at a ratio of 4:1, respectively. At day 5 post-transfection, supernatant is harvested, centrifuged for 5 min at 1200 rpm, followed by a second centrifugation for 10 min at 4000 rpm and kept at 4° C.
Generation of a Stable Mammalian Cell Line Expressing a Recombinant Anti-CD20 Antibody and a GalT-Fusion
The clone BHK-1502-28, constitutively expressing anti-CD20 monoclonal antibody genes and the neomycin resistance gene, is transfected with the expression vector by electroporation. The vector allows for constitutive expression of the ManII-GalT gene and a truncated form of human CD4, the latter IRES-dependently expressed. The vector also contains a puromycin-resistance gene expression cassette. Puromycin-resistant clones are first selected to obtain a set of clones that chromosomally integrated the vector DNA. Clones are then screened for surface expression of truncated CD4 (tCD4), which serves as a marker for expression level of the bicistronic ManII-GalT+tCD4 gene expression unit. Recombinant antibody production of the selected clones is verified using an ELISA assay.
Transfection and subsequent screening of tCD4 expression level is carried out as described in Example 1.
4. Production and Purification of Unmodified and Glycoengineered Antibodies
In the case of BHK cells transfected with an antibody expression vector or co-transfected with an antibody expression vector plus a GalT-fusion expression vector, the culture supernatant is harvested after culturing the transfected cells for 96 h post transfection. Depending on the expected productivity, several electroporations (10-15) are done for the same vector.
In the case of HEK293-EBNA cells transfected with an antibody expression vector or co-transfected with an expression vector plus a GalT-fusion expression vector, the culture medium is replaced by fresh culture medium approximately 16 hours post-transfection and the later medium is then harvested after culturing the transfected cells for a further 120 hours.

For the stable BHK-1502-28-11 cell line, a culture is seeded at 500,000 cells/ml and supernatant harvested after 4 days of culture.

Antibody Purification

Monoclonal antibody is purified from culture supernatant using two sequential chromatographic steps, Protein A chromatography and cation exchange chromatography as described in Example 1.

5. Oligosaccharide Analysis

Oligosaccharides are enzymatically released from the antibodies by PNGaseF digestion, with the antibodies being either immobilized on a PVDF membrane or in solution.

The resulting digest solution containing the released oligosaccharides are either prepared directly for MALDI/TOF-MS analysis or are further digested with EndoH glycosidase prior to sample preparation for MALDI/TOF-MS analysis. The oligosaccharide release method for PVDF membrane-immobilized antibodies and the oligosaccharide release method for antibodies in solution are carried out as described in Example 1.

Use of Endoglycosidase H Digestion of PNGaseF-Released Oligosaccharides for the Assignment of Hybrid Galactosylated Oligosaccharide Structures to MALDI/TOF-MS Neutral Oligosaccharide Peaks The PNGase released oligosaccharides are subsequently digested with Endoglycosidase H (EC 3.2.1.96) as described in Example 1.

MALDI/TOF-MS

Samples containing the enzymatic digests containing the released oligosaccharides are prepared for and subsequently run on a MALDI/TOF mass spectrometer as described in Example 1.

6. Cell Preparation and Isolation

Peripheral blood mononuclear cells (PBMC) are prepared using Histopaque-1077 (Sigma Diagnostics Inc., St. Louis, Mo. 63178 USA) following essentially the manufacturer's instructions and the protocol described in Example 1.

Human NK cells are isolated from PBMC applying a negative selection procedure as described in Example 1.

8. ADCC Assay

PBMC or NK as effector cells are prepared as described above and assayed for their ability to mediate cytotoxicity in an Antibody Dependent Cellular Cytotoxicity (ADCC) Assay as described in Example 1.

9. FcgammaRIIIA Binding on NK Cells and FcgammaRIIb Binding on Raji Lymphoma Cells The binding of FcgammaRIIIA on freshly isolated NK cells and the binding of FcgammaRIIb on Raji lymphoma cells is determined as described in Example 1.

10. Complement Dependent Cytotoxicity Assay

Complement dependent cytotoxicity assays are performed using antibody dilutions according to the method described in Example 1.

Results and Discussion

Assays are carried out in order to demonstrate the impact of the expression of genes encoding polypeptides with GalT activity on cell viability, cell growth or antibody production, relative to cells not producing such polypeptides.

The purified antibodies are analyzed for their glycosylation patterns by MALDI/TOF-MS as described in Example 1. Using this technique, it is possible to determine the fraction of different oligosaccharide species within the total, original Fc-oligosaccharide population, and it is also possible to assign structures to different peaks in the spectra (Umana, P. et al., Nature Biotechnol. 17:176-180(1999)).

The unmodified antibody oligosaccharide profile is determined. Specifically, it is determined if the engineering of the antibody producing cells by expression of wild-type GalT leads mainly to galactosylated, core-fucosylated, complex biantennary oligosaccharides. It is also determined if the engineering of the antibody-producing cells by expression of a nucleic acid encoding a GnTI-GalT fusion polypeptide, where the GalT catalytic domain is localized via the GnTI Golgi localization domain, leads mainly to galactosylated complex biantennary oligosaccharides relative to the wild-type GalT. If galactosylated, non-fucosylated and galactosylated, hybrid structures are synthesized, these may result from the competition between GalT and other glycosyltransferases or glycosidases. It is expected that once an oligosaccharide is modified with a galactose added via a GalT-catalyzed reaction, al α1,6-core fucosyltransferase, Golgi α-mannosidase II (ManII) and GnTII can no longer act to modify the galactosylated oligosaccharides.

EndoH glycosidase digestion, which can distinguish between hybrid and complex oligosaccharides is used evaluate the proportion of Fc-attached galactosylated, non-fucosylated and galactosylated, hybrid oligosaccharides.

Tests are carried out to determine if the engineering of the antibody-producing cells by expression of a nucleic acid encoding a ManII-GalT fusion polypeptide, where the GalT catalytic domain is localized via the ManII Golgi localization domain, leads mainly to galactosylated, non-fucosylated and galactosylated, hybrid. Specifically, it is determined whether, relative to the wild-type GalT and to the GnTI-GalT fusion, the ManII-GalT fusion is more efficient in the synthesis of Fc-attached galactosylated, non-fucosylated and galactosylated, hybrid oligosaccharides.

As mentioned above, endoglycosidase H (EndoH) is used to confirm the assignment of galactosylated non-fucosylated and galactosylated, hybrid structures to the different oligosaccharide peaks observed in the MALDI profiles. Of the oligosaccharide galactose residues that carry a galactose residue, the percentages of those structures that are non-fucosylated hybrid structures, fucosylated hybrid and fucosylated complex oligosaccharide structures are determined.

The impact of the level of GalT expression and the particular localization domain that is used to target the GalT catalytic domain to the Golgi, on the competition for GnTI-modified oligosaccharide substrates between the recombinant GalT-catalytic domain and the endogenous core □1,6-fucosyl-transferase, ManII and GnTII enzymes is determined. The level of antibody-dependent cellular cytotoxicity (ADCC) resulting from overexpression in the antibody-producing cells of a nucleic acid encoding a polypeptide with GalT activity that is localized to the Golgi via different localization domains is determined.

It is also determined whether glycoengineered antibodies produced by expression in the antibody producing cells of a nucleic acid encoding a fusion polypeptide with GalT activity have increased binding affinity to the human activating Fc receptor FcgammaRIIIA or for the inhibitory FcgammaRIIb.

The GalT constructs will outcompete the activity of the endogenous core □1,6-fucosyltransferase, glycoengineering the Fc region of an antibody and, consequently, increasing ADCC.

The oligosaccharide profile of an anti-CD20 antibody produced from BHK cells growing in suspension and engineered for constitutive, high-level expression of both the recombinant antibody and a fusion polypeptide with GalT activity is determined. The relative percentages of the oligosaccharides of the glycoengineered monoclonal antibody produced by the stable BHK-1502-28-11 cell line are also determined.

Example 5

Materials and Methods

1. Construction of ManII and GnTII Expression Vectors

For construction of the ManII expression vector, a human mannosidase II (SEQ ID NO:17) cDNA was subcloned into an expression vector plasmid downstream of the MPSV promoter and upstream of a synthetic rabbit beta-globin polyadenylation signal. For the GnTII expression, an expression vector plasmid is used with the human GnTII cDNA subcloned downstream of the human CMV promoter/enhancer and upstream of a bovine growth hormone polyadenylation signal.

Combination of the Expression Vectors with the Replication Origin oriP from Epstein Barr Virus.

A DNA fragment with oriP was subcloned as described in Example 1 into the ManII expression vector described above to give ManII expression vector pCLF9. A DNA fragment with oriP is subcloned as described in Example 1 into the GnTII expression vector described above to give GnTII expression vector pGnTII.

2. Transfection of HEK293-EBNA Cells

Exponentially growing HEK293-EBNA cells were transfected as described in Example 1. For the production of unmodified antibody "Cwt", the cells were transfected with antibody expression vector (pETR1520). For the production of the glycoengineered antibody "Cbrt", the cells were co-transfected with two plasmids, one for antibody expression (pETR1520) and another for fusion GnTIII polypeptide expression (PETR1519) at a ratio of 4:1, respectively. For the production of the glycoengineered antibody "Cm", the cells were co-transfected with three plasmids, one for antibody expression (PETR1520), one for fusion GnTIII polypeptide expression (PETR1519), and one for mannosidase II expression (pCLF9) at a ratio of 3:1:1, respectively. For the production of the glycoengineered antibody "Cmg", the cells are co-transfected with four plasmids, one for antibody expression (pETR1520), one for fusion GnTIII polypeptide expression (pETR1519), one for mannosidase II expression (pCLF9), and one for GnTII expression (pGnTII) at a ratio of 4:0.33:0.33:0.33, respectively.

3. Production and Purification of Unmodified and Glycoengineered Antibodies

The culture medium of the transfected cells above was replaced by fresh culture medium approximately 16 hours post-transfection and the later medium was then harvested after culturing the transfected cells for a further 120 hours. Harvested supernatants were centrifuged for 5 min at 1200 rpm, followed by a second centrifugation for 10 min at 4000 rpm and kept at 4° C.

Antibody Purification

Monoclonal antibodies were purified from culture supernatants using two sequential chromatographic steps, Protein A chromatography and cation exchange chromatography as described in Example 1. For antibodies cwt7, cbrt5, and cm1, an additional size exclusion chromatography step using a Superdex 200 column (Amersham Pharmacia) and phosphate buffer saline was added after the cation exchange step, and the monomeric antibody peak was collected.

4. Oligosaccharide Analysis

Oligosaccharides were enzymatically released from the antibodies in solution by PNGaseF digestion as described in Example 1.

Use of Endoglycosidase H Digestion of PNGaseF-Released Oligosaccharides for the Assignment of Hybrid Bisected Oligosaccharide Structures to MALDI/TOF-MS Neutral Oligosaccharide Peaks The PNGase released oligosaccharides were subsequently digested with Endoglycosidase H (EC 3.2.1.96) as described in Example 1.

MALDI/TOF-MS

Samples containing the enzymatic digests containing the released oligosaccharides were prepared for and subsequently ran on a MALDI/TOF mass spectrometer as described in Example 1.

5. Cell Preparation and Isolation

Peripheral blood mononuclear cells (PBMC) were prepared using Histopaque-1077 (Sigma Diagnostics Inc., St. Louis, Mo. 63178 USA) following essentially the manufacturer's instructions and the protocol described in Example 1.

6. NK Cell Isolation

Human NK cells were isolated from PBMC applying a negative selection procedure as described in Example 1.

7. ADCC Assay

PBMC as effector cells were prepared as described above and assayed for their ability to mediate cytotoxicity in an Antibody Dependent Cellular Cytotoxicity (ADCC) Assay as described in Example 1.

8. FcgammaRIIIA Binding on NK Cells

The binding of FcgammaRIIIA on freshly isolated NK cells and the binding of FcgammaRIIb was determined as described in Example 1.

9. Complement Dependent Cytotoxicity Assay

Complement dependent cytotoxicity assays were performed using antibody dilutions according to the method described in Example 1, with the following modification for the preparation of the human complement source. Briefly, normal human serum (NHS) was prepared from blood of healthy volunteers. The blood was allowed to clot for one hour and then centrifuged at 1200 g for 20 min. The cell-free supernatant serum was aliquoted and stored at −80° C. NHS was used at 20% of final assay volume.

Results and Discussion

Glycoengineered versions of an anti-CD20 chimeric IgG1 antibody (C2B8 chimeric antibody, also known as rituximab) were produced by co-transfecting cultures of mammalian cells with vectors for expression of antibody genes and with vectors for expression of genes encoding polypeptides with GnTIII activity and mannosidaseII. An additional glycoengineered antibody version is also made by co-transfecting cultures of mammalian cells with vectors for expression of antibody genes and with vectors for expression of genes encoding polypeptides with GnTIII activity, mannosidaseII activity, and GnTII activity. For glycoengineered antibody "Cbrt", cells were co-transfected with two plasmids, one for antibody expression (pETR1520), one for fusion GnTIII polypeptide expression (pETR1519). For glycoengineered antibody "Cm", cells were co-transfected with three plasmids, one for antibody expression (pETR1520), one for fusion GnTIII polypeptide expression (pETR1519), and one for mannosidase II expression (pCLF9). For glycoengineered antibody "Cmg", cells are co-transfected with four plasmids, one for antibody expression (PETR1520), one for fusion GnTIII polypeptide expression (PETR1519), one for mannosidase II expression (pCLF9), and one for GnTII expression (pGnTII) at. An unmodified (non-glycoengineered) version of the same antibody, "Cwt" was produced by transfecting mammalian cells only with the vector for antibody gene expression. The transfected cells were kept in culture for five days and the secreted, recombinant antibodies were purified from the culture medium. Expression of genes encoding polypeptides with GnTIII and ManII activity did not have any significant effect on cell viability, cell growth or antibody production, relative to cells not producing such glycosyltransferase or glycosidase polypeptides.

The purified antibodies were then analyzed for their glycosylation patterns. These antibodies carry N-linked oligosaccharides attached only to Asn297 residue of the human IgG1 Fc region. The oligosaccharides were enzymatically removed from antibodies by PNGaseF digestion and were subsequently analyzed by MALDI/TOF-MS. Using this technique, it is possible to determine the fraction of different oligosaccharide species within the total, original Fc-oligosaccharide population, and it is also possible to assign structures to different peaks in the spectra (Umana, P. et al., *Nature Biotechnol.* 17:176-180(1999)).

Figure 26:
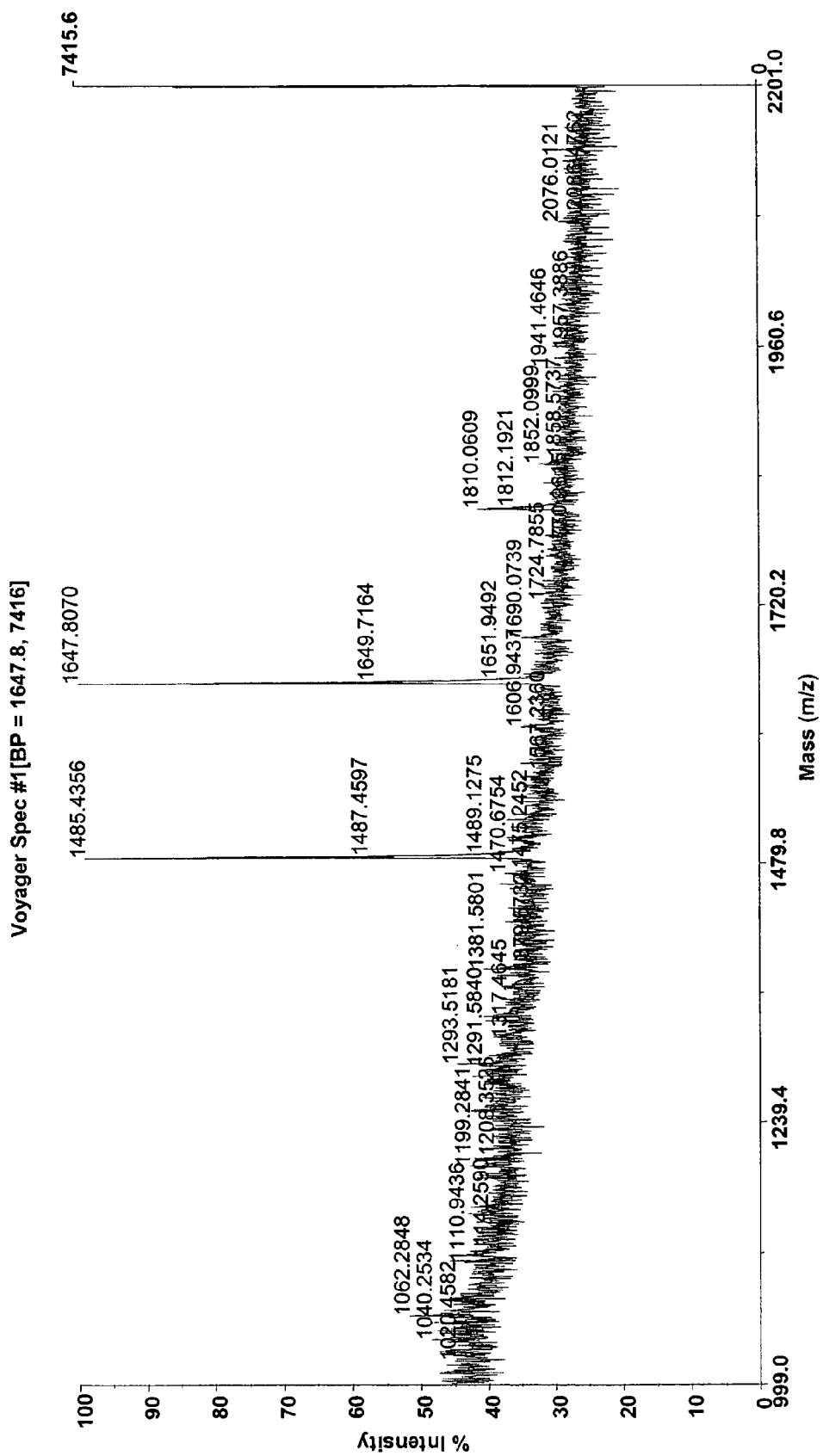
FIG. 26. MALDI/TOF-MS spectrum of neutral oligosaccharide mix from the unmodified, recombinant C2B8 anti-CD20 chimeric IgG1 antibody ("Cwt") produced in HEK293-EBNA cells transfected with antibody expression vector pETR1520. Antibody was purified from culture medium and oligosaccharides were prepared and analyzed as described in the Materials and Methods section of Example 5.
Figure 27A:
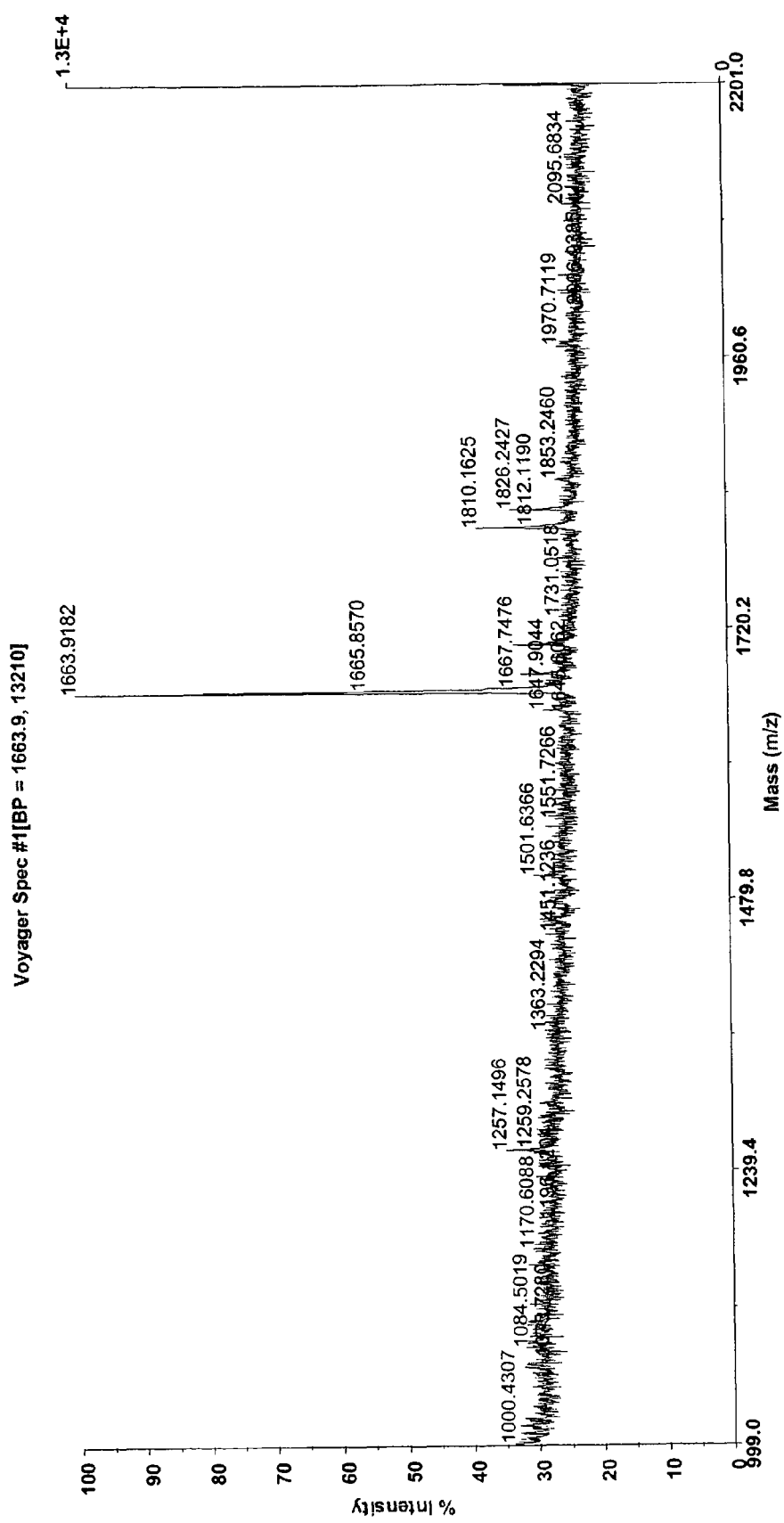
FIG. 27. MALDI/TOF-MS spectrum of neutral oligosaccharide mix derived from recombinant, glycoengineered C2B8 anti-CD20 chimeric IgG1 antibody ("Cbrt") produced in HEK293-EBNA cells co-transfected with antibody expression vector pETR1520 and fusion GnTIII polypeptide expression vector (PETR1519). Antibody was purified from culture medium and oligosaccharides were prepared and analyzed as described in the Materials and Methods section of Example 5. (A) Oligosaccharide profile of PNGaseF-release oligosaccharides with no additional enzymatic treatment. (B) Oligosaccharide profile of PNGaseF-release oligosaccharides further digested with EndoH.
Figure 27B:
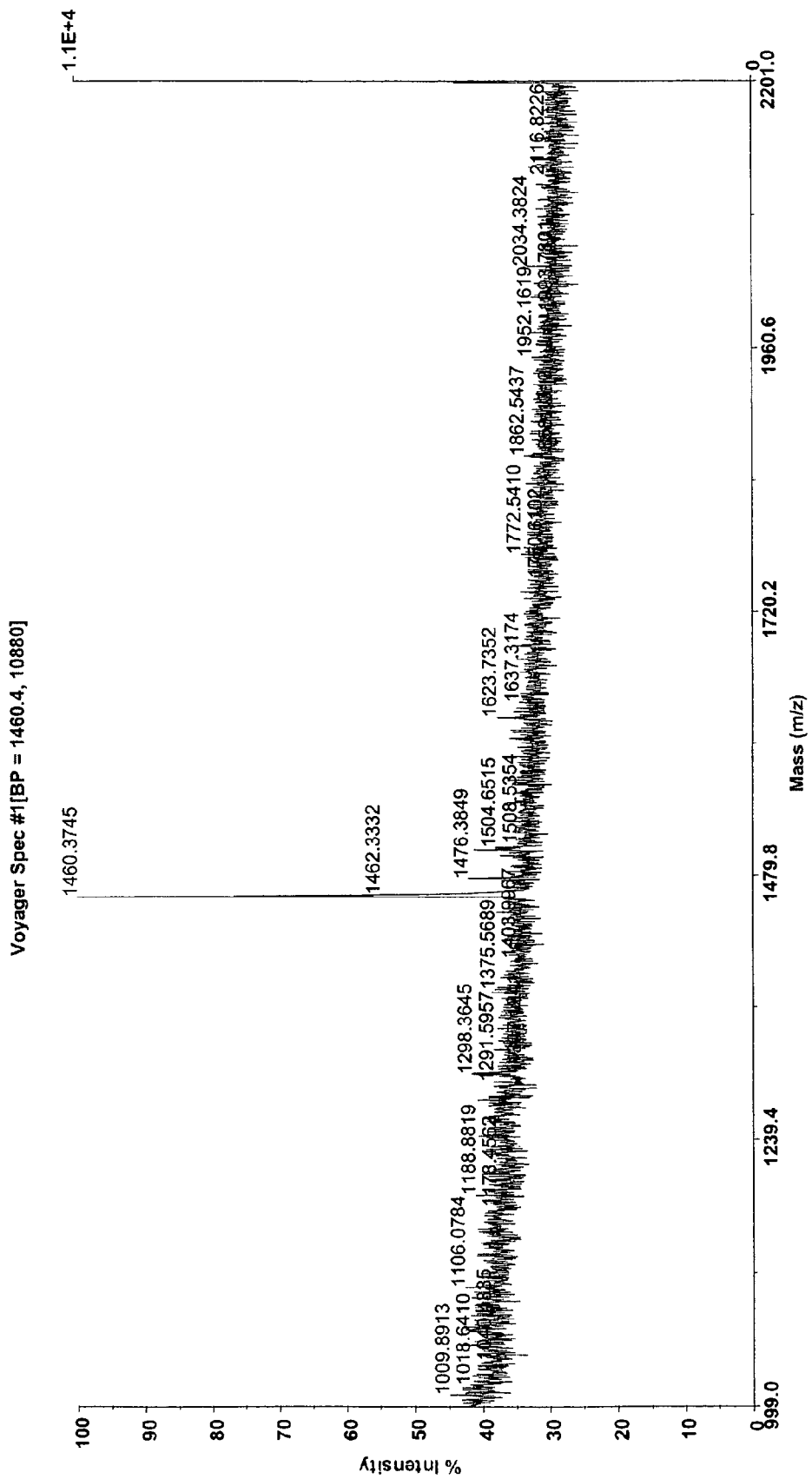

FIG. 26 shows the neutral oligosaccharide MALDI/TOF-MS profile from the unmodified, recombinant C2B8 anti-CD20 chimeric IgG1 antibody Cwt. As for the unmodified antibody previously described in Example 1, FIG. 5, Cwt had a typical oligosaccharide profile, with peaks at m/z ratios of 1485, 1648 and 1810 being consistent with biantennary, core-fucosylated, complex oligosaccharides with 0, 1- and 2-galactose residues, respectively. Engineering of the antibody-producing cells by expression of a nucleic acid encoding a ManII-GnTIII fusion polypeptide, where the GnTIII catalytic domain is localized via the ManII Golgi localization domain led to the production of an antibody (Cbrt) where the majority of the Fc-oligosaccharides were bisected, non-fucosylated hybrid (see FIG. 27). As described in Example 1, endoglycosidase H (EndoH) was used to confirm the assignment of bisected non-fucosylated and bisected, hybrid structures to the different oligosaccharide peaks observed in the MALDI profiles.

Figure 28A:
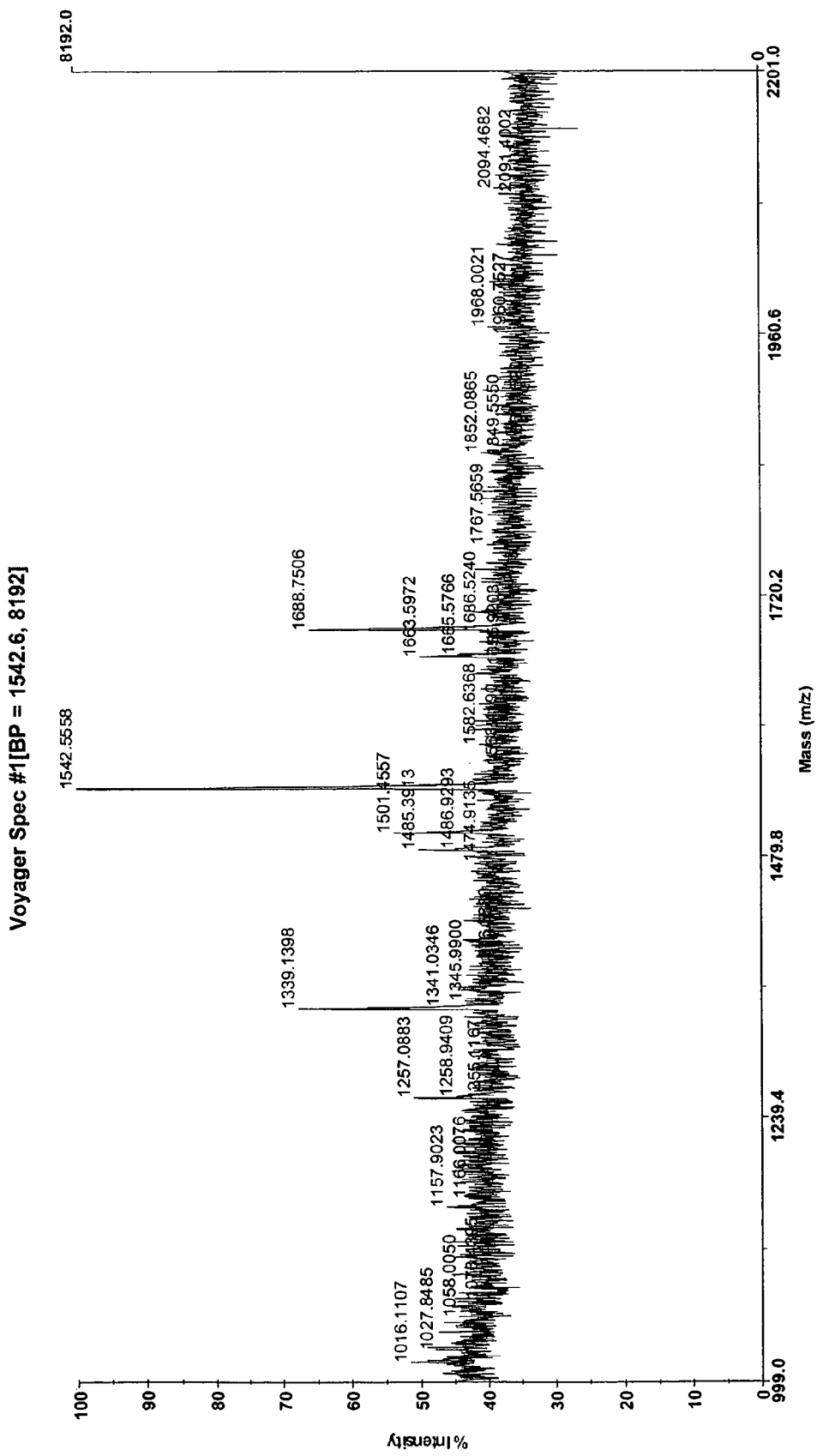
FIG. 28. MALDI/TOF-MS spectrum of neutral oligosaccharide mix derived from recombinant, glycoengineered C2B8 anti-CD20 chimeric IgG1 antibody ("Cm") produced in HEK293-EBNA cells co-transfected with antibody expression vector pETR1520, fusion GnTIII polypeptide expression vector (pETR1519) and mannosidase II polypeptide expression vector (pCLF9). Antibody was purified from culture medium and oligosaccharides were prepared and analyzed as described in the Materials and Methods section of Example 5. (A) Oligosaccharide profile of PNGaseF-release oligosaccharides with no additional enzymatic treatment. (B) Oligosaccharide profile of PNGaseF-release oligosaccharides further digested with EndoH.
Figure 28B:
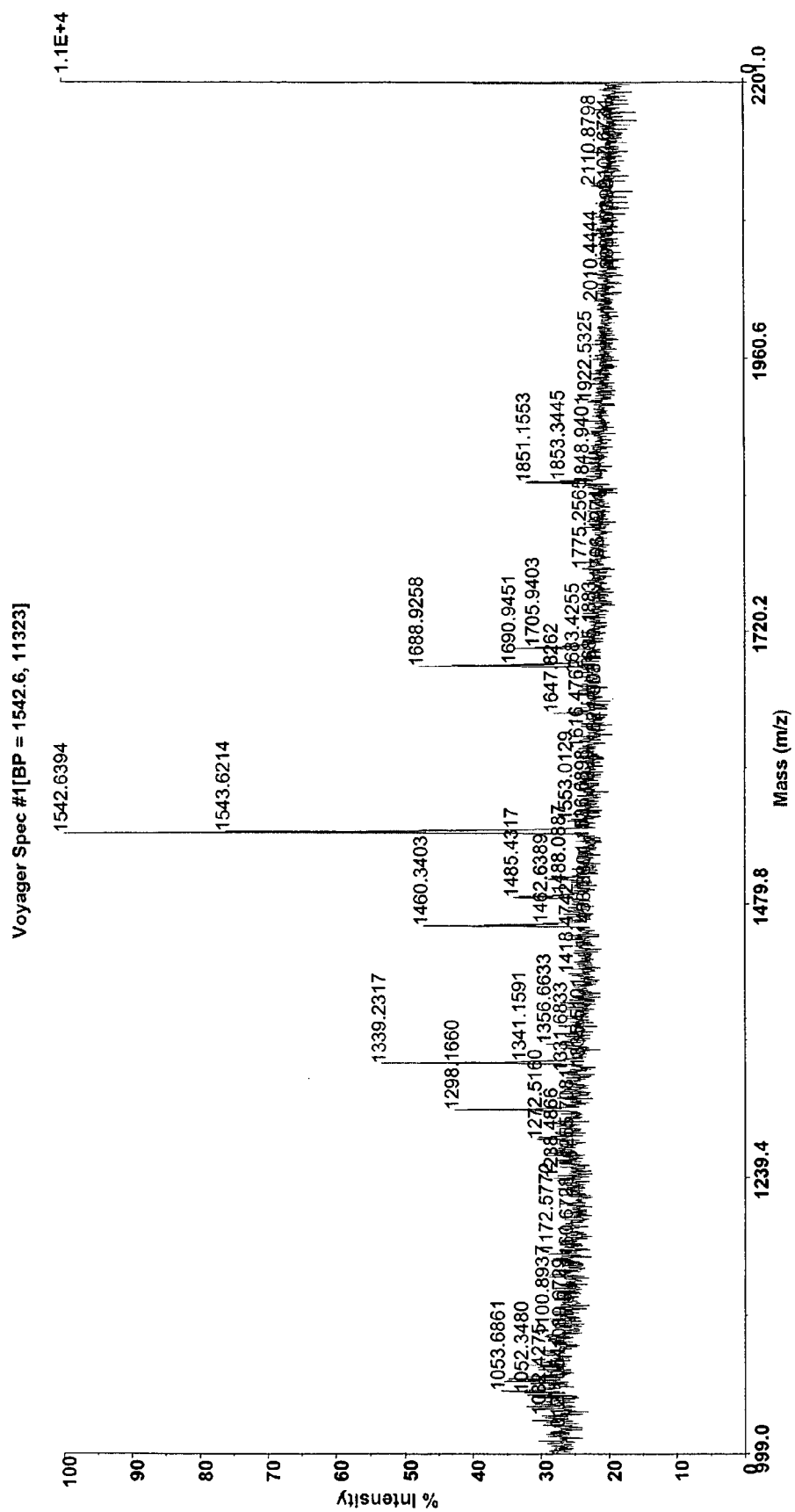

Engineering of the antibody-producing cells by co-expression of a nucleic acid encoding a ManII-GnTIII fusion polypeptide, where the GnTIII catalytic domain is localized via the ManII Golgi localization domain, and a nucleic acid encoding ManII, led to the production of an antibody (Cm) where the majority of the Fc-oligosaccharides were bisected, non-fucosylated complex (see FIG. 28). Engineering of the antibody-producing cells by co-expression of a nucleic acid encoding a ManII-GnTIII fusion polypeptide, where the GnTIII catalytic domain is localized via the ManII Golgi localization domain, a nucleic acid encoding ManII and a nucleic acid encoding GnTII, leads to the production of an antibody (Cmg) where the majority of the Fc-oligosaccharides are bisected, non-fucosylated complex, with a fraction of bisected, non-fucosylated complex Fc-attached oligosaccharides even higher than that of antibody Cm.

Figure 29:
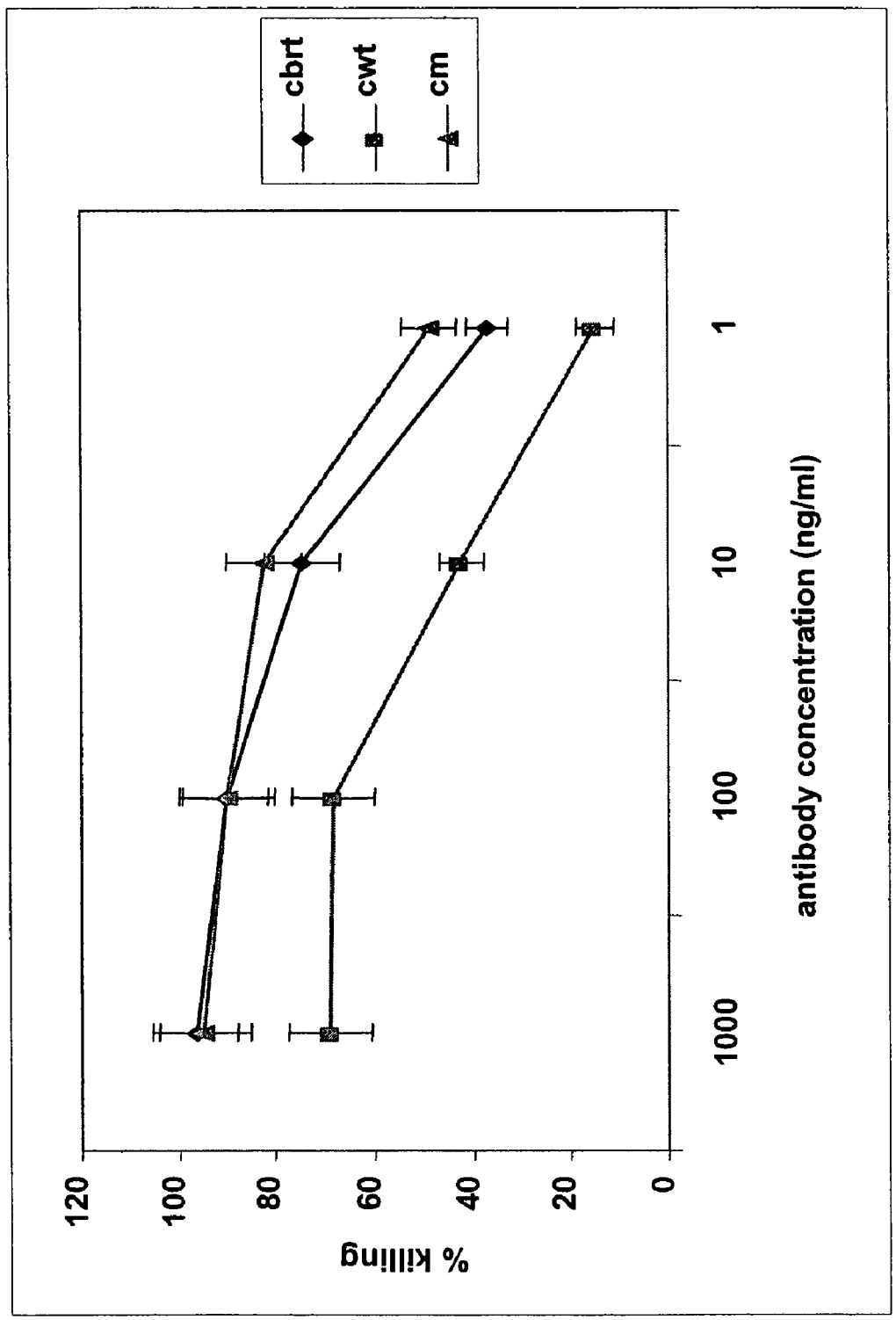
FIG. 29. Antibody-dependent cellular cytotoxicity (ADCC) mediated by chimeric anti-CD20 antibodies glycoengineered by expression in HEK293-EBNA cells of a nucleic acid encoding a ManII-GnTIII fusion polypeptide, where the GnTIII catalytic domain is localized via the ManII Golgi localization domain, where the ManII-GnTIII-encoding nucleic acid is expressed either on its own (antibody Cbrt) or co-expressed in the antibody producing cells together with a nucleic acid encoding ManII (Cm). Cwt is the unmodified, recombinant C2B8 anti-CD20 chimeric IgG1 antibody ("Cwt") produced in HEK293-EBNA cells transfected with antibody expression vector pETR1520. Assay details are described in Materials and Methods section of Example 1.

FIG. 29 shows data demonstrating increased antibody-dependent cellular cytotoxicity (ADCC) resulting from expression in the antibody-producing cells of a nucleic acid encoding a ManII-GnTIII fusion polypeptide, where the GnTIII catalytic domain is localized via the ManII Golgi localization domain, where the ManII-GnTIII-encoding nucleic acid is expressed either on its own (antibody Cbrt) or co-expressed in the antibody producing cells together with a nucleic acid encoding ManII (Cm). Therefore, increasing the level of bisected, non-fucosylated oligosaccharides of either the hybrid or complex type in the Fc region of the glycoengineered antibodies leads to increased ADCC activity.

Figure 30:
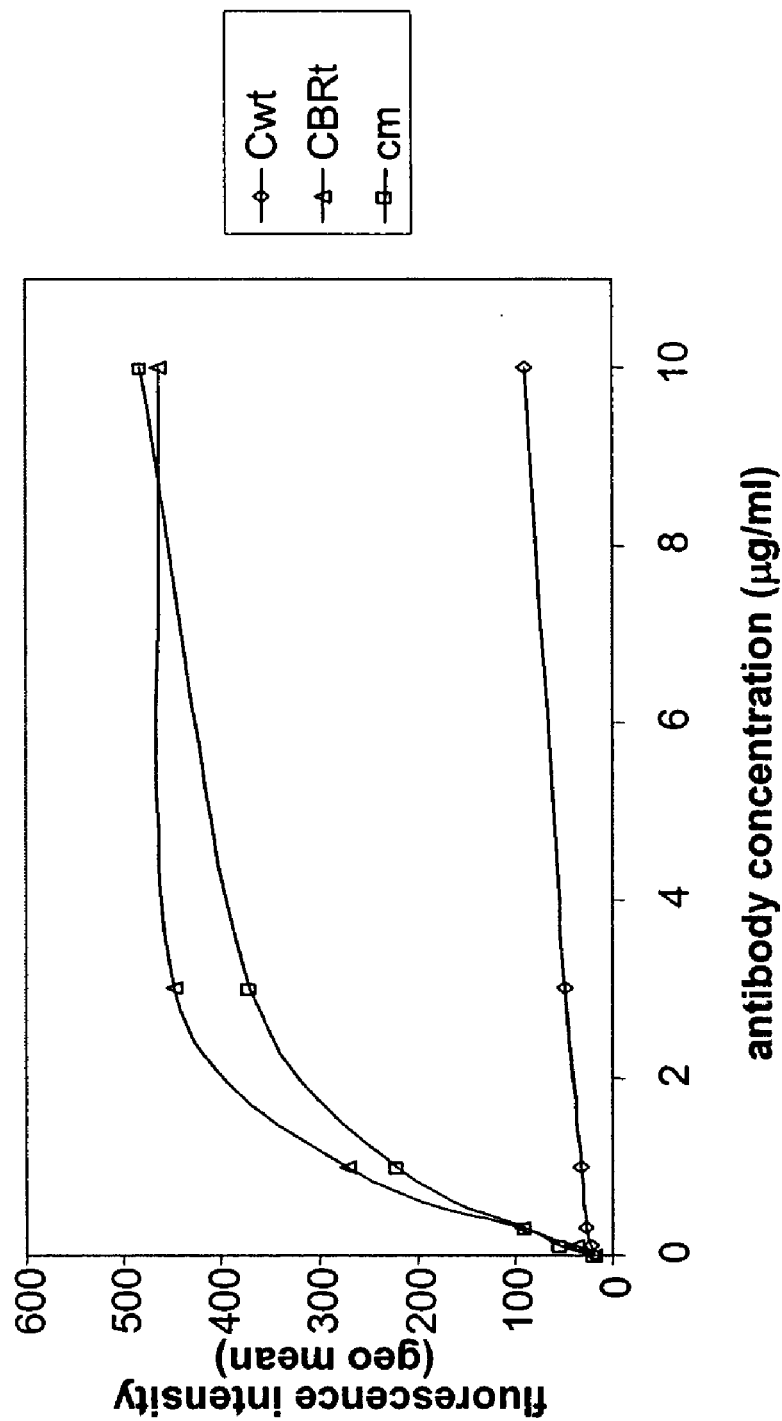
FIG. 30. FcgammaRIIIa receptor binding of chimeric anti-CD20 antibodies glycoengineered by expression in HEK293-EBNA cells of a nucleic acid encoding a ManII-GnTIII fusion polypeptide, where the GnTIII catalytic domain is localized via the ManII Golgi localization domain, where the ManII-GnTIII-encoding nucleic acid is expressed either on its own (antibody Cbrt) or co-expressed in the antibody producing cells together with a nucleic acid encoding ManII (Cm). Cwt is the unmodified, recombinant C2B8 anti-CD20 chimeric IgG1 antibody ("Cwt") produced in HEK293-EBNA cells transfected with antibody expression vector pETR1520. The binding assay was performed as described in the Materials and Methods section of Example 1. Human NK cells expressing FcgammaRIIIa receptor on their surface were isolated from a donor of a genotype known not to produce FcgammaRIIc receptor (i.e., homozygous for a gene variant that contains an in-frame stop codon within the FcgammaRIIc coding sequence). Geometric mean fluorescence intensity, measured by FACS using an FITC-labelled anti-human IgG antibody fragment, increases with the amount of recombinant antibody bound to the NK cells. Binding detected in this assay is FcgammaRIIIa-specific as demonstrated by use of a competing FcgammaRIIIa-specific antibody fragment (see FIG. 13).

Natural killer (NK) cells are known to be important mediators of ADCC. These cells carry on their surface the activating Fcgamma receptor IIIA, also known as CD16a. Binding of the Fc region, of the target-cell bound antibodies, to FcgammaRIIIA receptors on NK cells is essential for crosslinking of these receptors on the NK cell and subsequent induction of ADCC. Therefore it is important to evaluate the binding of the antibodies produced by the methods described here to Fc receptors, in particular to receptors in the native form in which the human immune effector cells display them. FIG. 30 demonstrates that glycoengineered antibodies produced by expression in the antibody producing cells of a nucleic acid encoding a fusion polypeptide with GnTIII activity, expressed either on its own (antibody Cbrt) or co-expressed in the antibody producing cells together with a nucleic acid encoding ManII (Cm), have increased binding affinity to the human activating Fc receptor FcgammaRIIIA. As mentioned above for the ADCC assays, these antibodies have increased levels of bisected, non-fucosylated oligosaccharides that result from the expression in the antibody-producing cells of the fusion polypeptide with GnTIII activity.

Therefore, increasing the level of bisected, non-fucosylated oligosaccharides of either the hybrid or complex type in the Fc region of the glycoengineered antibodies leads to increased ADCC activity. The NK cells used in this assay were from a donor of a genotype that does not express the FcgammaRIIc receptor on their NK cells (Metes, D. et al. *J. Immunol. Methods* 258(1-2):85-95 (2001)). Therefore the only Fc receptor on the surface of these cells is the activating FcgammaRIIIA receptor.

The binding domain of the activating FcgammaRIIIB receptor is almost identical to that of the FcgammaRIIIA. Therefore, the above data also indicates that glycoengineered antibodies described here can lead to increased effector functions mediated by effector cells displaying the FcgammaRIIIB, such as polymorphonuclear (PMN) cells, including release of toxic products and phagocytosis ((Reff, M. E. and Heard, C. *Crit Rev Oncol Hematol.* 40(1):25-35 (2001), Daeron, F M. *Annu. Rev. Immunol.* 15:203-34 (1997), Ravetch, J. V. and Bolland S. *Annu. Rev. Immunol.* 19:275-90 (2001)).

Figure 31:
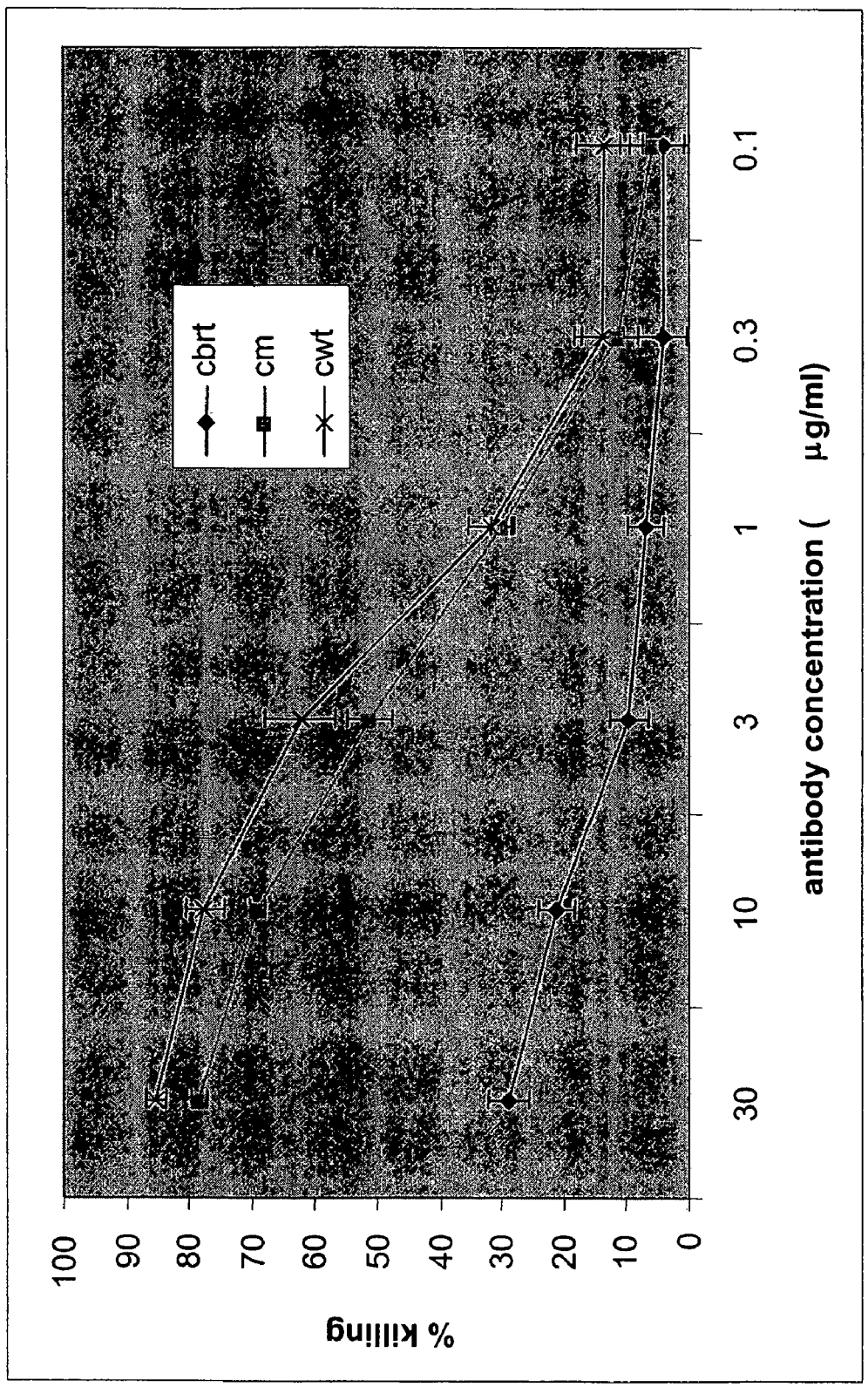
FIG. 31. Complement-mediated cytotoxicity of chimeric anti-CD20 antibodies glycoengineered by expression in HEK293-EBNA cells of a nucleic acid encoding a ManII-GnTIII fusion polypeptide, where the GnTIII catalytic domain is localized via the ManII Golgi localization domain, where the ManII-GntIII-encoding nucleic acid is expressed either on its own (antibody Cbrt) or co-expressed in the antibody producing cells together with a nucleic acid encoding ManII (Cm). Cwt is the unmodified, recombinant C2B8 anti-CD20 chimeric IgG1 antibody ("Cwt") produced in HEK293-EBNA cells transfected with antibody expression vector pETR1520.

Cbrt, an anti-CD20 antibody produced in cells engineered for expression of the nucleic acid encoding a fusion polypeptide with GnTIII activity and localized to the Golgi via the ManII localization domain was tested also for complement mediated lysis (CML), a different effector function that is not dependent on Fc receptors on immune effector cells. The vast majority of the oligosaccharides of this glycoengineered antibody were of bisected hybrid non-fucosylated type. Reduced CML activity was observed for the Cbrt antibody compared to the unmodified antibody Cwt (FIG. 31). For some applications antibodies with increased ADCC but with reduced CML may be desirable, for example to reduce side effects, such as vasculitis in the blood vessels at the tumor site, mediated by CML. Other significant CML-mediated side-effects have been observed for anti-CD20 antibody therapy (van der Kolk L. E. et al. *Br J Haematol.* 115(4):807-11 (2001)). However, it is possible to produce glycoengineered antibodies with increased ADCC activity and FcgammaRIII binding, but without significantly reducing CML activity relative to the unmodified antibody, as in the case of antibody Cm (FIG. 31). Such antibodies would be desirable for applications where maximal target cell elimination requires both high ADCC and high complement activation and CML activity. The oligosaccharide profiles described above show that is possible to engineer cells to produce antibodies where a majority of the Fc-attached oligosaccharides are of the bisected, non-fucosylated complex type instead of hybrid type by co-expressing the GnTIII fusion polypeptide together with a nucleic acid encoding ManII (antibody Cm) or together with a nucleic acid encoding ManII and with a nucleic acid encoding GnTII (antibody Cmg). The glycoengineered antibodies have increased ADCC activity and increased FcgammaRIII binding affinity that correlates with their increased levels of bisected non-fucosylated oligosaccharides, while their CML activity increased as the fraction of complex oligosaccharides increases relative to the fraction of hybrid oligosaccharides.

This and the previous examples have described the expression of fusion-polypeptide encoding nucleic acids, where the fusion polypeptide is localized to the Golgi complex and has a catalytic domain that competes with endogenous fucosyltransferases for oligosaccharide acceptors previously modified via GnTI-catalyzed reactions. Recombinant glycoproteins produced by such engineered host cells have increased levels of non-fucosylated oligosaccharides. This example demonstrates that co-expression in such host cells of nucleic acids encoding ManII and/or GnTII together with the above fusion-polypeptide encoding nucleic acids, leads to an increase in the biosynthetic flux towards complex instead of hybrid oligosaccharides and therefore to the synthesis of glycoproteins with increased levels of non-fucosylated complex oligosaccharides relative to glycoproteins produced in cells not co-expressing the ManII- and/or GnTII-encoding nucleic acids.

Example 6

Overexpression of α-Mannosidase

Molecular Cloning
Human α-Mannosidase II

Figure 32A:
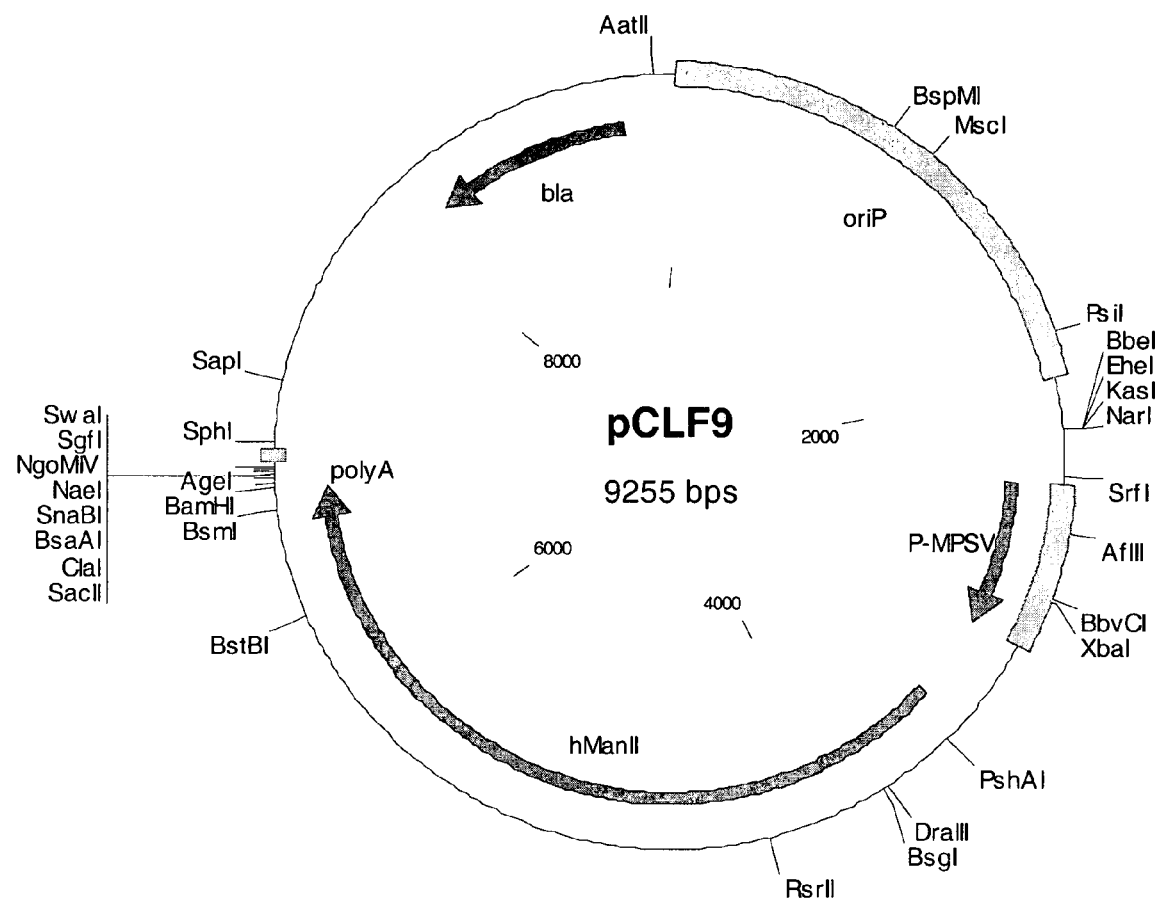
FIG. 32(A-C). Expression vectors pCLF9 (A), pETR1842 (B), and pETR1843 (C).
Figure 32B:
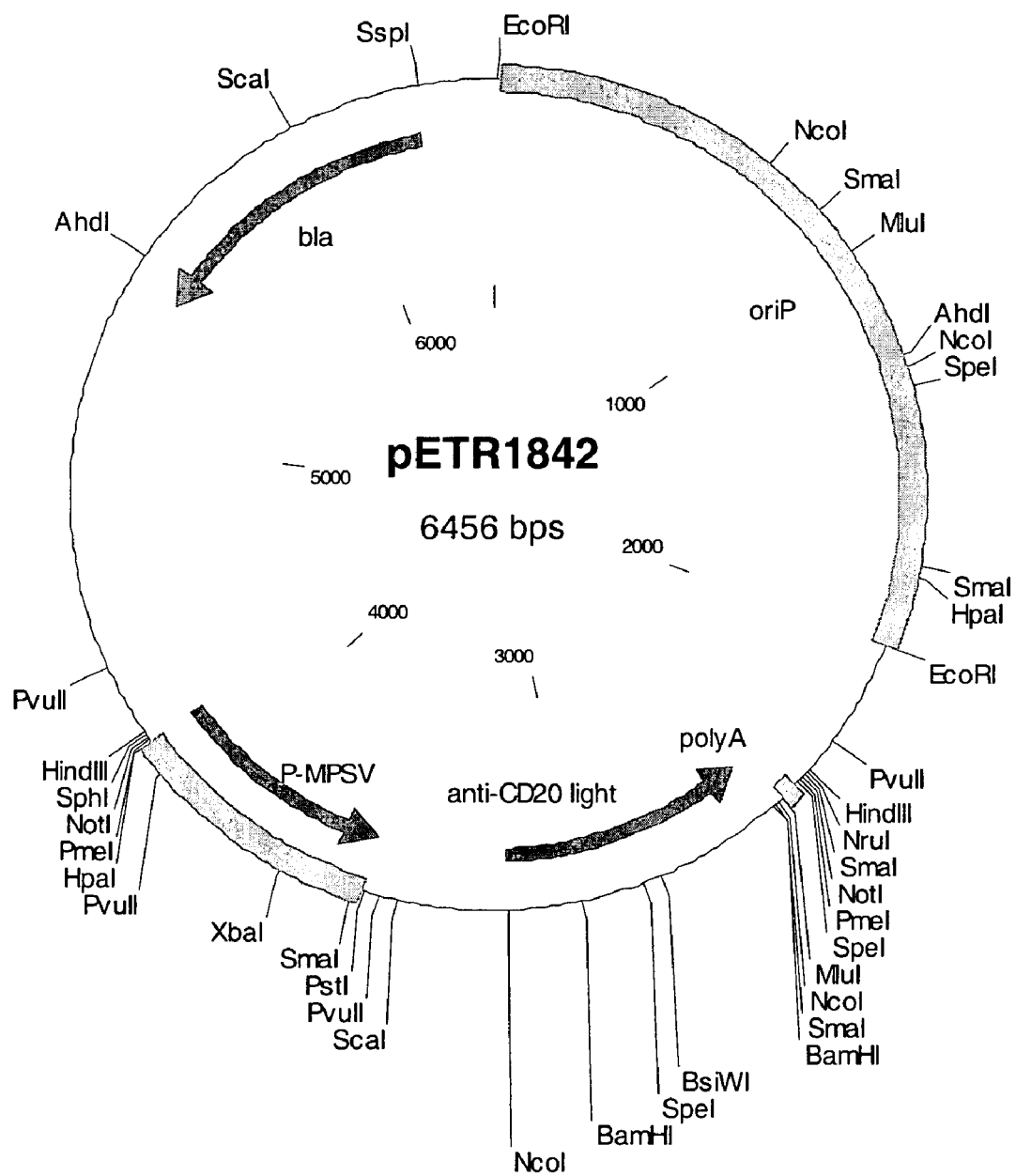
Figure 32C:
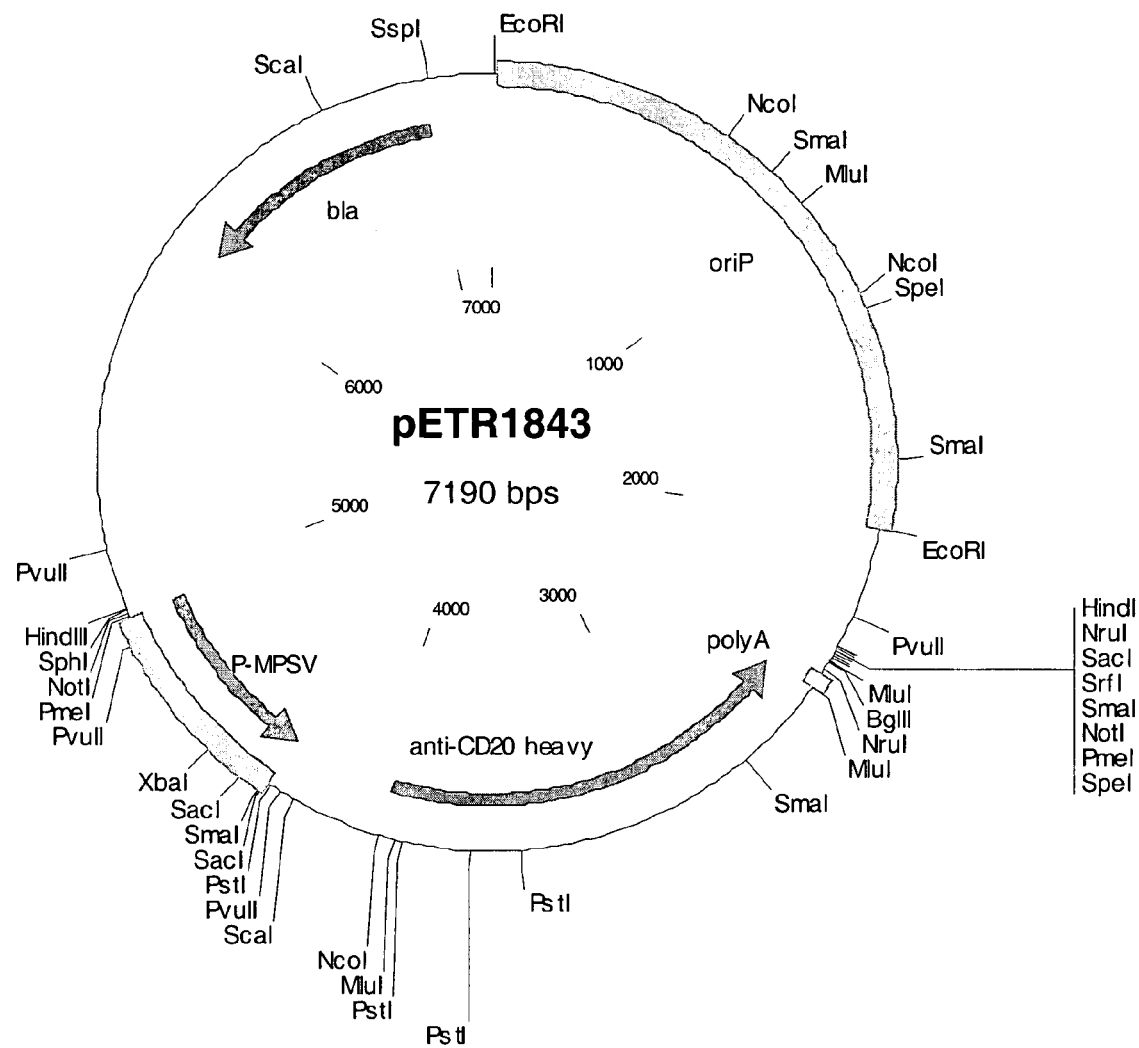

The gene coding for the human α-Mannosidase II ("hManII") (E.C. 3.2.1.114) (SEQ ID NO:17), under the control of the MPSV promoter, was cloned in an expression vector containing the OriP element. The resulting expression vector pCLF9 is shown in FIG. 32A. The expression vectors coding for the light and heavy chain of the anti-CD20 monoclonal antibody were respectively pETR1842 and pETR1843 (FIGS. 32B and 32C).
Fusion Protein ManII-GalT A fusion protein (SEQ ID NO:20), consisting of the hManII CTS and the catalytic domain of the human β1,4-galactosyltransferase (M22921, amino acids 126-397) was constructed as described below. The hManII CTS region was amplified by PCR from pETR1484 (CF33, GAB252). The catalytic domain of GalT (amino acids 126-397) was amplified using CF31 and CF35 from pBlueGalT. The hManII CTS was combined with the catalytic domain of GalT to obtain a fusion protein controlled by the MPSV promoter (pCLF24). The whole GalT gene was obtained from pBlueGalT. The gene coding for GalT was sequenced (SEQ ID NO:16):

MRLREPLLSGSAAMPGASLQRACRLLVAVCALHLGVTLVYYLAGRDLSRL

PQLVGVSTPLQGGSNSAAAIGQSSGELRTGGARPPPPLGASSQPRPGGDS

SPVVDSGPGPASNLTSVPVPHTTALSLPACPEESPLLVGPMLIEFNMPVD

LELVAKQNPNVKMGGRYAPRDCVSPHKVAIIIPFRNRQEHLKYWLYYLHP

VLQRQQLDYGIYVINQAGDTIFNRAKLLNVGFQEALKDYDYTCFVFSDVD

LIPMNDHNAYRCFSQPRHISVAMDKFGFSLPYVQYFGGVSALSKQQFLTI

NGFPNNYWGWGGEDDDIFNRLVFRGMSISRPNAVVGRCRMIRHSRDKKNE

PNPQRFDRIAHTKETMLSDGLNSLTYQVLDVQRYPLYTQITVDIGTPS

Figure 33A:
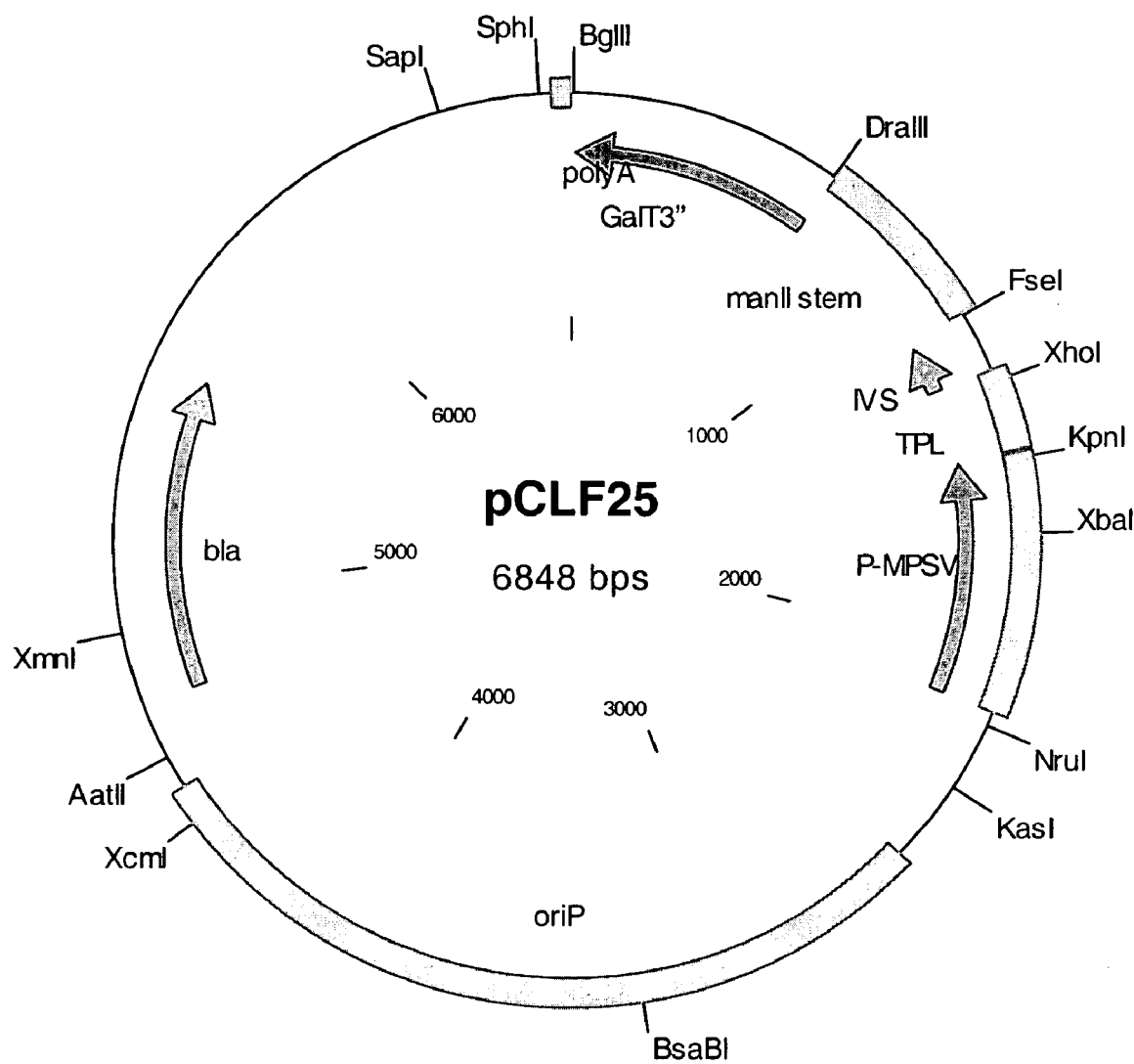
FIGS. 33(A and B). Expression vectors for fusion protein ManII-GalT (A) and GalT (B).
Figure 33B:
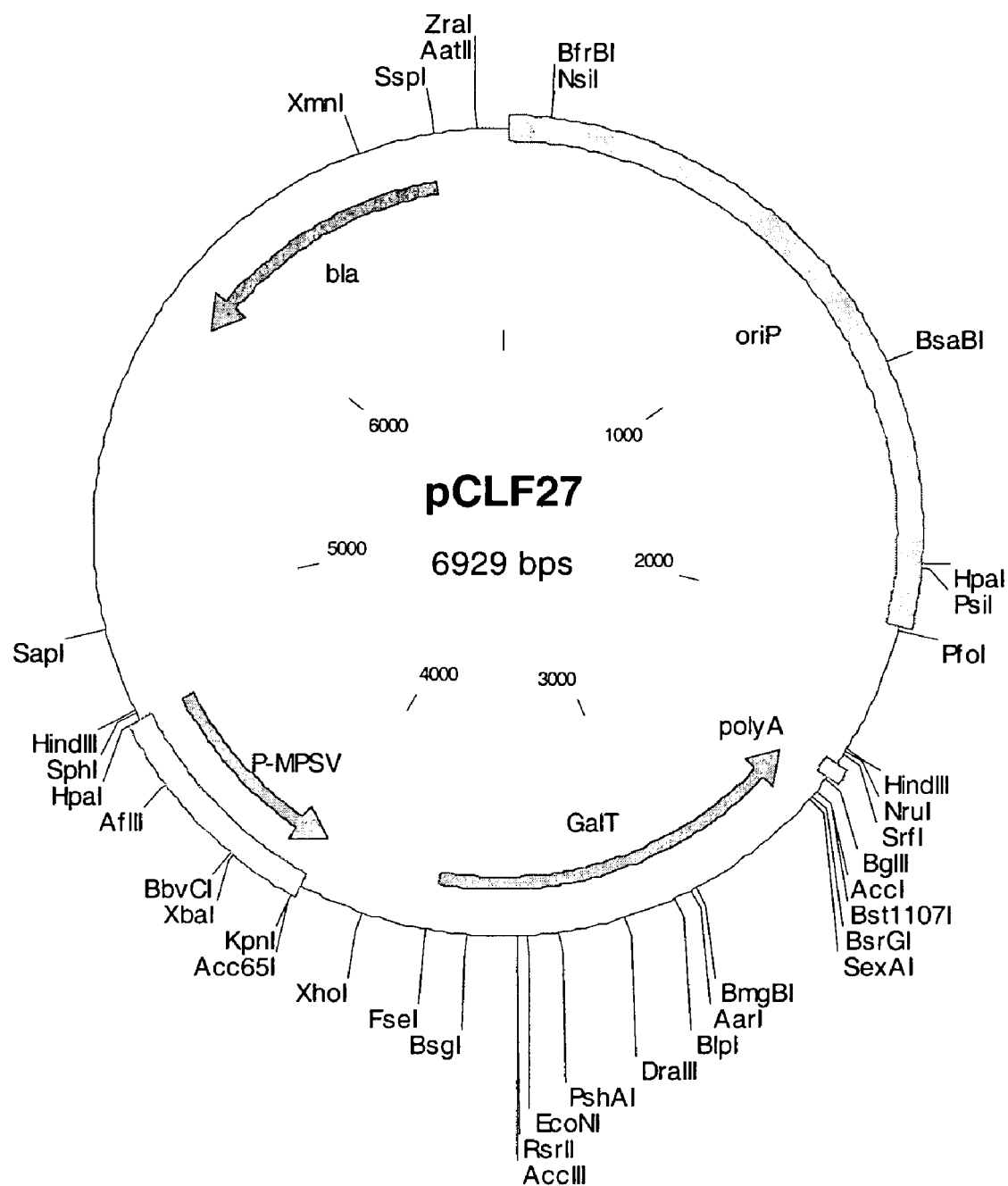

The 5' of GalT was amplified with CF32/CF38 and a FseI restriction site was added in front of the gene. The sequence was found correct by sequencing and exchanged in pCLF24 by FseI/DraIII digestion (pCLF26). The OriP was added to pCLF24 and pCLF26 to generate respectively pCLF25 and pCLF27 (FIGS. 33A and 33B).
Expression of α-Mannosidase and ManII-GalT in HEK 293-EBNA Cells HEK 293-EBNA cells were transfected with the calcium phosphate method. Briefly, for the transfection of a T150, 15 million cells were seeded 24 hours before transfection in 28 ml DMEM, 10% FCS, 250 µg/ml neomycin and incubated at 37° C., 5% $CO_2$ overnight.

For each T150 flask to be transfected, a solution of DNA, $CaCl_2$ and water was prepared by mixing 94 µg total plasmid vector DNA, 469 µl of a 1M $CaCl_2$ solution, and adding water to a final volume of 938 µl. To this solution, 938 µl of a 50 mM HEPES, 280 mM NaCl, 1.5 mM $Na_2HPO_4$ solution at pH 7.05 was added and mixed immediately for 10 sec and left to stand at room temperature for 20 sec. The suspension was diluted with 24 ml of DMEM supplemented with 2% FCS, and added to the T150 in place of the existing medium. The cells were incubated at 37° C., 5% $CO_2$ for about 17 to 20 hours, and the medium was replaced with 30 ml DMEM, 10% FCS.

For testing the α-Mannosidase II effect on core-fucosyltransferase competition, the cells were transfected with pETR1842, pETR1843 and pCLF9 at a ratio of 2:2:1 respectively. For the fusion protein ManII-GalT, the cells were transfected with pETR1842, pETR1843 and pCLF25 at a ratio of 2:2:1 respectively. At day 5 post-transfection, supernatant was harvested, centrifuged for 5 min at 1200 rpm, followed by a second centrifugation for 10 min at 4000 rpm, filtered and kept at 4° C.
Purification of Anti-CD20 Monoclonal Antibody The monoclonal antibody was purified from 30 ml of supernatant by two step chromatography, involving first a Protein A chromatography, to separate the monoclonal antibody from the cow antibody present in the serum, followed by a cation exchange chromatography, to buffer exchange the sample to PBS.
Oligosaccharide Analysis
PNGaseF Digestion The monoclonal antibody sample (50 µg) was incubated with N-Glycosidase F (recombinant, Roche, Switzerland) at 0.1 mU/µl. The digestion was performed in 2 mM Tris, pH7.0 buffer for 3 hours at 37° C. The released neutral oligosaccharides were then incubated at 150 mM acetic acid for 3 hours at room temperature. The samples were then desalted with 0.6 ml cation exchange resin (AG50W-X8 resin, hydrogen form, 100-200 mesh, BioRad, Hercules, Calif.) packed into a micro bio-spin chromatography column (BioRad, Hercules, Calif.).
EndoH Digestion The PNGaseF released oligosaccharides were digested with Endoglycosidase H (EC 3.2.1.96, ROCHE, Switzerland), an enzyme cleaving between the N-acetylglucosamine residues of the chitobiose core of N-linked oligosaccharides, prior to acetic acid treatment. The enzyme will cleave oligomannose and most hybrid type glycans, whereas complex type oligosaccharides are not hydrolyzed.

The oligosaccharides were digested with 0.2 mU/µl Endoglycosydase H in 2 mM Tris, pH 7.0. The digestion is performed at 37° C. for 3 hours. The oligosaccharides were incubated 3 h at room temperature at 150 mM acetic acid, and subsequently desalted with 0.6 ml cation exchange resin (AG50W-X8 resin, hydrogen form, 100-200 mesh, BioRad, Switzerland) packed into a micro bio-spin chromatography column (BioRad, Switzerland).

Matrix and Sample Preparation

The 2,5-dihydroxybenzoic acid matrix (sDHB) was prepared by dissolving 2 mg of 2,5-dihydroxybenzoic acid+0.1 mg of 5-methoxysalicylic acid in 1 ml of ethanol/10 mM aqueous sodium chloride 1:1 (v/v). 1 µl of sample was applied to a stainless steel target, and 1 µl of sDHB matrix was mixed. The samples were air-dried and 0.2 µl ethanol was applied.

MALDI/TOF Analysis

The MALDI-TOF mass spectrometer used to acquire the mass spectra was a Voyager Elite (Perspective Biosystems) equipped with delayed extraction. The instrument was operated in the reflector mode. Positive ions were accelerated to 20 kV after 75 ns delay. Five spectra of 40 shots (200 shots) were combined to obtain the final spectrum. External calibration using oligosaccharide standards was used for mass assignment of the ions.

Oligosaccharide Profile

Figure 34:
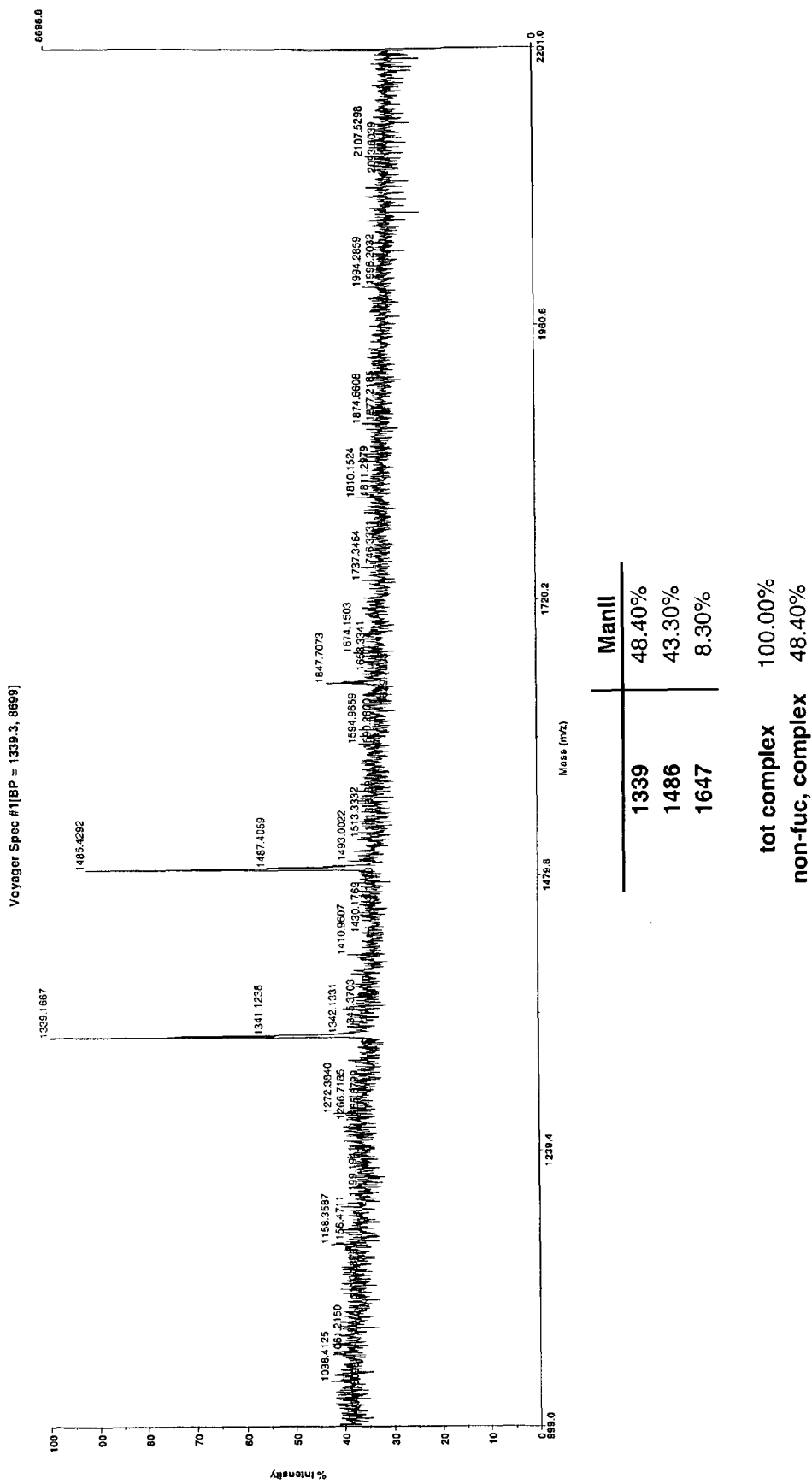
FIG. 34. Oligosaccharide profile of an anti-CD20 monoclonal antibody produced in the presence of α-Mannosidase II and relative percentages of the structures found associated to the Fc portion of the antibody.

The oligosaccharide profile of the anti-CD20 antibody produced in the presence of ManII is shown in FIG. 34. The oligosaccharides found associated to the Fc portion of the antibody are complex structures, 48% of which lack the core fucose. The α-Mannosidase II competes with the core-Fucosyltransferase, generating 48% of non-fucosylated oligosaccharide structures. In the absence of α-Mannosidase II, the oligosaccharides of the Fc portion of the antibody are composed only of fucosylated structures (wild type antibody).

Figure 35A:
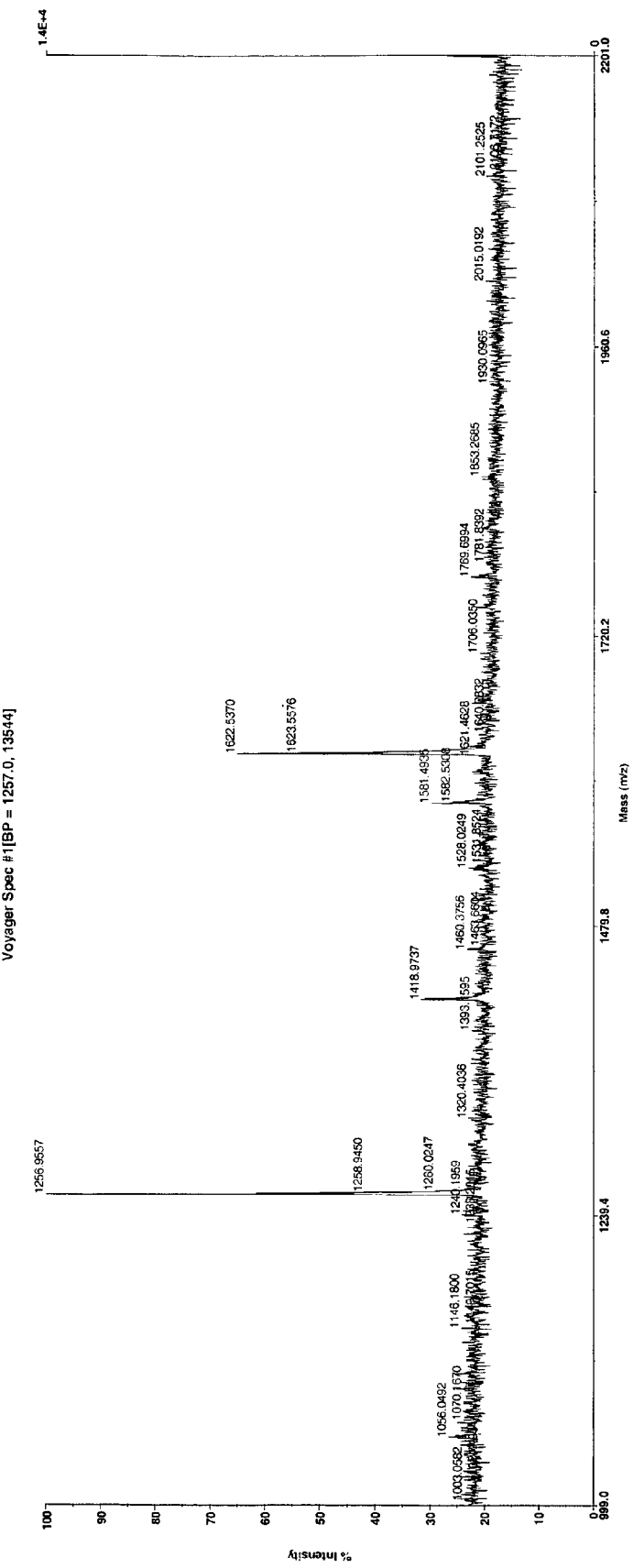
FIGS. 35(A and B). Oligosaccharide profile of an anti-CD20 monoclonal antibody produced in the presence of the fusion protein ManII-GalT and relative percentages of the structures found associated to the Fc portion of the antibody. Oligosaccharide profiles after PNGaseF (A) and EndoH (B) digestion.
Figure 35B:
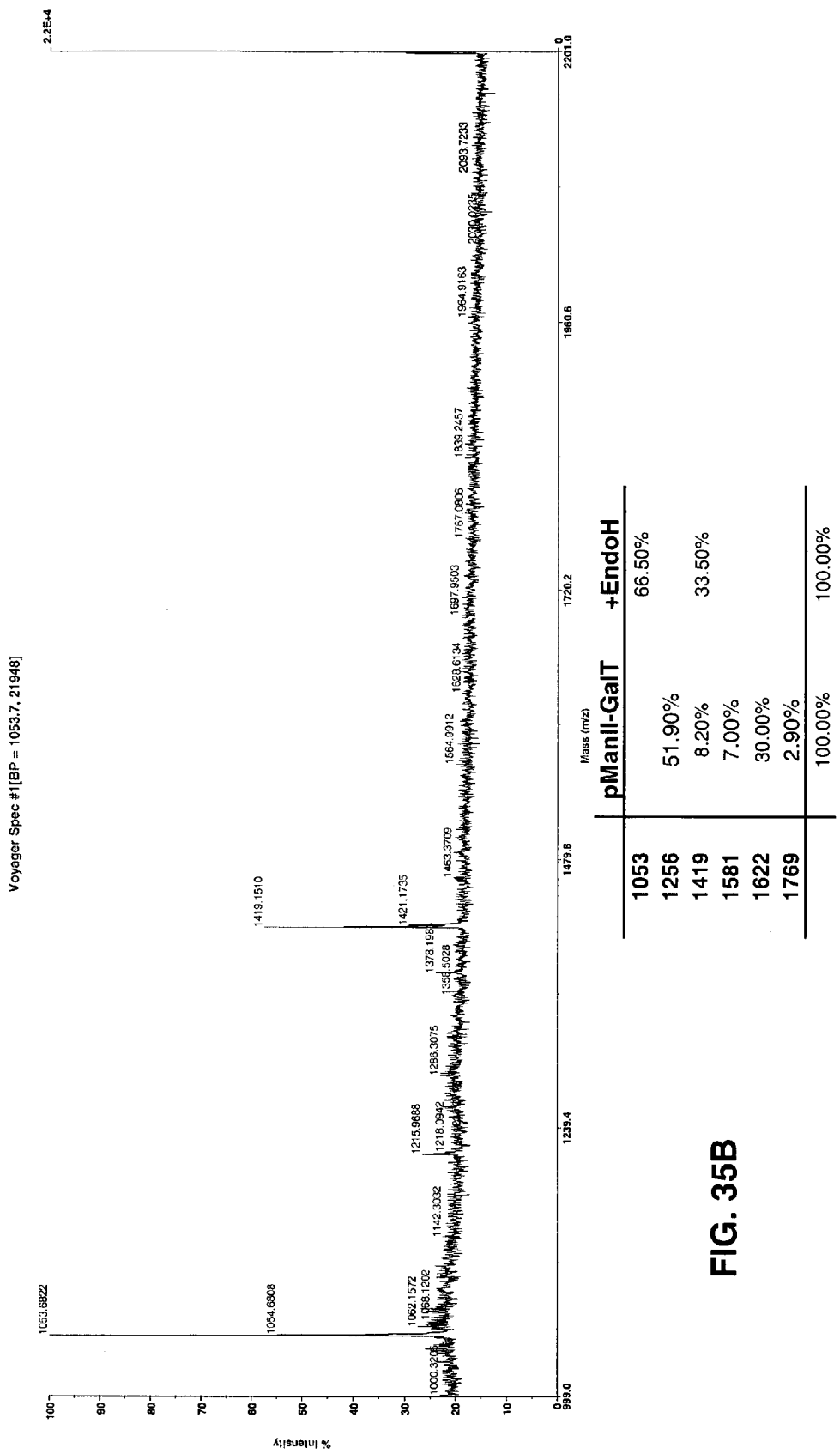

The oligosaccharide profile of an anti-CD20 antibody produced in the presence of the fusion protein ManII-GalT is shown in FIG. 35A-B. As for α-Mannosidase II, also in the case of the fusion protein ManII-GalT, the amount of non-fucosylated oligosaccharide structures increases. A high percentage of non-fucosylated structures consist in high mannose structures (m/z 1256, 1419 and 1581). To this 67% of non fucosylated sugars, an additional 30% of hybrid, non-fucosylated structures were found (m/z 1622). Therefore, the sample produced in the presence of the fusion protein ManII-GalT shows almost 100% of non-fucosylated structures.

Biological Activity of Antibodies Produced in the Presence of α-Mannosidase II or Fusion Protein ManII-GalT In order to determine the effect of the action of α-Mannosidase II and ManII-GalT enzyme in the competition of the core-fucosyltransferase, relevant biological assays were performed. The samples were tested for in vitro antibody-dependent cellular cytotoxicity (ADCC) and for binding to the CD16 receptor expressed on the surface of an engineered CHO cell line (CHO-1708-37).

IgG Binding on CHO-1708-37

Figure 36:
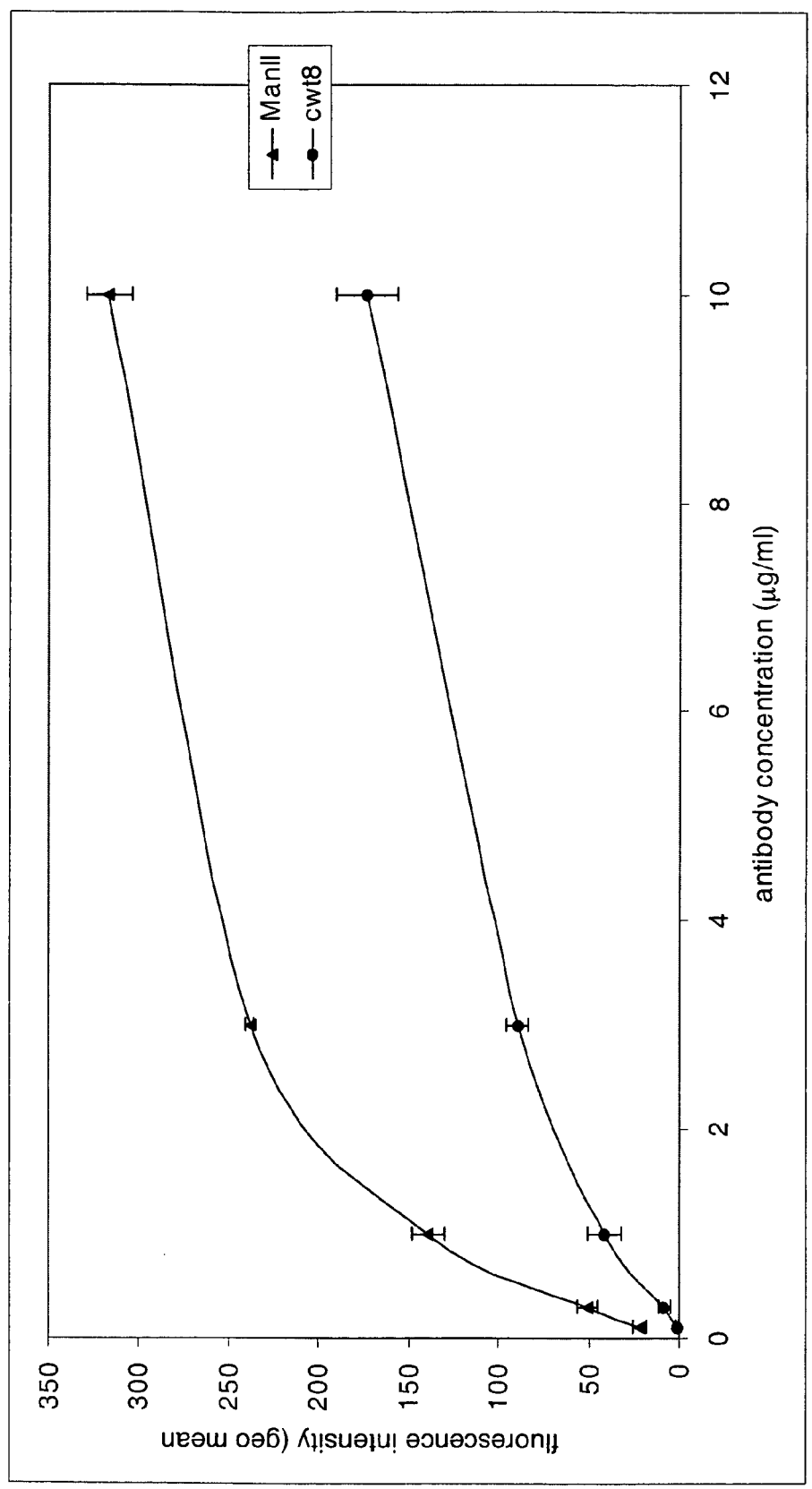
FIG. 36. Antibody produced in the presence of α-Mannosidase II (ManII) binds to the FcγRIIIA receptor with higher affinity than the wild type antibodies.

The cell line CHO-1708-37 expressed on its surface the FcγRIIIA receptor (CD16) and the γ chain of the FcγRI receptor. The expression of the FcγRIIIA receptor (CD16) was assessed by FACS analysis using the 3G8-FITC monoclonal antibody (FIG. 36). The CHO-1708-37 cells were incubated at 1 Mio/ml in PBS, 0.1% BSA with different antibody variants, at different concentrations (10, 3, 1, 0.3, 0.1 µg/ml) and in triplicates. The cells were incubated for 30 min at 4° C. and subsequently washed with PBS, 0.1% BSA. Antibody binding was detected by incubating with 1:200 fluorescein isothiocyanate-conjugated F(ab')$_2$ goat anti-human IgG (Jackson ImmunoReasearch, West Grove, Pa.) for 30 min at 4° C. The fluorescence intensity referring to the bound antibody variants was determined on a FACSCalibur (BD Bioscience, San Jose, Calif.) gating living cells.

The following antibody variants were included in the binding assay experiment:

Cwt8 (wild type 1)

ManII (α-Mannosidase II)

The antibody produced in the presence of α-Mannosidase II (ManII) binds to the FcγRIIIA receptor with higher affinity than the wild type antibodies.

In Vitro Antibody-Dependent Cellular Cytotoxicity (ADCC)

Peripheral blood mononuclear cells (PBMC) were prepared using Histopaque-1077 (Sigma Diagnostics Inc., St. Louis, Mo. 63178 USA) and following essentially the manufacturer's instructions. In brief, venous blood was taken with heparinized syringes from volunteers who were asked to run for 1 min at full power in order to increase the percentage of natural killer cells (NK) in the blood. The blood was diluted 1:0.75-1.3 with PBS not containing Ca or Mg and layered on Histopaque-1077. The gradient was centrifuged at 400 g for 30 min at room temperature (RT) without breaks. The interphase containing the PBMC was collected and washed with PBS (50 ml per cells from two gradients) and harvested by centrifugation at 300 g for 10 min at RT. After resuspension of the pellet with PBS the PBMC were counted and washed a second time by centrifugation at 200 g for 10 min at RT. The cells were then resuspended in the appropriate medium for the subsequent procedures.

Figure 37:
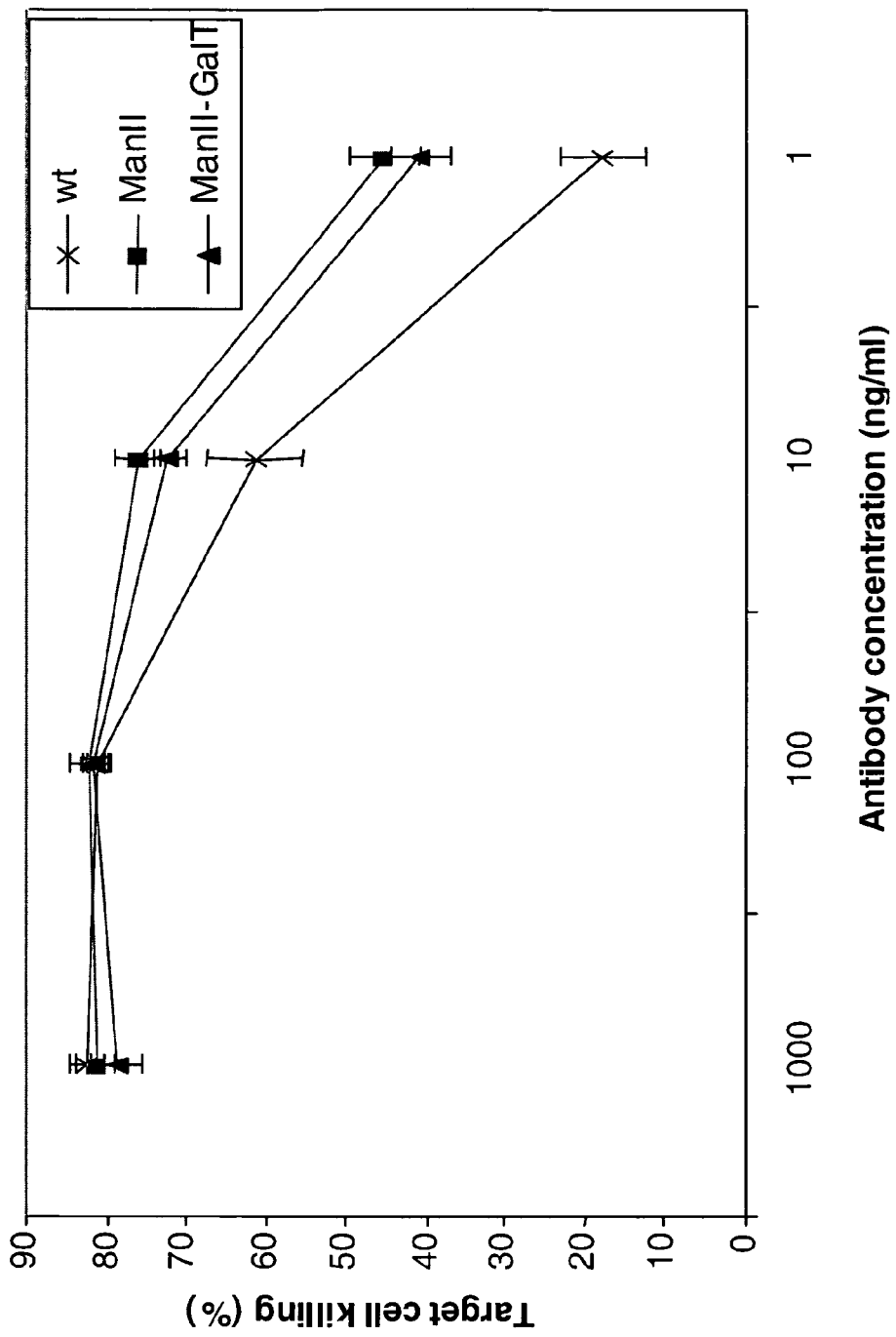
FIG. 37. Antibody-dependent cellular cytotoxicity mediated by glycoengineered chimeric anti-CD20.

The Raji target cells were washed in PBS, counted and resuspended in DMEM, 10% FCS, 1% Glutamax at 1 Mio per ml. To these, 1:100 calcein was added and cells were incubated for 30 min at 37° C. Cells were then washed in PBS, counted and resuspended in AIM-V at 0.3 Mio per ml. Of this cell suspension, 100 µl were added per well of a round bottom 96 well plate. Antibodies were diluted in AIM-V, added in 50 ul to the preplated target cells and allowed to bind to the targets for 10 min at RT. PBMC as effector cells were prepared as described above. The effector to target ratio was 25:1. The effector cells were prepared at 15 Mio per ml in AIM-V medium and 50 µl were added per well. The plate was incubated for 4 hours at 37° C. in a humified atmosphere containing 5% $CO_2$. Cells were washed twice in PBS and 200 µl of borate solution were added. Killing of target cells was assessed by measuring the calcein released in the medium after lysis with the borate solution (FIG. 37).

Spontaneous release was measured from wells containing only target and effector cells but no antibodies. Maximal release was determined from wells containing only target cells and 1% Triton X-100. Percentage of specific antibody-mediated killing was calculated as follows: $((x-SR)/(MR-SR))*100$, where x is the mean of Vmax at a specific antibody concentration, SR is the mean of Vmax of the spontaneous release and MR is the mean of Vmax of the maximal release.

Example 7

Use of Glycoengineered Anti-EGFR Monoclonal Antibody to Treat Psoriasis

Human patients with psoriasis can be treated with a glycoengineered anti-EGFR monoclonal antibody produced according to the methods of the invention. In particular, the patient receives weekly infusions of the glycoengineered antibody at a loading dose of 400 mg/m². Maintenance doses of 250 mg/m² are administered on a weekly basis until complete response is achieved.

Example 8

Use of Glycoengineered Anti-ErbB2 Monoclonal Antibody in the Treatment of Metastatic Prostate Cancer, Metastatic Breast Cancer, Metastatic Colorectal Cancer, and Stage IIIb or IV Non-Small Cell Lung Cancer RhuMAb2C4 is a full-length, humanized monoclonal antibody (produced in CHO cells) directed against ErbB2. RhuMab 2C4 blocks the associated of ErbB2 with other ErbB family members thereby inhibiting intracellular signaling through the ErbB pathway. RhuMAb 2C4 not only inhibits the growth of ErbB2 overexpressing tumors but also blocks growth of tumors that require ErbB ligand-dependent signaling.

A glycoengineered form of RhuMAb 2C4 made by the methods of the present invention can be used as a single agent for treatment of hormone-refractory (androgen independent) prostate cancer patients, metastatic breast cancer patients, metastatic colorectal cancer patients and patients with stage IIIb or IV non-small cell lung cancer. Specifically, the glycoengineered RhuMAb 2C4 is administered intravenously (IV) weekly or every three weeks at 2 or 4 mg/kg, respectively, until disease progression ceases. The antibody is supplied as a multi-dose liquid formulation (20 mL fill at a concentration of 20 mg/mL or higher concentration).

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference in their entirety.

---

What is claimed is:

1. A method for modifying the glycosylation profile of a polypeptide produced by a mammalian host cell, comprising introducing into said host cell an isolated nucleic acid comprising a sequence encoding a fusion polypeptide, wherein said fusion polypeptide has β(1,4)-N-acetylglucosaminyltransferase III activity and comprises the Golgi localization domain of mannosidase II, and wherein said modified polypeptide has increased Fc-receptor binding or effector function as a result of said modification.

2. A method for modifying the glycosylation profile of a polypeptide produced by a mammalian host cell, comprising introducing into said host cell an expression vector which comprises an isolated nucleic acid comprising a sequence encoding a fusion polypeptide, wherein said fusion polypeptide has β(1,4)-N-acetylglucosaminyltransferase III activity and comprises the Golgi localization domain of mannosidase II, and wherein said modified polypeptide has increased Fc-receptor binding or effector function as a result of said modification.

3. A method according to claim 1 or 2, wherein said polypeptide is IgG or a fragment thereof.

4. A method according to claim 3, wherein said polypeptide is IgG1 or a fragment thereof.

5. A method according to claim 3, wherein said polypeptide is a fusion protein that includes a region equivalent to the Fc region of a human IgG.

6. A method for producing a polypeptide in a mammalian host cell, comprising:
   a. culturing a mammalian host cell engineered to express at least one nucleic acid encoding a fusion polypeptide having β(1,4)-N-acetylglucosaminyltransferase III activity under conditions which permit the production of a polypeptide selected from the group consisting of a whole antibody molecule, an antibody fragment, and a fusion protein that includes a region equivalent to the Fc region of an immunoglobulin, wherein said fusion polypeptide is expressed in an amount sufficient to modify the oligosaccharides in the Fc region and increase the Fc-receptor binding or effector function of said polypeptide produced by said host cell and wherein said fusion polypeptide having β(1,4)-N-acetylglucosaminyltransferase III activity comprises the Golgi localization domain of mannosidase II; and
   b. isolating said polypeptide.

7. A method according to claim 6 wherein said fusion polypeptide consists essentially of the catalytic domain of β(1,4)-N-acetylglucosaminyltransferase III and the Golgi localization domain of mannosidase II.

8. A method according to claim 6, wherein said produced polypeptide selected from the group consisting of a whole antibody molecule, an antibody fragment, and a fusion protein that includes a region equivalent to the Fc region of an immunoglobulin exhibits at least 15% greater antibody-dependent cellular cytotoxicity compared to polypeptides produced in a host cell expressing wild-type β(1,4)-N-acetylglucosaminyltransferase III.

9. A method according to claim 6, wherein said increased effector function is increased Fc-mediated cellular cytotoxicity.

10. A method according to claim 6, wherein said polypeptide produced by said host cell exhibits increased Fc receptor binding affinity as a result of said modification.

11. A method according to claim 10, wherein said Fc receptor is Fc activating receptor.

12. A method according to claim 10, wherein said Fc receptor is FcγRIIIA receptor.

13. A method according to claim 6, wherein said polypeptide produced by said host cell has an increased proportion of bisected oligosaccharides in the Fc region of said polypeptide.

14. A method according to claim 6, wherein said polypeptide produced by said host cell has an increased proportion of nonfucosylated oligosaccharides in the Fc region of said polypeptide.

15. A method according to claim 14, wherein said nonfucosylated oligosaccharides are hybrid.

16. A method according to claim 14, wherein said nonfucosylated oligosaccharides are complex.

17. A method according to claim 6, wherein said polypeptide produced by said host cell has an increased proportion of bisected, nonfucosylated oligosaccharides in the Fc region of said polypeptide.

18. A method according to claim 17, wherein said bisected, nonfucosylated oligosaccharides are hybrid.

19. A method according to claim 17, wherein said bisected, nonfucosylated oligosaccharides are complex.

20. A method according to claim 17, wherein at least 20% of the oligosaccharides in the Fc region of said polypeptide are bisected, nonfucosylated.

21. A method according to claim 17, wherein at least 25% of the oligosaccharides in the Fc region of said polypeptide are bisected, nonfucosylated.

22. A method according to claim 17, wherein at least 30% of the oligosaccharides in the Fc region of said polypeptide are bisected, nonfucosylated.

23. A method according to claim 17, wherein at least 35% of the oligosaccharides in the Fc region of said polypeptide are bisected, nonfucosylated.

24. A method for producing a polypeptide in a mammalian host cell, comprising:
   a. culturing a mammalian host cell engineered to express at least one nucleic acid encoding a fusion polypeptide having GnT III activity and at least one nucleic acid encoding a polypeptide having Man II activity under conditions which permit the production of a polypeptide selected from the group consisting of a whole antibody molecule, an antibody fragment, and a fusion protein that includes a region equivalent to the Fc region of an immunoglobulin, wherein said fusion polypeptide is expressed in an amount sufficient to modify the oligosaccharides in the Fc region and increase the Fc-receptor binding or effector function of said polypeptide produced by said host cell and wherein said fusion polypeptide having GnT III activity comprises the Golgi localization domain of mannosidase II; and
   b. isolating said polypeptide.

25. A method according to claim 24 wherein said fusion polypeptide consists essentially of the catalytic domain of GnT III and the Golgi localization domain of mannosidase II.

26. A method according to claim 24, wherein said produced polypeptide selected from the group consisting of a whole antibody molecule, an antibody fragment, and a fusion protein that includes a region equivalent to the Fc region of an immunoglobulin exhibits at least 15% greater antibody-dependent cellular cytotoxicity compared to polypeptides produced in a host cell expressing wild-type β(1,4)-N-acetylglucosaminyltransferase III.

27. A method according to claim 24, wherein said polypeptide produced by said host cell has an increased proportion of bisected, nonfucosylated oligosaccharides in the Fc region of said polypeptide.

28. A method according to claim 27, wherein said bisected, nonfucosylated oligosaccharides are hybrid.

29. A method according to claim 27, wherein said bisected, nonfucosylated oligosaccharides are complex.

30. A method according to claim 27, wherein at least 20% of the oligosaccharides in the Fc region of said polypeptide are bisected, nonfucosylated.

31. A method according to claim 27, wherein at least 25% of the oligosaccharides in the Fc region of said polypeptide are bisected, nonfucosylated.

32. A method according to claim 27, wherein at least 30% of the oligosaccharides in the Fc region of said polypeptide are bisected, nonfucosylated.

33. A method according to claim 27, wherein at least 35% of the oligosaccharides in the Fc region of said polypeptide are bisected, nonfucosylated.

* * * * *